United States Patent
Gryaznov et al.

(10) Patent No.: US 12,077,757 B2
(45) Date of Patent: *Sep. 3, 2024

(54) MODIFIED OLIGONUCLEOTIDES AND METHODS OF USE

(71) Applicant: Janssen Biopharma, Inc., South San Francisco, CA (US)

(72) Inventors: Sergei Gryaznov, San Mateo, CA (US); Leonid Beigelman, San Mateo, CA (US); Antitsa Dimitrova Stoycheva, Half Moon Bay, CA (US); Saul Martinez Montero, Gijón (ES); Jin Hong, San Mateo, CA (US); Rajendra K. Pandey, Foster City, CA (US); Vivek Kumar Rajwanshi, Cupertino, CA (US); Lakshmipathi Pandarinathan, Boston, MA (US); Yi Jin, Carlsbad, CA (US); Bharat Baral, Vacaville, CA (US)

(73) Assignee: Janssen Pharmaceutica NV, Beerse (BE)

( * ) Notice: Subject to any disclaimer, the term of this patent is extended or adjusted under 35 U.S.C. 154(b) by 267 days.

This patent is subject to a terminal disclaimer.

(21) Appl. No.: 17/063,080

(22) Filed: Oct. 5, 2020

(65) Prior Publication Data

US 2021/0040483 A1 Feb. 11, 2021

Related U.S. Application Data

(63) Continuation of application No. 15/705,137, filed on Sep. 14, 2017, now Pat. No. 10,793,859.

(60) Provisional application No. 62/394,739, filed on Sep. 14, 2016, provisional application No. 62/394,738, filed on Sep. 14, 2016.

(51) Int. Cl.
| | | |
|---|---|---|
| *C07H 21/02* | (2006.01) | |
| *A61K 31/712* | (2006.01) | |
| *A61K 31/7125* | (2006.01) | |
| *A61K 47/54* | (2017.01) | |
| *A61P 31/20* | (2006.01) | |
| *C12N 15/11* | (2006.01) | |
| *C12N 15/113* | (2010.01) | |

(52) U.S. Cl.
CPC ........ *C12N 15/1131* (2013.01); *A61K 31/712* (2013.01); *A61K 31/7125* (2013.01); *A61K 47/549* (2017.08); *A61P 31/20* (2018.01); *C07H 21/02* (2013.01); *C12N 15/111* (2013.01); *C12N 2310/11* (2013.01); *C12N 2310/314* (2013.01); *C12N 2310/3145* (2013.01); *C12N 2310/315* (2013.01); *C12N 2310/3231* (2013.01); *C12N 2310/341* (2013.01); *C12N 2310/344* (2013.01); *C12N 2310/351* (2013.01); *C12N 2320/32* (2013.01)

(58) Field of Classification Search
CPC .............................. A61K 38/00; C12N 15/113
See application file for complete search history.

(56) References Cited

U.S. PATENT DOCUMENTS

| | | |
|---|---|---|
| 6,268,490 B1 | 7/2001 | Imanishi et al. |
| 6,525,191 B1 | 2/2003 | Ramasamy |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,084,125 B2 | 8/2006 | Wengel |
| 7,217,805 B2 | 5/2007 | Imanishi et al. |
| 7,314,923 B2 | 1/2008 | Kaneko et al. |
| 7,569,575 B2 | 8/2009 | Sorensen et al. |
| 7,696,345 B2 | 4/2010 | Allerson et al. |
| 8,268,986 B2 | 9/2012 | Beigelman et al. |
| 8,642,752 B2 | 2/2014 | Swayze et al. |
| 10,793,859 B2 | 10/2020 | Gryaznov et al. |
| 2009/0082975 A1 | 3/2009 | Balac Sipes et al. |
| 2013/0156845 A1 | 6/2013 | Manoharan et al. |
| 2014/0121261 A1 | 5/2014 | Gryaznov et al. |
| 2015/0218205 A1 | 8/2015 | Cedillo et al. |
| 2016/0215275 A1 | 7/2016 | Zhong |

FOREIGN PATENT DOCUMENTS

| | | | |
|---|---|---|---|
| JP | 2003-513887 | 4/2003 | |
| WO | WO-95/25814 A1 | 9/1995 | |
| WO | WO 01/18015 A1 | 3/2001 | |
| WO | WO-01/53307 A1 | 7/2001 | |
| WO | WO 02/081494 A1 | 10/2002 | |
| WO | WO 2005/047506 A1 | 5/2005 | |
| WO | WO 2007/022369 A2 | 2/2007 | |
| WO | WO 2008/011473 A2 * | 1/2008 | ........... C12N 15/113 |
| WO | WO-2011/047312 A1 | 4/2011 | |
| WO | WO 2011/060557 A1 | 5/2011 | |
| WO | WO-2012/145697 A1 | 10/2012 | |
| WO | WO 2013/003520 A1 | 1/2013 | |

(Continued)

OTHER PUBLICATIONS

Examination Report and Search Results Under Rule 164(2)(b) EPC, dated May 20, 2021 in EP 17772270.9.

(Continued)

*Primary Examiner* — Amy Rose Hudson

(74) *Attorney, Agent, or Firm* — Arnold & Porter Kaye Scholer LLP

(57) ABSTRACT

Modified oligonucleotides comprising modifications at the 2' and/or 3' position(s) along with methods of making and use, e.g., against HBV are disclosed.

15 Claims, 26 Drawing Sheets

Specification includes a Sequence Listing.

(56) References Cited

FOREIGN PATENT DOCUMENTS

| WO | WO-2013/159109 A1 | 10/2013 |
|----|-------------------|---------|
| WO | WO 2016/077321 A1 | 5/2016 |
| WO | WO/2018/053185 A1 | 3/2018 |

OTHER PUBLICATIONS

International Search Report and Written Opinion dated Feb. 7, 2018, in PCT/US2017/051644.
Banait et al. "DNA and RNA analogues—oligonucleotide phosphoramidates with bridging nitrogen," Expert Opinion on Therapeutic Patents, 2002, 12(4):543-559.
Bertrand et al., Biochemical and Biophysical Research Communications, 2002, 296:1000-1004.
Butz et al., "Peptide aptamers targeting the hepatitis B virus core protein: a new class of molecules with antiviral activity," Oncogene, 2001, 20:6579-6586.
Chen et al., "Synthesis of oligodeoxyribonucleotide N3'→ P5' phosphoramidates," Nucleic Acids Research, 1995, 23(14):2661-2668.
Gryaznov, Sergei M., "Oligonucleotide N3'→ P5' phosphoramidates as potential therapeutic agents," Biochimica et Biophysica Acta, 1999, 1489:131-140.
Matray et al., "Synthesis and properties of RNA analogs—oligoribonucleotide N3'→ P5' phosphoramidates," Nucleic Acids Research, 1999, 27(20):3976-3985.
Obika et al., "Synthesis and properties of 3'-amino-2',4'-BNA, a bridged nucleic acid with a N3'→ P5' phosphoramidate linkage," Bioorganic & Medicinal Chemistry, 2008, 16:9230-9237.
Pon et al., "Derivatization of Controlled Pore Glass Beads for Solid Phase Oligonucleotide Synthesis," BioTechniques, 1988, 6(8):768-775.
Prakash et al. "Targeted delivery of antisense oligonucleotides to hepatocytes using triantennary N-acetyl galactosamine improves potency 10-fold in mice," Nucleic Acids Research, 2014, 42(13):8796-8807.
Schultz et al., "Oligo-2'-fluoro-2'-deoxynucleotide N3'→ P5' phosphoramidates: synthesis and properties," Nucleic Acids Research, 1996, 24(15):2966-2973.
Russian Office Action with English translation and Search Report dated Jun. 22, 2021 in RU 2019111020.
Search Report dated Sep. 6, 2021 in TW 106131624.
Sharma et al., "Antisense oligonucleotides: modifications and clinical trials," MedChemComm, 2014, 5:1454-1471.
Dirks, "Brain Tumore Stem Cells: Bringing Order to the Chaos of Brain Cancer," Journal of Clinical Oncology, 26(71), pp. 2916-2924 (2008) (Alexandria, Virginia, US).
Lopez-Lazaro, "The migration ability of stem cells can explain the existence of cancer of unknown primary site. Rethinking metastasis," Oncoscience 2(5), pp. 467-475 (2015) (Washington, DC, US).
Tran et al., "Survival comparison between glioblastoma multiforme and other incurable cancers," Journal of Clinical Neuroscience, 17, pp. 417-421 (2010) (London, England, UK).
Wang et al., "Silence of MCL-1 upstream signaling by shRNA abrogates multiple myeloma growth," Experimental Hematology & Oncology 3(1):27 (2014) (London, England, UK).

\* cited by examiner

FIG. 7B

```
                          SEQUENCE LISTING

<160> NUMBER OF SEQ ID NOS: 598

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gcagaggtga agcgaagugc                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
gcagaggtga agcgaagugc                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gcagaggtga agcgaagugc                                                   20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gauuaggcag aggtgaaaaa g                                                 21

<210> SEQ ID NO 5
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
gauuaggcag aggtgaaaaa g                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
gauuaggcag aggtgaaaaa g                                           21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
gauuaggcag aggtgaaaaa g                                           21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gauuaggcag aggtgaaaaa g                                           21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
gauuaggcag aggtgaaaaa g                                           21

<210> SEQ ID NO 10
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine

<400> SEQUENCE: 10
gnuunggcag aggtgaaaaa g                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(20)
<223> OTHER INFORMATION: 2,6-diaminopurine

<400> SEQUENCE: 11
gauuaggcag aggtgaannn g                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(20)
<223> OTHER INFORMATION: 2,6-diaminopurine

<400> SEQUENCE: 12
gauuaggcag aggtgnnnnn g                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
```

```
<221> NAME/KEY: modified_base
<222> LOCATION: (18)..(20)
<223> OTHER INFORMATION: 2,6-diaminopurine

<400> SEQUENCE: 13
gnuunggcag aggtgaannn g                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (16)..(20)
<223> OTHER INFORMATION: 2,6-diaminopurine

<400> SEQUENCE: 14
gnuunggcag aggtgnnnnn g                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine

<400> SEQUENCE: 15
gnuunggcag aggtgaaaaa g                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(20)
<223> OTHER INFORMATION: 2,6-diaminopurine

<400> SEQUENCE: 16
gauuaggcag aggtgaannn g                                              21
```

```
<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(20)
<223> OTHER INFORMATION: 2,6-diaminopurine

<400> SEQUENCE: 17
gauuaggcag aggtgnnnnn g                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (18)..(20)
<223> OTHER INFORMATION: 2,6-diaminopurine

<400> SEQUENCE: 18
gnuunggcag aggtgaannn g                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (16)..(20)
<223> OTHER INFORMATION: 2,6-diaminopurine

<400> SEQUENCE: 19
gnuunggcag aggtgnnnnn g                                              21

<210> SEQ ID NO 20
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2,6-diaminopurine

<400> SEQUENCE: 20
gcagaggtga agcgangugc                                                 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(16)
<223> OTHER INFORMATION: 2,6-diaminopurine

<400> SEQUENCE: 21
gcagaggtga agcgnngugc                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (15)..(16)
<223> OTHER INFORMATION: 2,6-diaminopurine

<400> SEQUENCE: 22
gcagnggtga agcgnngugc                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2,6-diaminopurine
<220> FEATURE:
<221> NAME/KEY: modified_base
```

```
<222> LOCATION: (5)..(5)
<223> OTHER INFORMATION: 2,6-diaminopurine
<220> FEATURE:
<221> NAME/KEY: modified_base
<222> LOCATION: (15)..(16)
<223> OTHER INFORMATION: 2,6-diaminopurine

<400> SEQUENCE: 23
gcngnggtga agcgnngugc                                                     20

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgtgcagagg tgaagc                                                         16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcagaggtga agcgaa                                                         16

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgacgtgcag aggtgaag                                                       18

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcagaggtga agcgaagtg                                                      19

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcagaggtga agc                                                            13

<210> SEQ ID NO 29
<211> LENGTH: 15
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgtgcagagg tgaag                                                    15

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcagaggtga agcgaagtg                                                19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcagaggtga agcgaagtg                                                19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcagaggtga agcgaagtg                                                19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcagaggtga agcgaagtg                                                19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcagaggtga agcgaagtg                                                19

<210> SEQ ID NO 35
<211> LENGTH: 19
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 35
gcagaggtga agcgaagtg                                                 19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcagaggtga agcgaagtg                                                 19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcagaggtga agcgaagtg                                                 19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcagaggtga agcgaagtg                                                 19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcagaggtga agcgaagtg                                                 19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcagaggtga agcgaagtg                                                 19

<210> SEQ ID NO 41
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 41
gcagaggtga agcgaagtg                                                       19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcagaggtga agcgaagtg                                                       19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
aagagaggtg cgccccgugg                                                      20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
ggugaagcga agtgcacacg                                                      20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
cgugcagagg tgaagcgaag                                                      20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 46
agaggtgaag cgaagugcac                                          20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
uggcactagt aaactgagcc                                          20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
cuaggagttc cgcaguaugg                                          20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
agaggtgcgc cccgtggucg                                          20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
gaggugcgcc ccgtggucgg                                          20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 51
gaaagcccta cgaaccacug                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
guuccgcagt atggaucggc                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
uccgcagtat ggatcggcag                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
accactgaac aaatggcacu                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
ugcagaggtg aagcgaagug                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 56
acugaacaaa tggcacuagu                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
aguccaccac gagtcuagac                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
cacugaacaa atggcacuag                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
cagaggtgaa gcgaagugca                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
aagagaggtg cgccccgugg                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide
<220> FEATURE:
<223> OTHER INFORMATION: Description of Combined DNA/RNA Molecule:
      Synthetic oligonucleotide

<400> SEQUENCE: 61
ggugaagcga agtgcacacg                                                 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
uggcactagt aaactgagcc                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
cuaggagttc cgcaguaugg                                                 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
agaggtgcgc cccgtggucg                                                 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
uccgcagtat ggatcggcag                                                 20

<210> SEQ ID NO 66
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
ugcagaggtg aagcgaagug                                                    20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
aguccaccac gagtcuagac                                                    20

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
gcgggtgaag cggug                                                         15

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
gcgggtgaag cggug                                                         15

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
gcgggtgaag cggug                                                         15

<210> SEQ ID NO 71
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 71
gcagaggtga agcgaagtg                                                      19

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gcagaggtga agcgagtg                                                       18

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcagaggtga agcgaagtg                                                      19

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
gcagaggtga agcgaagugc                                                     20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
gcagaggtga agcgaagugc                                                     20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
```
gcagaggtga agcgaagugc                                              20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
gcuccaaatt ctttauaagg g                                            21

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
aagagaggtg cgccccgugg                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
ggugaagcga agtgcacacg                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
cgugcagagg tgaagcgaag                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 81
gugaagcgaa gtgcacacgg                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
agaggtgaag cgaagugcac                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
uggcactagt aaactgagcc                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
cuaggagttc cgcaguaugg                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
gcagaggtga agcgaagugc                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 86
agaggtgcgc cccgtggucg                                                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
gaggugcgcc ccgtggucgg                                                    20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
gaaagcccta cgaaccacug                                                    20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
guuccgcagt atggaucggc                                                    20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
uccgcagtat ggatcggcag                                                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

Synthetic oligonucleotide

<400> SEQUENCE: 91
accactgaac aaatggcacu                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
ugcagaggtg aagcgaagug                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
acugaacaaa tggcacuagu                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
aguccaccac gagtcuagac                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
cacugaacaa atggcacuag                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 96
cagaggtgaa gcgaagugca                                                  20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
aagagaggtg cgccccgugg                                                  20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
aagagaggtg cgccccgugg                                                  20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
ggugaagcga agtgcacacg                                                  20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
ggugaagcga agtgcacacg                                                  20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 101
uggcactagt aaactgagcc                                                    20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
uggcactagt aaactgagcc                                                    20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
cuaggagttc cgcaguaugg                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
cuaggagttc cgcaguaugg                                                    20

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gcagaggtga agcgaag                                                       17

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
```
gcagaggtga agcgaagtgc                              20

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cgtgcagagg tgaagcg                                 17

<210> SEQ ID NO 108
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gcagaggtga agcgaag                                 17

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cgacgtgcag aggtgaagc                               19

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gcagaggtga agcgaagtgc                              20

<210> SEQ ID NO 111
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gcagaggtga agcg                                    14

<210> SEQ ID NO 112
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cgtgcagagg tgaagc                                                        16

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcagaggtga agcgaagtg                                                     19

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
uccgcagtat ggatcggcag                                                    20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
cuaggagttc cgcaguaugg                                                    20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
aagagaggtg cgccccgugg                                                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
agaggtgcgc cccgtggucg                                                    20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
ugcagaggtg aagcgaagug                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
gcuccaaatt ctttauaagg                                                    20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
gcuccaaatt ctttauaagg                                                    20

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
gcuccaaatt ctttauaagg g                                                  21

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
gcuccaaatt ctttauaagg                                                    20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
gcuccaaatt ctttauaagg                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
gcuccaaatt ctttauaagg                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
gcuccaaatt ctttauaagg                                              20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
gcuccaaatt ctttauaagg g                                            21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
gcagaggtga agcgaagugc                                          20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
gcagaggtga agcgaagugc                                          20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
gcagaggtga agcgaagugc                                          20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
gcagaggtga agcgaagugc                                          20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gcagaggtga agcgaagugc                                          20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
gcagaggtga agcgaagugc                                            20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
gcagaggtga agcgaagugc                                            20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
gcagaggtga agcgaagugc                                            20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gcagaggtga agcgaagugc                                            20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
gcagaggtga agcgaagugc                                            20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 137
gcagaggtga agcgaagugc                                                    20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
gcagaggtga agcgaagugc                                                    20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
gcagaggtga agcgaagugc                                                    20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
gcagaggtga agcgaagugc                                                    20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
gcagaggtga agcgaagugc                                                    20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 142
gcagaggtga agcgaagugc                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
gcagaggtga agcgaagugc                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
gcagaggtga agcgaagugc                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
gcagaggtga agcgaagugc                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
gcagaggtga agcgaagugc                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 147
gcagaggtga agcgaagugc                                           20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
gcagaggtga agcgaagugc                                           20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
gcagaggtga agcgaagugc                                           20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgcagaggtg aagcgaagtg                                           20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
tgcagaggtg aagcgaagug                                           20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 152
gcagaggtga agcgaagugc                                              20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
gcagaggtga agcgaagugc                                              20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
gcagaggtga agcgaagugc                                              20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
gcagaggtga agcgaagugc                                              20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
gcagaggtga agcgaagugc                                              20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 157
gcagaggtga agcgaagugc                                           20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
gcagaggtga agcgaagugc                                           20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
gcagaggtga agcgaagugc                                           20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
gcagaggtga agcgaagugc                                           20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
gcagaggtga agcgaagugc                                           20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 162
gcagaggtga agcgaagugc                                              20

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
gauuaggcag aggtgaaaaa g                                            21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
gauuaggcag aggtgaaaaa g                                            21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
gauuaggcag aggtgaaaaa g                                            21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
gauuaggcag aggtgaaaaa g                                            21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 167
gauuaggcag aggtgaaaaa g                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
gauuaggcag aggtgaaaaa g                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine

<400> SEQUENCE: 169
gnuunggcag aggtgaaaaa g                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(20)
<223> OTHER INFORMATION: 2,6-diaminopurine

<400> SEQUENCE: 170
gauuaggcag aggtgaannn g                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<221> NAME/KEY: modified_base
<222> LOCATION: (16)..(20)
<223> OTHER INFORMATION: 2,6-diaminopurine

<400> SEQUENCE: 171
gauuaggcag aggtgnnnnn g                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (18)..(20)
<223> OTHER INFORMATION: 2,6-diaminopurine

<400> SEQUENCE: 172
gnuunggcag aggtgaannn g                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (16)..(20)
<223> OTHER INFORMATION: 2,6-diaminopurine

<400> SEQUENCE: 173
gnuunggcag aggtgnnnnn g                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
```

```
<220> FEATURE:
<221> NAME/KEY: modified_base
<222> LOCATION: (5)..(5)
<223> OTHER INFORMATION: 2,6-diaminopurine

<400> SEQUENCE: 174
gnuunggcag aggtgaaaaa g                                                 21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(20)
<223> OTHER INFORMATION: 2,6-diaminopurine

<400> SEQUENCE: 175
gauuaggcag aggtgaannn g                                                 21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(20)
<223> OTHER INFORMATION: 2,6-diaminopurine

<400> SEQUENCE: 176
gauuaggcag aggtgnnnnn g                                                 21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (18)..(20)
<223> OTHER INFORMATION: 2,6-diaminopurine

<400> SEQUENCE: 177
gnuunggcag aggtgaannn g                                                 21

<210> SEQ ID NO 178
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (16)..(20)
<223> OTHER INFORMATION: 2,6-diaminopurine

<400> SEQUENCE: 178
gnuunggcag aggtgnnnnn g                                          21

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2,6-diaminopurine

<400> SEQUENCE: 179
gcagaggtga agcgangugc                                            20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(16)
<223> OTHER INFORMATION: 2,6-diaminopurine

<400> SEQUENCE: 180
gcagaggtga agcgnngugc                                            20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (5)..(5)
<223> OTHER INFORMATION: 2,6-diaminopurine
<220> FEATURE:
<221> NAME/KEY: modified_base
<222> LOCATION: (15)..(16)
<223> OTHER INFORMATION: 2,6-diaminopurine

<400> SEQUENCE: 181
gcagnggtga agcgnngugc                                          20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (15)..(16)
<223> OTHER INFORMATION: 2,6-diaminopurine

<400> SEQUENCE: 182
gcngnggtga agcgnngugc                                          20

<210> SEQ ID NO 183
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
cgtgcagagg tgaagc                                              16

<210> SEQ ID NO 184
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gcagaggtga agcgaa                                              16

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cgacgtgcag aggtgaag                                            18
```

```
<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gcagaggtga agcgaagtg                                                  19

<210> SEQ ID NO 187
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gcagaggtga agc                                                        13

<210> SEQ ID NO 188
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cgtgcagagg tgaag                                                      15

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gcagaggtga agcgaagtg                                                  19

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gcagaggtga agcgaagtg                                                  19

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gcagaggtga agcgaagtg                                                  19

<210> SEQ ID NO 192
```

<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gcagaggtga agcgaagtg                                              19

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gcagaggtga agcgaagtg                                              19

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gcagaggtga agcgaagtg                                              19

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gcagaggtga agcgaagtg                                              19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gcagaggtga agcgaagtg                                              19

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gcagaggtga agcgaagtg                                              19

<210> SEQ ID NO 198
<211> LENGTH: 19

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gcagaggtga agcgaagtg                                                   19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gcagaggtga agcgaagtg                                                   19

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gcagaggtga agcgaagtg                                                   19

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
aagagaggtg cgccccgugg                                                  20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
ggugaagcga agtgcacacg                                                  20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 203
cgugcagagg tgaagcgaag                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
agaggtgaag cgaagugcac                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
uggcactagt aaactgagcc                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
cuaggagttc cgcaguaugg                                              20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
agaggtgcgc cccgtggucg                                              20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 208
gaggugcgcc ccgtggucgg					20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
gaaagcccta cgaaccacug					20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
guuccgcagt atggaucggc					20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
uccgcagtat ggatcggcag					20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
accactgaac aaatggcacu					20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 213
ugcagaggtg aagcgaagug                                                      20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
acugaacaaa tggcacuagu                                                      20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
aguccaccac gagtcuagac                                                      20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
cacugaacaa atggcacuag                                                      20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
cagaggtgaa gcgaagugca                                                      20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 218
aagagaggtg cgccccgugg                                                  20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
ggugaagcga agtgcacacg                                                  20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
uggcactagt aaactgagcc                                                  20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
cuaggagttc cgcaguaugg                                                  20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
agaggtgcgc cccgtggucg                                                  20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 223
uccgcagtat ggatcggcag                                                   20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
ugcagaggtg aagcgaagug                                                   20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
aguccaccac gagtcuagac                                                   20

<210> SEQ ID NO 226
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
gcagaggtga agcgaagug                                                    19

<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
gcagaggtga agcgaagug                                                    19

<210> SEQ ID NO 228
<211> LENGTH: 19
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
gcagaggtga agcgaagug                                                19

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gcagaggtga agcgaagtg                                                19

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gcagaggtga agcgaagtg                                                19

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcagaggtga agcgaagtg                                                19

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
gcagaggtga agcgaagugc                                               20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
gcagaggtga agcgaagugc                                          20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
gcagaggtga agcgaagugc                                          20

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
gcuccaaatt ctttauaagg g                                        21

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
aagagaggtg cgccccgugg                                          20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
ggugaagcga agtgcacacg                                          20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
cgugcagagg tgaagcgaag                                                    20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
gugaagcgaa gtgcacacgg                                                    20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
agaggtgaag cgaagugcac                                                    20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
uggcactagt aaactgagcc                                                    20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
cuaggagttc cgcaguaugg                                                    20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 243
gcagaggtga agcgaagugc                                              20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
agaggtgcgc cccgtggucg                                              20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
gaggugcgcc ccgtggucgg                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
gaaagcccta cgaaccacug                                              20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
guuccgcagt atggaucggc                                              20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 248
uccgcagtat ggatcggcag                                               20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
accactgaac aaatggcacu                                               20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
ugcagaggtg aagcgaagug                                               20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
acugaacaaa tggcacuagu                                               20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
aguccaccac gagtcuagac                                               20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 253
cacugaacaa atggcacuag    20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
cagaggtgaa gcgaagugca    20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
aagagaggtg cgccccgugg    20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
aagagaggtg cgccccgugg    20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
ggugaagcga agtgcacacg    20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 258
ggugaagcga agtgcacacg                                                     20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
uggcactagt aaactgagcc                                                     20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
uggcactagt aaactgagcc                                                     20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
cuaggagttc cgcaguaugg                                                     20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
cuaggagttc cgcaguaugg                                                     20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 263
uccgcagtat ggatcggcag                                                    20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
cuaggagttc cgcaguaugg                                                    20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
aagagaggtg cgccccgugg                                                    20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
agaggtgcgc cccgtggucg                                                    20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
ugcagaggtg aagcgaagug                                                    20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
    Synthetic oligonucleotide

<400> SEQUENCE: 268
gcuccaaatt ctttauaagg                                              20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 269
gcuccaaatt ctttauaagg                                              20

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 270
gcuccaaatt ctttauaagg g                                            21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 271
gcuccaaatt ctttauaagg                                              20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 272
gcuccaaatt ctttauaagg                                              20

<210> SEQ ID NO 273
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
gcuccaaatt ctttauaagg                                               20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
gcuccaaatt ctttauaagg                                               20

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
gcuccaaatt ctttauaagg g                                             21

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
gcagaggtga agcgaagugc                                               20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
gcagaggtga agcgaagugc                                               20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
gcagaggtga agcgaagugc                                              20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
gcagaggtga agcgaagugc                                              20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
gcagaggtga agcgaagugc                                              20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
gcagaggtga agcgaagugc                                              20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
gcagaggtga agcgaagugc                                              20

<210> SEQ ID NO 283
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
gcagaggtga agcgaagugc                                                   20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
gcagaggtga agcgaagugc                                                   20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
gcagaggtga agcgaagugc                                                   20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
gcagaggtga agcgaagugc                                                   20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
gcagaggtga agcgaagugc                                                   20

<210> SEQ ID NO 288
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
gcagaggtga agcgaagugc                                             20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
gcagaggtga agcgaagugc                                             20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
gcagaggtga agcgaagugc                                             20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
gcagaggtga agcgaagugc                                             20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
gcagaggtga agcgaagugc                                             20

<210> SEQ ID NO 293
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
gcagaggtga agcgaagugc                                              20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
gcagaggtga agcgaagugc                                              20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
gcagaggtga agcgaagugc                                              20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
gcagaggtga agcgaagugc                                              20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
gcagaggtga agcgaagugc                                              20
```

```
<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
gcagaggtga agcgaagugc                                               20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tgcagaggtg aagcgaagtg                                               20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
tgcagaggtg aagcgaagug                                               20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
gcagaggtga agcgaagugc                                               20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
gcagaggtga agcgaagugc                                               20

<210> SEQ ID NO 303
<211> LENGTH: 20
```

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
gcagaggtga agcgaagugc                                                    20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
gcagaggtga agcgaagugc                                                    20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
gcagaggtga agcgaagugc                                                    20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
gcagaggtga agcgaagugc                                                    20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
gcagaggtga agcgaagugc                                                    20

<210> SEQ ID NO 308

```
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
gcagaggtga agcgaag                                                   17

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gcagaggtga agcgaagtgc                                                20

<210> SEQ ID NO 310
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
cgtgcagagg tgaagcg                                                   17

<210> SEQ ID NO 311
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
cgtgcagagg tgaagcg                                                   17

<210> SEQ ID NO 312
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gcagaggtga agcgaag                                                   17

<210> SEQ ID NO 313
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cgacgtgcag aggtgaagc                                                 19

<210> SEQ ID NO 314
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gcagaggtga agcgaagtgc                                                 20

<210> SEQ ID NO 315
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gcagaggtga agcg                                                       14

<210> SEQ ID NO 316
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cgtgcagagg tgaagc                                                     16

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
gcagaggtga agcgaagugc                                                 20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gcagaggtga agcgaagtgc                                                 20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
```
gcagaggtga agcgaagugc                                         20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
gcagaggtga agcgaagugc                                         20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
gcagaggtga agcgaagugc                                         20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gcagaggtga agcgaagtgc                                         20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 323
gcagaggtga agcgaagugc                                         20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
gcagaggtga agcgaagugc                                         20

```
<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
gcagaggtga agcgaagugc                                                    20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gcagaggtga agcgaagtgc                                                    20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
gcagaggtga agcgaagugc                                                    20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gcagaggtga agcgaagtgc                                                    20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
gcagaggtga agcgaagugc                                                    20

<210> SEQ ID NO 330
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 330
gcagaggtga agcgaagtgc                                               20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
gcagaggtga agcgaagugc                                               20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
gcagaggtga agcgaagugc                                               20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
gcagaggtga agcgaagugc                                               20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
gcagaggtga agcgaagugc                                               20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 335
gcagaggtga agcgaagtgc                                              20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
gcagaggtga agcgaagtgc                                              20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
gcagaggtga agcgaagugc                                              20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
gcagaggtga agcgaagugc                                              20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
gcagaggtga agcgaagugc                                              20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 340
gcagaggtga agcgaagugc                                              20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
gcagaggtga agcgaagugc                                              20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gcagaggtga agcgaagtgc                                              20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
gcagaggtga agcgaagugc                                              20

<210> SEQ ID NO 344
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
gcagaggtga agcgaagug                                               19

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gcagaggtga agcgaagtgc                                              20
```

```
<210> SEQ ID NO 346
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tgcagaggtg aagcgaagt                                                  19

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
ugcagaggtg aagcgaagug                                                 20

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
ugcagaggtg aagcgaagu                                                  19

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
gcuccaaatt ctttauaagg g                                               21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
gcuccaaatt ctttauaagg g                                               21

<210> SEQ ID NO 351
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gcagaggtga agcgaagtgc                                                  20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
gcagaggtga agcgaagugc                                                  20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
gcagaggtga agcgaagtgc                                                  20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
gcagaggtga agcgaagugc                                                  20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
gcagaggtga agcgaagugc                                                  20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 356
gcagaggtga agcgaagugc                                                    20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
gcagaggtga agcgaagugc                                                    20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358
gcagaggtga agcgaagugc                                                    20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
gcagaggtga agcgaagugc                                                    20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gcagaggtga agcgaagtgc                                                    20

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

Synthetic oligonucleotide

<400> SEQUENCE: 361
gcagaggtga agcgaagug                                                19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
gcagaggtga agcgaagug                                                19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 363
gcagaggtga agcgaagug                                                19

<210> SEQ ID NO 364
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
gcagaggtga agcgaagug                                                19

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
gcuccaaatt ctttauaagg                                               20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 366 gcuccaaaatt ctttauaagg                                              20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 367 gcuccaaaatt ctttauaagg                                              20

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
gcagaggtga agcgaagug                                                19

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
gcagaggtga agcgaagug                                                19

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
gcagaggtga agcgaagug                                                19

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 371
gcuccaaatt ctttauaagg                                                 20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372
gcuccaaatt ctttauaagg                                                 20

<210> SEQ ID NO 373
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
gcagaggtga agcgaagug                                                  19

<210> SEQ ID NO 374
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gcagaggtga agcgaagtg                                                  19

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gcagaggtga agcgaagtg                                                  19

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gctccaaatt ctttataagg                                                 20
```

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
gcuccaaauu cuuuauaagg                                               20

<210> SEQ ID NO 378
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
ttgccttctg acttctttcc ttct                                          24

<210> SEQ ID NO 379
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
tgcctgagtg ctgtatggtg ag                                            22

<210> SEQ ID NO 380
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
tcgggaagcc ttagagtctc ctga                                          24

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 381
gcagaggtga agcgaagugc                                               20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 382
gcagaggtga agcgaagugc                                              20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 383
gcagaggtga agcgaagugc                                              20

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
gauuaggcag aggtgaaaaa g                                            21

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
gauuaggcag aggtgaaaaa g                                            21

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 386
gauuaggcag aggtgaaaaa g                                            21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 387
gauuaggcag aggtgaaaaa g                                              21

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 388
gauuaggcag aggtgaaaaa g                                              21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 389
gauuaggcag aggtgaaaaa g                                              21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine

<400> SEQUENCE: 390
gnuunggcag aggtgaaaaa g                                              21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(20)

<223> OTHER INFORMATION: 2,6-diaminopurine

<400> SEQUENCE: 391
gauuaggcag aggtgaannn g                                              21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(20)
<223> OTHER INFORMATION: 2,6-diaminopurine

<400> SEQUENCE: 392
gauuaggcag aggtgnnnnn g                                              21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (18)..(20)
<223> OTHER INFORMATION: 2,6-diaminopurine

<400> SEQUENCE: 393
gnuunggcag aggtgaannn g                                              21

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (16)..(20)
<223> OTHER INFORMATION: 2,6-diaminopurine

<400> SEQUENCE: 394
gnuunggcag aggtgnnnnn g                                      21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine

<400> SEQUENCE: 395
gnuunggcag aggtgaaaaa g                                      21

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (18)..(20)
<223> OTHER INFORMATION: 2,6-diaminopurine

<400> SEQUENCE: 396
gauuaggcag aggtgaannn g                                      21

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(20)
<223> OTHER INFORMATION: 2,6-diaminopurine

<400> SEQUENCE: 397
gauuaggcag aggtgnnnnn g                                      21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (18)..(20)
<223> OTHER INFORMATION: 2,6-diaminopurine

<400> SEQUENCE: 398
gnuunggcag aggtgaannn g                                      21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (16)..(20)
<223> OTHER INFORMATION: 2,6-diaminopurine

<400> SEQUENCE: 399
gnuunggcag aggtgnnnnn g                                      21

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: 2,6-diaminopurine

<400> SEQUENCE: 400
gcagaggtga agcgangugc                                        20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(16)
<223> OTHER INFORMATION: 2,6-diaminopurine

<400> SEQUENCE: 401
gcagaggtga agcgnngugc				20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (15)..(16)
<223> OTHER INFORMATION: 2,6-diaminopurine

<400> SEQUENCE: 402
gcagnggtga agcgnngugc				20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2,6-diaminopurine
<220> FEATURE:
<221> NAME/KEY: modified_base
<222> LOCATION: (5)..(5)
<223> OTHER INFORMATION: 2,6-diaminopurine
<220> FEATURE:
<221> NAME/KEY: modified_base
<222> LOCATION: (15)..(16)
<223> OTHER INFORMATION: 2,6-diaminopurine

<400> SEQUENCE: 403
gcngnggtga agcgnngugc				20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 404
aagagaggtg cgccccgugg				20

<210> SEQ ID NO 405
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 405
ggugaagcga agtgcacacg                                                   20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 406
uggcactagt aaactgagcc                                                   20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 407
cuaggagttc cgcaguaugg                                                   20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 408
agaggtgcgc cccgtggucg                                                   20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 409
uccgcagtat ggatcggcag                                                   20

<210> SEQ ID NO 410
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 410
ugcagaggtg aagcgaagug                                                    20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 411
aguccaccac gagtcuagac                                                    20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
gcagaggtga agcgaagtgc                                                    20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
gcagaggtga agcgaagtgc                                                    20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
gcagaggtga agcgaagtgc                                                    20

<210> SEQ ID NO 415
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
```
gcagaggtga agcgaagug                                                        19

<210> SEQ ID NO 416
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 416
gcagaggtga agcgaagug                                                        19

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 417
gcagaggtga agcgaagug                                                        19

<210> SEQ ID NO 418
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gcagaggtga agcgaagtg                                                        19

<210> SEQ ID NO 419
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
gcagaggtga agcgaagtg                                                        19

<210> SEQ ID NO 420
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
gcagaggtga agcgaagtg                                                        19

<210> SEQ ID NO 421
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 421
gcagaggtga agcgaagugc                                            20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 422
gcagaggtga agcgaagugc                                            20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
gcagaggtga agcgaagugc                                            20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
uccgcagtat ggatcggcag                                            20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 425
cuaggagttc cgcaguaugg                                            20

<210> SEQ ID NO 426
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
aagagaggtg cgccccgugg                                                  20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 427
agaggtgcgc cccgtggucg                                                  20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
ugcagaggtg aagcgaagug                                                  20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
gcuccaaatt ctttauaagg                                                  20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
gcuccaaatt ctttauaagg                                                  20

<210> SEQ ID NO 431
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 431
gcuccaaatt ctttauaagg g                                                 21

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 432
gcuccaaatt ctttauaagg                                                   20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 433
gcuccaaatt ctttauaagg                                                   20

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 434
gcuccaaatt ctttauaagg g                                                 21

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 435
gcuccaaatt ctttauaagg                                                   20

<210> SEQ ID NO 436
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 436
gcuccaaatt ctttauaagg                                         20

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 437
gcuccaaatt ctttauaagg g                                       21

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
gcagaggtga agcgaagugc                                         20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
gcagaggtga agcgaagugc                                         20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
gcagaggtga agcgaagugc                                         20
```

```
<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
gcagaggtga agcgaagugc                                            20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
gcagaggtga agcgaagugc                                            20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443
gcagaggtga agcgaagugc                                            20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
gcagaggtga agcgaagugc                                            20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
gcagaggtga agcgaagugc                                            20
```

```
<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
gcagaggtga agcgaagugc                                                   20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
gcagaggtga agcgaagugc                                                   20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
gcagaggtga agcgaagugc                                                   20

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
gcagaggtga agcgaagugc                                                   20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
gcagaggtga agcgaagugc                                                   20
```

-continued

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
gcagaggtga agcgaagugc                                                  20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452
gcagaggtga agcgaagugc                                                  20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
gcagaggtga agcgaagugc                                                  20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
gcagaggtga agcgaagugc                                                  20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
gcagaggtga agcgaagugc                                            20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 456
gcagaggtga agcgaagugc                                            20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 457
gcagaggtga agcgaagugc                                            20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 458
gcagaggtga agcgaagugc                                            20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 459
gcagaggtga agcgaagugc                                            20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 460
gcagaggtga agcgaagugc                                        20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
tgcagaggtg aagcgaagtg                                        20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
tgcagaggtg aagcgaagug                                        20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
gcagaggtga agcgaagugc                                        20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
gcagaggtga agcgaagugc                                        20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
gcagaggtga agcgaagugc                                        20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 466
gcagaggtga agcgaagugc                                              20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 467
gcagaggtga agcgaagugc                                              20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 468
gcagaggtga agcgaagugc                                              20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 469
gcagaggtga agcgaagugc                                              20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 470
aagagaggtg cgccccgugg                                       20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
aagagaggtg cgccccgugg                                       20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
aagagaggtg cgccccgugg                                       20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
ggugaagcga agtgcacacg                                       20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
ggugaagcga agtgcacacg                                       20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
ggugaagcga agtgcacacg                                              20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
uggcactagt aaactgagcc                                              20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
uggcactagt aaactgagcc                                              20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
uggcactagt aaactgagcc                                              20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
cuaggagttc cgcaguaugg                                              20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 480
cuaggaguuc cgcaguaugg                                               20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
cuaggaguuc cgcaguaugg                                               20

<210> SEQ ID NO 482
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
gcagaggtga agc                                                      13

<210> SEQ ID NO 483
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
cgtgcagagg tgaag                                                    15

<210> SEQ ID NO 484
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
gcagaggtga agcgaagtg                                                19

<210> SEQ ID NO 485
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
gcagaggtga agcgaagtg                                                19

<210> SEQ ID NO 486
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 486
gcagaggtga agcgaagtg                                              19

<210> SEQ ID NO 487
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
gcagaggtga agcgaagtg                                              19

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
gcagaggtga agcgaagtg                                              19

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
gcagaggtga agcgaagtg                                              19

<210> SEQ ID NO 490
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gcagaggtga agcgaagtg                                              19

<210> SEQ ID NO 491
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
gcagaggtga agcgaagtg                                              19

<210> SEQ ID NO 492
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 492
gcagaggtga agcgaagtg                                               19

<210> SEQ ID NO 493
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gcagaggtga agcgaagtg                                               19

<210> SEQ ID NO 494
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
gcagaggtga agcgaagtg                                               19

<210> SEQ ID NO 495
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
gcagaggtga agcgaagtg                                               19

<210> SEQ ID NO 496
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
gcagaggtga agcgaagtg                                               19

<210> SEQ ID NO 497
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
gcagaggtga agcgaagtg                                               19

<210> SEQ ID NO 498
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 498
gcagaggtga agcgaagtg                                               19

<210> SEQ ID NO 499
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
gcagaggtga agcgaagtg                                               19

<210> SEQ ID NO 500
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
gcagaggtga agcgaagtg                                               19

<210> SEQ ID NO 501
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
gcagaggtga agcgaagtg                                               19

<210> SEQ ID NO 502
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
gcagaggtga agcgaagtg                                               19

<210> SEQ ID NO 503
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gcagaggtga agcgaagtg                                               19

<210> SEQ ID NO 504
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
```

```
gcagaggtga agcgaagtg                                                19
```

<210> SEQ ID NO 505
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505

```
gcagaggtga agcgaagtg                                                19
```

<210> SEQ ID NO 506
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506

```
gcagaggtga agcgaagtg                                                19
```

<210> SEQ ID NO 507
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507

```
gcagaggtga agcgaagtg                                                19
```

<210> SEQ ID NO 508
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508

```
gcagaggtga agcgaagtg                                                19
```

<210> SEQ ID NO 509
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509

```
gcagaggtga agcgaagtg                                                19
```

<210> SEQ ID NO 510
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
gcagaggtga agcgaagtg                                            19

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
gcagaggtga agcgaagugc                                           20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
gcagaggtga agcgaagtgc                                           20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
gcagaggtga agcgaagugc                                           20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gcagaggtga agcgaagtgc                                           20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
gcagaggtga agcgaagugc                                           20

<210> SEQ ID NO 516
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
gcagaggtga agcgaagugc                                                  20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
gcagaggtga agcgaagugc                                                  20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
gcagaggtga agcgaagtgc                                                  20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
gcagaggtga agcgaagugc                                                  20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
gcagaggtga agcgaagtgc                                                  20

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Description of Combined DNA/RNA Molecule:
      Synthetic oligonucleotide

<400> SEQUENCE: 521
gcagaggtga agcgaagugc                                              20

<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
gcagaggtga agcgaagtgc                                              20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
gcagaggtga agcgaagugc                                              20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
gcagaggtga agcgaagugc                                              20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
gcagaggtga agcgaagugc                                              20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 526
gcagaggtga agcgaagugc                                         20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
gcagaggtga agcgaagtgc                                         20

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
gcagaggtga agcgaagtgc                                         20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
gcagaggtga agcgaagugc                                         20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
gcagaggtga agcgaagugc                                         20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
gcagaggtga agcgaagugc                                         20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gcagaggtga agcgaagtgc                                              20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
gcagaggtga agcgaagugc                                              20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gcagaggtga agcgaagtgc                                              20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
gcagaggtga agcgaagugc                                              20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
gcagaggtga agcgaagugc                                              20

<210> SEQ ID NO 537
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 537
gcagaggtga agcgaagtgc                                                    20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
gcagaggtga agcgaagugc                                                    20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
gcagaggtga agcgaagtgc                                                    20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
gcagaggtga agcgaagugc                                                    20

<210> SEQ ID NO 541
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
gcagaggtga agcgaagug                                                     19

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 542
gcagaggtga agcgaagtgc                                                     20

<210> SEQ ID NO 543
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
tgcagaggtg aagcgaagt                                                      19

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
ugcagaggtg aagcgaagug                                                     20

<210> SEQ ID NO 545
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
ugcagaggtg aagcgaagu                                                      19

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
gcuccaaatt ctttauaagg g                                                   21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
```
gcuccaaatt ctttauaagg g                                              21

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gcagaggtga agcgaagtgc                                                20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 549
gcagaggtga agcgaagugc                                                20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
gcagaggtga agcgaagtgc                                                20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
gcagaggtga agcgaagugc                                                20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
gcagaggtga agcgaagugc                                                20

<210> SEQ ID NO 553
<211> LENGTH: 20

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
gcagaggtga agcgaagugc                                              20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 554
gcagaggtga agcgaagugc                                              20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
gcagaggtga agcgaagugc                                              20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 556
gcagaggtga agcgaagugc                                              20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
gcagaggtga agcgaagtgc                                              20

<210> SEQ ID NO 558
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
gcagaggtga agcgaagug                                                19

<210> SEQ ID NO 559
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 559
gcagaggtga agcgaagug                                                19

<210> SEQ ID NO 560
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
gcagaggtga agcgaagug                                                19

<210> SEQ ID NO 561
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 561
gcagaggtga agcgaagug                                                19

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
gcuccaaatt ctttauaagg                                               20

<210> SEQ ID NO 563
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
gcuccaaatt ctttauaagg                                                20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 564
gcuccaaatt ctttauaagg                                                20

<210> SEQ ID NO 565
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
gcagaggtga agcgaagug                                                 19

<210> SEQ ID NO 566
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
gcagaggtga agcgaagug                                                 19

<210> SEQ ID NO 567
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
gcagaggtga agcgaagug                                                 19

<210> SEQ ID NO 568
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
gcagaggtga agcgaagug                                                19

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 569
gcuccaaatt ctttauaagg                                               20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
gcuccaaatt ctttauaagg                                               20

<210> SEQ ID NO 571
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
gcagaggtga agcgaagug                                                19

<210> SEQ ID NO 572
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
gcagaggtga agcgaagtg                                                19

<210> SEQ ID NO 573
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 573
gcagaggtga agcgaagtg                                                    19

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
gctccaaatt ctttataagg                                                   20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
gcuccaaatt ctttataagg                                                   20

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
gauuaggcag aggtgaaaaa g                                                 21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
gauuaggcag aggtgaaaaa g                                                 21

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 578
aagagaggtg cgccccgtgg					20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
cuaggaguuc cgcaguaugg					20

<210> SEQ ID NO 580
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
agtctagact cgtggtggac tt					22

<210> SEQ ID NO 581
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
tggctcagtt tactagtgcc atttgttcag tggttcgtag ggctttcc					48

<210> SEQ ID NO 582
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
tctgccgatc catactgcgg aactcctagc					30

<210> SEQ ID NO 583
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
gccgaccacg gggcgcacct ctcttt					26

<210> SEQ ID NO 584
<211> LENGTH: 33
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 584
ccgtgtgcac ttcgcttcac ctctgcacgt cgc                              33

<210> SEQ ID NO 585
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585 acttttttcac ctctgcctaa tca                                        23

<210> SEQ ID NO 586
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
acccttataa agaatttgga gct                                         23

<210> SEQ ID NO 587
<211> LENGTH: 22
<212> TYPE: DNA
<213> ORGANISM: Hepatitis B virus

<400> SEQUENCE: 587
agtctagact cgtggtggac tt                                          22

<210> SEQ ID NO 588
<211> LENGTH: 48
<212> TYPE: DNA
<213> ORGANISM: Hepatitis B virus

<400> SEQUENCE: 588
tggctcagtt tactagtgcc atttgttcag tggttcgtag ggctttcc              48

<210> SEQ ID NO 589
<211> LENGTH: 30
<212> TYPE: DNA
<213> ORGANISM: Hepatitis B virus

<400> SEQUENCE: 589
tctgccgatc catactgcgg aactcctagc                                  30

<210> SEQ ID NO 590
<211> LENGTH: 26
<212> TYPE: DNA
<213> ORGANISM: Hepatitis B virus

<400> SEQUENCE: 590
accgaccacg gggcgcacct ctcttt                                      26

<210> SEQ ID NO 591
<211> LENGTH: 38
<212> TYPE: DNA
<213> ORGANISM: Hepatitis B virus
```

```
<400> SEQUENCE: 591
ccgtgtgcac ttcgcttcac ctctgcacgt cgcatgga                           38

<210> SEQ ID NO 592
<211> LENGTH: 34
<212> TYPE: DNA
<213> ORGANISM: Hepatitis B virus

<400> SEQUENCE: 592 acttttttcac ctctgcctaa tcatctcttg ttca                              34

<210> SEQ ID NO 593
<211> LENGTH: 22
<212> TYPE: RNA
<213> ORGANISM: Hepatitis B virus

<400> SEQUENCE: 593
agucuagacu cgugguggac uu                                            22

<210> SEQ ID NO 594
<211> LENGTH: 48
<212> TYPE: RNA
<213> ORGANISM: Hepatitis B virus

<400> SEQUENCE: 594
uggcucaguu acuagugcc auuuguucag ugguucguag ggcuuucc                 48

<210> SEQ ID NO 595
<211> LENGTH: 30
<212> TYPE: RNA
<213> ORGANISM: Hepatitis B virus

<400> SEQUENCE: 595
ucugccgauc cauacugcgg aacuccuagc                                    30

<210> SEQ ID NO 596
<211> LENGTH: 26
<212> TYPE: RNA
<213> ORGANISM: Hepatitis B virus

<400> SEQUENCE: 596
accgaccacg gggcgcaccu cucuuu                                        26

<210> SEQ ID NO 597
<211> LENGTH: 38
<212> TYPE: RNA
<213> ORGANISM: Hepatitis B virus

<400> SEQUENCE: 597
ccgugugcac uucgcuucac cucugcacgu cgcaugga                           38

<210> SEQ ID NO 598
<211> LENGTH: 34
<212> TYPE: RNA
<213> ORGANISM: Hepatitis B virus

<400> SEQUENCE: 598
acuuuuucac cucugccuaa ucaucucuug uuca                               34
```

MODIFIED OLIGONUCLEOTIDES AND METHODS OF USE

CROSS-REFERENCE TO RELATED APPLICATIONS

The present application is a Continuation of U.S. application Ser. No. 15/705,137, filed Sep. 14, 2017 (now U.S. Pat. No. 10,793,859), which claims the benefit of priority to U.S. Provisional Application No. 62/394,738, filed Sep. 14, 2016, and U.S. Provisional Application No. 62/394,739, filed Sep. 14, 2016, the entireties of each of which are hereby incorporated by reference.

SEQUENCE LISTING

The instant application contains a Sequence Listing which has been submitted electronically in ASCII format and is hereby incorporated by reference in its entirety. Said ASCII copy, created on Oct. 2, 2020, is named 112059-0210 SL.txt and is 186,888 bytes in size.

BACKGROUND

Antisense oligonucleotide therapies have been considered for treatment or prevention of various diseases and conditions such as viral diseases, neurological diseases, neurodegenerative diseases, fibrotic diseases, hyperproliferative diseases.

Certain viral diseases such as hepatitis B (HBV) remain elusive from conventional therapies while continuing to infect an estimated 240 million people (defined as HBV surface antigen positive for at least 6 months) and contributing to the deaths of more than 686,000 people every year. Conventional therapies including oral anti-viral nucleotide analog treatments, such as tenofovir or entecavir, only suppresses the replication of the virus and do not cure the HBV infection. Therefore, even those treated with current HBV therapies must continue their treatment for life.

Oligonucleotides can bind a complimentary RNA or DNA sequence. This feature enables oligonucleotides to bind specific nucleic acid targets involved in many aspects of cellular processes such as metabolism, differentiation, proliferation, viral replication, etc. Oligonucleotides can also be engineered to cleave target RNA through RNase H mechanism or RISC pathway; block micro RNA binding, change RNA splicing pattern, or bind to targets as aptamers once they bind to their specific target. For example, chimeric oligonucleotides, such as "gapmers" include a portion of the oligonucleotide that attracts RNase H enzyme to the site where the oligonucleotide binds to the RNA region. Subsequent activation of RNase H results in cleavage of the genetic target, thereby inhibiting the function of the genetic target such as gene expression or replication of a virus.

Accordingly, there is a need in the art to discover and develop new therapies with different mechanisms of action, increased potency, increased affinity and/or decreased side-effects.

SUMMARY

The present disclosure relates to compounds and compositions containing oligonucleotides and their use in preventing or treating diseases and conditions, e.g., HBV.

Some embodiments include an oligonucleotide comprising one or more nucleotides of Formula (I):

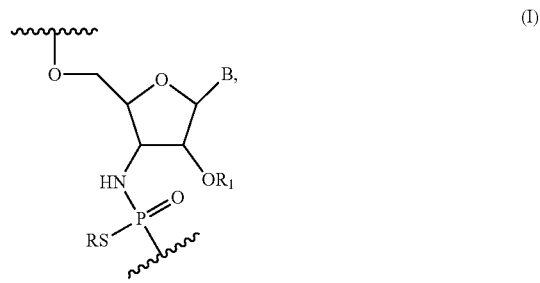

(I)

wherein R is H or a positively charged counter ion, B is a nucleobase, $R_1$ is $-(CR'_2)_2OCR'_3$, and R' is independently in each instance H or F. In some embodiments, each nucleotide of said oligonucleotide is a nucleotide of Formula (I). In some embodiments, the oligonucleotide comprises 2 to 40 nucleotides. In some embodiments, the oligonucleotide comprises 2-26 nucleotides of Formula (I). In some embodiments, the oligonucleotide comprises 5-10 nucleotides of Formula (I). In some embodiments, B is an unmodified nucleobase in at least one nucleotide of Formula (I). In some embodiments, B is a modified nucleobase in at least one nucleotide of Formula (I). In some embodiments, B is an unmodified nucleobase in each nucleotide of Formula (I). In some embodiments, B is a modified nucleobase in each nucleotide of Formula (I). In some embodiments, each R' is H in at least one nucleotide of Formula (I). In some embodiments, each R' is H in each nucleotide of Formula (I). In some embodiments, $R_1$ is $-(CH_2)_2OCH_3$ in at least one nucleotide of Formula (I). In some embodiments, $R_1$ is $-(CH_2)_2OCH_3$ in each nucleotide of Formula (I). In some embodiments, the oligonucleotide further comprises one or more nucleotides of Formula (II):

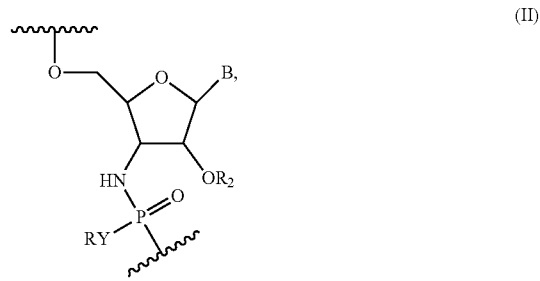

(II)

wherein Y is S or O, R is H or a positively charged counter ion, B is a nucleobase, $R_2$ is $-CR'_3$, $-CR'_2OCR'_3$, $-(CR'_2)_3OCR'_3$ or $-(CR'_2)_{1-2}CR'_3$, or $R_2$ is $-(CR'_2)_2OCR'_3$ and Y is O, and R' is independently in each instance H or F. In some embodiments, the oligonucleotide comprises at least one nucleotide of Formula (II), where $R_2$ is $-CR'_3$. In some embodiments, the oligonucleotide comprises at least one nucleotide of Formula (II), where $R_2$ is $-(CR'_2)_{1-2}OCR'_3$. In some embodiments, the oligonucleotide comprises at least one nucleotide of Formula (II), where $R_2$ is $-(CR'_2)_{1-2}CR'_3$. In some embodiments, B is a modified nucleobase in at least one nucleotide of Formula (II). In some embodiments, Y is S in at least one nucleotide of Formula (II). In some embodiments, Y is O in at least one nucleotide of Formula (II). In some embodiments, Y is S in each nucleotide of Formula (II). In some embodiments, Y is O in each nucleotide of Formula (II). In some embodiments, the oligonucleotide further comprises one or more nucleotides of Formula (IIIa) or Formula (IIIb):

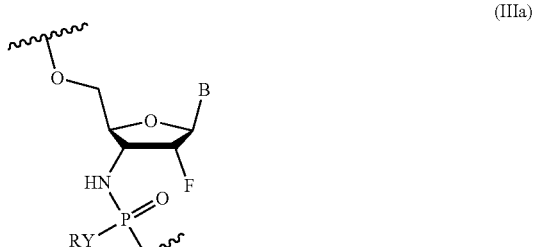

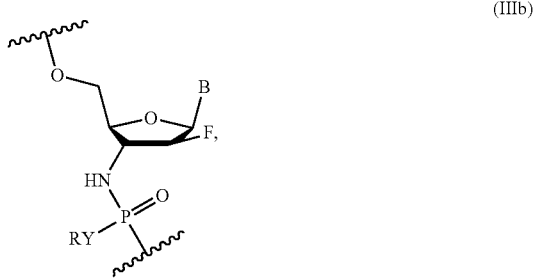

wherein Y is S or O, R is H or a positively charged counter ion, and B is a nucleobase. In some embodiments, the oligonucleotide further comprises one or more nucleotides of Formula (V'):

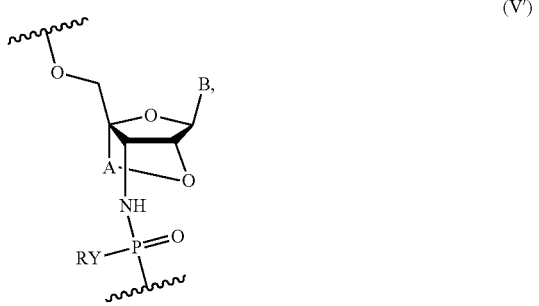

wherein Y is S or O, R is H or a positively charged counter ion, B is independently in each instance a natural or an unmodified nucleobase or a modified nucleobase, A is —(CR"R")$_{1-2}$— and R" is independently in each instance H, F or Me. In some embodiments, the oligonucleotide is arranged in a construct of Formula (VI): 5' X—Y—Z 3' (VI), wherein each of X, Y and Z is a domain comprising 2-14 nucleotides, at least one of the X and Z domains comprising at least one nucleotide of Formula (I), and wherein each of the nucleotides of the Y domain is a 2'-deoxynucleotide. In some embodiments, the oligonucleotide comprises 18 to 22 nucleosides. In some embodiments, the X and Z domains each comprise 5-10 nucleotides. In some embodiments, the Y domain comprises 5-10 nucleotides. In some embodiments, the X and Z domains each comprise 5-10 nucleotides, and the Y domain comprises 10 nucleotides. In some embodiments, the X and Z domains each comprise 5 nucleotides, and the Y domain comprises 10 nucleotides. In some embodiments, each nucleotide of the X and Z domains is a nucleotide of Formula (I). In some embodiments, at least one nucleotide of the X domain and at least one nucleotide of the Z domain are each independently selected from the group consisting of a nucleotide of Formula (II), a nucleotide of Formula (IIIa), and a nucleotide of Formula (IIIb). In some embodiments, each of the at least one nucleotide of the X and Z domains are the same nucleotide. In some embodiments, each nucleotide of the Y domain is linked through thiophosphate intersubunit linkages. In some embodiments, the oligonucleotide is single stranded. In some embodiments, the oligonucleotide is an antisense oligonucleotide. In some embodiments, the oligonucleotide is complementary to a sequence of the HBV genome.

Another embodiments include a chimeric oligonucleotide represented by Formula (VI):

$$5'\text{-}X\text{—}Y\text{—}Z\text{-}3' \qquad (VI),$$

wherein X—Y—Z is a chimeric oligonucleotide comprising a sequence of 18 to 22 nucleosides, and is optionally conjugated at the 5' and/or 3' end to a ligand targeting group or a pharmacophore; X is a domain comprising a sequence of modified nucleosides that is 3-10 nucleosides in length; Z is a domain comprising a sequence of modified nucleosides that is 3-10 nucleosides in length; and Y is a domain comprising a sequence of 2 to 14 2'-deoxy-nucleosides linked through thiophosphate intersubunit linkages. In some embodiments, the Y domain is 6 to 10 nucleosides in length. In some embodiments, X and/or Z domains comprise a sequence of modified nucleosides linked through N3'→P5' phosphoramidate or N3'→P5' thiophosphoramidate intersubunit linkages. In some embodiments, the Y domain comprises at least one phosphodiester intersubunit linkage. In some embodiments, the Y domain consists of 2'-deoxy-nucleosides linked through thiophosphate intersubunit linkages, and optionally one or two phosphodiester intersubunit linkage. In some embodiments, the X domain comprises modified nucleosides where the modification is independently selected from the group consisting of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleosides, 2'-OH—N3'→P5' thiophosphoramidate and 2'-OH—N3'→P5' phosphoramidate. In some embodiments, the functional domain of Z comprises modified nucleosides where the modification is selected from the group consisting of 2'-F, 2'-F—N3'→P5', 2'-OMe, 2'-OMe-N3'→P5', 2'-O-methoxyethoxy, 2'-O-methoxyethoxy-N3'→P5', conformationally restricted nucleosides, 2'-OH—N3'→P5' thiophosphoramidate and 2'-OH—N3'→P5' phosphoramidate. In some embodiments, the X and/or Z domains comprise one or more 2'-deoxy-nucleosides linked through a N3'→P5' phosphoramidate intersubunit linkage. In some embodiments, the X and Z domains comprise one or more 2'-ara-bino-F and/or 2'-ribo-F modified nucleoside, wherein each said nucleoside is independently linked through at least one of an N3'→P5' phosphoramidate or N3'→P5' thiophosphoramidate intersubunit linkage. In some embodiments, the X and Z domains comprise one or more 2'-OMe modified nucleosides, wherein each said nucleoside is independently linked through at least one of N3'→P5' phosphoramidate, N3'→P5' thiophosphoramidate, or thiophosphate intersubunit linkages. In some embodiments, the modified nucleosides in each of the X and Z domains are 2'-OMe modified nucleosides linked through thiophosphate intersubunit linkages, and wherein the modified nucleosides include 5-methylcytosine nucleobases, but optionally not cytosine. In some embodiments, the modified nucleosides include 2,6-diaminopurine nucleobases, but optionally not adenine. In some embodiments, the modified nucleosides include 5-methyluracil nucleobases, but optionally not uracil. In some embodiments, the modified nucleosides include 2,6-diaminopurine nucleobases, but not adenine and 5-methyluracil nucleobases, but optionally not uracil. In some embodiments, the Y domain comprises 6-8 2'-deoxy-nucleosides. In some embodiments, the modified nucleosides in each of the X and Z domains comprise 2'-OMe modified nucleosides and conformationally restricted nucleosides optionally linked through thiophosphate intersubunit linkages, and wherein the 2'-OMe modified nucleosides include 5-methylcytosine nucleobases, but optionally not cytosine. In some embodiments, the modified nucleosides in each of the X and Z domains comprise 2'-OMe and conformationally restricted nucleosides. In some embodiments, the modified nucleosides in each of the X and Z domains comprise conformationally restricted nucleosides and, wherein at least one modified nucleoside includes a N3'→P5' phosphoramidate or a N3'→P5' thiophosphoramidate intersubunit linkage. In some embodiments, the Y domain comprises 7-8 2'-deoxy-nucleosides. In some embodiments, the 2'-OMe modified nucleosides include 5-methyluracil nucleobases, but optionally not uracil. In some embodiments, the Y domain comprises 9-10 2'-deoxy-nucleosides. In some embodiments, the X and Z domains comprise nucleotides represented by the Formula (Ix):

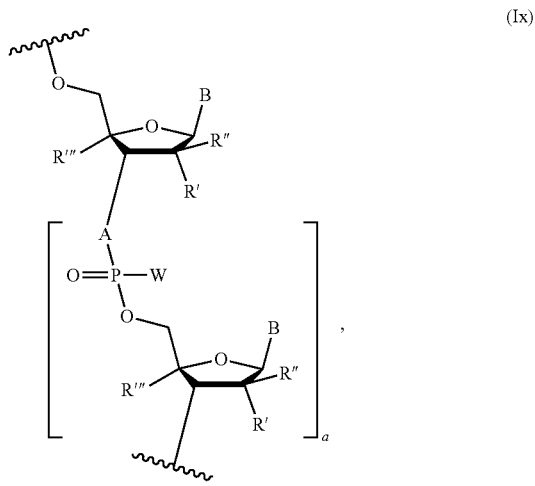

(Ix)

wherein A is independently in each instance NH or O; B is independently in each instance an unmodified or modified nucleobase; W is independently in each instance OR or SR, where R is H or a positively charged counter ion; R' and R" are each independently in each instance selected from the group consisting of H, F, Cl, OH, OMe, Me, and O-methoxyethoxy; R'" is H, or R' and R'" together form —O—CH$_2$— or —O—(CH$_2$)$_2$—, and a is an integer of 3 to 9, wherein when R', R" and R'" are each H, then A is NH, and optionally when A is O, then W is SR. In some embodiments, the ligand targeting group or a pharmacophore is selected from the group consisting of Chol., Toco, Palm, GalNAc, MGB-1, MGB-2, Acr-, Pyr-, Steroyl, HEG linker, a C7 amino linker, and combinations thereof. In some embodiments, the X and/or Z domain comprises one or more oligonucleotide where the modification is 2'-O-methoxy-ethoxy-N3'→P5'. In some embodiments, the X domain comprises one or more oligonucleotide where the modification is 2'-O-methoxyethoxy-N3'→P5'. In some embodiments, the Z domain comprises one or more oligonucleotide where the modification is 2'-O-methoxyethoxy-N3'→P5'. In some embodiments, the construct of said oligonucleotide corresponds to a construct of Table B.

Other embodiments include a chimeric oligonucleotide represented by Formula (VII):

5'-X'—Y'—Z'-3' (VII), wherein X'—Y'—Z' is a chimeric oligonucleotide comprising a sequence of 16 to 22 nucleosides, and is optionally conjugated at the 5' and/or 3' end; X' is a domain comprising a sequence of modified nucleosides that is 3-10 nucleosides in length; Z' is a domain comprising a sequence of modified nucleosides that is 3-10 nucleosides in length; and Y' is a domain comprising a sequence of 2 to 4 2'-deoxy-nucleosides linked through intersubunit linkages, wherein the X' and/or Z' domains comprise a sequence of modified nucleosides linked through N3'→P5' phosphoramidate or N3'→P5' thiophosphoramidate intersubunit linkages. In some embodiments, the Y' domain consists of 2'-deoxy-nucleosides linked through thiophosphate intersubunit linkages, and optionally one phosphodiester intersubunit linkage. In some embodiments, the X' domain is 9 or 10 nucleosides in length. In some embodiments, the X' domain comprises modified nucleosides where the modification is selected from the group consisting of 2'-F, 2'-F—N3'→P5', 2'-OMe, 2'-OMe-N3'→P5', 2'-O-methoxyethoxy, 2'-O-methoxyethoxy-N3'→P5', and conformationally restricted nucleosides. In some embodiments, the Z' domain comprises modified nucleosides where the modification is selected from the group consisting of 2'-F, 2'-F—N3'→P5', 2'-OH, 2'-OMe, 2'-OMe-N3'→P5', 2'-O-methoxyethoxy, 2'-O-methoxyethoxy-N3'→P5', and conformationally restricted nucleosides. In some embodiments, the X' and/or Z' domains comprise one or more 2'-arabino-F and/or 2'-ribo-F modified nucleoside. In some embodiments, the modified nucleosides in the X' and/or Z' domains comprise 2'-OMe and conformationally restricted nucleosides. In some embodiments, the modified nucleosides in the X' and/or Z' domains comprise conformationally restricted nucleosides and a N3'→P5' modification. In some embodiments, the sequence is selected from those in Table C having a 2-4 nucleotide Y domain. Other embodiments include a chimeric oligonucleotide, wherein the sequence of said oligonucleotide corresponds to a sequence listed in Table C.

Other embodiments include an oligonucleotide comprising one or more nucleotides of the following Formula (A):

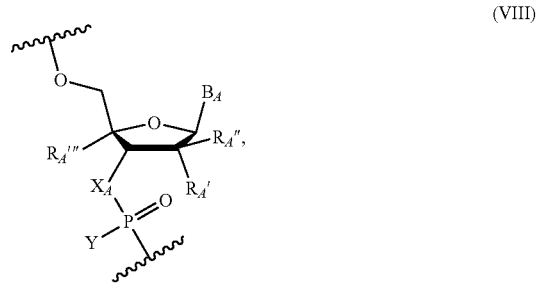

(VIII)

wherein $X_A$ is NH or O, Y is OR or SR, where R is H or a positively charged counter ion, $B_A$ is independently in each instance a natural or an unmodified nucleobase or a modified nucleobase, $R_A'$ and $R_A''$ are each independently in each instance selected from H, F, OH, OMe, Me, 0-methoxyethoxy, and $R_A'''$ is H or $R_A'$ and $R_A'''$ together form —O—CH$_2$— or —O—(CH$_2$)$_2$—. In some embodiments, $R_A'$ and $R_A'''$ are H; and $R_A''$ is F. In some embodiments, $R_A'$ and $R_A''$ are H; and $R_A'''$ is F, OH, H or OMe. In some embodiments, $X_A$ is NH; $B_A$ is an unmodified or modified nucleobase; $R_A'$ and $R_A'''$ together form a conformationally restricted nucleoside (e.g., —O—CH$_2$— or —O—(CH$_2$)$_2$—); and $R_A''$ is H. In some embodiments, at least one of $R_A'$ and $R_A''$ is H. In some embodiments, when $B_A$ is a purine nucleobase at least one of $R_A'$ and $R_A''$ is OH or F, and/or when $B_A$ is a pyrimidine nucleobase at least one of $R_A'$ and $R_A''$ is OMe, OH or F. In some embodiments, the modified nucleobase is selected from 5-methylcytosine, 2,6-diaminopurine, 5-methyluracil, and a g-clamp. In some embodiments, the nucleotides of Formula (A) include those in Table G. In some embodiments, the nucleotide of Formula (A) includes a sequence listed in Table H. In some embodiments, the nucleotide of Formula (A) includes a sequence 1, 2, 3, 4, or 5 nucleobases different from a sequence selected from those in Table B.

Other embodiments include an oligonucleotide comprising ten or more nucleotides of the following Formula (IX):

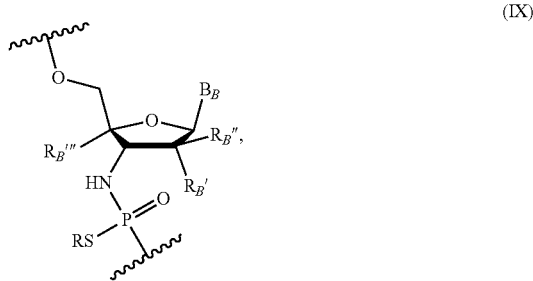

(IX)

wherein R is H or a positively charged counter ion, $B_B$ is independently in each instance a natural or an unmodified nucleobase or a modified nucleobase, $R_B'$ and $R_B''$ are each independently in each instance selected from H, F, OMe, Me, O-methoxyethoxy, and $R_B'''$ is H or $R_B'$ and $R_B'''$ together form —O—CH$_2$— or —O—(CH$_2$)$_2$—. In some embodiments, $R_B'$ and $R_B''$ are H; and $R_B''$ is F. In some embodiments, $R_B'$ and $R_B''$ are H; and $R_B'''$ is F, OH, H or OMe. In some embodiments, $B_B$ is an unmodified or modified nucleobase; $R_B'$ and $R_B'''$ together form a conformationally restricted nucleoside (e.g., —O—CH$_2$— or —O—(CH$_2$)$_2$—); and $R_B''$ is H. In some embodiments, at least one of $R_B'$ and $R_B''$ is H. In some embodiments, when $B_B$ is a purine nucleobase at least one of $R_B'$ and $R_B''$ is OH or F, and/or when $B_B$ is a pyrimidine nucleobase at least one of $R_B'$ and $R_B''$ is OMe, OH or F. In some embodiments, the modified nucleobase is selected from 5-methylcytosine, 2,6-diaminopurine, 5-methyluracil, and a g-clamp. In some embodiments, the nucleotides of Formula (B) include those in Table A where $X_A$ is NH. In some embodiments, the nucleotide of Formula (B) includes a sequence listed in Table B. In some embodiments, the nucleotide of Formula (B) includes a sequence 1, 2, 3, 4, or 5 nucleobases different from a sequence selected from those in Table B. In some embodiments, every oligonucleotide is a nucleotide of the Formula (B).

Other embodiments include a pharmaceutical composition comprising an oligonucleotide of any of the preceding embodiments and a pharmaceutically acceptable excipient. In some embodiments, the composition is suitable for intravenous or subcutaneous delivery. Other embodiments include a method of inhibiting Hepatitis B virus (HBV) gene expression in a cell comprising contacting the cell with an oligonucleotide or composition of any of the preceding embodiments. Other embodiments include a method of inhibiting replication of a Hepatitis B virus (HBV) in a cell comprising contacting the cell with an oligonucleotide or composition of any of the preceding embodiments. Other embodiments include a method of treating a subject having a Hepatitis B virus (HBV) infection, comprising administering to the subject a therapeutically effective amount of an oligonucleotide or composition of any of the preceding embodiments. Other embodiments include a, oligonucleotide of any of the preceding embodiments, wherein said oligonucleotide complexed with an HBV genome sequence has a melting temperature (Tm) of >37° C. Other embodiments include a method of treating a subject having a Hepatitis B virus (HBV) infection, comprising administering to the subject a therapeutically effective amount of an oligonucleotide or composition of any of the preceding embodiments. Other embodiments include a method of inhibiting expression of a target RNA in a cell comprising contacting the cell with an oligonucleotide or composition comprising said oligonucleotide of any of the preceding embodiments, wherein the chimeric oligonucleotide contains a nucleobase sequence that is complementary or hybridizes to a portion of the target RNA. Other embodiments include a method of inhibiting replication of a virus in a cell comprising contacting the cell with an oligonucleotide or composition comprising said oligonucleotide of any of the preceding embodiments, comprising said oligonucleotide contains a nucleobase sequence that is complementary or hybridizes to a portion a viral target RNA. Other embodiments include a method of treating a subject having a viral infection, comprising administering to the subject a therapeutically effective amount of an oligonucleotide or composition comprising said oligonucleotide of any of the preceding embodiments, wherein the oligonucleotide contains a nucleobase sequence that is complementary or hybridizes to a portion of viral target RNA. Other embodiments include a method of modulating expression of a target by contacting a target nucleic acid with an antisense compound comprising an oligonucleotide or composition comprising said oligonucleotide of any of the preceding embodiments, wherein the oligonucleotide contains a nucleobase sequence that is complementary or hybridizes to a portion of target nucleic acid.

BRIEF DESCRIPTION OF THE DRAWINGS

FIG. 3 discloses SEQ ID NOS 576-579, respectively, in order of appearance.

FIG. 4A shows HBsAg serum levels. FIG. 4B shows HBeAg serum levels. FIG. 4C shows HBV DNA levels.

FIG. 5A shows HBsAg serum levels. FIG. 5B shows HBeAg serum levels. FIG. 5C shows HBV DNA levels.

FIG. 6A shows HBsAg serum levels. FIG. 6B shows HBeAg serum levels. FIG. 6C shows HBV DNA levels.

FIGS. 7A-7B show various compounds of the present disclosure (SEQ ID NOS 580-586, respectively, in order of appearance) and their respective complimentary sites for the HBV (+) strand genome.

DETAILED DESCRIPTION

Figure 1A:
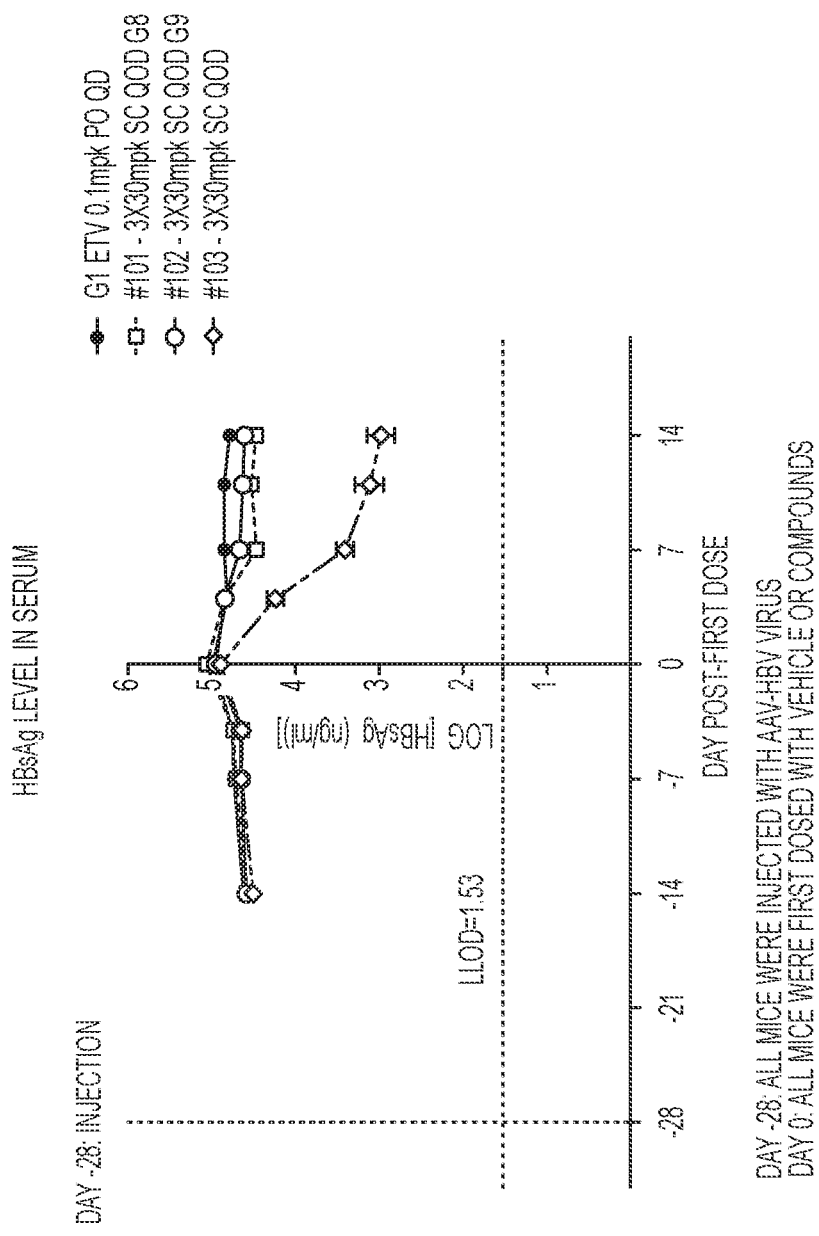
FIG. 1A shows HBsAg serum levels.

The present disclosure is directed to modified nucleotides and oligonucleotides comprising the modified nucleotides and modified linkages between nucleotides. The present disclosure is also directed to constructs of the oligonucleotides, which include domains, regions or portions within the oligonucleotide having common features and additional components conjugated to the oligonucleotide such as targeting moieties. The present disclosure is further directed to methods of using and preparing the oligonucleotides and their constructs.

As known in the art and as set forth in the present disclosure, a modified nucleotide is any nucleotide that is not a deoxyribonucleotide. For example, the 2' carbon of the deoxyribose may be substituted by a substituent other than the hydroxy (OH); the 3' carbon of the deoxyribose may be substituted by a substituent other than the oxygen atom (O). As known in the art and as set forth in the present disclosure, a modified linkage between two nucleotides is any linkage that is not a phosphodiester bond between the 3' carbon of the deoxyribose of the first nucleotide and the 5' carbon of the deoxyribose of the second nucleotide.

1. 2', 3'-Modified Nucleotides and Related Oligonucleotides

Compounds of the present disclosure include modified nucleotides with particular 2' and 3' modifications. In embodiments, compounds of the present disclosure include replacement of the hydroxy, or substitution, at the 2' carbon of the deoxyribose sugar. In addition, these compounds of the present disclosure include modifications of the linkage between two nucleosides, which includes replacement of the oxygen atom, or substitution, with a nitrogen atom (N) at the 3' carbon of the deoxyribose sugar. Modifications of the linkage further include replacement of another oxygen atom, or substitution, in the phosphodiester bond.

These modified nucleotides may be used, e.g., in oligonucleotides such as chimeric oligonucleotides allowing for enzymatic cleavage of the genetic target by RNase H or modified antisense oligonucleotides.

A. 2', 3'-Modified Nucleotides

Accordingly, compounds of the present disclosure include nucleotides of Formula (I):

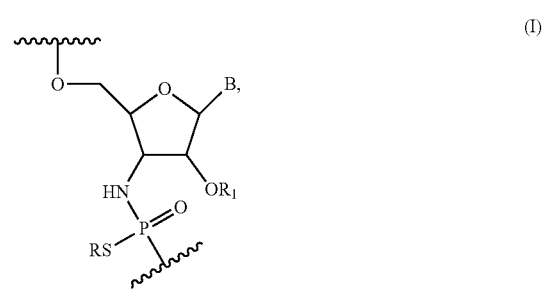

(I)

wherein R is H or a positively charged counter ion, B is independently in each instance a natural or an unmodified nucleobase or a modified nucleobase, $R_1$ is —$(CR'_2)_2OCR'_3$, and R' is independently in each instance H or F.

In nucleotides of Formula (I), $R_1$ is —$(CR'_2)_2OCR'_3$. In some embodiments, R' is H in each instance. In other embodiments, at least one R' is F, for example, 1, 2, 3, 4, 5, 6, or 7 R's are F. In some embodiments, $CR'_3$ contains 1, 2 or 3 F moieties. For example, in embodiments, $R_1$ is selected from the group consisting of —$CH_2CH_2OCH_3$ (or MOE), —$CF_2CH_2OCH_3$, —$CH_2CF_2OCH_3$, —$CH_2CH_2OCF_3$, —$CF_2CF_2OCH_3$, —$CH_2CF_2OCF_3$, —$CF_2CH_2OCF_3$, —$CF_2CF_2OCF_3$, —$CHFCH_2OCH_3$, —$CHFCHFOCH_3$, —$CHFCH_2OCFH_2$, —$CHFCH_2OCHF_2$ and —$CH_2CHFOCH_3$.

In embodiments, the nucleotide of Formula I is:

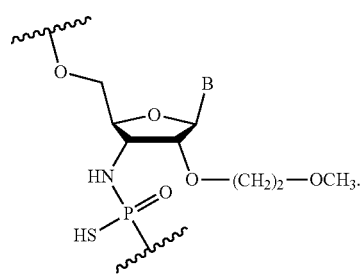

In embodiments, compounds of the present disclosure include at least one nucleotide of Formula (I) and at least one nucleotide of Formula (II):

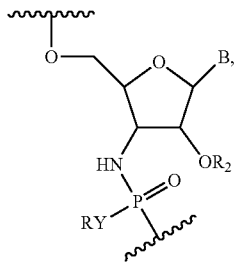

(II)

wherein Y is S or O, R is H or a positively charged counter ion, B is a nucleobase, R$_2$ is —CR'$_3$, —CR'$_2$OCR'$_3$, —(CR'$_2$)$_3$OCR'$_3$ or —(CR'$_2$)$_{1-2}$CR'$_3$, or R$_2$ is —(CR'$_2$)$_2$OCR'$_3$ and Y is O and R' is independently in each instance H or F.

In the nucleotide of Formula (II), R$_2$ is —CR'$_3$, —(CR'$_2$)$_{1-3}$OCR'$_3$, or —(CR'$_2$)$_{1-2}$CR'$_3$. In some embodiments, R$_2$ is-CR'$_3$ or —CR'$_2$CR'$_3$. In some embodiments, R' is H in each instance. In other embodiments, at least one R' is F, for example, 1, 2, 3, 4, or 5 R's are F. In some embodiments, CR'$_3$ contains 1, 2 or 3 F moieties. For example, in embodiments, R$_1$ is selected from the group consisting of —CH$_3$ (or Me), —CFH$_2$, —CHF$_2$, CF$_3$, —CH$_2$OCH$_3$, —CFH$_2$OCH$_3$, —CHF$_2$OCH$_3$, —CF$_3$OCH$_3$, —CH$_2$OCFH$_2$, —CH$_2$OCHF$_2$, —CH$_2$OCF$_3$, —CFH$_2$OCH$_3$, —CFH$_2$OCFH$_2$, —CFH$_2$OCHF$_2$, —CFH$_2$OCF$_3$, —CHF$_2$OCH$_3$, —CHF$_2$OCFH$_2$, —CHF$_2$OCHF$_2$, —CHF$_2$OCF$_3$, —(CR'$_2$)$_3$OCR'$_3$, —CH$_2$CH$_3$ (or Et), —CFH$_2$CH$_3$, —CHF$_2$CH$_3$, —CF$_3$CH$_3$, —CH$_2$CFH$_2$, —CH$_2$CHF$_2$, —CH$_2$CF$_3$, —CFH$_2$CH$_3$, —CFH$_2$CFH$_2$, —CFH$_2$CHF$_2$, —CFH$_2$CF$_3$, —CHF$_2$CH$_3$, —CHF$_2$CFH$_2$, —CHF$_2$CHF$_2$, —CHF$_2$CF$_3$, —CH$_2$CH$_2$CH$_3$, CF$_2$CH$_2$CH$_3$, CH$_2$CF$_2$CH$_3$, CH$_2$CH$_2$CF$_3$, CF$_2$CF$_2$CH$_3$, CH$_2$CF$_2$CF$_3$, CF$_2$CH$_2$CF$_3$, CF$_2$CF$_2$CF$_3$, CHFCH$_2$CH$_3$, CHFCHFOCH$_3$, CHFCH$_2$CFH$_2$, CHFCH$_2$CHF$_2$ and CH$_2$CHFCH$_3$. In embodiments, R$_1$ is —CH$_3$ (or Me) or —CH$_2$CH$_3$ (or Et). In embodiments, the nucleotides of Formula II are selected from the group consisting of

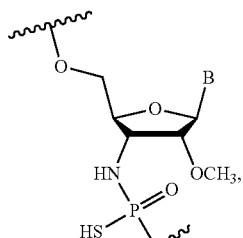

and

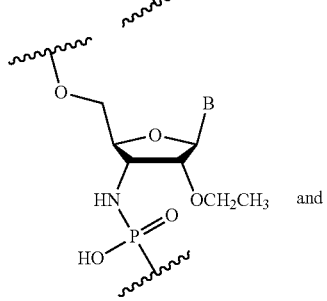

-continued

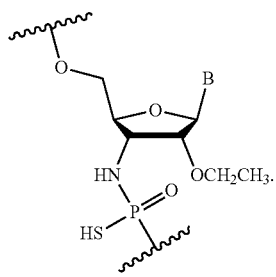

In compounds of Formulae (I) or (II), Y may be O or S. In some embodiments, Y is S in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.). In other embodiments, Y is S in at least one instance and O in at least another instance. In other embodiments, Y is S in each instance. In some embodiments, Y is O in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.).

The disclosed oligonucleotides comprise at least one nucleotide of Formula (I). In embodiments, the disclosed oligonucleotides comprise 1, 2, 3, 4, 5, 6, 7, 8, 9, 10, 11, 12, 13, 14, 15, 16, 17, 18, 19, 20, 21, 22, 23, 24 nucleotides of Formula (I). In embodiments, the disclosed oligonucleotides comprise 1, 2, 3, 4, 5, 6, 7, 8, 9, 10, 11, 12, 13, 14, 15, 16, 17, 18, 19, 20, 21, 22, 23, 24 nucleotides of Formula (II). In some embodiments, the oligonucleotide comprises from 2 to 40 nucleotides, for example, 8 to 26 nucleotides or integers there between.

In embodiments where more than one nucleotide of Formula (I) are included, the nucleotide may be the same or different. In some embodiments one or more nucleotides of Formula (II) are included, and may be the same or different. For example, in some embodiments, the oligonucleotide comprises at least one nucleotide of Formula (I) and at least one nucleotide of Formula (II). In some embodiments, the oligonucleotide comprises at least one nucleotide of Formula (I), wherein at least one R$_1$ is MOE and at least one nucleotide of Formula (II), wherein R$_2$ is Me or Et. In some embodiments, the oligonucleotide comprises at least 2 alternating nucleotides of Formula (I) and Formula (II). For example, 2, 3, 4, 5, 6, 7, 8, 9, 10, 11, 12, 13, 14, 15, 16, 17, 18, 19, 20, 21, 22, 23, 24 nucleotides with alternating 2' modification (e.g., Me-MOE-Me-MOE . . . or Et-MOE-Et-MOE-Et-MOE . . . ).

In some embodiments, the nucleotide of Formula (I) and/or Formula (II) is represented by the following:

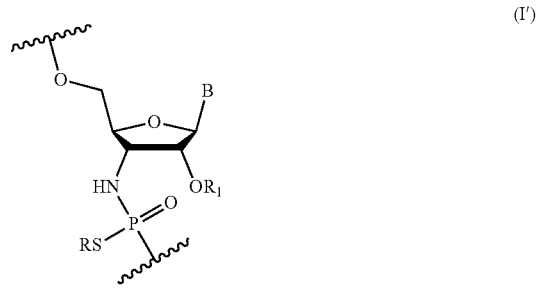

(I')

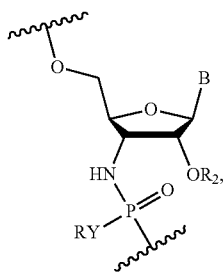
(II')

In some embodiments, the oligonucleotide comprising the nucleotide of Formula (I) further comprises a 2'-fluoronucleotide of the Formula (IIIa) and/or (IIIb):

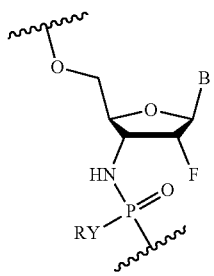
(IIIa)

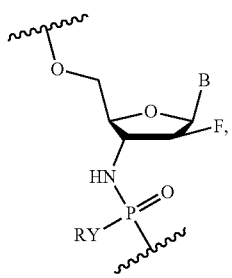
(IIIb)

wherein Y is S or O, R is H or a positively charged counter ion, and B is a nucleobase.

In some embodiments, the oligonucleotide comprises at least 4 alternating nucleotides of Formulae (I) and (IIIa). For example, the oligonucleotide comprises 4, 5, 6, 7, 8, 9, 10, 11, 12, 13, 14, 15, 16, 17, 18, 19, 20, 21, 22, 23, 24 alternating nucleotides.

Certain embodiments include an oligonucleotide comprising 4-40 nucleotides, and comprising Formula (IV):

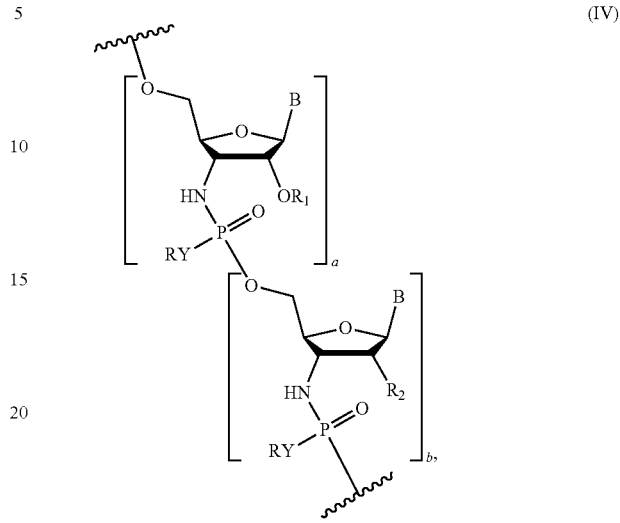
(IV)

wherein Y is S or O, R is H or a positively charged counter ion, B is a nucleobase, $R_1$ is —$(CR'_2)_2OCR'_3$, $R_2$ is selected from —$OCR'_3$, —$OCR'_2OCR'_3$, —$O(CR'_2)_3OCR'_3$ or —$O(CR'_2)_{1-2}CR'_3$ and F, R' is independently in each instance H or F, and a is an integer of 1-10 and b is an integer from 1-10, where the to 20, e.g., 1, 2, 3, 4, 5, 6, 7, 8, 9, 10, 11, 12, 13, 14, 15, 16, 17, 18, 19 and 20.

Compounds of the present disclosure include compounds comprising the following Formula (III'):

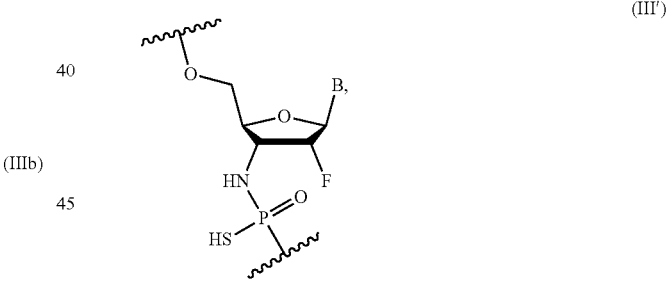
(III')

wherein Y is S or O, R is H or a positively charged counter ion, and B is independently in each instance a natural or an unmodified nucleobase or a modified nucleobase; and optionally comprising one or more of formula (I), (II), and/or (IV).

The nucleobases, B, of the nucleotides of Formulae (I), (II), (IIIa), (IIIb), (IV) and (V) may each independently be a natural or an unmodified nucleobase or a modified nucleobase. In some embodiments, the modified nucleotides include 2,6-diaminopurine nucleobases, but optionally not adenine. In some embodiments, the modified nucleotides include 5-methyluracil nucleobases, but optionally not uracil. In some embodiments, the modified nucleotides include 2,6-diaminopurine nucleobases, but not adenine and 5-methyluracil nucleobases, but optionally not uracil.

Y in each nucleotide of Formulae (II), (IIIa), (IIIb), (IV) and (V) may be independently 0 or S. In some embodiments, Y is S in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.). In other embodiments, Y is S in at least one instance and O in at least another instance. In other embodiments, Y is S in each instance. In some embodiments, Y is O in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.).

In embodiments where more than one nucleotide of each of Formulae (I), (II), (IIIa), (IIIb), (IV) and (V) are included, the more than one nucleotides such Formulae may be the same or different. For example, in some embodiments, the nucleotide comprises at least one nucleotide of Formula (II), (III), (IV), (V) and/or (V') in addition to at least one nucleotide of Formula (I). In some embodiments, the nucleotide comprises at least 2 alternating nucleotides of Formula (I) and/or Formula (II) and/or (III) and/or (IV), (V) and/or (V'). For example, disclosed oligonucleotides may include 2, 3, 4, 5, 6, 7, 8, 9, 10, 11, 12, 13, 14, 15, 16, 17, 18, 19, 20, 21, 22, 23, 24 nucleotides with alternating 2' modifications.

In embodiments, the nucleotides of the oligonucleotide are selected from the group consisting of:

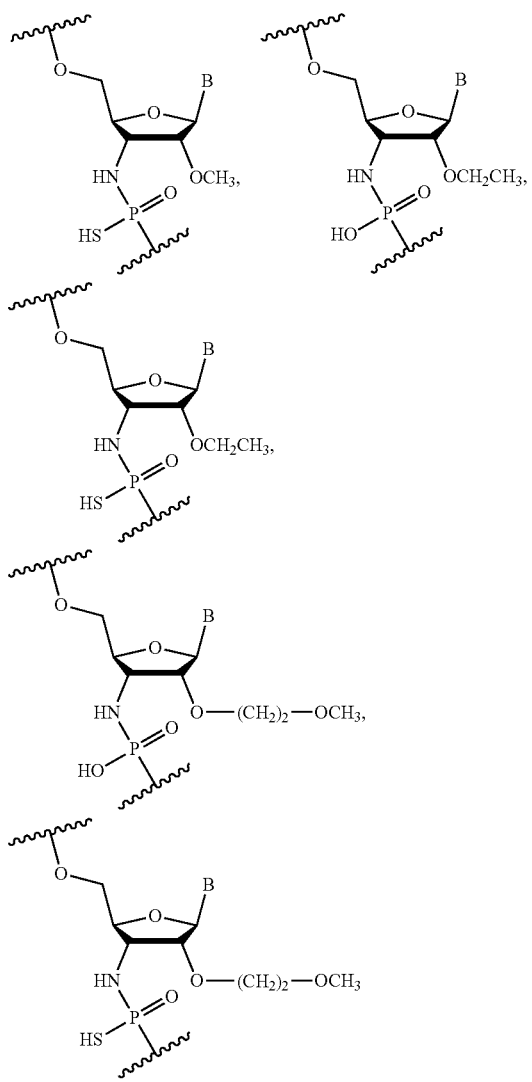

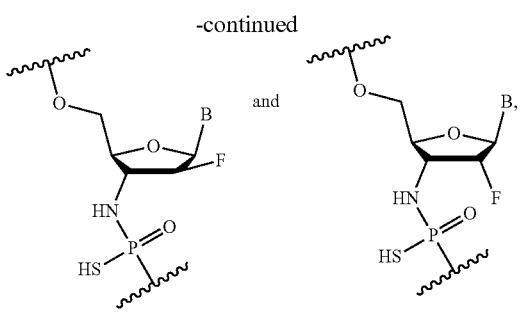

where B can be any natural or modified base.

Compounds of the present disclosure include compounds comprising the following Formula (V'):

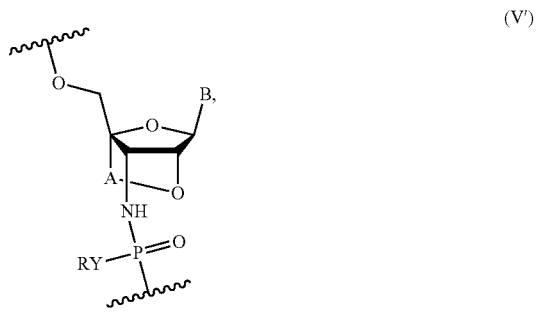

wherein Y is S or O, R is H or a positively charged counter ion, B is independently in each instance a natural or an unmodified nucleobase or a modified nucleobase, A is —(CR"R")$_{1-2}$— and R" is independently in each instance H, F or Me, and optionally comprising one or more of Formulae (I), (II), (III), (IV) or (V).

In the compound comprising formula (V'), A is —(CR"R")$_{1-2}$—. In some embodiments, A is —(CR"R")— in other embodiments, A is —(CR"R")$_2$—. R" is independently in each instance H or Me. In some embodiments, one R" is Me and remaining are H. In other embodiments, all R" are H.

In some embodiments, when A is $CH_2$, then Y is S. In other embodiments, when A is $CH_2CH_2$, then Y is O or S. In some embodiments, A is $CH_2CH(Me)$ or $CH(Me)$ and Y is O or S.

In the compound comprising formula (V'), Y is O or S. In some embodiments, Y is S in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.). In other embodiments, Y is S in at least one instance and O in at least another instance. In other embodiments, Y is S in each instance. In some embodiments, Y is O in at least one instance (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.).

The compound of Formula (V') (and optionally Formulae (I), (II), (III), (IV), (V) and/or (V') may be part of an oligonucleotide. In some embodiments, the compound comprising Formula (IV) (and optionally Formulae (I), (II), (III), (IV), (V) and/or (V')) is an oligonucleotide comprising 1, 2, 3, 4, 5, 6, 7, 8, 9, 10, 11, 12, 13, 14, 15, 16, 17, 18, 19, 20, 21, 22, 23, 24 nucleotides of Formula (V') (and Formulae (I), (II), (III), (IV), (V) and/or (V')). In some embodiments, the oligonucleotide comprises from 2 to 40 nucleotides, for example, 8 to 26 nucleotides or integers there between.

In embodiments where more than one nucleotides of Formula (V') are included, the more than one nucleotides of Formula (V') may be the same or different. In some embodiments one or more nucleotides of Formulae (I), (II), (III), (IV), (V) and/or (V') are included, and may be the same or different. For example, in some embodiments, the nucleotide comprises at least one nucleotide of Formula (V') and at least one nucleotide of Formulae (I), (II), (III), (IV), (V) and/or (V'). In some embodiments, the nucleotide comprises at least 2 alternating nucleotides of Formula (V') and Formula (I) and/or (II). For example, 2, 3, 4, 5, 6, 7, 8, 9, 10, 11, 12, 13, 14, 15, 16, 17, 18, 19, 20, 21, 22, 23, 24 nucleotides with alternating 2' modification.

In some embodiments, the nucleotide comprising the nucleotide of Formula (V') (and optionally Formulae (I), (II), (III), (IV), (V) and/or (V')) further comprises a 2-fluoronucleotide of the following structures:

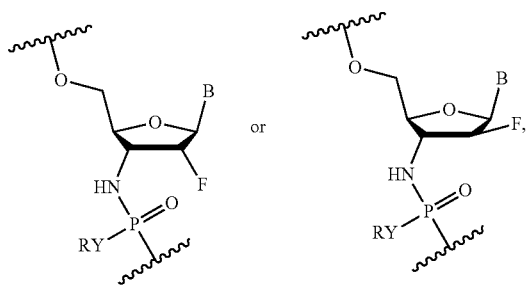

where Y, R and B are the same as for Formula (I). In some embodiments, the nucleotide comprises at least 4 alternating nucleotides of Formula (V') and 2-fluoronucleotides.

Compounds of the present disclosure include compounds comprising the following Formula (V):

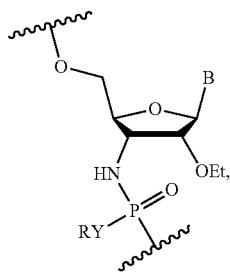

wherein Y is S or O, R is H or a positively charged counter ion, and B is independently in each instance a natural or an unmodified nucleobase or a modified nucleobase; and optionally comprising one or more of formula (I), (II), (III), (IV) and/or (V').

B. Chimeric Oligonucleotides

The present disclosure is directed to constructs of oligonucleotides, which include domains, regions or portions within the oligonucleotide having common features.

Oligonucleotides having these domains are referred to herein as chimeric oligonucleotides. In some embodiments, chimeric oligonucleotides are represented by Formula (VI):

$$5'-X-Y-Z-3' \quad (VI),$$

wherein the chimeric oligonucleotide comprises a sequence of 14 to 22 nucleosides, wherein X is a domain comprising a sequence of modified nucleotides that is 3-10 nucleotides in length; Z is a domain comprising a sequence of modified nucleotides that is 3-10 nucleosides in length; and Y is a domain comprising a sequence of 2-10 2'-deoxy-nucleotides, or unmodified nucleotides. Each of the nucleosides in each of the domains is linked through intersubunit linkages.

In some embodiments, chimeric oligonucleotides are represented by Formula (VI'):

$$5'-X-Y-Z-3' \quad (VI'),$$

wherein the chimeric oligonucleotide comprises a sequence of 14 to 22 nucleosides, wherein X is a domain comprising a sequence of modified nucleotides that is 2-10 nucleotides in length; Z is a domain comprising a sequence of modified nucleotides that is 2-10 nucleosides in length; and Y is a domain comprising a sequence of 6-14 2'-deoxy-nucleotides, or unmodified nucleotides. Each of the nucleosides in each of the domains is linked through intersubunit linkages.

Nucleotides of formula (I), (II), (IIIa), (IIIb), (IV), (V) and/or (V') may be present in the X and/or Z domain. Chimeric oligonucleotide may be conjugated at the 5' and/or 3' end to a ligand-targeting group or a pharmacophore.

In some embodiments, the Y domain contains 2'deoxy-nucleosides linked by thiophosphate intersubunit linkages. In embodiments, the Y domain contains 2'deoxy-nucleosides linked by at least one phosphodiester intersubunit linkage. In embodiments, the Y domain contains 2'deoxy-nucleosides linked by two phosphodiester intersubunit linkages. In embodiments, the Y domain contains 2'deoxy-nucleosides linked by thiophosphate intersubunit linkages and one or two phosphodiester intersubunit linkages. In some embodiments, the Y domain is 6 to 10 nucleotides in length.

In some embodiments, the X domain comprises nucleotides of formulae (I), (II), (IIIa), (IIIb), (IV), (V) and/or (V'). In some embodiments, the X domain comprises modified nucleotides where the modification is independently selected from 2'-OMe, 2'-OEt, 2'-O-methoxyethoxy, and conformationally restricted nucleotides. In some embodiments, the X domain is 9 or 10 nucleotides in length.

In some embodiments, the Z domain comprises nucleotides of formulae (I), (II), (IIIa), (IIIb), (IV), (V) and/or (V'). In some embodiments, the Z domain comprises 2' modified nucleotides where the modification is 2'-OMe, 2'-OEt or 2'-MOE. In some embodiments, the Z domain is 9 or 10 nucleotides in length.

In embodiments, the chimeric oligonucleotide comprises a sequence of 14 to 22 nucleotides. For example, the oligonucleotide may include 14, 15, 16, 17, 18, 19, 20, 21 or 22 nucleotides.

In embodiments, X is a domain consisting of a sequence containing one or more modified nucleotides that is 3-10 nucleotides in length; Z is a domain consisting of a sequence containing one or more modified nucleotides that is 3-10 nucleotides in length; and Y is a domain consisting of a sequence of 2 to 10 2'-deoxy-nucleosides linked through thiophosphate intersubunit linkages and optionally one or two phosphodiester intersubunit linkages. In some embodiments, X is 5-9, Y is 6-10 and Z is 5-9. In some embodiments, the number of nucleotides in each of X, Y and Z, respectively is: 6/6/6, 6/6/7, 6/6/8, 6/7/6, 6/7/7, 6/7/8, 6/8/6, 6/8/7, 6/8/8, 3/10/3, 4/10/4, 5/10/5, 5/10/6, 2/12/2, 3/12/3, 2/14/2, 5/9/5, 5/9/6, 5/8/5, 5/8/6, 5/8/7, 7/5/7, 7/5/8, 7/5/9, 7/6/6, 7/6/7, 7/6/8, 7/6/9, 7/7/6, 7/7/7, 7/7/8, 7/7/9, 7/5/7, 7/5/8, 7/5/9, 7/4/7, 7/4/8, 7/4/9, 8/4/7, 8/4/8, 8/4/9, 7/3/7, 7/3/8, 7/3/9, 8/3/7, 8/3/8, 8/3/9, 8/3/10, 9/3/7, 9/3/8, 9/3/9, 9/3/10, 8/2/7, 8/2/8, 8/2/9, 8/2/10, 9/2/7, 9/2/8, 9/2/9, 9/2/10, 10/2/8, 10/2/9, 10/2/10. The X domain and the Z domain each, respectively, comprise a sequence of modified nucleotides, where the domain is 4-10 nucleotides in length. For example, the X domain and/or Z domain may comprise a sequence of 4, 5, 6, 7, 8, 9, or 10 nucleotides. One or more of these nucleotides is modified (e.g., 1, 2, 3, 4, 5, 6, 7, 8, 9 or 10). For example, in some embodiments, all the nucleotides in each of the X domain and/or Z domain are modified.

The nucleotides of the X and Z domains may be modified according to Formulae (I), (II), (IIIa), (IIIb), (IV), (V) and/or (V') with respect to one or more of their nucleobases, the 2' and/or 3' positions on the ribose sugar and their intersubunit linkages. Embodiments include wherein the 2' position is modified with an F (ribo or arabino) and the 3' position is O or NH. Embodiments also include wherein the 2' position is modified with an OMe and the 3' position is O or NH. Embodiments include wherein the 2' position is modified with an F (ribo or arabino) as well as Me or OMe, and the 3' position is O or NH. Embodiments include wherein the 2' position is modified with an F (ribo or arabino) and the 3' position is O or NH. Embodiments include wherein the 2' position is modified with an O-methoxyethoxy and the 3' position is O or NH. Embodiments also include wherein the 2' position is modified with an F (ribo or arabino) and the 3' position is O or NH. Embodiments include wherein the 2' and 4' positions are modified bridging group (as described elsewhere herein) to form a conformationally restricted nucleotide and the 3' position is O or NH. Each of these embodiments may include thiophosphate (or thiophosphoramidate depending on the 3' substitution) and phosphoramidate intersubunit linkages.

Embodiments also include where the 2' position is H, and the 3' position is NH. Each of these embodiments may include thiophosphoramidate and/or phosphoramidate intersubunit linkages.

In some embodiments, the modified nucleotides of the X domain and the Z domain each, respectively, include a modification independently selected from at least one of 2'-F, 2'-F—N3'→P5', 2'-OMe, 2'-OMe-N3' →P5', 2'-O-methoxyethoxy, 2'-O-methoxyethoxy-N3' conformationally restricted nucleotides.

In some embodiments, the modified nucleotide contains a nucleoside represented by the following Formula (A):

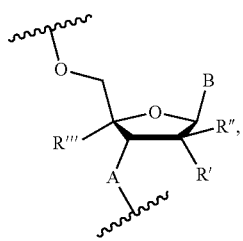

(A)

wherein A is independently in each instance NH or O, B is independently in each instance a natural or an unmodified nucleobase or a modified nucleobase, and R' and R" are each independently in each instance selected from H, F, OH, OMe, OEt, O-methoxyethoxy, and R''' is H, or R' and R''' together form a 2-4 atom bridge to form a conformationally restricted nucleoside (e.g., —O—CH$_2$—, —O—CH(Me)-, or —O—(CH$_2$)$_2$—).

In some embodiments, R' is selected from F, OH, —OMe, —OEt, O-methoxyethoxy; R" is H and F; and R''' is H, Me or —OMe. In other embodiments, R" and R''' are H; and R' is selected from F, OMe, OEt and O-methoxyethoxy. In some embodiments, A is NH in each instance.

Some embodiments include one or more modified nucleosides represented by Formula (A), wherein A is NH; B is a G-clamp; R' is F or OMe and R" is H; or R' is H and R" is H or F; and R''' is H.

Some embodiments include one or more modified nucleosides represented by Formula (A), wherein A is NH; B is an unmodified or modified nucleobase; R' and R''' together form a conformationally restricted nucleoside (e.g., —O—CH$_2$—, —O—CH(Me)-, or —O—(CH$_2$)$_2$—); and R" is H. In some embodiments, B is an unmodified or a modified nucleobase selected from the group consisting of 5-methylcytosine, 2,6-diaminopurine, and 5-methyluracil.

Some embodiments include one or more modified nucleosides represented by Formula (A), wherein A is NH; B is an unmodified or modified nucleobase; R' is F or OMe, R" is H and R''' is H.

Some embodiments include one or more modified nucleosides represented by Formula (A), wherein A is NH; B is an unmodified or modified nucleobase; R' is H, R" is F and R''' is H.

In some embodiments, the X and Z domains are represented by the Formula (Ix):

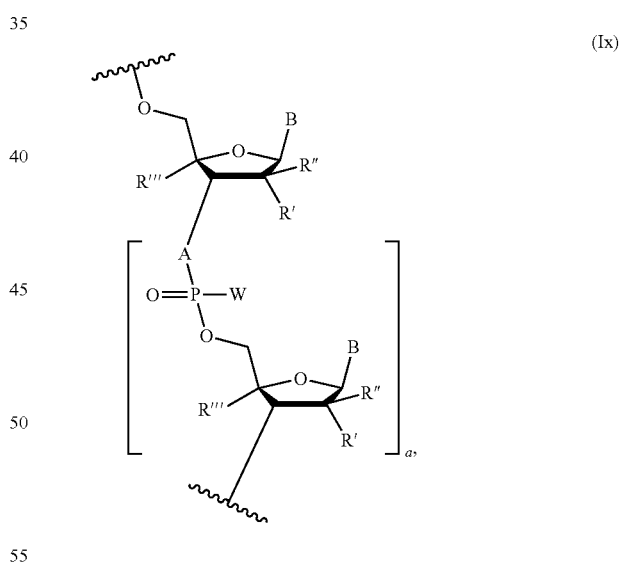

(Ix)

wherein W is independently in each instance OR or SR, where R is H or a positively charged counter ion; R', R", R''', A and B are as described for Formula (A). In other embodiments, A is O and R', R" are independently H or OEt, where at least one of R', R" is OEt.

For example, the nucleotides of X and/or Z may include one or more of the nucleotides in Table A in addition to at least one nucleotide in each of the X and Z domains where A is NH, W is S, and R' is MOE.

TABLE A

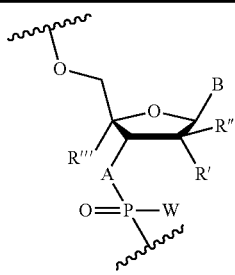

| Nucleotide No. | R' | R" | R''' | A | W |
|---|---|---|---|---|---|
| 1 | F | H | H | NH | S |
| 2 | F | H | H | NH | O |
| 3 | F | H | H | O | S |
| 4 | F | H | H | O | O |
| 5 | H | F | H | NH | S |
| 6 | H | F | H | NH | O |
| 7 | H | F | H | O | S |
| 8 | H | F | H | O | O |
| 9 | OMe | H | H | NH | S |
| 10 | OMe | H | H | NH | O |
| 11 | OMe | H | H | O | S |
| 12 | OMe | H | H | O | O |
| 13 | H | F | H | NH | S |
| 14 | H | F | H | NH | O |
| 15 | H | F | H | O | S |
| 16 | H | F | H | O | O |
| 17 | O-methoxyethoxy | H | H | NH | S |
| 18 | O-methoxyethoxy | H | H | NH | O |
| 19 | O-methoxyethoxy | H | H | O | S |
| 20 | O-methoxyethoxy | H | H | O | O |
| 21 | H | H | H | NH | S |
| 22 | H | H | H | NH | O |
| 23 | OH | H | H | NH | S |
| 24 | OH | H | H | NH | O |
| 25 | OH | H | H | O | S |
| 26 | H | OH | H | NH | O |
| 27 | H | OH | H | NH | S |
| 28 | H | OEt | H | NH | O |
| 29 | H | OEt | H | NH | S |
| 30 | H | OEt | H | O | O |
| 31 | H | OEt | H | O | S |
| 32 | OEt | H | H | NH | O |
| 33 | OEt | H | H | NH | S |
| 34 | OEt | H | H | O | O |
| 35 | OEt | H | H | O | S |

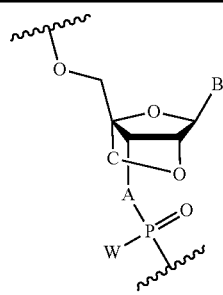

| Nucleotide No. | C | A | W |
|---|---|---|---|
| 36 | —O—CH$_2$— | NH | S |
| 37 | —O—CH$_2$— | NH | O |
| 38 | —O—CH$_2$— | O | S |
| 39 | —O—CH$_2$— | O | O |
| 40 | —O—(CH$_2$)$_2$— | NH | S |
| 41 | —O—(CH$_2$)$_2$— | NH | O |
| 42 | —O—(CH$_2$)$_2$— | O | S |
| 43 | —O—(CH$_2$)$_2$— | O | O |
| 44 | —O—CH(Me)— | NH | S |
| 45 | —O—CH(Me)— | NH | O |

TABLE A-continued

| | | | |
|---|---|---|---|
| 46 | —O—CH(Me)— | O | S |
| 47 | —O—CH(Me)— | O | O |

In some embodiments, the X domain and Z domain each independently comprise two, three or more different nucleotides 1-47.

The nucleosides of the X domain are linked through intersubunit linkages, for example, N3'→P5' phosphoramidate, N3'→P5' thiophosphoramidate, thiophosphate, phosphodiester intersubunit linkages or combinations thereof. In some embodiments, the X domain is linked through intersubunit linkages selected from N3'→P5' phosphoramidate, N3'→P5' thiophosphoramidate, and combinations thereof.

The X domain of the chimeric oligonucleotide may include a certain arrangement of modified nucleotides. For example, in some embodiments, the X domain comprises one or more conformationally restricted nucleotides. Conformationally restricted nucleotides can include BNA, such as, LNA and ENA. (e.g., 1, 2, 3, 4, 5, 6, 7, 8, 9, 10 conformationally restricted nucleotides). In some embodiments, the X domain comprises one or more 2'-F and/or 2'-OMe modified nucleotides. In some embodiments, the X domain comprises alternating conformationally restricted nucleotides, e.g., every other nucleotide is a conformationally restricted nucleotide. In some embodiments, the X domain comprises one or more 2'-F and/or 2'—OMe modified nucleotide (e.g., 1, 2, 3, 4, 5, 6, 7, 8, 9, 10 2'-F and/or 2'-OMe modified nucleotides). In some embodiments, the X domain comprises alternating 2'-F and 2'-OMe modified nucleotides. In embodiments, the X domain comprises 2'-F or 2'-OMe and conformationally restricted nucleotides, for example, in an alternating sequence.

The Y domain comprises a sequence of 2 to 14 2'-deoxynucleotides. For example, the Y domain may comprise a sequence of 2, 3, 4, 5, 6, 7, 8, 9, 10, 11, 12, 13 or 14 2'-deoxynucleotides. One or more of the 2'-deoxynucleosides may be linked through thiophosphate intersubunit linkages (e.g., 1, 2, 3, 4, 5, 6, 7, 8, 9, 10, 11, 12, 13 or 14 thiophosphate intersubunit linkages). In some embodiments, each of the 2'-deoxynucleosides is linked through a thiophosphate intersubunit linkage. In some embodiments, the Y domain comprises at least one phosphodiester intersubunit linkage (e.g., 1, 2 or 3 phosphodiester intersubunit linkages). In other embodiments, the Y domain consists of 2'-deoxynucleosides linked through thiophosphate intersubunit linkages, and optionally one or two phosphodiester intersubunit linkages.

In embodiments, the Y domain comprises nucleotides that induce RNase H cleavage.

In some embodiments, the 2'-deoxynucleoside linked through a thiophosphate intersubunit linkage may be represented by the following Formula (B):

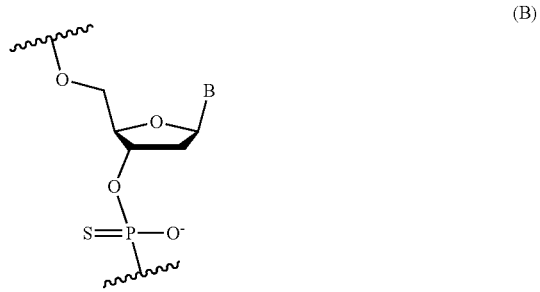

(B)

where B is independently in each instance an unmodified or modified nucleobase. In some embodiments, B is an unmodified or a modified nucleobase selected from the group consisting of 5-methylcytosine, 2,6-diaminopurine, and 5-methyluracil.

In other embodiments, the 2'-deoxynucleoside linked through a thiophosphate intersubunit linkage comprises a modified 2'-deoxynucleoside, which may be modified in the same manner as in the X and Z domain. For example, the modified 2'-deoxynucleoside linked through a thiophosphate intersubunit linkage may be represented by the following Formula (C):

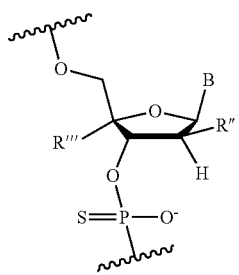

(C)

wherein B is independently in each instance an unmodified or modified nucleobase, and R'' and R''' are each independently in each instance selected from H, F, Cl, OH, OMe, Me, 0-methoxyethoxy, or R' and R''' together form a 2-4 atom bridge to form a conformationally restricted nucleoside. In some embodiments, B is an unmodified or a modified nucleobase selected from the group consisting of 5-methylcytosine, 2,6-diaminopurine, and 5-methyluracil.

The Z domain comprises a sequence of modified nucleotides, where the Z domain is 4-10 nucleotides in length. For example, the Z domain may comprise a sequence of 4, 5, 6, 7, 8, 9, or 10 nucleotides. One or more of these nucleotides is modified (e.g., 1, 2, 3, 4, 5, 6, 7, 8, 9, 10, 11, 12, 13, 14, 15, 16, 17, 18, 19, 20, 21 or 22). For example, in some embodiments, all the nucleotides in the Z domain are modified.

The modified nucleotides of the Z domain include, for example, a modification independently selected from at least one of 2'-F, 2'-F—N3'-P5', 2'-OMe, 2'-OMe-N3'-P5', 2'-OEt-N3'→P5', 2'-O-methoxyethoxy, 2'-O-methoxyethoxy-N3'→P5', conformationally restricted nucleotides, 2'-OH—N3'→P5' thiophosphoramidate and 2'-OH—N3'→P5' phosphoramidate.

In some embodiments, the modified nucleotide may include a nucleoside represented by Formula (A).

The nucleotides of the Z domain are linked through intersubunit linkages, for example, N3'→P5' phosphoramidate, N3'→P5' thiophosphoramidate, thiophosphate or phosphodiester intersubunit linkages. In some embodiments, the Z domain is linked through N3'→P5' phosphoramidate, N3'→P5' thiophosphoramidate, intersubunit linkages, and combinations thereof.

The Z domain of the chimeric oligonucleotide may include a certain arrangement of modified nucleotides. For example, in some embodiments, the Z domain comprises one or more (e.g., 1, 2, 3, 4, 5, 6, 7, 8, 9 or 10, or more) conformationally restricted nucleotides (e.g., BNA, such as, LNA, ENA, each of which may be optionally substituted). In some embodiments, the Z domain comprises alternating conformationally restricted nucleotides, e.g., every other nucleotide is a conformationally restricted nucleotide (e.g., BNA, such as, LNA, ENA, each of which may be optionally substituted). In some embodiments, the Z domain comprises one or more (e.g., 1, 2, 3, 4, 5, 6, 7, 8, 9 or 10, or more) 2'-F and/or 2'-OMe modified nucleotide. For example, some embodiments include where the Z domain comprises alternating 2'-F and 2'-OMe modified nucleotides, or the Z domain comprises alternating 2'-F or 2'-OMe and conformationally restricted nucleotides.

In some embodiments, the modified nucleotides of Formula (VI) or (VI') include 5-methylcytosine nucleobases, but not cytosine. In some embodiments, the modified nucleotides of Formula (VI) or (VI') include 2,6-diaminopurine nucleobases, but not adenine. In some embodiments, the modified nucleotides of Formula (VI) or (VI') include 5-methyluracil nucleobases, but not uracil. In some embodiments, the modified nucleotides of Formula (VI) or (VI') include 2'-OMe and conformationally restricted nucleotides, and are linked through thiophosphate intersubunit linkages, and the modified nucleotides include 5-methylcytosine nucleobases, but not cytosine. In some embodiments, the modified nucleotides of Formula (VI) or (VI') include the 2'-OMe modified nucleotides with 5-methyluracil nucleobases, but not uracil.

In certain embodiments, the chimeric oligonucleotide represented by Formula (VI) or (VI') is arranged according to at least one of the constructs of Table B where at least one intersubunit linkage in the X and Z domains is an NPS linkage.

TABLE B

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 6 | np, nps, ps, PO | A, G, C, T, U, DAP, 5 meC, 5 meU, G clamp, DAP | 2 | ps | A, G, C, T, U | 11 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 2 | ps | A, G, C, T, U | 10 | np, nps, ps, PO | A, G, C, T, U, DAP, 5 meC, 5 meU, G clamp, DAP, |
| 8 | np, nps, ps, PO | A, G, C, T, U, DAP, 5 meC, 5 meU, G clamp, DAP | 2 | ps | A, G, C, T, U | 9 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 9 | np, nps, ps, PO | A, G, C, T, U, DAP, 5 meC, 5 meU, G clam, DAP | 2 | ps | A, G, C, T, U | 8 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp | 2 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 3 | ps | A, G, C, T, U | 10 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 3 | ps | A, G, C, T, U | 9 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 3 | ps | A, G, C, T, U | 8 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 3 | ps | A, G, C, T, U | 7 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 3 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 4 | ps | A, G, C, T, U | 9 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 4 | ps | A, G, C, T, U | 8 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 4 | ps | A, G, C, T, U | 7 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 4 | ps | A, G, C, T, U | 6 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 4 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 5 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 5 | ps | A, G, C, T, U | 9 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 5 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 5 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 5 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 6 | ps | A, G, C, T, U | 8 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 7 | np, nps, ps, PO | A, G, C, T, U, DAP, 5 meC, 5 meU, G clamp, DAP | 6 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 6 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 6 | ps | A, G, C, T, U | 5 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 6 | ps | A, G, C, T, U | 4 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 6 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 6 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 6 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 6 | ps | A, G, C, T, U | 5 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 6 | ps | A, G, C, T, U | 4 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 6 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 6 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 6 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 6 | ps | A, G, C, T, U | 5 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 6 | ps | A, G, C, T, U | 4 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 7 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 7 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 7 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 7 | ps | A, G, C, T, U | 5 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 10 | np, nps, ps, PO | A, G, C, T, U, DAP, 5 meC, 5 meU, G clamp, DAP | 7 | ps | A, G, C, T, U | 4 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 7 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 7 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 7 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 7 | ps | A, G, C, T, U | 5 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 7 | ps | A, G, C, T, U | 4 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 7 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 7 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 7 | ps | A, G, C, T, U | 6 | np, nps, ps, PO | A, G, C, T, U, DAP, 5 meC, 5 meU, G clamp, DAP |
| 9 | np, nps, ps, PO | A, G, C, T, U, DAP, 5 meC, 5 meU, G clamp, DAP | 7 | ps | A, G, C, T, U | 5 | np, nps, ps, PO | A, G, C, T, U, DAP, 5 meC, 5 meU, G clamp, DAP |
| 10 | np, nps, ps, PO | A, G, C, T, U, DAP, 5 meC, 5 meU, G clamp, DAP | 7 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 6 | np, nps, ps, PO | A, G, C, T, U, DAP, 5 meC, 5 meU, G clamp, DAP | 8 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 7 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 8 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 8 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 8 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 8 | ps | A, G, C, T, U | 6 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 8 | np, nps, ps, PO | A, G, C, T, U, DAP, 5 meC, 5 meU, G clamp, DAP | 8 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 5 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 9 | ps | A, G, C, T, U | 9 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 6 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 9 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 9 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 9 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 3 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 10 | ps | A, G, C, T, U | 9 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 3 | np, nps, ps, PO | A, G, C, T, U, DAP, 5 meC, 5 meU, G clamp, DAP | 10 | ps | A, G, C, T, U | 10 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 3 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 9 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 10 | ps | A, G, C, T, U | 10 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 6 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 7 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 10 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 10 | ps | A, G, C, T, U | 8 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |
| 7 | np, nps, ps, PO | A, G, C, T, U, DAP, 5 meC, 5 meU, G clamp, DAP | 10 | ps | A, G, C, T, U | 7 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 6 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 8 | np, nps, ps, PO | A, G, C, T, U, DAP, 5 meC, 5 meU, G clamp, DAP | 10 | ps | A, G, C, T, U | 5 | np, nps, ps, PO | A, G, C, T, U, DAP, 5 meC, 5 meU, G clamp, DAP |
| 8 | np, nps, ps, PO | A, G, C, T, U, DAP, 5 meC, 5 meU, G clamp, DAP | 10 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 3 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 5 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 6 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 7 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 8 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 9 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 11 | ps | A, G, C, T, U | 10 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 3 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 4 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 5 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 6 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 7 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 8 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 9 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 11 | ps | A, G, C, T, U | 10 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 5 | np, nps, ps, PO | A, G, C, T, U, DAP, 5 meC, 5 meU, G clamp, DAP | 11 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 11 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 11 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 11 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 11 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 11 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 11 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 11 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 11 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 11 | ps | A, G, C, T, U | 8 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 2 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 3 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 4 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 5 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 6 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 7 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 8 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 12 | ps | A, G, C, T, U | 9 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 2 | np, nps, ps, PO | A, G, C, T, U, DAP, 5 meC, 5 meU, G clamp, DAP | 12 | ps | A, G, C, T, U | 10 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 2 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 3 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 5 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 6 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 7 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 8 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 9 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 12 | ps | A, G, C, T, U | 10 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 2 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 3 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 4 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 5 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 6 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 7 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 8 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 12 | ps | A, G, C, T, U | 9 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 4 | np, nps, ps, PO | A, G, C, T, U, DAP, 5 meC, 5 meU, G clamp, DAP | 12 | ps | A, G, C, T, U | 10 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 12 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 12 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 12 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 12 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 12 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 12 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 12 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 12 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 12 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 12 | ps | A, G, C, T, U | 8 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 2 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 3 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 4 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 5 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 6 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 7 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 8 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 2 | np, nps, ps, PO | A, G, C, T, U, DAP, 5 meC, 5 meU, G clamp, DAP | 13 | ps | A, G, C, T, U | 9 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 13 | ps | A, G, C, T, U | 10 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 2 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 3 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 5 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 6 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 7 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 8 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 9 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 13 | ps | A, G, C, T, U | 10 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 2 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 3 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 4 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 5 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 6 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 7 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 8 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 4 | np, nps, ps, PO | A, G, C, T, U, DAP, 5 meC, 5 meU, G clamp, DAP | 13 | ps | A, G, C, T, U | 9 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 13 | ps | A, G, C, T, U | 10 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 13 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 13 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 13 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 13 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 13 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 13 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 13 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 13 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 13 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 13 | ps | A, G, C, T, U | 8 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 2 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 3 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 4 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 5 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 6 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 7 | np, nps, ps, PO | A, G, C, T, U, DAP, 5 meC, 5 meU, G clamp, DAP |

TABLE B-continued

| X Domain | | | Y Domain | | | Z Domain | | |
| --- | --- | --- | --- | --- | --- | --- | --- | --- |
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 2 | np, nps, ps, PO | A, G, C, T, U, DAP, 5 meC, 5 meU, G clamp, DAP | 14 | ps | A, G, C, T, U | 8 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 9 | np, nps, ps, PO | A, G, C, T, U, DAP, 5 meC, 5 meU, G clamp, DAP |
| 2 | np, nps, ps, PO | A, G, C, T, U, DAP, 5 meC, 5 meU, G clamp, DAP | 14 | ps | A, G, C, T, U | 10 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 2 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 3 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 4 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 5 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 6 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 7 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 8 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 9 | np, nps, ps, PO | A, G, C, T, U, DAP, 5 meC, 5 meU, G clamp, DAP |
| 3 | np, nps, ps, PO | A, G, C, T, U, DAP, 5 meC, 5 meU, G clamp, DAP | 14 | ps | A, G, C, T, U | 10 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 2 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 3 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 4 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 5 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 6 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 7 | np, nps, ps, PO | A, G, C, T, U, DAP, 5 meC, 5 meU, G clamp, DAP |

TABLE B-continued

| X Domain | | | Y Domain | | | Z Domain | | |
|---|---|---|---|---|---|---|---|---|
| Number of Nucs | Intersubunit Linkages | Nucleobase Substitutions | Number of Nucs | Intersubunit Linkages | Nucleobase | Number of Nucs | Intersubunit Linkages | Nucleobase Substitutions |
| 4 | np, nps, ps, PO | A, G, C, T, U, DAP, 5 meC, 5 meU, G clamp, DAP | 14 | ps | A, G, C, T, U | 8 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 9 | np, nps, ps, PO | A, G, C, T, U, DAP, 5 meC, 5 meU, G clamp, DAP |
| 4 | np, nps, ps, PO | A, G, C, T, U, DAP, 5 meC, 5 meU, G clamp, DAP | 14 | ps | A, G, C, T, U | 10 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 14 | ps | A, G, C, T, U | 4 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 14 | ps | A, G, C, T, U | 5 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 14 | ps | A, G, C, T, U | 6 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 14 | ps | A, G, C, T, U | 7 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 14 | ps | A, G, C, T, U | 8 | np, nps, ps, PO | A, G, C, T, U, DAP, 5 meC, 5 meU, G clamp, DAP |
| 5 | np, nps, ps, PO | A, G, C, T, U, DAP, 5 meC, 5 meU, G clamp, DAP | 14 | ps | A, G, C, T, U | 9 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 14 | ps | A, G, C, T, U | 5 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 14 | ps | A, G, C, T, U | 6 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 14 | ps | A, G, C, T, U | 7 | np, nps, ps, PO | A, G, C, T, U, DAP, 5 meC, 5 meU, G clamp, DAP |
| 6 | np, nps, ps, PO | A, G, C, T, U, DAP, 5 meC, 5 meU, G clamp, DAP | 14 | ps | A, G, C, T, U | 8 | np, nps, ps, PO | A, G, C, T, U, DAP, 5 meC, 5 meU, G clamp, DAP |

In Table B, the nucleotides in each of the X and Z domains can be one or more of the numbered nucleotides in Table A. In some embodiments, the chimeric oligonucleotides of Table B include at least 1, 2, 3, 4, 5, 6, 7, 8 or more of the modified nucleotides in Table A. In some embodiments, all of the nucleotides of X and/or Z are modified nucleotides. In some embodiments, the nucleotides in Table B are selected from certain modified nucleotides listed in Table A such as nucleotide numbers 1-4 or 5-8 or 9-12 or 13-16 or 17-20 or 21-24 or 25-28 or 29-30 or 31-32 or 33. In some embodiments the nucleotides in Table B are selected from certain modified nucleotides listed in Table A such as nucleotide numbers 9-12 and 21-28, or 9-12 and 21-24, or 1-4 and 21-28, or 1-4 and 21-24, or 5-8 and 21-28, or 5-8 and 21-24. In some embodiments, the nucleotides in Table B are selected from one or two or three modified nucleotides listed in Table A such as nucleotide numbers 29-31 or 31-32 or 33. In some embodiments, the nucleotides in Table B are selected from certain modified nucleotides listed in Table A such as nucleotide numbers 29 or 31 or 33. The nucleotides in the Y domain of Table B can include nucleotides of Formula B.

In some embodiments, the oligonucleotide of Table B is conjugated at the 5' and/or 3' end to a ligand-targeting group or a pharmacophore.

In some embodiments, the nucleotide compounds of the present disclosure include one of the following sequence: 5'-GCAGAGGTGAAGCGAAGUGC-3' (SEQ ID NO: 159), or other sequences in Table H (below).

In some embodiments, the oligonucleotide comprises a sequence in Table C. In table C, X is independently in each instance a natural or an unmodified nucleobase or a modified nucleobase. In some embodiments, each X is independently selected from A, C, G, U, T, 2,6-diaminopurine, a 5-Me pyrimidine (e.g., 5-methylcytosine, 5-methyluracil), and a g-clamp.

TABLE C

| Modified Sequence (5'-3') |
|---|
| 5'-mXpsmXpsmXpsmXpsmXpsmXpsXpsXpsXpsXpsXpsmXpsmXpsmXpsmXpsmXpsmXpsmX-3' |
| 5'-mXpsmXpsmXpsmXpsmXpsmXpsXpsXpsXpsXpsXpsmXpsmXpsmXpsmXpsmXpsmXps-Chol-3' |
| 5'-mXpsmXpsmXpsmXpsmXpsmXpsXpsXpsXpsXpsXpsmXpsmXpsmXpsmXpsmXpsmXpsmX-GalNAc-3' |
| 5'-mXpsmXpsmXpsmXpsmXpsmXpsXpsXpsXpsXpsXpsXpsXpsmXpsmXpsmXpsmXpsmXpsmX-3' |
| 5'-mXpsmXpsmXpsmXpsmXpsmXpsXpsXpsXpsXpsXpsXpsXpsmXpsmXpsmXpsmXpsmXpsmX-Chol-3' |
| 5'-mXpsmXpsmXpsmXpsmXpsmXpsXpsXpsXpsXpsXpsXpsXpsmXpsmXpsmXpsmXpsmXpsmX-GalNAc-3' |
| 5'-mXpsmXpsmXpsmXpsmXpsXpsXpsXpsXpsXpsXpsXpsXpsXpsmXpsmXpsmXpsmXpsmXpsmX |
| 5'-mXpsmXpsmXpsmXpsmXpsXpsXpsXpsXpsXpsXpsXpsXpsXpsmXpsmXpsmXpsmXpsmXpsmX-Chol-3' |
| 5'-mXpsmXpsmXpsmXpsmXpsXpsXpsXpsXpsXpsXpsXpsXpsXpsmXpsmXpsmXpsmXpsmXpsmX-GalNAc-3' |
| 5'-XnpsXnpsXnpsXnpsXnpsXpsXpsXpsXpsXpsXpsXpsXnpsXnpsXnpsXnps-3-NH$_2$-X-3' |
| 5'-XnpsXnpsXnpsXnpsXnpsXpsXpsXpsXpsXpsXpsXnpsXnpsXnpsXnpsXnps-3-NH$_2$-X-3 |
| 5'-XnpsXnpsXnpsXnpsXnpsXnpsXpsXpsXpsXpsXpsXpsXnpsXnpsXnpsXnpsXnps-3-NH$_2$-X-3' |
| 5'-XnpsXnpsXnpsXnpsXnpsXpsXpsXpsXpsXpsXnpsXnpsXnpsXnps-3-NH$_2$-X-3' |
| 5'-XnpsXnpsXnpsXnpsXnpsXpsXpsXpsXpsXpsXnpsXnpsXnpsXnpsXnps-3-NH$_2$-X-3' |
| 5'-XnpsXnpsXnpsXnpsXnpsXnpsXnpsXnpsXpsXpsXnpsXnpsXnpsXnpsXnpsXnpsXnpsXnps-3 NH$_2$-X-3' |
| 5'-XnpsXnpsXnpsXnpsXnpsXnpsXnpsXpsXpsXnpsXnpsXnpsXnpsXnpsXnpsXnpsXnpsXnps-3 NH$_2$-X-3' |
| 5'-XnpsXnpsXnpsXnpsXnpsXnpsXpsXpsXnpsXnpsXnpsXnpsXnpsXnpsXnpsXnpsXnps-3 NH$_2$-X-3' |
| 5'-XnpsXnpsXnpsXnpsXnpsXnpsXnpsXnpsXnpsXpsXpsXnpsXnpsXnpsXnpsXnpsXnpsXnps-3 NH$_2$-X-3' |
| 5'-XnpsXnpsXnpsXnpsXnpsXnpsXnpsXnpsXnpsXpsXpsXnpsXnpsXnpsXnpsXnpsXnpsXnps-3 NH$_2$-X-3' |
| 5'-XnpsXnpsXnpsXnpsXnpsXnpsXpsXpsXpsXnpsXnpsXnpsXnpsXnpsXnpsXnpsXnpsXnps-3 NH$_2$-X-3' |
| 5'-XnpsXnpsXnpsXnpsXnpsXnpsXnpsXpsXpsXpsXnpsXnpsXnpsXnpsXnpsXnpsXnpsXnps-3 NH$_2$-X-3' |
| 5'-XnpsXnpsXnpsXnpsXnpsXnpsXnpsXnpsXpsXpsXpsXnpsXnpsXnpsXnpsXnpsXnpsXnps-3 NH$_2$-X-3' |
| 5'-XnpsXnpsXnpsXnpsXnpsXnpsXnpsXnpsXnpsXpsXpsXpsXnpsXnpsXnpsXnpsXnpsXnps-3 NH$_2$-X-3' |
| 5'-XnpsXnpsXnpsXnpsXnpsXnpsXnpsXnpsXpsXpsXpsXpsXnpsXnpsXnpsXnpsXnpsXnps-3 NH$_2$-X-3' |
| 5'-XnpsXnpsXnpsXnpsXnpsXnpsXnpsXpsXpsXpsXpsXpsXnpsXnpsXnpsXnpsXnpsXnps-3 NH$_2$-X-3' |
| 5'-XnpsXnpsXnpsXnpsXnpsXnpsXpsXpsXpsXpsXpsXpsXnpsXnpsXnpsXnpsXnpsXnps-3 NH$_2$-X-3' |
| 5'-XnpsXnpsXnpsXnpsXnpsXpsXpsXpsXpsXpsXpsXpsXnpsXnpsXnpsXnpsXnpsXnps-3-NH$_2$-X-3' |
| 5'-mXpsmXpsmXpsmXpsmXpsXpsXpsXpsXpsXpsXpsXpsXpsXpsXpsmXpsmXpsmXpsmXpsmX-3' |
| 5'-mXpsmXpsmXpsmXpsmXpsXpsXpsXpsXpsXpsXpsXpsXpsXpsXpsmXpsmXpsmXpsmeXps mX-GalNAc-3' |

TABLE C-continued

| Modified Sequence (5'-3') |
|---|

5'-mXpsmXpsmXpsmXpsmXpsXpsXpsXpsXpsXpsXpsXpsXpsXpsXpsmXpsmXpsmXpsmXpsmXpoGalNAc-3'

5'-mXpsmXpsmXpsmXmXpsXpsXpsXpsXpsXpsXpsXpsXpsXpsXpsmXpsmXpsmXpsmXpsmXpoGalNAc-3'

5'-mXpsmXpsmXpsmXpsmXpsXpsXpsXpsXpsXpsXpsXpsXpsXpsXpsmXpsmXpsmXpsmXpsmXpoGalNAc-3'

5'-mXpsmXpsmXpsmXpsmXpsXpsXpsXpsXpsXpsXpsXpsXpsXpsXpsmXpsmXpsmXpsmXpsmXpoGalNAc-3'

5'-fXnpsfXnpsfXnpsfXnpsfXnpsfXnpsXpsXpsXpsXpsXpsfXnpsfXnpsfXnpsfXnpsfXnpsfXnpsfXnps-3-NH$_2$-fX-3'

5'-fXnpsfXnpsfXnpsfXnpsfXnpsXpsXpsXpsXpsXpsXpsXpsfXnpsfXnpsfXnpsfXnpsfXnpsfXnps-3-NH$_2$-fX-3'

5'-fXnpsfXnpsfXnpsfXnpsfXnpsfXnpsXpsXpsXpsXpsXpsXpsXpsfXnpsfXnpsfXnpsfXnps-3-NH$_2$-fX-3'

5'-XnpXnpXnpXnpXnpXnpXpsXpsXpsXpsXpsXpsXnpXnpXnpXnpXnpXnpXnp-3 NH$_2$-X-3'

5'-XnpsfXnpsfXnpsXnpsfXnpsXnpXpsXpsXpsXpsXpsfXnpsXnpsfXnpsfXnpsXnpsfXnpsXnps-3 NH$_2$-fX-3'

5'-XnpfXnpfXnpXnpfXnpXnpXpsXpsXpsXpsXpsXpsfXnpXnpfXnpfXnpfXnpXnpfXnpXnp-3 NH$_2$-fX-3'

5'-XnpsXfXnpsXfXnpsXnspXfXnpsXnpsXpsXpsXpsXpsXpsXpsXfXnpsXnpsXfXnpsXfXnpsXnpsXfXnpsXnpsXfX-3'

5'-XnpXfXnpXfXnpXnpXfXnpXnpXpsXpsXpsXpsXpsXpsXfXnpXnpXfXnpXfXnpXnpXfXnpXnpXfX-3'

5'-XnpXfXnpXfXnpXnpXfXnpXnpXpsXpsXpsXpsXpsXpsXnpXfXnpXfXnpXnpXfXnpXnpXfX-3'

5-mXpsmXpsmXpsmXpsmXpsmXpsXpsXpsXpsXpsXpsXpsXpsXpsmXpsmXpsmXpsmXpsmXpsmX-GalNAc-3

5'-mXpsmXpsmXpsmXpsmXpsmXpsXpsXpsXpsXpsXpsXpsXpsXpsmXpsmXpsmXpsmXpsmXpsmX 3'

5'-mXpsmXpsmXpsmXpsmXpsmXpsmXpsXpsXpsXpsXpsXpsXpsmXpsmXpsmXpsmXpsmXpsmX 3'

5'-mXpsmXpsmXpsmXpsmXpsmXpsXpsXpsXpsXpsXpsXpsXpsXpsmXpsmXpsmXpsmXpsmeXpsmX 3'

5'-mXpsmXpsmXpsmXpsmXpsmXpsmXpsXpsXpsXpsXpsXpsXpsXpsmXpsmXpsmXpsmXpsmeXpsmX 3'

5'-mXpsmXpsmXpsmXpsmXpsmXpsXpsXpsXpsXpsXpsXpsXpsXpsmXpsmXpsmXpsmXpsmX 3'

5'-mXpsmXpsmXpsmXmXpsmXpsXpsXpsXpsXpsXpsXpsXpsmXpsmXpsmXpsmXpsmXpsmX 3'

5'-mXpsmXpsmXpsmXmXpsmXpsmXpsXpsXpsXpsXpsXpsXpsXpsmXpsmXpsmXpsmXpsmXpsmX 3'

5'-GalNAc-NHC6-psmXpsm5meXpsm5meXpsmXpsm5meXpsXpsXpsXpsXpsXpsXpsXpsXpsXps5meXpsmXpsmXpsm5meXpsmX 3'

5'-GalNAc-NHC6-psm5meXpsmXpsmXpsmXpsmXpsXpsXpsXpsXps5meXps5meXpsXps5meXpsXpsmXpsmXpsmXpsmX 3'

5'-GalNAc-NHC6-psmXpsmXpsmXpsmXpsXpsXpsXpsXps5meXpsXps5meXps5meXps5meXpsm5meXpsmXpsmXpsmX 3'

5' GalNAc-NHC6-psmXpsmXpsmXpsXpsXps5meXpsXps5meXps5meXps5meXps5meXpsXpsXpsmXpsmXpsm5meXpsmX 3'

5' GalNAc-NHC6-psmXpsmXpsm5meXpsmXpsXpsXpsXpsXpsXpsXpsXps5meXpsXpsmXpsmXpsmXpsmXpsmX 3' mXpsmXpsmXpsmXpsmXpsmXpsmXpsXpsXpsXpsXpsXpsXpsXpsmXpsmXpsmXpsmXpsmXpsmX

TABLE C-continued

| Modified Sequence (5'-3') |
|---| mXpsmXpsmXpsmXpsmXpsmXps<u>XpsXpsXpsXpsXpsXpsXpsXps</u>mXpsmXpsmXpsmXpsmXpsmX mXpsmXpsmXpsmXpsmXpsmXps<u>XpsXpsXpsXpsXpsXpsXps</u>mXpsmXpsmXpsmXpsmXpsmX mXpsmXpsmXpsmXpsmXpsmXps<u>XpsXpsXpsXpsXpsXps</u>mXpsmXpsmXpsmXpsmXpsmX/GalNAc/ mXpsmXpsmXpsmXpsmXpsmXps<u>XpsXpsXpsXpsXpsXpsXps</u>mXpsmXpsmXpsmXpsmXpsmX/GalNAc/ mXpsmXpsmXpsmXpsmXpsmXps<u>XpsXpsXpsXpsXpsXps</u>mXpsmXpsmXpsmXpsmXpsmX/3CholTEG/ mXpsmXpsmXpsmXpsmXpsmXps<u>XpsXpsXpsXpsXpsXpsXps</u>mXpsmXpsmXpsmXpsmXpsmX/3CholTEG/ mXpsmXpsmXpsmXpsmXpsmXps<u>XpsXpsXpsXpsXpsXpsXpsXps</u>mXpsmXpsmXpsmXpsmXpsmX/3CholTEG/

5'-mXps5mmXpsmXpsmXpsmXpsmXpsXpsXpsXpsXpsXpsXp5mmXpsmXpsmXpsmXpsmXpsmXpsm5meX-3

5'-mXps5mmXpsmXpsmXpsmXpsmXpsXpsXpsXpsXpsXpsXps5mmXpsmXpsmXpsmXpsmXpsmXps5mmX-CholesXerol-3'

5'-mXps5mmXpsmXpsmXpsmXpsmXpsXpsXpsXpsXpsXpsXp5mmXpsmXpsmXpsmXpsmXpsmXps5mmX-TEG-CholesXerol-3'

5'-mXps5mmXpsmXpsmXpsmXpsmXpsXpsXpsXpsXpsXpsXps5mmXpsmXpsmXpsmXpsmXpsmXps5mmX-Tocopherol-3'

5'-mXps5mmXpsmXpsmXpsmXpsmXpsXpsXpsXpsXpsXpsXps5mmXpsmXpsmXpsmXpsmXpsmXps5mmX-TEG-Tocopherol-3'

5'-mXps5mmXpsmXpsmXpsmXpsmXpsXpsXpsXpsXpsXpsXps5mmXpsmXpsmXpsmXpsmXpsmXps5mmX-GalNAc-3'

5'-mXpsm5meXpsmXpsmXpsmXpsmXpsXpsXpsXpsXpsXpsXps5meXpsmXpsmXpsmXpsmXpsmXpsm5meX-3'

5'-mXpsm5meXpsmXpsmXpsmXpsmXpsXpsXpsXpsXpsXpsXps5meXpsmXpsmXpsmXpsmXpsmXpsm5meX-po-Chol-3'

5'-mXpsm5meXpsmXpsmXpsmXpsmXpsXpsXpsXpsXpsXpsXps5meXpsmXpsmXpsmXpsmXpsmXpsm5meX-po-Tocopherol-3'

5'-mXpsm5meXpsmXpsmXpsmXpsmXpsXpsXpsXpsXpsXpsXps5meXpsmXpsmXpsmXpsmXpsmXpsm5meX-po-GalNAc-3'

5'-mXpsm5meXpsmXpsmXpsmXpsmXpsXpsXpsXpsXpsXpsXps5meXpsXpsmXpsmXpsmXpsmXpsmXpsm5meX-3'

5'-mXpsm5meXpsmXpsmXpsmXpsmXpsXpsXpsXpsXpsXpsXps5meXpsXpsmXpsmXpsmXpsmXpsmXpsm5meX-po-Chol-3'

5'-mXpsm5meXpsmXpsmXpsmXpsmXpsXpsXpsXpsXpsXpsXps5meXpsXpsmXpsmXpsmXpsmXpsmXpsm5meX-po-Tocopherol-3'

5'-mXpsm5meXpsmXpsmXpsmXpsmXpsXpsXpsXpsXpsXpsXps5meXpsXpsmXpsmXpsmXpsmXpsmXpsm5meX-po-GalNAc-3'

5-mXps2-4-OXH$_2$-XpsmXps 2-4-OXH$_2$-XpsmXps2-4-OXH$_2$-XpsXpsXpsXpsXpsXpsXpsmXpsmXps2-4-OXH$_2$-XpsmXps2-4-OXH$_2$-XpsmXps2-4-OXH$_2$-Xps mX-3

5-mXps2-4-OXH$_2$-XpsmXps 2-4-OXH$_2$-XpsmXps2-4-OXH$_2$-XpsXpsXpsXpsXpsXpsXpsmXpsmXps2-4-OXH$_2$-XpsmXps2-4-OXH$_2$-XpsmXps2-4-OXH$_2$-Xps mX-Chol-3

5-mXps2-4-OXH$_2$-XpsmXps 2-4-OXH$_2$-XpsmXps2-4-OXH$_2$-XpsXpsXpsXpsXpsXpsXpsmXpsmXps2-4-OXH$_2$-XpsmXps2-4-OXH$_2$-XpsmXps2-4-OXH$_2$-Xps mX-XoXo-3

5-mXps2-4-OXH$_2$-XpsmXps 2-4-OXH$_2$-XpsmXps2-4-OXH$_2$-XpsXpsXpsXpsXpsXpsXpsmXpsmXps2-4-OXH$_2$-XpsmXps2-4-OXH$_2$-XpsmXps2-4-OXH$_2$-Xps mX-GalNAc-3

5-mXps2-4-OXH$_2$-XpsmXps 2-4-OXH$_2$-XpsmXps2-4-OXH$_2$-XpsXpsXpsXpsXpsXpsXpsmXpsmXps2-4-OXH$_2$-XpsmXps2-4-OXH$_2$-XpsmXps2-4-OXH$_2$-Xps mX-3

5-mXps2-4-OXH$_2$-XpsmXps 2-4-OXH$_2$-XpsmXps2-4-OXH$_2$-XpsXpsXpsXpsXpsXpsXpsmXpsmXps2-4-OXH$_2$-XpsmXps2-4-OXH$_2$-XpsmXps2-4-OXH$_2$-Xps mX-Chol-3

5-mXps2-4-OXH$_2$-XpsmXps2-4-OXH$_2$-XpsmXps2-4-OXH$_2$-XpsmXps2-4-OXH$_2$-XpsXpsXpsXpsXpsXpsXpsmXps2-4-OXH$_2$-XpsmXps2-4-OXH$_2$-XpsmXps2-4-OXH$_2$-Xps mX-XoXo-3

TABLE C-continued

Modified Sequence (5'-3')

5-mXps2-4-OXH$_2$-XpsmXps 2-4-OXH$_2$-XpsmXps2-4-OXH$_2$-XpsXpsXpsXpsXpsXpsXpsXpsmXps2-4-OXH$_2$-XpsmXps2-4-OXH$_2$-XpsmXps2-4-OXH2-Xps mX-GalNAc-3

5-mXps2-4-OXH$_2$-XpsmXps2-4-OXH$_2$-XpsmXps2-4-OXH$_2$-XpsXpsXpsXpsXpsXpsXpsXpsmXps2-4-OXH$_2$-XpsmXps2-4-OXH$_2$-XpsmXps2-4-OXH$_2$-XpsmX-3

5-dXnpsXnpsXnpsXnpsXnps<u>XpsXpsXpsXpsXpsXpsXpsXpsXpsXps</u>XnpsXnpsXnpsXnpsXn-3

5-dXnpsfXnpsXnpsfXnpsfXnps<u>XpsXpsXpsXpsXpsXpsXpsXpsXpsXps</u>fXnpsfXnpsfXnpsfXnpsfXn 3'

5-fXnpsXnpsfXnpsfXnpsfXnpsfXnps<u>XpsXpsXpsXpsXpsXps</u>XnpsfXnpsfXnpsfXnpsfXnpsfXnpsXn-3'

5-fXnpsXnpsfXnpsfXnpsfXnpsfXnps<u>XpsXpsXpsXpsXpsXpsXps</u>fXnpsfXnpsfXnpsfXnpsXn-3'

5'-dXnpmXnpmXnpmXnpmXnpmXnpXpsXpsXpsXpsXpsXpsmXnpmXnpmXnpmXnpmXnpmXnpmXnp-3'

5'-dXnpmXnpmXnpmXnpmXnpmXnpXpsXpsXpsXpsXpsXpsmXnpmXnpmXnpmXnpmXnpmXnp-3'

5'-dXnpmXnpmXnpmXnpmXnpmXnpXpsXpsXpsXpsXpsXpsmXnpsmXnpmXnpmXnpmXnp-3'

5'-dXnpmXnpmXnpmXnpmXnpXpsXpsXpsXpsXpsXpsXpsmXnpmXnpmXnpmXnpmXnpmXnp-3'

5'-dXnpmXnpmXnpmXnpmXnpXpsXpsXpsXpsXpsXpsXpsXpsmXnpmXnpmXnpmXnpmXnp-3, mXnpsmoeXnpsmoeXnpsmXnpsmoeXnpsXpsXpsXpsXpsXpsXpsXpsXpsXpsmoeXnpsmXnpsmoeXnpsmXnpsmoeXnp-C6-NH-GalNAc 6 moeXpsmoeXpsmoeXpsmoeXpsmoeXpsXpsXpsXpsXpsXpsXpsXpsXpsXpsmoeXpsmoeXpsmoeXpsmoeXpsmoeX-po-GalNAc2 mXnpsmoeXnpsmoeXnpsmXnpsmoeXnpsXpsXpsXpsXpsXpsXpsXpsXpsXpsmoeXnpsmXnpsmoeXnpsmXnpsmoeXnpo-C6-NH-GalNAc-6

GalNAc-2-pofXnpsfXnpsfXnpsfXnpsfXnpsXpsXpsXpsXpsXpsXpsXpsXpsXpsfXnpsfXnpsfXnpsfXnpsfXn GalNAc2-moeXnpsmoeXnpsmoeXnpsmoeXnpsmoeXnpsXpsXpsXpsXpsXpsXpsXpsXpsXpsmoeXnpsmoeXnpsmoeXnpsmoeXnpsmoeXn moeXpsmoeXpsmoeXpsmoeXpsmoeXpsXpsXpsXpsXpsXpsXpsXpsXpsXpsmoeXpsmoeXpsmoeXpsmoeXpsmoeX-GalNAc2

GalNAc2-moeXnpsmoeXnpsmoeXnpsmoeXnpsmoeXnpsXpsXpsXpsXpsXpsXpsXpsXpsXpsmoeXnpsmoeXnpsmoeXnpsmoeXn GalNac-moeXnpsmoeXnpsmoeXnpsmoeXnpsmoeXnpsXpsXpsXpsXpsXpsXpsXpsXpsXpsmoeXnpsmoeXnpsmoeXnpsmoeXn GalNAc2-mXnpsmXnpsmXnpsmXnpsXpsXpsXpsXpsXpsXpsXpsXpsXpsmoeXnpsmoeXnpsmoeXnpsmoeXnpsmoeXn GaLNac6-NH-C6-moeXpsmoeXpsmoeXpsmoeXpsmoeXpsXpsXpsXpsXpsXpsXpsXpsXpsXpsmoeXpsmoeXpsmoeXpsmoeX GalNAc2-mXnpsmXnpsmXnpsmXnpsmXnpsXpsXpsXpsXpsXpsXpsXpsXpsXpsmXnpsmXnpsmXnpsmXnpsmXn GalNAc2-etoXnpsetoXnpsetoXnpsetoXnpsetoXnpsXpsXpsXpsXpsXpsXpsXpsXpsXpsetoXnpsetoXnpsetoXnpsetoXnpsetoXn GalNAc2-moeXnpsmoeXnpsmoeXnpsmoeXnpsmoeXnpsXpsXpsXpsXpsXpsXpsXpsXpsXpsmXnpsmXnpsmXnpsmXnpsmXn moeXpsmoemXpsmoeXpsmoeXpsmoeXpsXpsXpsXpsXpsXpsXps5mXpsXpsXpsmoeXpsmoeXpsmoeXpsmoeXpsmoemX moeXnpsmoeXnpsmoeXnpsmoeXnpsmoeXnpsXpsXpsXpsXpsXpsXpsXpsXpsXpsmoeXnpsmoeXnpsmoeXnpsmoeXnpsmoeXn TABLE C-continued Modified Sequence (5'-3')

mXps5mmXpsmXpsmXpsmXpsXpsXpsXpsXpsXpsXpsXps5mXpsXpsXpsmXpsmXpsmXpsmXps5mmX mXnpsmXnpsmXnpsmXnps
mXnpsXpsXpsXpsXpsXpsXpsXpsXpsmXnpsmXnpsmXnpsmXnpsmXn GalNAc2-moeXnpsmoeXnpsmoeXnps moeXnpsmoeXnpsXps XpsXpsXps XpsXpsXps
moeXnpsmoeXnpsmoeXnps moeXnpsmoeXn GalNAc6-NH-C6-
moeXpsmoeXpsmoeXpsmoeXpsmoeXpsXpsXpsXpsXpsXpsXpsXpsXpsXpsmoeXpsmoeXpsmoeXp
smoeXpsmoeX 5'moeXpsmoeXpsmoeXpsmoeXpsmoeXpsXpsXpsXpsXpsXpsXpsXpsXpsXpsmoeXpsmoeXpsmoe
XpsmoeXpsmoeX-GalNAc2

GalNAc2-
mXnpsmXnpsmXnpsmXnpsmXnpsXpsXpsXpsXpsXpsXpsXpsXpsXpsmXnpsmXnpsmXnpsmXnps
mXn' mXpsmXpsmXpsmXpsXpsXpsXpsXpsXpsXpsXpsXpsXpsmXpsmXpsmXpsmXpsmX-
GalNAc

GalNAc2-moeXnpsmoeXnpsmoeXnps moeXnpsmoeXnpsXpsXpsXpsXpsXpsXps
XpsXpsXpsmoeXnpsmoeXnpsmoeXnps moeXnpsmoeXn moeXnpsmoeXnpsmoeXnpsmoeXnpsmoeXnpsXpsXpsXpsXpsXpsXpsXpsXpsXpsmoeXnpsmoeXn
psmoeXnpsmoeXnpsmoeXnp-C6-NH-GalNAc6

GalNAc2-
moeXnpsmoeXnpsmoeXnpsmoeXnpsmoeXnpsXpsXpsXpsXpsXpsXpsXpsXpsXpsmoeXnpsmoeXn
psmoeXnps moeXnpsmoeXn GalNAc-XnpsXnpsXnpsXnpsXnpsXps XpsXpsXpsXpsXpsXpsXpsXpsXnpsXnpsXnpsXnpsXn GalNAc-
mXnpsmXnpsmXnpsmXnpsmXnpsXpsXpsXpsXpsXpsXpsXpsXpsXpsmXnpsmXnpsmXnpsmXnps
mXn GalNAc-fXnpsfXnpsfXnpsfXnpsfXnpsXpsXpsXpsXpsXpsXpsXpsXpsXpsfXnpsfXnpsfXnpsfXnps-
3nh2-fX GalNAc-
afXnpsafXnpsafXnpsafXnpsafXnpsXpsXpsXpsXpsXpsXpsXpsXpsXpsafXnpsafXnpsafXnpsaf
Xn GalNAc-dXnpsXnpsXnpsXnpsXnpsXpsXpsXpsXpsXpsXpsXpsXpsXpsXnpsXnpsXnpsXnps-3nh2-
X GalNAc-mXnpsmXnpsmXnpsmXnpsmXnpsXpsXpsXpsXpsXpsXpsXpsXps
XpsmXnpsmXnpsmXnpsmXnpsmXn GalNAc-fXnpsfXnpsfXnpsfXnpsfXnpsXpsXpsXpsXpsXpsXpsXpsXpsXpsfXnpsfXnpsfXnpsfXnps-
3nh2-fX GalNAc-
mXnpsmXnpsmXnpsmXnpsmXnpsXpsXpsXpsXpsXps5MeXpsXpsXpsXpsXpsmXnpsmXnpsmXnpsm
XnpsmXnpsmXn GalNAc-
moeXnpsmoeXnpsmoeXnpsmoeXnpsmoeXnpsXpsXpsXpsXpsXps5MeXpsXpsXpsXpsXpsmoeXnpsmoe
XnpsmoeXnpsmoeXnpsmoeXnpsmoeXn moeXpsmoeXpsmoeXpsmoeXpsmoeXpsXpsXpsXpsXpsXpsXpsXpsXpsXpsmoeXpsmoeXpsmoeXpsmoe
XpsmoeX moeXnpsmoeXnpsmoeXnpsmoeXnpsmoeXnpsXpsXpsXpsXpsXpsXpsXpsXpsXpsmoeXnpsmoeXnpsmoe
XnpsmoeXnpsmoeXn fXnpsfXnpsfXnpsfXnpsfXnpsXpsXpsXpsXpsXpsXpsXpsXpsXpsfXnpsfXnpsfXnpsfXnpsfX-C6-
NH-GalNAc6 fXnpsfXnpsfXnpsfXnpsfXnpsXpsXpsXpsXpsXpsXpsXpsXpsXpsfXnpsfXnpsfXnpsfXnpsfXnp-C6-
NH-GalNAc6 mXnpsmXnpsmXnpsmXnpsmXnpsXpsXpsXpsXpsXpsXpsXpsXpsXps mXnpsmXnpsmXnps
mXnpsmXnp-C6-NH-GalNAc6

TABLE C-continued

Modified Sequence (5'-3')

mXnpsmXnpsmXnpsmXnpsmXnpsXpXpsXpsXpsXpsXpsXpsXpsXpsXps
mXnpsmXnpsmXnpsmXnpsmX-C6-NH-GalNAc6 moeXnpsmoeXnpsmoeXnpsmoeXnpsmoeXnpsXps XpsXpsXps XpsXpsXps XpsXpsXpsmoe
XnpsmoeXnpsmoeXnpsmoeXnpsmoeXnp-C6-NH-GalNAc6 moeXnpsmoeXnpsmoeXnpsmoeXnpsmoeXnpsmoeXnpsXpsXpsXpsXpsXpsXpsXpsXpsXpsXpsmoeXnpsmoeXnpsmoe
XnpsmoeXnpsmoeX-C6-NH-GalNAc6

GalNAc2-moeXnpsmoeXnpsmoeXnpsmoeXnpsmoeXnpsXpsXpsXpsXps XpsXpsXps
XpsXpsXpsmoeXnpsmoeXnpsmoeXnpsmoeXn GalNAc2-etoXnpsetoXnpsetoXnps etoXnpsetoXnpsXpsXpsXpsXpsXpsXpsXps XpsXpsXps
etoXnpsetoXnpsetoXnps etoXnpsetoXn mXnpsmXnps2-4-OCH$_2$XnpsmXnpsmXnpsXpsXpsXpsXpsXpsXpsXpsXpsXpsXps2-4-
OCH$_2$XnpsmXnpsmXnpsmXnps3-NH$_2$mX mXnpsmXnps2-4-OCH$_2$CH$_2$XnpsmXnpsmXnpsXpsXpsXpsXpsXpsXpsXpsXpsXpsXps2-4-
OCH$_2$CH$_2$XnpsmXnpsmXnpsmXnps3-NH$_2$mX mXnpsmXnps2-4-OCH$_2$CH$_2$XnpsmXnps2-4OCH2CH2XnpsXpsXpsXpsXpsXpsXpsXpsXpsXpsXps2-4-
OCH$_2$CH$_2$XnpsmXnpsmXnpsmXnps3-NH$_2$mX mXnpsmXnpsmXnpsmXnps2-4-OCH$_2$CH$_2$XnpsXpsXpsXpsXpsXpsXpsXpsXpsXps2-4-
OCH$_2$CH$_2$XnpsmXnpsmXnpsmXnps3-NH$_2$mX 5-mXnpsmCnpsmXnpsmXnpsmXnpsmXnps2-4-OCH$_2$CH$_2$XnpsXpsXpsXpsXpsXpsXpsXpsXps
mXnpsmXnpsmXnps2-4-OCH$_2$CH$_2$XnpsmXnpsmXnps3-NH$_2$mX-3 mXnpsmXnpsmXnpsmCnpsmXnps2-4-OCH$_2$CH$_2$XnpsXpsXpsXpsXpsXpsXpsXpsXps2-4-
OCH$_2$CH$_2$XnpsmXnpsmXnps2-4-OCH$_2$ CH$_2$XnpsmXnpsmXnps3-NH$_2$mX mXnpsmXnpsmXnpsmXnpsmXnps2-4-OCH$_2$CH$_2$XnpsXpsXpsXpsXpsXpsXpsXpsXps2-4-OCH$_2$
CH$_2$XnpsmXnps2-4-OCH$_2$CH$_2$XnpsmXnpsmXnpsmXnps3-NH$_2$mX 2-
4OCH$_2$CH$_2$XnpsmXnpsmXnpsmXnpsmXnpsXpsXpsXpsXpsXpsXpsXpsXpsXpsXpsmXnpsmXnpsmXn
ps2-4OCH$_2$CH$_2$Xnps3-NH$_2$mX 2-4 OCH$_2$CH$_2$XnpsmXnpsmXnps2-
4OCH$_2$CH$_2$XnpsmXnpsXpsXpsXpsXpsXpsXpsXpsXpsXpsXpsmXnps2-4 OCH2CH2XnpsmXnps2-
4OCH$_2$CH$_2$Xnps3-NH$_2$mX 2-4OCH$_2$CH$_2$XnpsmXnps2-4-
OCH$_2$CH$_2$XnpsmXnpsmXnpsXpsXpsXpsXpsXpsXpsXpsXpsXpsXpsmXnpsmXnpsmXnpsmXnps3-
NH$_2$mX 2-4OCH$_2$CH$_2$XnpsmXnpsmXnpsmXnpsmXnps2-4-
OCH$_2$CH$_2$XnpsXpsXpsXpsXpsXpsXpsXpsXpsXpsXpsmXnpsmXnpsmXnps2-4-OCH$_2$CH$_2$XnpsmXnpsm2-
4OCH$_2$CH$_2$Xnps3-NH$_2$mX 2-4 OCH$_2$CH$_2$XnpsmXnpsmXnpsmXnpsmXnpsmXnpsXpsXpsXpsXpsXpsXpsXpsXps
mXnpsmXnpsmXnpsmXnpsmXnpsm2-4 OCH$_2$CH$_2$Xnps3-NH$_2$mX mXnpsmXnpsmXnpsmXnpsmXnpsXpsXpsXpsXpsXpsXpsXpsXpsXpsmXnpsmXnpsmXnpsmXnps
3-NH$_2$mX mXnps2-4 OCH$_2$CH$_2$XnpsmXnps2-4
OCH$_2$CH$_2$XnpsmXnpsXpsXpsXpsXpsXpsXpsXpsXpsXpsmXnpsmXnps2-4
OCH$_2$CH$_2$XnpsmXnps3-NH$_2$mX 2-4 OCH$_2$CH$_2$XnpsmXnps2-
4OCH$_2$CH$_2$XnpsmXnpsmXnpsXpsXpsXpsXpsXpsXpsXpsXpsXpsmXnpsmXnps2-4
OCH$_2$CH$_2$XnpsmXnps2-OCH$_2$CH$_2$3-NH$_2$X 2-4 OCH$_2$CH$_2$XnpsmXnps2-4
OCH$_2$CH$_2$XnpsmXnpsmCnpsmXnpsXpsXpsXpsXpsXpsXpsXpsXpsmXnps2-4
OCH$_2$CH$_2$XnpsmXnpsmXnpsmXnps2-4 OCH$_2$CH$_2$Xnps3-NH$_2$mX mXnps2-4OCH$_2$CH$_2$XnpsmXnps2-4 OCH$_2$CH$_2$
XnpsmXnpsmXnpsXpsXpsXpsXpsXpsXpsXpsmXnps2-4 OCH$_2$CH$_2$XnpsmXnpsmXnps2-
4OCH$_2$CH$_2$XnpsmXnps3-NH$_2$mX In embodiments, each of the nucleotides of a domain are modified. In embodiments, each of the nucleotides of a domain have the same modifications. In embodiments, each of the nucleotides of the X and Z domains are modified. In embodiments, each of the nucleotides of the X and Z domains have the same modifications. In embodiments, each of the nucleotides of a domain are modified with 2' MOE. In embodiments, each of the nucleotides of the X and Z domains are modified with 2' MOE. In embodiments, each of the nucleotides of a domain are modified with 2' OMe. In embodiments, each of the nucleotides of the X and Z domains are modified with 2' OMe. In embodiments, each of the nucleotides of a domain are modified with 2' OEt. In embodiments, each of the nucleotides of the X and Z domains are modified with 2' OEt. In embodiments, each of the nucleotides of the X and Z domains are linked by an NPS linkage. In embodiments, the X and Z domains have the same number of nucleotides. In embodiments, the X and Z domains each have 4-8 nucleotides. In embodiments, the X and Z domains each have 5-6 nucleotides. In embodiments, the X and Z domains each have 5 nucleotides. In embodiments, the Y domain has at least twice the number of nucleotides as each of the X and Z domains. In embodiments, the Y domain has 8-12 nucleotides. In embodiments, the Y domain has 10 nucleotides. In embodiments, each of the nucleotides of the Y domain are linked by a PS linkage. In embodiments, at least one nucleobase of the oligonucleotide is modified. In embodiments, at least one nucleobase adjacent to the 3' terminal end of the oligonucleotide is modified. In embodiments, at least one nucleobase in the Z domain of the oligonucleotide is modified. In embodiments, at least one nucleobase in the Y domain of the oligonucleotide is modified.

In some embodiments, the oligonucleotide represented by Formula (VI) or (VI') is selected from Table D. In other embodiments, the oligonucleotide represented by Formula (VI) or (VI') has a sequence that differs from a chimeric oligonucleotide of Table D by one modified nucleotide. In other embodiments, the oligonucleotide represented by Formula (VI) or (VI') has a sequence that differs from an oligonucleotide of Table D by 1, 2, 3 or 4 nucleotides. Specific embodiments of the chimeric oligonucleotide represented by Formula (VI) or (VI') are listed below in Table D:

TABLE D

| #ID | SEQ ID NO: | Modified Sequence (5'-3') |
|---|---|---|
| 101 | 160 | 5'-mGpsmCpsmApsmGpsmApsmGpsGpsTpsGpsApsApsGpsmCpsmGpsmApsmApsmGpsmUpsmGpsmC-3' |
| 102 | 161 | 5'-mGpsmCpsmApsmGpsmApsmGpsGpsTpsGpsApsApsGpsmCpsmGpsmApsmApsmGpsmUpsmGpsmCps-Chol-3' |
| 103 | 162 | 5'-mGpsmCpsmApsmGpsmApsmGpsGpsTpsGpsApsApsGpsmCpsmGpsmApsmApsmGpsmUpsmGpsmC-GalNAc-3' |
| 104 | 163 | mGpsmApsmUpsmUpsmApsmGpsGpsCpsApsGpsApsGpsGpsTpsmGpsmApsmApsmApsmApsmApsmG |
| 105 | 164 | 5'-mGpsmApsmUpsmUpsmApsmGpsGpsCpsApsGpsApsGpsGpsTpsmGpsmApsmApsmApsmApsmApsmG-Chol-3' |
| 106 | 165 | 5'-mGpsmApsmUpsmUpsmApsmGpsGpsCpsApsGpsApsGpsGpsTpsmGpsmApsmApsmApsmApsmApsmG-GalNAc-3' |
| 107 | 166 | 5'-mGpsmApsmUpsmUpsmApsGpsGpsCpsApsGpsApsGpsGpsTpsmGpsmApsmApsmApsmApsmApsmG |
| 108 | 167 | 5'-mGpsmApsmUpsmUpsmApsGpsGpsCpsApsGpsApsGpsGpsTpsmGpsmApsmApsmApsmApsmApsmG-Chol-3' |
| 109 | 168 | 5'-mGpsmApsmUpsmUpsmApsGpsGpsCpsApsGpsApsGpsGpsTpsmGpsmApsmApsmApsmApsmApsmG-GalNAc-3' |
| 110 | 169 | 5'-mGpsmDAPpsmUpsmUpsmDAPpsmGpsGpsCpsApsGpsApsGpsGpsTpsmGpsmApsmApsmApsmApsmG-3' |
| 111 | 170 | 5'-mGpsmApsmUpsmUpsmApsmGpsGpsCpsApsGpsApsGpsGpsTpsmGpsmApsmApsmDAPpsmDAPpsmDAPpsmG-3' |
| 112 | 171 | 5'-mGpsmApsmUpsmUpsmApsmGpsGpsCpsApsGpsApsGpsGpsTpsmGpsmDAPpsmDAPpsmDAPpsmDAPpsmDAPpsmG-3' |
| 113 | 172 | 5'-mGpsmDAPpsmUpsmUpsmDAPpsmGpsGpsCpsApsGpsApsGpsGpsTpsmGpsmApsmApsmDAPpsmDAPpsmDAPpsmG-3' |
| 114 | 173 | 5'-mGpsmDAPpsmUpsmUpsmDAPpsmGpsGpsCpsApsGpsApsGpsGpsTpsmGpsmDAPpsmDAPpsmDAPpsmDAPpsmDAPpsmG-3' |
| 115 | 174 | 5'-mGpsmApsmUpsmUpsmApsGpsGpsCpsApsGpsApsGpsGpsTpsmGpsmApsmApsmApsmApsmApsmG-3' |
| 116 | 175 | 5'-mGpsmApsmUpsmUpsmApsGpsGpsCpsApsGpsApsGpsGpsTpsmGpsmApsmDAPpsmDAPpsmDAPpsmG-3' |

TABLE D-continued

| #ID | SEQ ID NO: | Modified Sequence (5'-3') |
|---|---|---|
| 117 | 176 | 5'-mGpsmApsmUpsmUpsmApsGpsGpsCpsApsGpsApsGpsGpsTpsmGpsmDAPpsmDAPpsmDAPpsmDAPpsmG-3' |
| 118 | 177 | 5'-mGpsmDAPpsmUpsmUpsmDAPpsGpsGpsCpsApsGpsApsGpsGpsTpsmGpsmApsmApsmDAPpsmDAPpsmDAPpsmG-3' |
| 119 | 178 | 5'-mGpsmDAPpsmUpsmUpsmDAPpsGpsGpsCpsApsGpsApsGpsGpsTpsmGpsmDAPpsmDAPpsmDAPpsmDAPpsmDAPpsmG-3' |
| 120 | 179 | 5'-mGpsmCpsmApsmGpsmApsmGpsGpsTpsGpsApsApsGpsmCpsmGpsmApsmDAPpsmGpsmUpsmGpsmC-3' |
| 121 | 180 | 5'-mGpsmCpsmApsmGpsmApsmGpsTpsGpsApsApsGpsmCpsmGpsmDAPpsmDAPpsmGpsmUpsmGpsmC-3' |
| 122 | 181 | 5'-mGpsmCpsmApsmGpsmDAPpsmGpsGpsTpsGpsApsApsGpsmCpsmGpsmDAPpsmDAPpsmGpsmUpsmGpsmC-3' |
| 123 | 182 | 5'-mGpsmCpsmDAPpsmGpsmDAPpsmGpsGpsTpsGpsApsApsGpsmCpsmGpsmDAPpsmDAPpsmGpsmUpsmGpsmC-3' |
| 124 | 183 | 5'-CnpsGnpsTnpsGnpsCnpsApsGpsApsGpsGpsTpsGpsAnpsAnpsGnpsCnps-3-NH$_2$-G-3' |
| 125 | 184 | 5'-GnpsCnpsAnpsGnpsAnpsGpsGpsTpsGpsApsApsGnpsCnpsGnpsAnpsAnps-3-NH$_2$-G-3 |
| 126 | 185 | 5'-CnpsGnpsAnpsCnpsGnpsTnpsGpsCpsApsGpsApsGpsGnpsTnpsGnpsAnpsAnpsGnps-3-NH$_2$-C-3' |
| 127 | 186 | 5'-GnpsCnpsAnpsGnpsAnpsGnpsGpsTpsGpsApsApsGpsCnpsGnpsAnpsAnpsGnpsTnpsGnps-3-NH$_2$-C-3' |
| 128 | 187 | 5'-GnpsCnpsAnpsGnpsApsGpsGpsTpsGpsAnpsAnpsGnpsCnps-3-NH$_2$-G-3' |
| 129 | 188 | 5'-CnpsGnpsTnpsGnpsCnpsApsGpsApsGpsGpsTnpsGnpsAnpsAnpsGnps-3-NH$_2$-C-3' |
| 130 | 189 | 5'-GnpsCnpsAnpsGnpsAnpsGnpsGnpsTnpsGpsApsAnpsGnpsCnpsGnpsAnpsAnpsGnpsTnpsGnps-3NH$_2$-C-3' |
| 131 | 190 | 5'-GnpsCnpsAnpsGnpsAnpsGnpsGnpsTpsGpsAnpsAnpsGnpsCnpsGnpsAnpsAnpsGnpsTnpsGnps-3NH$_2$-C-3' |
| 132 | 191 | 5'-GnpsCnpsAnpsGnpsAnpsGnpsGpsTpsGnpsAnpsAnpsGnpsCnpsGnpsAnpsAnpsGnpsTnpsGnps-3NH$_2$-C-3' |
| 133 | 192 | 5'-GnpsCnpsAnpsGnpsAnpsGnpsGnpsTnpsGnpsApsApsGnpsCnpsGnpsAnpsAnpsGnpsTnpsGnps-3NH$_2$-C-3' |
| 134 | 193 | 5'-GnpsCnpsAnpsGnpsAnpsGnpsGnpsTnpsGnpsAnpsApsGpsCnpsGnpsAnpsAnpsGnpsTnpsGnps-3NH$_2$-C-3' |
| 135 | 194 | 5'-GnpsCnpsAnpsGnpsAnpsGnpsGpsTpsGpsAnpsAnpsGnpsCnpsGnpsAnpsAnpsGnpsTnpsGnps-3NH$_2$-C-3' |
| 136 | 195 | 5'-GnpsCnpsAnpsGnpsAnpsGnpsGnpsTnpsGpsApsApsGnpsCnpsGnpsAnpsAnpsGnpsTnpsGnps-3NH$_2$-C-3' |
| 137 | 196 | 5'-GnpsCnpsAnpsGnpsAnpsGnpsGnpsTpsGpsApsAnpsGnpsCnpsGnpsAnpsAnpsGnpsTnpsGnps-3NH$_2$-C-3' |
| 138 | 197 | 5'-GnpsCnpsAnpsGnpsAnpsGnpsGnpsTnpsGnpsApsApsGpsCnpsGnpsAnpsAnpsGnpsTnpsGnps-3NH$_2$-C-3' |
| 139 | 198 | 5'-GnpsCnpsAnpsGnpsAnpsGnpsGnpsTnpsGpsApsApsGpsCnpsGnpsAnpsAnpsGnpsTnpsGnps-3NH$_2$-C-3' |
| 140 | 199 | 5'-GnpsCnpsAnpsGnpsAnpsGnpsGnpsTpsGpsApsApsGpsCnpsGnpsAnpsAnpsGnpsTnpsGnps-3NH$_2$-C-3' |
| 141 | 200 | 5'-GnpsCnpsAnpsGnpsAnpsGnpsGpsTpsGpsApsApsGpsCpsGnpsAnpsAnpsGnpsTnpsGnps-3NH$_2$-C-3' |
| 142 | 201 | 5'-mApsmApsmGpsmApsmGpsApsGpsGpsTpsGps5mCpsGps5mCps5mCps5mCps5mmCpsmGpsmUpsmGpsmG-3' |

TABLE D-continued

| #ID | SEQ ID NO: | Modified Sequence (5'-3') |
|---|---|---|
| 143 | 202 | 5'-mGpsmGpsmUpsmGpsmApsApsGps5mCpsGpsApsApsGpsTpsGps5mCpsmAps5mmCpsmAps5mmCpsmG-3' |
| 144 | 203 | 5'-5mmCpsmGpsmUpsmGps5mmCpsApsGpsApsGpsGpsTpsGpsApsApsGps5mmCpsmGpsmApsmApsmG-3' |
| 145 | 204 | 5'-mApsmGpsmApsmGpsmGpsTpsGpsApsApsGps5mCpsGpsApsApsGpsmUpsmGps5mmCpsmAps5mmC-3' |
| 146 | 205 | 5'-mUpsmGps5mmCpsmAps5mCpsTpsApsGpsTpsApsApsApsAps5mCpsTpsmGpsmApsmGps5mmCps5mmC-3' |
| 147 | 206 | 5'-5mmCpsmUpsmApsmGpsmGpsApsGpsTpsTps5mCps5mCpsGps5mCpsApsGpsmUpsmApsmUpsmGpsmG-3' |
| 148 | 207 | 5'-mApsmGpsmApsmGpsmGpsTpsGps5mCpsGps5mCps5mCps5mCps5mCpsGpsTpsmGpsmGpsmUps5mmCpsmG-3' |
| 149 | 208 | 5'-mGpsmApsmGpsmGpsmUpsGps5mCpsGps5mCps5mCps5mCps5mCpsGpsTpsGpsmGpsmUps5mmCpsmGpsmG-3' |
| 150 | 209 | 5'-mGpsmApsmGpsmApsmGps5mCps5mCps5mCpsTpsAps5mCpsGpsApsAps5mCps5mmCpsmAps5mmCpsmUpsmG-3' |
| 151 | 210 | 5'-mGpsmUpsmUps5mmCps5mmCpsGps5mCpsApsGpsTpsApsTpsGpsGpsApsmUps5mmCpsmGpsmGps5mmC-3' |
| 152 | 211 | 5'-mUps5mmCps5mmCpsmGps5mmCpsApsGpsTpsApsTpsGpsGpsApsTps5mCpsmGpsmGps5mmCpsmApsmG-3' |
| 153 | 212 | 5'-mAps5mmCps5mmCpsmAps5mmCpsTpsGpsApsAps5mCpsApsApsApsTpsGpsGps5mmCpsmAps5mmCpsmU-3' |
| 154 | 213 | 5'-mUpsmGps5mmCpsmApsmGpsApsGpsGpsTpsGpsApsApsGps5mCpsGpsmApsmApsmGpsmUpsmG-3' |
| 155 | 214 | 5'-mAps5mmCpsmUpsmGpsmApsAps5mCpsApsApsApsTpsGpsGps5mCpsAps5mmCpsmUpsmApsmGpsmU-3' |
| 156 | 215 | 5'-mApsmGpsmUps5mmCps5mmCpsAps5mCps5mCpsAps5mCpsGpsApsGpsTps5mCpsmUpsmApsmGpsmAps5mmC-3' |
| 157 | 216 | 5'-5mmCpsmAps5mmCpsmUpsmGpsApsAps5mCpsApsApsApsTpsGpsGps5mCpsmAps5mmCpsmUpsmApsmG-3' |
| 158 | 217 | 5'-5mmCpsmApsmGpsmApsmGpsGpsTpsGpsApsApsGps5mCpsGpsApsApsmGpsmUpsmGps5mmCpsmA-3' |
| 159 | 218 | 5'-mApsmApsmGpsmApsmGpsApsGpsGpsTpsGps5meCpsGps5meCps5meCps5meCps5memCpsmGpsmUpsmGpsmG-GalNAc-3' |
| 160 | 219 | 5'-mGpsmGpsmUpsmGpsmApsApsGps5meCpsGpsApsApsGpsTpsGps5mCpsmAps5memCpsmAps5memeCpsmG-GalNAc-3' |
| 161 | 220 | 5'-mUpsmGpsmGps5memCpsmAps5meCpsTpsApsGpsTpsApsApsAps5meCpsTpsmGpsmApsmGps5meCps5memCpoGalNAc-3' |
| 162 | 221 | 5'-5memCpsmUpsmApsmGmGpsApsGpsTpsTps5meCps5meCpsGps5meCpsApsGpsmUpsmApsmUpsmGpsmGpoGalNAc-3' |
| 163 | 222 | 5'-mApsmGpsmApsmGpsmGpsTpsGps5meCpsGps5meCps5meCps5meCps5meCpsGpsTpsmGpsmGpsmUps5memCpsmGpoGalNAc-3' |
| 164 | 223 | 5'-mUps5memCps5memCpsmGps5memCpsApsGpsTpsApsTpsGpsGpsApsTps5meCpsmGpsmGps5memCpsmApsmGpoGalNAc-3' |
| 165 | 224 | 5'-mUpsmGps5memCpsmApsmGpsApsGpsGpsTpsGpsApsApsGps5meCpsGpsmApsmApsmGpsmUpsmGpoGalNAc-3' |
| 166 | 225 | 5'-mApsmGpsmUps5memCps5memCpsAps5meCps5meCAps5meCpsGpsApsGpsTps5meCpsmUpsmApsmGpsmAps5memCpoGalNAc-3' |
| 167 | 226 | 5'-fGnpsfCnpsfAnpsfGnpsfAnpsfGnpsGpsTpsGpsApsApsGpsfCnpsfGnpsfAnpsfAnpsfGnpsfUnpsfGnps-3-NH$_2$-fC-3' |

TABLE D-continued

| #ID | SEQ ID NO: | Modified Sequence (5'-3') |
|---|---|---|
| 168 | 227 | 5'-fGnpsfCnpsfAnpsfGnpsfAnpsfGnpsGpsTpsGpsApsApsGpsCpsfGnpsfAnpsfAnpsfGnpsfUnpsfGnps-3-NH₂4C-3' |
| 169 | 228 | 5'-fGnpsfCnpsfAnpsfGnpsfAnpsfGnpsGpsTpsGpsApsApsGpsCpsGpsfAnpsfAnpsfGnpsfUnpsfGnps-3-NH₂-fC-3' |
| 170 | 229 | 5'-GnpCnpAnpGnpAnpGnpGpsTpsGpsApsApsGpsCnpGnpAnpAnpGnpTnpGnp-3NH₂-C-3' |
| 171 | 230 | 5'-GnpsfCnpsfAnpsGnpsfAnpsGnpsGpsTpsGpsApsApsGpsfCnpsGnpsfAnpsfAnpsGnpsfTnpsGnps-3NH₂-fC-3' |
| 172 | 231 | 5'-GnpfCnpfAnpGnpfAnpGnpGpsTpsGpsApsApsGpsfCnpGnpfAnpfAnpGnpfTnpGnp-3NH₂-fC-3' |
| 173 | 232 | 5'-GnpsafCnpsafAnpsGnspafAnpsGnpsGpsTpsGpsApsApsGpsafCnpsGnpsafAnpsafAnpsGnpsafUnpsGnpsafC-3' |
| 174 | 233 | 5'-GnpafCnpafAnpGnpafAnpGnpGpsTpsGpsApsApsGpsafCnpGnpafAnpafAnpGnpafUnpGnpafC-3' |
| 175 | 234 | 5'-GnpafCnpafAnpGnpafAnpGnpGpsTpsGpsApsApsGpsCpsGnpafAnpafAnpGnpafUnpGnpafC-3' |
| 176 | 235 | 5-mGpsmCpsmUpsmCpsmCpsmApsApsApsTpsTpsCpsTpsTpsTpsApsmUpsmApsmApsmGpsmGpsmG-GalNAc-3 |
| 177 | 236 | 5'-mApsmApsmGpsmApsmGpsApsGpsGpsTpsGps5mCpsGps5mCps5mCps5mCps5mmCpsmGpsmUpsmGpsmG-3' |
| 178 | 237 | 5'-mGpsmGpsmUpsmGpsmApsApsGps5mCpsGpsApsApsGpsTpsGps5mCpsmAps5mmCpsmAps5mmCpsmG-3' |
| 179 | 238 | 5-5mmCpsmGpsmUpsmGps5mmCpsApsGpsApsGpsGpsTpsGpsApsApsGps5mmCpsmGpsmApsmApsmG-3' |
| 180 | 239 | 5'-mGpsmUpsmGpsmApsmApsGps5mCpsGpsApsApsGpsTpsGps5mCpsAps5mmCpsAps5mmCpsmGpsmG-3' |
| 181 | 240 | 5'-mApsmGpsmApsmGpsmGpsTpsGpsApsApsGps5mCpsGpsApsApsGpsmUpsmGps5mmCpsmAps5mmC-3' |
| 182 | 241 | 5'-mUpsmGpsmGps5mmCpsmAps5mCpsTpsApsGpsTpsApsApsAps5mCpsTpsmGpsmApsmGps5mmCps5mmC-3' |
| 183 | 242 | 5'-5mmCpsmUpsmApsmGpsmGpsApsGpsTpsTps5mCps5mCpsGps5mCpsApsGpsmUpsmApsmUpsmGpsmG-3' |
| 184 | 243 | 5'-mGps5mmCpsmApsmGpsmApsGpsGpsTpsGpsApsApsGps5mCpsGpsApsmApsmGpsmUpsmGps5mmC-3' |
| 185 | 244 | 5'-mApsmGpsmApsmGpsmGpsTpsGps5mCpsGps5mCps5mCps5mCps5mCpsGpsTpsmGpsmGpsmUps5mmCpsmG-3' |
| 186 | 245 | 5'-mGpsmApsmGpsmGpsmUpsGps5mCpsGps5mCps5mCps5mCps5mCpsGpsTpsGpsmGpsmUps5mmCpsmGpsmG-3' |
| 187 | 246 | 5'-mGpsmApsmApsmApsmGps5mCps5mCps5mCpsTpsAps5mCpsGpsApsAps5mCps5mmCpsmAps5mmCpsmUpsmG-31 |
| 188 | 247 | 5'-mGpsmUpsmUps5mmCps5mmCpsGps5mCpsApsGpsTpsApsTpsGpsGpsApsmUps5mmCpsmGpsmGps5mmC-3' |
| 189 | 248 | 5'-mUps5mmCps5mmCpsmGps5mmCpsApsGpsTpsApsTpsGpsGpsApsTps5mCpsmGpsmGps5mmCpsmApsmG-3' |
| 190 | 249 | 5'-mAps5mmCps5mmCpsmAps5mmCpsTpsGpsApsAps5mCpsApsApsApsTpsGpsGps5mmCpsmAps5mmCpsmU-31 |
| 191 | 250 | 5'-mUpsmGps5mmCpsmApsmGpsApsGpsGpsTpsGpsApsApsGps5mCpsGpsmApsmApsmGpsmUpsmG-3' |
| 192 | 251 | 5'-mAps5mmCpsmUpsmGpsmApsAps5mCpsApsApsApsTpsGpsGps5mCpsAps5mmCpsmUpsmApsmGpsmU-31 |
| 193 | 252 | 5'-mApsmGpsmUps5mmCps5mmCpsAps5mCps5mCpsAps5mCpsGpsApsGpsTps5mCpsmUpsmApsmGpsmAps5mmC-3' |

TABLE D-continued

| #ID | SEQ ID NO: | Modified Sequence (5'-3') |
|---|---|---|
| 194 | 253 | 5'-5mmCpsmAps5mmCpsmUpsmGpsApsAps5mCpsApsApsApsTpsGps Gps5mCpsmAps5mmCpsmUpsmApsmG-3' |
| 195 | 254 | 5'-5mmCpsmApsmGpsmApsmGpsGpsTpsGpsApsApsGps5mCpsGpsAps ApsmGpsmUpsmGps5mmCpsmA-3' |
| 196 | 255 | 5'-mApsmApsmGpsmApsmGpsmApsGpsGpsTpsGps5meCpsGps5meCps 5meCps5memCps5memCpsmGpsmUpsmGpsmG3' |
| 197 | 256 | 5'-mApsmApsmGpsmApsmGpsmApsmGpsGpsTpsGps5meCpsGps5me Cps5memCps5memCps5memCpsmGpsmUpsmGpsmG3' |
| 198 | 257 | 5'-mGpsmGpsmUpsmGpsmApsmApsGps5meCpsGpsApsApsGpsTpsGps 5memCpsmAps5memCpsmAps5memeCpsmG3' |
| 199 | 258 | 5'-mGpsmGpsmUpsmGpsmApsmApsmGps5meCpsGpsApsApsGpsTps Gps5memCpsmAps5memCpsmAps5memeCpsmG3' |
| 200 | 259 | 5'-mUpsmGpsmGps5memCpsmAps5memCpsTpsApsGpsTpsApsApsAps 5meCpsTpsmGpsmApsmGps5memCps5memC3' |
| 201 | 260 | 5'-mUpsmGpsmGps5memCpsmAps5meCpsTpsApsGpsTpsApsApsAps 5meCpsTpsmGpsmApsmGps5memCps5memC3' |
| 202 | 261 | 5'-5memCpsmUpsmApsmGmGpsmApsGpsTpsTps5meCps5meCpsGps 5meCpsApsmGpsmUpsmApsmUpsmGpsmG3' |
| 203 | 262 | 5'-5memCpsmUpsmApsmGmGpsmApsmGpsTpsTps5meCps5meCpsGps 5meCpsApsmGpsmUpsmApsmUpsmGpsmG3' |
| 204 | 263 | 5'-GalNAc-NHC6-psmUpsm5meCpsm5meCpsmGpsm5meCpsApsGps TpsApsTpsGpsGpsApsTps5meCpsmGpsmGpsm5meCpsmApsmG3' |
| 205 | 264 | 5'-GalNAc-NHC6-psm5meCpsmUpsmApsmGpsmGpsApsGpsTpsTps 5meCps5meCpsGps5meCpsApsGpsmUpsmApsmUpsmGpsmG3' |
| 206 | 265 | 5'-GalNAc-NHC6-psmApsmApsmGpsmApsmGpsApsGpsGpsTpsGps 5meCpsGps5meCps5meCps5meCpsm5meCpsmGpsmUpsmGpsmG3' |
| 207 | 266 | 5'GalNAc-NHC6-psmApsmGpsmApsmGpsmGpsGpsTpsGps5meCpsGps5me Cps5meCps5meCps5meCpsGpsTpsmGpsmGpsmUpsm5meCpsmG3' |
| 208 | 267 | 5'GalNAc-NHC6-psmUpsmGpsm5meCpsmApsmGpsApsGpsGpsTpsGps ApsApsGps5meCpsGpsmApsmApsmGpsmUpsmG3' |
| 209 | 268 | mGpsmCpsmUpsmCpsmCpsmApsmApsApsTpsTpsCpsTpsTpsTpsmApsm UpsmApsmApsmGpsmG |
| 210 | 269 | mGpsmCpsmUpsmCpsmCpsmApsApsApsTpsTpsCpsTpsTpsTpsmApsm UpsmApsmApsmGpsmG |
| 211 | 270 | mGpsmCpsmUpsmCpsmCpsmApsApsApsTpsTpsCpsTpsTpsTpsApsm UpsmApsmApsmGpsmGpsmG |
| 212 | 271 | mGpsmCpsmUpsmCpsmCpsmApsmApsApsTpsTpsCpsTpsTpsTpsmApsm UpsmApsmApsmGpsmG/GalNAc/ |
| 213 | 272 | mGpsmCpsmUpsmCpsmCpsmApsmApsApsTpsTpsCpsTpsTpsTpsmApsmU psmApsmApsmGpsmG/GalNAc/ |
| 214 | 273 | mGpsmCpsmUpsmCpsmCpsmApsmApsApsTpsTpsCpsTpsTpsTpsmApsm UpsmApsmApsmGpsmG/3CholTEG/ |
| 215 | 274 | mGpsmCpsmUpsmCpsmCpsmApsApsApsTpsTpsCpsTpsTpsTpsmApsm UpsmApsmApsmGpsmG/3CholTEG/ |
| 216 | 275 | mGpsmCpsmUpsmCpsmCpsmApsApsApsTpsTpsCpsTpsTpsTpsApsm UpsmApsmApsmGpsmGpsmG/3CholTEG/ |
| 217 | 276 | 5'-mGps5mmCpsmApsmGpsmApsmGpsGpsTpsGpsApsApsGp5mmCpsm GpsmApsmApsmGpsmUpsmGpsm5meC-3 |
| 218 | 277 | 5'-mGps5mmCpsmApsmGpsmApsmGpsGpsTpsGpsApsApsGps5mmCpsm GpsmApsmApsmGpsmUpsmGps5mmC-Cholesterol-3' |

TABLE D-continued

| #ID | SEQ ID NO: | Modified Sequence (5'-3') |
|---|---|---|
| 219 | 278 | 5'-mGps5mmCpsmApsmGpsmApsmGpsGpsTpsGpsApsApsGp5mmCpsm GpsmApsmApsmGpsmUpsmGps5mmC-TEG-Cholesterol-3' |
| 220 | 279 | 5'-mGps5mmCpsmApsmGpsmApsmGpsGpsTpsGpsApsApsGps5mmCpsm GpsmApsmApsmGpsmUpsmGps5mmC-Tocopherol-3' |
| 221 | 280 | 5'-mGps5mmCpsmApsmGpsmApsmGpsGpsTpsGpsApsApsGps5mmCpsm GpsmApsmApsmGpsmUpsmGps5mmC-TEG-Tocopherol-3' |
| 222 | 281 | 5'-mGps5mmCpsmApsmGpsmApsmGpsGpsTpsGpsApsApsGps5mmCpsm GpsmApsmApsmGpsmUpsmGps5mmC-GalNAc-3' |
| 223 | 282 | 5'-mGps5meCpsmApsmGpsmApsmGpsGpsTpsGpsApsApsGps5meCps mGpsmApsmApsmGpsmUpsmGpsm5meC-3' |
| 224 | 283 | 5'-mGps5meCpsmApsmGpsmApsmGpsGpsTpsGpsApsApsGps5meCps mGpsmApsmApsmGpsmUpsmGpsm5meC-po-Chol-3' |
| 225 | 284 | 5'-mGps5meCpsmApsmGpsmApsmGpsGpsTpsGpsApsApsGps5meCps mGpsmApsmApsmGpsmUpsmGpsm5meC-po-Tocopherol-3' |
| 226 | 285 | 5'-mGps5meCpsmApsmGpsmApsmGpsGpsTpsGpsApsApsGps5meCps mGpsmApsmApsmGpsmUpsmGpsm5meC-po-GalNAc-3' |
| 227 | 286 | 5'-mGps5meCpsmApsmGpsmApsmGpsGpsTpsGpsApsApsGps5meCps GpsmApsmApsmGpsmUpsmGpsm5meC-3' |
| 228 | 287 | 5'-mGps5meCpsmApsmGpsmApsmGpsGpsTpsGpsApsApsGps5meCps GpsmApsmApsmGpsmUpsmGpsm5meC-po-Chol-3' |
| 229 | 288 | 5'-mGps5meCpsmApsmGpsmApsmGpsGpsTpsGpsApsApsGps5meCps GpsmApsmApsmGpsmUpsmGpsm5meC-po-Tocopherol-3' |
| 230 | 289 | 5'-mGps5meCpsmApsmGpsmApsmGpsGpsTpsGpsApsApsGps5meCps GpsmApsmApsmGpsmUpsmGpsm5meC-po-GalNAc-3' |
| 231 | 290 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-3 |
| 232 | 291 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-Chol-3 |
| 233 | 292 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-Toco-3 |
| 234 | 293 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-GalNAc-3 |
| 235 | 294 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-3 |
| 236 | 295 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-Chol-3 |
| 237 | 296 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-Toco-3 |
| 238 | 297 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-GalNAc-3 |
| 239 | 298 | 5-mGps2-4-OCH$_2$-(5m)CpsmAps2-4-OCH$_2$-GpsmAps2-4-OCH$_2$-Gps GpsTpsGpsApsApsGps(5m)CpsmGps2-4-OCH$_2$-ApsmAps2-4-OCH$_2$-GpsmUps2-4-OCH$_2$-Gps(5m)mC-3 |
| 240 | 299 | 5-dTnpsGnpsCnpsAnpsGnpsApsGpsGpsTpsGpsApsApsGpsCpsGps AnpsAnpsGnpsTnpsGn-3 |
| 241 | 300 | 5-dTnpsfGnpsCnpsfAnpsfGnpsApsGpsGpsTpsGpsApsApsGpsCps GpsfAnpsfAnpsfGnpsfUnpsfGn3' |

TABLE D-continued

| #ID | SEQ ID NO: | Modified Sequence (5'-3') |
|---|---|---|
| 242 | 301 | 5-fGnpsCnpsfAnpsfGnpsfAnpsfGnpsGpsTpsGpsApsApsGpsCnpsfGnpsfAnpsfAnpsfGnpsfUnpsfGnpsCn-3' |
| 243 | 302 | 5-fGnpsCnpsfAnpsfGnpsfAnpsfGnpsGpsTpsGpsApsApsGpsCpsGpsfAnpsfAnpsfGnpsfUnpsfGnpsCn-3' |
| 244 | 303 | 5'-dGnpmCnpmAnpmGnpmAnpmGnpGpsTpsGpsApsApsGpsmCnpmGnpmAnpmAnpmGnpmUnpmGnpmCnp-3' |
| 245 | 304 | 5'-dGnpmCnpmAnpmGnpmAnpmGnpGpsTpsGpsApsApsGpsCpsmGnpmAnpmAnpmGnpmUnpmGnpmCnp-3' |
| 246 | 305 | 5'-dGnpmCnpmAnpmGnpmAnpmGnpGpsTpsGpsApsApsGpsCpsGpsmAnpsmAnpmGnpmUnpmGnpmCnP-3' |
| 247 | 306 | 5'-dGnpmCnpmAnpmGnpmAnpGpsGpsTpsGpsApsApsGpsCpsmGnpmAnpmAnpmGnpmUnpmGnpmCnp-3' |
| 248 | 307 | 5'-dGnpmCnpmAnpmGnpmAnpGpsGpsTpsGpsApsApsGpsCpsGpsmAnpmAnpmGnpmUnpmGnpmCnp-3' |
| 249 | 308 | GnpsCnpsAnpsGnpsAnpsGnpsGnpsTnpsGnpsAnpsAnpsGnpsCnpsGnpsAnpsAnpsG |
| 250 | 309 | GnpsCnpsAnpsGnpsAnpsGnpsGnpsTnpsGnpsAnpsAnpsGnpsCnpsGnpsAnpsAnpsGnpsTnpsGnpsC |
| 251 | 310 | CnpsGnpsTnpsGnpsCnpsAnpsGnpsAnpsGnpsGnpsTnpsGnpsAnpsAnpsGnpsCnpsG |
| 252 | 311 | CnpsGnpsTnpsGnpsCnpsApsGpsApsGpsGpsTpsGpsAnpsAnpsGnpsCnpsG |
| 253 | 312 | GnpsCnpsAnpsGnpsAnpsGpsGpsTpsGpsApsApsGnpsCnpsGnpsAnpsAnpsG |
| 254 | 313 | CnpsGnpsAnpsCnpsGnpsTnpsGpsCpsApsGpsApsGpsGnpsTnpsGnpsAnpsAnpsGnpsC |
| 255 | 314 | GnpsCnpsAnpsGnpsAnpsGnpsGpsTpsGpsApsApsGpsCnpsGnpsAnpsAnpsGnpsTnpsGnpsC |
| 256 | 315 | GnpsCnpsAnpsGnpsApsGpsGpsTpsGpsAnpsAnpsGnpsCnpsG |
| 257 | 316 | CnpsGnpsTnpsGnpsCnpsApsGpsApsGpsGpsTnpsGnpsAnpsAnpsGnpsC |
| 258 | 317 | mGnpsmoeCnpsmoeAnpsmGnpsmoeAnpsGpsGpsTpsGpsApsApsGpsCpsGpsApsmoeAnpsmGnpsmoeUnpsmGnpsmoeCnp-C6-NH-GalNAc6 |
| 259 | 318 | moeGps(5me)moeCpsmoeApsmoeGpsmoeApsGpsGpsTpsGpsApsApsGps(5me)CpsGpsApsmoeApsmoeGpsmoeTpsmoeGps(5me)moeC-po-GalNAc2 |
| 260 | 319 | mGnpsmoeCnpsmoeAnpsmGnpsmoeAnpsGpsGpsTpsGpsApsApsGps(5me)CpsGpsApsmoeAnpsmGnpsmoeUnpsmGnpsmoeCnpo-C6-NH-GalNAc-6 |
| 261 | 320 | GalNAc-2-pofGnpsfCnpsfAnpsfGnpsfAnpsGpsGpsTpsGpsApsApsGps(5me)CpsGpsApsfAnpsfGnpsfUnpsfGnpsfCn |
| 262 | 321 | GalNAc2-moeGnpsmoeCnpsmoeAnpsmoeGnpsmoeAnpsGpsGpsTpsGpsApsApsGpsCpsGpsApsmoeAnpsmoeGnpsmoeUnpsmoeGnpsmoeCn |
| 263 | 322 | moeGps(5me)moeCpsmoeApsmoeGpsmoeApsGpsGpsTpsGpsApsApsGps(5me)CpsGpsApsmoeApsmoeGpsmoeTpsmoeGps(5me)moeC-GalNAc2 |
| 264 | 323 | GalNac2-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn |
| 265 | 324 | GalNac-moeGnpsmoeCnpsmoeAnpsmoeGnpsmoeAnpsGpsGpsTpsGpsApsApsGpsCpsGpsApsmoeAnpsmoeGnpsmoeUnpsmoeGnpsmoeCn |

TABLE D-continued

| #ID | SEQ ID NO: | Modified Sequence (5'-3') |
|---|---|---|
| 266 | 325 | GalNAc2-mGnpsmCnpsmAnpsmGnpsmAnpsGpsGpsTpsGpsApsApsGps(5m)CpsGpsApsmoeAnpsmoeGnpsmoeUnpsmoeGnpsmoeCn |
| 267 | 326 | GalNac6-NH-C6-moeGps(5m)moeCpsmoeApsmoeGpsmoeApsGpsGpsTpsGpsApsApsGps(5m)CpsGpsApsmoeApsmoeGpsmoeTpsmoeGps(5m)moeC |
| 268 | 327 | GalNAc2-mGnpsmCnpsmAnpsmGnpsmAnpsGpsGpsTpsGpsApsApsGps(5m)CpsGpsApsmAnpsmGnpsmUnpsmGnpsmCn |
| 269 | 328 | GalNAc2-etoGnps(5m)etoCnpsetoAnpsetoGnpsetoAnpsGpsGpsTpsGpsApsApsGps(5m)CpsGpsApsetoAnpsetoGnpsetoTnpsetoGnps(5m)etoCn |
| 270 | 329 | GalNAc2-moeGnpsmoeCnpsmoeAnpsmoeGnpsmoeAnpsGpsGpsTpsGpsApsApsGps(5m)CpsGpsApsmAnpsmGnpsmUnpsmGnpsmCn |
| 271 | 330 | moeGpsmoemCpsmoeApsmoeGpsmoeApsGpsGpsTpsGpsApsApsGps5mCpsGpsApsmoeApsmoeGpsmoeTpsmoeGpsmoemC |
| 272 | 331 | moeGnpsmoeCnpsmoeAnpsmoeGnpsmoeAnpsGpsGpsTpsGpsApsApsGpsCpsGpsApsmoeAnpsmoeGnpsmoeUnpsmoeGnpsmoeCn |
| 273 | 332 | mGps5mmCpsmApsmGpsmApsGpsGpsTpsGpsApsApsGps5mCpsGpsApsmApsmGpsmUpsmGps5mmC |
| 274 | 333 | mGnpsmCnpsmAnpsmGnpsmAnpsGpsGpsTpsGpsApsApsGpsCpsGpsApsmAnpsmGnpsmUnpsmGnpsmCn |
| 275 | 334 | GalNAc2-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn |
| 276 | 335 | GalNac6-NH-C6-moeGps(5m)moeCpsmoeApsmoeGpsmoeApsGpsGpsTpsGpsApsApsGps(5m)CpsGpsApsmoeApsmoeGpsmoeTpsmoeGps(5m)moeC |
| 277 | 336 | 5'moeGps(5m)moeCpsmoeApsmoeGpsmoeApsGpsGpsTpsGpsApsApsGps(5m)CpsGpsApsmoeApsmoeGpsmoeTpsmoeGps(5me)moeC-GalNAc2 |
| 278 | 337 | GalNAc2-mGnpsmCnpsmAnpsmGnpsmAnpsGpsGpsTpsGpsApsApsGpsCpsGpsApsmAnpsmGnpsmUnpsmGnpsmCn' |
| 279 | 338 | mGps(5m)mCpsmApsmGpsmApsGpsGpsTpsGpsApsApsGps(5m)CpsGpsApsmApsmGpsmUpsmGps(5m)mC-GalNAc |
| 280 | 339 | GalNAc2-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn |
| 281 | 340 | moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCnp-C6-NH-GalNAc6 |
| 282 | 341 | GalNAc2-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn |
| 283 | 342 | GalNAc-GnpsCnpsAnpsGnpsAnpsGpsGpsTpsGpsApsApsGpsCpsGpsApsAnpsGnpsTnpsGnpsCn |
| 284 | 343 | GalNAc-mGnpsmCnpsmAnpsmGnpsmAnpsGpsGpsTpsGpsApsApsGpsCpsGpsApsmAnpsmGnpsmUnpsmGnpsmCn |
| 285 | 344 | GalNAc-fGnpsfCnpsfAnpsfGnpsfAnpsGpsGpsTpsGpsApsApsGpsCpsGpsApsfAnpsfGnpsfUnpsfGnps-3nh2-fC |
| 286 | 345 | GalNAc-afGnpsafCnpsafAnpsafGnpsafAnpsGpsGpsTpsGpsApsApsGpsCpsGpsApsafAnpsafGnpsafTnpsafGnpsafCn |
| 287 | 346 | GalNAc-dTnpsGnpsCnpsAnpsGnpsApsGpsGpsTpsGpsApsApsGpsCpsGpsAnpsAnpsGnpsTnps-3nh2-G |
| 288 | 347 | GalNAc-mUnpsmGnpsmCnpsmAnpsmGnpsApsGpsGpsTpsGpsApsApsGpsCpsGpsmAnpsmAnpsmGnpsmUnpsmGn |

TABLE D-continued

| #ID | SEQ ID NO: | Modified Sequence (5'-3') |
|---|---|---|
| 289 | 348 | GalNAc-fUnpsfGnpsfCnpsfAnpsfGnpsApsGpsGpsTpsGpsApsAps GpsCpsGpsfAnpsfAnpsfGnpsfUnps-3nh2-fG |
| 290 | 349 | GalNAc-mGnpsmCnpsmUnpsmCnpsmCnpsApsApsApsTpsTps5MeCps TpsTpsTpsApsmUnpsmAnpsmAnpsmGnpsmGnpsmGn |
| 291 | 350 | GalNAc-moeGnpsmoeCnpsmoeUnpsmoeCnpsmoeCnpsApsApsApsTps Tps5MeCpsTpsTpsTpsApsmoeUnpsmoeAnpsmoeAnpsmoeGnpsmoe GnpsmoeGn |
| 292 | 351 | moeGps(5m)moeCpsmoeApsmoeGpsmoeApsGpsGpsTpsGpsApsAps Gps(5m)CpsGpsApsmoeApsmoeGpsmoETpsmoeGps(5m)moeC |
| 293 | 352 | moeGnpsmoeCnpsmoeAnpsmoeGnpsmoeAnpsGpsGpsTpsGpsApsAps Gps(5m)CpsGpsApsmoeAnpsmoeGnpsmoeUnpsmoeGnpsmoeCn |
| 294 | 353 | fGnps(5m)fCnpsfAnpsfGnpsfAnpsGpsGpsTpsGpsApsApsGpsCps GpsApsfAnpsfGnpsfTnpsfGnpsfC-C6-NH-GalNac6 |
| 295 | 354 | fGnpsfCnpsfAnpsfGnpsfAnpsGpsGpsTpsGpsApsApsGps(5m)Cps GpsApsfAnpsfGnpsfUnpsfGnpsfCnp-C6-NH-GalNAc6 |
| 296 | 355 | mGnpsmCnpsmAnpsmGnpsmAnpsGpsGpsTpsGpsApsApsGps(5m)Cps GpsApsmAnpsmGnpsmUnpsmGnpsmCnp-C6-NH-GalNAc6 |
| 297 | 356 | mGnpsmCnpsmAnpsmGnpsmAnpsGpGpsTpsGpsApsApsGps(5m)Cps GpsApsmAnpsmGnpsmUnpsmGnpsmC-C6-NH-GalNAc6 |
| 298 | 357 | moeGnpsmoeCnpsmoeAnpsmoeGnpsmoeAnpsGpsGpsTpsGpsApsAps Gps(5m)CpsGpsApsmoeAnpsmoeGnpsmoeUnpsmoeGnpsmoeCnp- C6-NH-GalNAc6 |
| 299 | 358 | moeGnpsmoeCnpsmoeAnpsmoeGnpsmoeAnpsGpsGpsTpsGpsApsAps Gps(5m)CpsGpsApsmoeAnpsmoeGnpsmoeUnpsmoeGnps(5m)moeC- C6-NH-GalNAc6 |
| 300 | 359 | GalNAc2-moeGnpsmoeCnpsmoeAnpsmoeGnpsmoeAnpsGpsGpsTps GpsApsApsGps(5m)CpsGpsApsmoeAnpsmoeGnpsmoeUnpsmoeGnps moeCn |
| 301 | 360 | GalNAc2-etoGnpseto(5m)CnpsetoAnpsetoGnpsetoAnpsGpsGps TpsGpsApsApsGps(5m)CpsGpsApsetoAnpsetoGnpsetoTnpseto Gnpseto(5m)Cn |
| 302 | 361 | mGnpsmCnps2-4-OCH$_2$AnpsmGnpsmAnpsGpsGpsTpsGpsApsApsGps CpsGpsAps2-4-OCH$_2$AnpsmGnpsmUnpsmGnps3-NH$_2$mC |
| 303 | 362 | mGnpsmCnps2-4-OCH$_2$CH$_2$AnpsmGnpsmAnpsGpsGpsTpsGpsApsAps GpsCpsGpsAps2-4-OCH$_2$CH$_2$AnpsmGnpsmUnpsmGnps3-NH$_2$mC |
| 304 | 363 | mGnpsmCnps2-4-OCH$_2$CH$_2$AnpsmGnps2-4OCH$_2$CH$_2$AnpsGpsGpsTps GpsApsApsGpsCpsGpsAps2-4-OCH$_2$CH$_2$AnpsmGnpsmUnpsmGnps3- NH$_2$mC |
| 305 | 364 | mGnpsmCnpsmAnpsmGnps2-4-OCH$_2$CH$_2$AnpsGpsGpsTpsGpsApsAps GpsCpsGpsAps2-4-OCH$_2$CH$_2$AnpsmGnpsmUnpsmGnps3-NH$_2$mC |
| 306 | 365 | 5-mGnpsmCnpsmUnpsmCnpsmCnps2-4-OCH$_2$CH$_2$AnpsApsApsTpsTps CpsTpsTpsTps2-4-OCH$_2$CH$_2$AnpsmUnpsmAnps2-4-OCH$_2$CH$_2$AnpsmGnpsmGnps3- NH$_2$mG-3 |
| 307 | 366 | mGnpsmCnpsmUnpsmCnpsmCnps2-4-OCH$_2$CH$_2$AnpsApsApsTpsTps CpsTpsTpsTps2-4-OCH$_2$CH$_2$AnpsmUnpsmAnps2-4-OCH$_2$CH$_2$Anpsm GnpsmGnps3-NH$_2$mG |
| 308 | 367 | mGnpsmCnpsmUnpsmCnpsmCnps2-4-OCH$_2$CH$_2$AnpsApsApsTpsTps CpsTpsTpsTps2-4-OCH$_2$CH$_2$AnpsmUnps2-4-OCH$_2$CH$_2$AnpsmAnps mGnpsmGnps3-NH$_2$mG |
| 309 | 368 | 2-4OCH$_2$CH$_2$GnpsmCnpsmAnpsmGnpsmAnpsGpsGpsTpsGpsApsAps GpsCpsGpsApsmAnpsmGnpsmUnps2-4OCH$_2$CH$_2$Gnps3-NH$_2$mC |
| 310 | 369 | 2-4OCH$_2$CH$_2$GnpsmCnpsmAnps2-4OCH$_2$CH$_2$GnpsmAnpsGpsGpsTps GpsApsApsGpsCpsGpsApsmAnps2-4OCH$_2$CH$_2$GnpsmUnps2-4OCH$_2$ CH$_2$Gnps3-NH$_2$mC |

TABLE D-continued

| #ID | SEQ ID NO: | Modified Sequence (5'-3') |
|---|---|---|
| 311 | 370 | 2-4OCH$_2$CH$_2$GnpsmCnps2-4-OCH$_2$CH$_2$AnpsmGnpsmAnpsGpsGpsTps GpsApsApsGpsCpsGpsApsmAnpsmGnpsmUnpsmGnps3-NH$_2$mC |
| 312 | 371 | 2-4OCH$_2$CH$_2$GnpsmCnpsmUnpsmCnpsmCnps2-4-OCH$_2$CH$_2$AnpsAps ApsTpsTpsCpsTpsTpsTpsmAnpsmUnpsmAnps2-4-OCH$_2$CH$_2$Anpsm Gnpsm2-4OCH$_2$CH$_2$Gnps3-NH$_2$mG |
| 313 | 372 | 2-4OCH$_2$CH$_2$GnpsmCnpsmUnpsmCnpsmCnpsmAnpsApsApsTpsTpsCps TpsTpsTpsmAnpsmUnpsmAnpsmAnpsmGnpsm2-4OCH$_2$CH$_2$Gnps3-NH$_2$mG |
| 314 | 373 | mGnpsmCnpsmAnpsmGnpsmAnpsGpsGpsTpsGpsApsApsGpsCpsGpsAp smAnpsmGnpsmUnpsmGnps3-NH$_2$mC |
| 315 | 374 | mGnps2-4OCH$_2$CH$_2$(5me)CnpsmAnps2-4OCH$_2$CH$_2$GnpsmAnpsGpsGps TpsGpsApsApsGpsCpsGpsApsmAnpsmGnps2-4OCH$_2$CH$_2$TnpsmGnps 3-NH$_2$mC |
| 316 | 375 | 2-4OCH$_2$CH$_2$GnpsmCnps2-4OCH$_2$CH$_2$AnpsmGnpsmAnpsGpsGpsTps GpsApsApsGpsCpsGpsApsmAnpsmGnps2-4OCH$_2$CH$_2$TnpsmGnps2-OCH$_2$CH$_2$3-NH$_2$(5me)C |
| 317 | 376 | 2-4OCH$_2$CH$_2$GnpsmCnps2-4OCH$_2$CH$_2$TnpsmCnpsmCnpsmAnpsApsAps TpsTpsCpsTpsTpsTpsmAnps2-4OCH$_2$CH$_2$TnpsmAnpsmAnpsmGnps2-4OCH$_2$CH$_2$Gnps3-NH$_2$mG |
| 318 | 377 | mGnps2-4OCH$_2$CH$_2$(5me)CnpsmUnps2-4OCH$_2$CH$_2$(5me)CnpsmCnpsm AnpsApsApsTpsTpsCpsTpsTpsTpsmAnps2-4OCH$_2$CH$_2$TnpsmAnpsm Anps2-4OCH$_2$CH$_2$GnpsmGnps3-NH$_2$mG |

In some embodiments, the oligonucleotide represented by Formula (VI) or (VI') is selected from the above Table C. In other embodiments, the oligonucleotide represented by Formula (VI) or (VI') has a sequence that differs from a chimeric oligonucleotide of the above list by one nucleotide. In other embodiments, the oligonucleotide represented by Formula (VI) or (VI') has a sequence that differs from a chimeric oligonucleotide of the above list by 1, 2, 3 or 4 nucleotides. In embodiments, the oligonucleotide represented by Formula (VI) or (VI') has a sequence that differs from a chimeric oligonucleotide of the above list but has the same construct as the chimeric oligonucleotide of the above list. In embodiments, the disclosed oligonucleotides display an increased affinity for a target nucleic acid sequence compared to an unmodified oligonucleotide of the same sequence. For example, in some sequences the disclosed oligonucleotides has a nucleobase sequence that is complementary or hybridizes to a target nucleic acid sequence at a higher affinity than an unmodified oligonucleotide of the same sequence. In embodiments, the disclosed oligonucleotide complexed with a complementary target nucleic acid sequence has a melting Temperature™ of >37° C. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with a target nucleic acid sequence under physiological conditions or nearly physiological conditions is >50° C.

In certain embodiments, the target nucleic acid sequence may be selected from a nucleic acid sequence of a known viral DNA or RNA sequence such as the HBV genome, for example those listed in Table E, F, or J.

In embodiments, the disclosed oligonucleotides display an affinity for at least one of the following six sequences of the HBV genome or its RNA equivalents and/or display stability complexed to at least one of the following six sequences of the HBV genome (Table E) or its RNA equivalents (Table F). In embodiments, the oligonucleotide complexed with a complementary HBV genome sequence has a melting temperature (Tm) of >37° C. The HBV genome may be an RNA sequence such as DR-1 and/or DR-2 RNA sequence. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with an HBV RNA under physiological conditions or nearly physiological conditions is >50° C.

TABLE E

| 1 (SEQ ID NO: 587) | | 2 (SEQ ID NO: 588) | | 3 (SEQ ID NO: 589) | | 4 (SEQ ID NO: 590) | | 5 (SEQ ID NO: 591) | | 6 (SEQ ID NO: 592) | |
|---|---|---|---|---|---|---|---|---|---|---|---|
| 245 | A | 668 | T | 1257 | T | 1512 | A | 1575 | C | 1819 | A |
| 246 | G | 669 | G | 1258 | C | 1513 | C | 1576 | C | 1820 | C |
| 247 | T | 670 | G | 1259 | T | 1514 | C | 1577 | G | 1821 | T |
| 248 | C | 671 | C | 1260 | G | 1515 | G | 1578 | T | 1822 | T |
| 249 | T | 672 | T | 1261 | C | 1516 | A | 1579 | G | 1823 | T |
| 250 | A | 673 | C | 1262 | C | 1517 | C | 1580 | T | 1824 | T |

TABLE E-continued

| 1 (SEQ ID NO: 587) | | 2 (SEQ ID NO: 588) | | 3 (SEQ ID NO: 589) | | 4 (SEQ ID NO: 590) | | 5 (SEQ ID NO: 591) | | 6 (SEQ ID NO: 592) | |
|---|---|---|---|---|---|---|---|---|---|---|---|
| 251 | G | 674 | A | 1263 | G | 1518 | C | 1581 | G | 1825 | T |
| 252 | A | 675 | G | 1264 | A | 1519 | A | 1582 | C | 1826 | C |
| 253 | C | 676 | T | 1265 | T | 1520 | C | 1583 | A | 1827 | A |
| 254 | T | 677 | T | 1266 | C | 1521 | G | 1584 | C | 1828 | C |
| 255 | C | 678 | T | 1267 | C | 1522 | G | 1585 | T | 1829 | C |
| 256 | G | 679 | A | 1268 | A | 1523 | G | 1586 | T | 1830 | T |
| 257 | T | 680 | C | 1269 | T | 1524 | G | 1587 | C | 1831 | C |
| 258 | G | 681 | T | 1270 | A | 1525 | C | 1588 | G | 1832 | T |
| 259 | G | 682 | A | 1271 | C | 1526 | G | 1589 | C | 1833 | G |
| 260 | T | 683 | G | 1272 | T | 1527 | C | 1590 | T | 1834 | C |
| 261 | G | 684 | T | 1273 | G | 1528 | A | 1591 | T | 1835 | C |
| 262 | G | 685 | G | 1274 | C | 1529 | C | 1592 | C | 1836 | T |
| 263 | A | 686 | C | 1275 | G | 1530 | G | 1593 | A | 1837 | A |
| 264 | C | 687 | C | 1276 | G | 1531 | T | 1594 | C | 1838 | A |
| 265 | T | 688 | A | 1277 | A | 1532 | C | 1595 | C | 1839 | T |
| 266 | T | 689 | T | 1278 | A | 1533 | T | 1596 | T | 1840 | C |
|  |  | 690 | T | 1279 | C | 1534 | C | 1597 | C | 1841 | A |
|  |  | 691 | T | 1280 | T | 1535 | T | 1598 | T | 1842 | T |
|  |  | 692 | G | 1281 | C | 1536 | T | 1599 | G | 1843 | C |
|  |  | 693 | T | 1282 | C | 1537 | T | 1600 | C | 1844 | T |
|  |  | 694 | T | 1283 | T |  |  | 1601 | A | 1845 | C |
|  |  | 695 | C | 1284 | A |  |  | 1602 | C | 1846 | T |
|  |  | 696 | A | 1285 | G |  |  | 1603 | G | 1847 | T |
|  |  | 697 | G | 1286 | C |  |  | 1604 | T | 1848 | G |
|  |  | 698 | T |  |  |  |  | 1605 | C | 1849 | T |
|  |  | 699 | G |  |  |  |  | 1606 | G | 1850 | T |
|  |  | 700 | G |  |  |  |  | 1607 | C | 1851 | C |
|  |  | 701 | T |  |  |  |  | 1608 | A | 1852 | A |
|  |  | 702 | T |  |  |  |  | 1609 | T |  |  |
|  |  | 703 | C |  |  |  |  | 1610 | G |  |  |
|  |  | 704 | G |  |  |  |  | 1611 | G |  |  |
|  |  | 705 | T |  |  |  |  | 1612 | A |  |  |
|  |  | 706 | A |  |  |  |  |  |  |  |  |
|  |  | 707 | G |  |  |  |  |  |  |  |  |
|  |  | 708 | G |  |  |  |  |  |  |  |  |
|  |  | 709 | G |  |  |  |  |  |  |  |  |
|  |  | 710 | C |  |  |  |  |  |  |  |  |
|  |  | 711 | T |  |  |  |  |  |  |  |  |
|  |  | 712 | T |  |  |  |  |  |  |  |  |
|  |  | 713 | T |  |  |  |  |  |  |  |  |
|  |  | 714 | C |  |  |  |  |  |  |  |  |
|  |  | 715 | C |  |  |  |  |  |  |  |  |

TABLE F

| 1 (SEQ ID NO: 593) | | 2 (SEQ ID NO: 594) | | 3 (SEQ ID NO: 595) | | 4 (SEQ ID NO: 596) | | 5 (SEQ ID NO: 597) | | 6 (SEQ ID NO: 598) | |
|---|---|---|---|---|---|---|---|---|---|---|---|
| 245 | A | 668 | U | 1257 | U | 1512 | A | 1575 | C | 1819 | A |
| 246 | G | 669 | G | 1258 | C | 1513 | C | 1576 | C | 1820 | C |
| 247 | U | 670 | G | 1259 | U | 1514 | C | 1577 | G | 1821 | U |
| 248 | C | 671 | C | 1260 | G | 1515 | G | 1578 | U | 1822 | U |
| 249 | U | 672 | U | 1261 | C | 1516 | A | 1579 | G | 1823 | U |
| 250 | A | 673 | C | 1262 | C | 1517 | C | 1580 | U | 1824 | U |
| 251 | G | 674 | A | 1263 | G | 1518 | C | 1581 | G | 1825 | U |
| 252 | A | 675 | G | 1264 | A | 1519 | A | 1582 | C | 1826 | C |
| 253 | C | 676 | U | 1265 | U | 1520 | C | 1583 | A | 1827 | A |
| 254 | U | 677 | U | 1266 | C | 1521 | G | 1584 | C | 1828 | C |
| 255 | C | 678 | U | 1267 | C | 1522 | G | 1585 | U | 1829 | C |
| 256 | G | 679 | A | 1268 | A | 1523 | G | 1586 | U | 1830 | U |
| 257 | U | 680 | C | 1269 | U | 1524 | G | 1587 | C | 1831 | C |
| 258 | G | 681 | U | 1270 | A | 1525 | C | 1588 | G | 1832 | U |
| 259 | G | 682 | A | 1271 | C | 1526 | G | 1589 | C | 1833 | G |
| 260 | U | 683 | G | 1272 | U | 1527 | C | 1590 | U | 1834 | C |
| 261 | G | 684 | U | 1273 | G | 1528 | A | 1591 | U | 1835 | C |
| 262 | G | 685 | G | 1274 | C | 1529 | C | 1592 | C | 1836 | U |
| 263 | A | 686 | C | 1275 | G | 1530 | G | 1593 | A | 1837 | A |
| 264 | C | 687 | C | 1276 | G | 1531 | U | 1594 | C | 1838 | A |
| 265 | U | 688 | A | 1277 | A | 1532 | C | 1595 | C | 1839 | U |
| 266 | U | 689 | U | 1278 | A | 1533 | U | 1596 | U | 1840 | C |
|  |  | 690 | U | 1279 | C | 1534 | C | 1597 | C | 1841 | A |
|  |  | 691 | U | 1280 | U | 1535 | U | 1598 | U | 1842 | U |

TABLE F-continued

| 1 (SEQ ID NO: 593) | 2 (SEQ ID NO: 594) | 3 (SEQ ID NO: 595) | | 4 (SEQ ID NO: 596) | | 5 (SEQ ID NO: 597) | | 6 (SEQ ID NO: 598) | |
|---|---|---|---|---|---|---|---|---|---|
| | 692 | G | 1281 | C | 1536 | U | 1599 | G | 1843 | C |
| | 693 | U | 1282 | C | 1537 | U | 1600 | C | 1844 | U |
| | 694 | U | 1283 | U | | | 1601 | A | 1845 | C |
| | 695 | C | 1284 | A | | | 1602 | C | 1846 | U |
| | 696 | A | 1285 | G | | | 1603 | G | 1847 | U |
| | 697 | G | 1286 | C | | | 1604 | U | 1848 | G |
| | 698 | U | | | | | 1605 | C | 1849 | U |
| | 699 | G | | | | | 1606 | G | 1850 | U |
| | 700 | G | | | | | 1607 | C | 1851 | C |
| | 701 | U | | | | | 1608 | A | 1852 | A |
| | 702 | U | | | | | 1609 | U | | |
| | 703 | C | | | | | 1610 | G | | |
| | 704 | G | | | | | 1611 | G | | |
| | 705 | U | | | | | 1612 | A | | |
| | 706 | A | | | | | | | | |
| | 707 | G | | | | | | | | |
| | 708 | G | | | | | | | | |
| | 709 | G | | | | | | | | |
| | 710 | C | | | | | | | | |
| | 711 | U | | | | | | | | |
| | 712 | U | | | | | | | | |
| | 713 | U | | | | | | | | |
| | 714 | C | | | | | | | | |
| | 715 | C | | | | | | | | |

Compounds of the present disclosure include compounds comprising the following Formula (VII):

$$5'\text{-}X'\text{—}Y'\text{—}Z'\text{-}3' \quad \text{(VII)}$$

wherein X'—Y'—Z' is a chimeric oligonucleotide comprising a sequence of 14 to 22 nucleosides, and is optionally conjugated at the 5' and/or 3' end to a ligand targeting group or a pharmacophore, X' is a domain comprising a sequence of modified nucleosides that is 3-14 nucleosides in length; Y' is a domain comprising a sequence of 2 to 4 2'-deoxynucleosides linked through intersubunit linkages; and Z' is a domain comprising a sequence of modified nucleosides that is 3-14 nucleosides in length, wherein the X' and/or Y' domains comprise one or more modified nucleoside which is linked through a N3'→P5' phosphoramidate or a N3'→P5' thiophosphoramidate intersubunit linkage.

The chimeric oligonucleotide represented by X'—Y'—Z' of Formula (VII) comprises a sequence of 14 to 22 nucleotides, for example, 14, 15, 16, 17, 18, 19, 20, 21, or 22 nucleotides. In some embodiments, the number of nucleotides in each of X', Y' and Z', respectively is: 8/2/10, 9/2/10, 10/2/10, 7/3/10, 8/3/10, 9/3/10, 8/4/8, 9/4/9, 6/4/8. In some embodiments, X' is 6-10, Y' is 2-4 and Z' is 8-10.

In some embodiments, the compound of Formula (VII) consists of the X'—Y'—Z' chimeric oligonucleotide consisting of a sequence of 14 to 22 nucleotides, and is optionally conjugated at the 5' and/or 3' end (e.g., 5' end, 3' end or both 5' and 3' ends) to a ligand targeting group and/or a pharmacophore, where X' is a domain consisting of a sequence containing one or more modified nucleotides that is 3-10 nucleotides in length; Z' is a domain consisting of a sequence containing one or more modified nucleotides that is 3-10 nucleotides in length; and Y' is a domain consisting of a sequence of 2 to 4 2'-deoxy-nucleotides linked through thiophosphate intersubunit linkages and optionally one phosphodiester intersubunit linkage, wherein the X' and/or Y' domains contain one or more modified nucleotide which is linked through a N3'→P5' phosphoramidate or a N3'→P5' thiophosphoramidate intersubunit linkage.

The X' domain comprises a sequence of modified nucleotides, where the X' domain is 4-10 nucleotides in length. For example, the X' domain may comprise a sequence of 4, 5, 6, 7, 8, 9, or 10 nucleotides. One or more (e.g., 1, 2, 3, 4, 5, 6, 7, 8, 9, 10, 11, 12, 13, 14, 15, 16, 17, 18, 19, 20, 21 or 22) of these nucleotides is modified. For example, in some embodiments, all the nucleotides in the X' domain are modified.

The modified nucleotides of the X' domain may be the same as disclosed for X in Formula (VI) or (VI'). For example, the nucleotides of the X' domain may be modified with respect to one or more of their nucleobases, the 2' and/or 3' positions on the ribose sugar and their intersubunit linkages. Embodiments include wherein the 2' position is modified with an F (ribo or arabino) and the 3' position is O or NH. Embodiments also include wherein the 2' position is modified with an OMe and the 3' position is O or NH. Embodiments include wherein the 2' position is modified with an F (ribo or arabino) as well as Me or OMe, and the 3' position is O or NH. Embodiments include wherein the 2' position is modified with an F (ribo or arabino) and the 3' position is O or NH. Embodiments include wherein the 2' position is modified with an O-methoxyethoxy and the 3' position is O or NH. Embodiments also include wherein the 2' position is modified with an F (ribo or arabino) and the 3' position is O or NH. Embodiments include wherein the 2' and 4' positions are modified bridging group (as described elsewhere herein) to form a conformationally restricted nucleotide and the 3' position is O or NH. Each of these embodiments may include thiophosphate (or thiophosphoramidate depending on the 3' substitution) and phosphoramidate intersubunit linkages.

Embodiments also include where the 2' position is OH, and the 3' position is NH, or where the 2' position is H, and the 3' position is NH. Each of these embodiments may include thiophosphoramidate and/or phosphoramidate intersubunit linkages.

The nucleotides of the X' domain are linked through intersubunit linkages, for example, N3'→P5' phosphoramidate, N3'→P5' thiophosphoramidate, thiophosphate or phosphodiester intersubunit linkages. In some embodiments, the X' domain is linked through intersubunit linkages selected from N3'→P5' phosphoramidate, N3'→P5' thiophosphoramidate, and combinations thereof. In some embodiments, the X' domain comprises at least 1, 2, 3, 4, 5, 6, 7, 8, 9 or 10 from N3'→P5' phosphoramidate and/or N3'→P5' thiophosphoramidate intersubunit linkages.

The Y' domain comprises a sequence of 2 to 4 2'-deoxynucleotides. For example, the Y' domain may comprise a sequence of 2, 3, or 4 2'-deoxynucleotides. One or more of the 2'-deoxynucleotides may be linked through thiophosphate or phosphodiester intersubunit linkages (e.g., 1, 2, 3, 4, 5, 6, 7, 8, 9, 10, 11, 12, 13, 14, 15, 16, 17, 18, 19, 20, 21 or 22). In some embodiments, each of the 2'-deoxynucleotides is linked through a thiophosphate intersubunit linkage. In other embodiments, each of the 2'-deoxynucleotides is linked through a phosphodiester intersubunit linkage. In other embodiments, the Y' domain consists of 2'-deoxynucleotides linked through thiophosphate intersubunit linkages, and optionally one phosphodiester intersubunit linkage.

The Z' domain comprises a sequence of modified nucleotides, where the Z' domain is 4-10 nucleotides in length. For example, the Z' domain may comprise a sequence of 4, 5, 6, 7, 8, 9, or 10 nucleotides. One or more of these nucleotides is modified (e.g., 1, 2, 3, 4, 5, 6, 7, 8, 9, 10, 11, 12, 13, 14, 15, 16, 17, 18, 19, 20, 21 or 22). For example, in some embodiments, all the nucleotides in the Z' domain are modified.

The modified nucleotides of the Z' domain may be the same as disclosed for Z in Formula (VI) or (VI'). For example, the nucleotides of the Z' domain may be modified with respect to one or more of their nucleobases, the 2' and/or 3' positions on the ribose sugar and their intersubunit linkages. Embodiments include wherein the 2' position is modified with an F (ribo or arabino) and the 3' position is O or NH. Embodiments also include wherein the 2' position is modified with an OMe and the 3' position is O or NH. Embodiments include wherein the 2' position is modified with an F (ribo or arabino) as well as Me or OMe, and the 3' position is O or NH. Embodiments include wherein the 2' position is modified with an F (ribo or arabino) and the 3' position is O or NH. Embodiments include wherein the 2' position is modified with an O-methoxyethoxy and the 3' position is O or NH. Embodiments also include wherein the 2' position is modified with an F (ribo or arabino) and the 3' position is O or NH. Embodiments include wherein the 2' and 4' positions are modified bridging group (as described elsewhere herein) to form a conformationally restricted nucleotide and the 3' position is O or NH. Each of these embodiments may include thiophosphate (or thiophosphoramidate depending on the 3' substitution) and phosphoramidate intersubunit linkages.

Embodiments also include where the 2' position is OH, and the 3' position is NH, or where the 2' position is H, and the 3' position is NH. Each of these embodiments may include thiophosphoramidate and/or phosphoramidate intersubunit linkages.

The nucleotides of the Z' domain are linked through intersubunit linkages, for example, N3'→P5' phosphoramidate, N3'→P5' thiophosphoramidate, thiophosphate or phosphodiester intersubunit linkages. In some embodiments, the Z' domain is linked through intersubunit linkages selected from N3'→P5' phosphoramidate, N3'→P5' thiophosphoramidate, and combinations thereof. In some embodiments, the Z' domain comprises at least 1, 2, 3, 4, 5, 6, 7, 8, 9 or 10 from N3'→P5' phosphoramidate and/or N3'→P5' thiophosphoramidate intersubunit linkages.

C. Modified Antisense Oligonucleotides

Other compounds include modified antisense oligonucleotides. In some embodiments the ASO includes the nucleotide of formula (I), (II), (IIIa), (IIIb), (IV), (V) and/or (V').

Other compounds of the present disclosure include compounds comprising the following Formula (VIII):

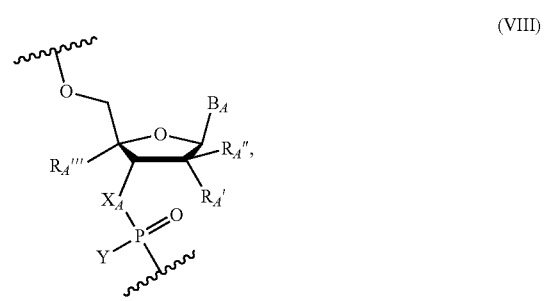

(VIII)

wherein $X_A$ is NH or O, Y is OR or SR, where R is H or a positively charged counter ion, $B_A$ is independently in each instance a natural or an unmodified nucleobase or a modified nucleobase, $R_A'$ and $R_A''$ are each independently in each instance selected from H, F, OH, OMe, 0-methoxyethoxy, and $R_A'''$ is H or $R_A'$ and $R_A'''$ together form —O—CH$_2$—, —O—CH(Me)- or —O—(CH$_2$)$_2$—.

In some embodiments, $R_A'$ and $R_A'''$ are H; and $R_A''$ is selected from F, OH, OMe, Me, O-methoxyethoxy. In other embodiments, $R_A''$ and $R_A'''$ are H; and $R_A'$ is selected from F, OMe, Me, O-methoxyethoxy. In some embodiments, $X_A$ is NH in each instance.

Some embodiments include one or more modified nucleotides represented by Formula (VIII), wherein $X_A$ is NH; $B_A$ is a G-clamp; $R_A'$ is F or OMe and $R_A''$ is H; or $R_A'$ is H and $R_A''$ is H or F; and $R_A'''$ is H.

Some embodiments include one or more modified nucleotides represented by Formula (VIII), wherein $X_A$ is NH; $B_A$ is an unmodified or modified nucleobase; $R_A'$ and $R_A'''$ together form a conformationally restricted nucleotide (e.g., —O—CH$_2$— or —O—(CH$_2$)$_2$—); and $R_A''$ is H. In some embodiments, $B_A$ is an unmodified or a modified nucleobase selected from the group consisting of 5-methylcytosine, 2,6-diaminopurine, and 5-methyluracil.

Some embodiments include one or more modified nucleotides represented by Formula (VIII), wherein $X_A$ is NH; B is an unmodified or modified nucleobase; $R_A'$ is F or OMe, $R_A''$ is H and $R_A'''$ is H.

Some embodiments include one or more modified nucleotides represented by Formula (VIII), wherein $X_A$ is NH; $B_A$ is an unmodified or modified nucleobase; $R_A'$ is H, $R_A''$ is F and $R_A'''$ is H.

In some embodiments, $X_A$ is NH. In other embodiments, Y is O'' or S'' (with a positively charged counter ion). In some embodiments, $R_A'$ or $R_A''$ is H and the other is F, OH, OMe, Me, O-methoxyethoxy (e.g. arabino-F or ribo-F or OMe).

In some embodiments, $B_A$ is selected from A, C, G, U and T. In additional embodiments, $B_A$ is selected from A, C, G, U, T, 2,6-diaminopurine, a 5-Me pyrimidine (e.g., 5-methylcytosine, 5-methyluracil). In some embodiments, at least one of $R_A'$ and $R_A''$ is H. For example, in some embodiments, $R_A'$ is F, OH, OMe, Me, O-methoxyethoxy and $R_A''$ is H. In other embodiments, $R_A'$ is H and $R_A''$ is F.

In some embodiments, when $B_A$ is a purine nucleobase at least one of $R_A'$ and $R_A''$ is OH or F, and/or when $B_A$ is a pyrimidine nucleobase at least one of $R_A'$ and $R_A''$ is OMe, OH or F.

In other embodiments, the nucleotides include one or more of the nucleotides in Table G.

TABLE G

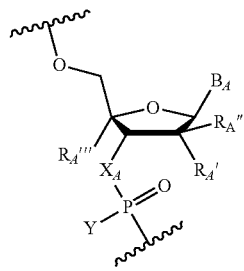

| Nucleotide No. | R' | R'' | R''' | A | W |
|---|---|---|---|---|---|
| 48 | F | H | H | NH | S |
| 49 | F | H | H | NH | O |
| 50 | F | H | H | O | S |
| 51 | F | H | H | O | O |
| 52 | H | F | H | NH | S |
| 53 | H | F | H | NH | O |
| 54 | H | F | H | O | S |
| 55 | H | F | H | O | O |
| 56 | OMe | H | H | NH | S |
| 57 | OMe | H | H | NH | O |
| 58 | OMe | H | H | O | S |
| 59 | OMe | H | H | O | O |
| 60 | H | F | H | NH | S |
| 61 | H | F | H | NH | O |
| 62 | H | F | H | O | S |
| 63 | H | F | H | O | O |
| 64 | O-methoxyethoxy | H | H | NH | S |
| 65 | O-methoxyethoxy | H | H | NH | O |
| 66 | O-methoxyethoxy | H | H | O | S |
| 67 | O-methoxyethoxy | H | H | O | O |
| 68 | H | H | H | NH | S |
| 69 | H | H | H | NH | O |
| 70 | OH | H | H | NH | S |
| 71 | OH | H | H | NH | O |
| 72 | OH | H | H | O | S |
| 73 | H | OH | H | NH | O |
| 74 | H | OH | H | NH | S |
| 75 | H | OEt | H | NH | O |
| 76 | H | OEt | H | NH | S |
| 77 | H | OEt | H | O | O |
| 78 | H | OEt | H | O | S |
| 79 | OEt | H | H | NH | O |
| 80 | OEt | H | H | NH | S |
| 81 | OEt | H | H | O | O |
| 82 | OEt | H | H | O | S |

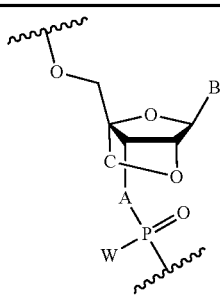

| Nucleotide No. | C | A | W |
|---|---|---|---|
| 83 | —O—$CH_2$— | NH | S |
| 84 | —O—$CH_2$— | NH | O |
| 85 | —O—$CH_2$— | O | S |
| 86 | —O—$CH_2$— | O | O |
| 87 | —O—$(CH_2)_2$— | NH | S |
| 88 | —O—$(CH_2)_2$— | NH | O |
| 89 | —O—$(CH_2)_2$— | O | S |
| 90 | —O—$(CH_2)_2$— | O | O |
| 91 | —O—CH(Me)— | NH | S |
| 92 | —O—CH(Me)— | NH | O |
| 93 | —O—CH(Me)— | O | S |
| 94 | —O—CH(Me)— | O | O |

Compounds of the present disclosure also include oligonucleotides comprising ten or more nucleotides of the following Formula (IX):

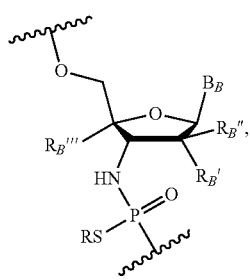

(IX)

wherein R is H or a positively charged counter ion, $B_B$ is independently in each instance a natural or an unmodified nucleobase or a modified nucleobase, $R_B'$ and $R_B''$ are each independently in each instance selected from H, F, OMe, O-methoxyethoxy, and $R_B'''$ is H or $R_B'$ and $R_B'''$ together form —O—$CH_2$—, —O—CH(Me)-, or —O—$(CH_2)_2$—.

In some embodiments, every oligonucleotide is a nucleotide of the Formula (IX).

In some embodiments, $R_B'$ and $R_B'''$ are H and $R_B''$ is selected from F, OH, OMe, Me, O-methoxyethoxy. In other embodiments, $R_B''$ and $R_B'''$ are H; and $R_B'$ is selected from F, OMe, Me, O-methoxyethoxy.

Some embodiments include one or more modified nucleotides represented by Formula (IX), wherein $B_A$ is a G-clamp; $R_B'$ is F or OMe and $R_B''$ is H; or $R_B'$ is H and $R_B''$ is H or F; and $R_B'''$ is H.

Some embodiments include one or more modified nucleotides represented by Formula (IX), wherein $B_A$ is an unmodified or modified nucleobase; $R_B'$ and $R_B''$ together form a conformationally restricted nucleotide (e.g., —O—$CH_2$— or —O—$(CH_2)_2$—); and $R_B'''$ is H. In some embodiments, $B_A$ is an unmodified or a modified nucleobase selected from the group consisting of 5-methylcytosine, 2,6-diaminopurine, and 5-methyluracil.

Some embodiments include one or more modified nucleotides represented by Formula (IX), wherein B is an unmodified or modified nucleobase; $R_B'$ is F or OMe, $R_B''$ is H and $R_B'''$ is H.

Some embodiments include one or more modified nucleotides represented by Formula (IX), wherein $B_A$ is an unmodified or modified nucleobase; $R_B'$ is H, $R_B''$ is F and $R_B'''$ is H.

In other embodiments, Y is 5" (with a positively charged counter ion). In some embodiments, $R_B'$ or $R_B''$ is H and the other is F, OH, OMe, Me, O-methoxyethoxy (e.g. arabino-F or ribo-F or OMe).

In some embodiments, $B_B$ is selected from A, C, G, U and T. In additional embodiments, $B_B$ is selected from A, C, G, U, T, 2,6-diaminopurine, a 5-Me pyrimidine (e.g., 5-methylcytosine). In some embodiments, at least one of $R_B'$ and $R_B"$ is H. For example, in some embodiments, $R_A'$ is F, OH, OMe, Me, O-methoxyethoxy and $R_B"$ is H. In other embodiments, $R_B'$ is H and $R_B"$ is F.

In some embodiments, when $B_B$ is a purine nucleobase at least one of $R_B'$ and $R_B"$ is OH or F, and/or when $B_B$ is a pyrimidine nucleobase at least one of $R_B'$ and $R_B"$ is OMe, OH or F.

In some embodiments, the nucleobase sequence of the oligonucleotide of Formulae (VIII) or (IX) comprises a sequence selected from those in Table A. In some embodiments, the nucleobase sequence of the oligonucleotide of Formulae (VIII) or (IX) comprises a sequence 1, 2, 3, 4, or 5 nucleobases different from a sequence selected from those in Table H.

TABLE H

| Nucleobase Sequence (5'-3') | SEQ. ID NO. |
|---|---|
| 5'-GCAGAGGTGAAGCGAAGUGC-3' | 1 |
| 5'-GCAGAGGTGAAGCGAAGUGC-Chol-3' | 2 |
| 5'-GCAGAGGTGAAGCGAAGUGC-GalNAc-3' | 3 |
| 5'-GAUUAGGCAGAGGTGAAAAAG-3' | 4 |
| 5'-GAUUAGGCAGAGGTGAAAAAG-Chol-3' | 5 |
| 5'-GAUUAGGCAGAGGTGAAAAAG-GalNAc-3' | 6 |
| 5'-GAUUAGGCAGAGGTGAAAAAG-3' | 7 |
| 5'-GAUUAGGCAGAGGTGAAAAAG-Chol-3' | 8 |
| 5'-GAUUAGGCAGAGGTGAAAAAG-GalNAc-3' | 9 |
| 5'-GDAPUUDAPGGCAGAGGTGAAAAAG-3' | 10 |
| 5'-GAUUAGGCAGAGGTGAADAPDAPDAPG-3' | 11 |
| 5'-GAUUAGGCAGAGGTGDAPDAPDAPDAPDAPG-3' | 12 |
| 5'-GDAPUUDAPGGCAGAGGTGAADAPDAPDAPG-3' | 13 |
| 5'-GDAPUUDAPGGCAGAGGTGDAPDAPDAPDAPDAPG-3' | 14 |
| 5'-GDAPUUDAPGGCAGAGGTGAAAAAG-3' | 15 |
| 5'-GAUUAGGCAGAGGTGAADAPDAPDAPG-3' | 16 |
| 5'-GAUUAGGCAGAGGTGDAPDAPDAPDAPDAPG-3' | 17 |
| 5'-GDAPUUDAPGGCAGAGGTGAADAPDAPDAPG-3' | 18 |
| 5'-GDAPUUDAPGGCAGAGGTGDAPDAPDAPDAPDAPG-3' | 19 |
| 5'-GCAGAGGTGAAGCGADAPGUGC-3' | 20 |
| 5'-GCAGAGGTGAAGCGDAPDAPGUGC-3' | 21 |
| 5'-GCAGDAPGGTGAAGCGDAPDAPGUGC-3' | 22 |
| 5'-GCDAPGDAPGGTGAAGCGDAPDAPGUGC-3' | 23 |
| 5'-CGTGCAGAGGTGAAGC-3-NH$_2$-G-3' | 24 |
| 5'-GCAGAGGTGAAGCGAA-3-NH$_2$-G-3 | 25 |
| 5'-CGACGTGCAGAGGTGAAG-3-NH$_2$-C-3' | 26 |
| 5'-GCAGAGGTGAAGCGAAGTG-3-NH$_2$-C-3' | 27 |
| 5'-GCAGAGGTGAAGC-3-NH$_2$-G-3' | 28 |
| 5'-CGTGCAGAGGTGAAG-3-NH$_2$-C-3' | 29 |
| 5'-GCAGAGGTGAAGCGAAGTG-3NH$_2$-C-3' | 30 |
| 5'-GCAGAGGTGAAGCGAAGTG-3NH$_2$-C-3' | 31 |
| 5'-GCAGAGGTGAAGCGAAGTG-3NH$_2$-C-3' | 32 |
| 5'-GCAGAGGTGAAGCGAAGTG-3NH$_2$-C-3' | 33 |
| 5'-GCAGAGGTGAAGCGAAGTG-3NH$_2$-C-3' | 34 |

TABLE H-continued

| Nucleobase Sequence (5'-3') | SEQ. ID NO. |
|---|---|
| 5'-GCAGAGGTGAAGCGAAGTG-3NH$_2$-C-3' | 35 |
| 5'-GCAGAGGTGAAGCGAAGTG-3NH$_2$-C-3' | 36 |
| 5'-GCAGAGGTGAAGCGAAGTG-3NH$_2$-C-3' | 37 |
| 5'-GCAGAGGTGAAGCGAAGTG-3NH$_2$-C-3' | 38 |
| 5'-GCAGAGGTGAAGCGAAGTG-3NH$_2$-C-3' | 39 |
| 5'-GCAGAGGTGAAGCGAAGTG-3NH$_2$-C-3' | 40 |
| 5'-GCAGAGGTGAAGCGAAGTG-3NH$_2$-C-3' | 41 |
| 5'-GCAGAGGTGAAGCGAAGTG-3-NH$_2$-C-3' | 42 |
| 5'-AAGAGAGGTG5meCG5meC5meC5meCGUGG-3' | 43 |
| 5'-GGUGAAG5meCGAAGTG5meCA5meCA5meCG-3' | 44 |
| 5'-5meCGUG5meCAGAGGTGAAG5meCGAAG-3' | 45 |
| 5'-AGAGGTGAAG5meCGAAGUG5meCA5meC-3' | 46 |
| 5'-UGG5meCA5meCTAGTAAA5meCTGAG5meC5meC-3' | 47 |
| 5'-5meCUAGGAGTT5meC5meCG5meCAGUAUGG-3' | 48 |
| 5'-AGAGGTG5meCG5meC5meC5meC5meCGTGGU5meCG-3' | 49 |
| 5'-GAGGUG5meCG5meC5meC5meC5meCGTGGU5meCGG-3' | 50 |
| 5'-GAAAG5meC5meC5meCTA5meCGAA5meC5meCA5meCUG-3' | 51 |
| 5'-GUU5meC5meCG5meCAGTATGGAU5meCGG5meC-3' | 52 |
| 5'-U5meC5meCG5meCAGTATGGAT5meCGG5meCAG-3' | 53 |
| 5'-A5meC5meCA5meCTGAA5meCAAATGG5meCA5meCU-3' | 54 |
| 5'-UG5meCAGAGGTGAAG5meCGAAGUG-3' | 55 |
| 5'-A5meCUGAA5meCAAATGG5meCA5meCUAGU-3' | 56 |
| 5'-AGU5meC5meCA5meC5meCA5meCGAGT5meCUAGA5meC-3' | 57 |
| 5'-5meCA5meCUGAA5meCAAATGG5meCA5meCUAG-3' | 58 |
| 5'-5meCAGAGGTGAAG5meCGAAGUG5meCA-3' | 59 |
| 5'-AAGAGAGGTG5meCG5meC5meC5meC5meCGUGG-GalNAc-3' | 60 |
| 5'-GGUGAAG5meCGAAGTG5meCA5meCA5meCG-GalNAc-3' | 61 |
| 5'-UGG5meCA5meCTAGTAAA5meCTGAG5meC5meC-GalNAc-3' | 62 |
| 5'-5meCUAGGAGTT5meC5meCG5meCAGUAUGGGalNAc-3' | 63 |
| 5'-AGAGGTG5meCG5meC5meC5meC5meCGTGGU5meCGGalNAc-3' | 64 |
| 5'-U5meC5meCG5meCAGTATGGAT5meCGG5meCAG-GalNAc-3' | 65 |
| 5'-UG5meCAGAGGTGAAG5meCGAAGUGGalNAc-3' | 66 |
| 5'-AGU5meC5meCA5meC5meCA5meCGAGT5meCUAGA5meC-GalNAc-3' | 67 |
| 5'-GCGGGTGAAGCGGUG-3-NH$_2$-C-3' | 68 |
| 5'-GCGGGTGAAGCGGUG-3-NH$_2$-C-3' | 69 |
| 5'-GCGGGTGAAGCGGUG-3-NH$_2$-C-3' | 70 |
| 5'-GCAGAGGTGAAGCGAAGTG-3NH$_2$-C-3' | 71 |
| 5'-GCAGAGGTGAAGCGAGTG-3NH$_2$-C-3' | 72 |

TABLE H-continued

| Nucleobase Sequence (5'-3') | SEQ. ID NO. |
|---|---|
| 5'-GCAGAGGTGAAGCGAAGTG-3NH$_2$-C-3' | 73 |
| 5'-GCAGnspAGGTGAAGCGAAGUGC-3' | 74 |
| 5'-GCAGAGGTGAAGCGAAGUGC-3' | 75 |
| 5'-GCAGAGGTGAAGCGAAGUGC-3' | 76 |
| 5-GCUCCAAATTCTTTAUAAGGG-GalNAc-3 | 77 |
| 5'-AAGAGAGGTG5meCG5meC5meC5meC5meCGUGG-3' | 78 |
| 5'-GGUGAAG5meCGAAGTG5meCA5meCA5meCG-3' | 79 |
| 5-5meCGUG5meCAGAGGTGAAG5meCGAAG-3' | 80 |
| 5'-GUGAAG5meCGAAGTG5meCA5meCA5meCGG-3' | 81 |
| 5'-AGAGGTGAAG5meCGAAGUG5meCA5meC-3' | 82 |
| 5'-UGG5meCA5meCTAGTAAA5meCTGAG5meC5meC-3' | 83 |
| 5'-5meCUAGGAGTT5meC5meCG5meCAGUAUGG-3' | 84 |
| 5'-G5meCAGAGGTGAAG5meCGAAGUG5meC-3' | 85 |
| 5'-AGAGGTG5meCG5meC5meC5meC5meCGTGGU5meCG-3' | 86 |
| 5'-GAGGUG5meCG5meC5meC5meC5meCGTGGU5meCGG-3' | 87 |
| 5'-GAAAG5meC5meC5meCTA5meCGAA5meC5meCA5meCUG-3' | 88 |
| 5'-GUU5meC5meCG5meCAGTATGGAU5meCGG5meC-3' | 89 |
| 5'-U5meC5meCG5meCAGTATGGAT5meCGG5meCAG-3' | 90 |
| 5'-A5meC5meCA5meCTGAA5meCAAATGG5meCA5meCU-3' | 91 |
| 5'-UG5meCAGAGGTGAAG5meCGAAGUG-3' | 92 |
| 5'-A5meCUGAA5meCAAATGG5meCA5meCUAGU-3' | 93 |
| 5'-AGU5meC5meCA5meC5meCA5meCGAGT5meCUAGA5meC-3' | 94 |
| 5'-5meCA5meCUGAA5meCAAATGG5meCA5meCUAG-3' | 95 |
| 5'-5meCAGAGGTGAAG5meCGAAGUG5meCA-3' | 96 |
| 5'-AAGAGAGGTG5meCG5meC5meC5meC5meCGUGG3' | 97 |
| 5'-AAGAGAGGTG5meCG5meC5meC5meC5meCGUGG-3' | 98 |
| 5'-GGUGAAG5meCGAAGTG5meCA5meCA5meCG3' | 99 |
| 5'-GGUGAAG5meCGAAGTG5meCA5meCA5meCG3' | 100 |
| 5'-UGG5meCA5meCTAGTAAA5meCTGAG5meC5meC3' | 101 |
| 5'-UGG5meCA5meCTAGTAAA5meCTGAG5meC5meC3' | 102 |
| 5'-5meCUAGGAGTT5meC5meCG5meCAGUAUGG3' | 103 |
| 5'-5meCUAGGAGTT5meC5meCG5meCAGUAUGG3' | 104 |
| 5'-GCAGAGGTGAAGCGAAG-3' | 105 |
| 5'-GCAGAGGTGAAGCGAAGTGC-3' | 106 |
| 5'-CGTGCAGAGGTGAAGCG-3' | 107 |
| 5'-GCAGAGGTGAAGCGAAG-3' | 108 |
| 5'-CGACGTGCAGAGGTGAAGC-3' | 109 |
| 5'-GCAGAGGTGAAGCGAAGTGC-3' | 110 |

TABLE H-continued

| Nucleobase Sequence (5'-3') | SEQ. ID NO. |
|---|---|
| 5'-GCAGAGGTGAAGCG-3' | 111 |
| 5'-CGTGCAGAGGTGAAGC-3' | 112 |
| 5'-GCAGAGGTGAAGCGAAGTG-3nh2-C-3' | 113 |
| 5'-GalNAc-NHC6-U5meC5meCG5meCAGTATGGAT5meCGG5meCAG3' | 114 |
| 5'-GalNAc-NHC6-5meCUAGGAGTT5meC5meCG5meCAGUAUGG3' | 115 |
| 5'-GalNAc-NHC6-AAGAGAGGTG5meCG5meC5meC5meC5meCGUGG3' | 116 |
| 5'GalNAc-NHC6-AGAGGTG5meCG5meC5meC5meC5meCGTGGU5meCG3' | 117 |
| 5'GalNAc-NHC6-UG5meCAGAGGTGAAG5meCGAAGUG3' | 118 |
| mGCUCCAAATTCTTTAUAAGG | 119 |
| mGCUCCAAATTCTTTAUAAGG | 120 |
| mGCUCCAAATTCTTTAUAAGGG | 121 |
| mGCUCCAAATTCTTTAUAAGG/GalNAc/ | 122 |
| mGCUCCAAATTCTTTAUAAGG/GalNAc/ | 123 |
| mGCUCCAAATTCTTTAUAAGG/3CholTEG/ | 124 |
| mGCUCCAAATTCTTTAUAAGG/3CholTEG/ | 125 |
| mGCUCCAAATTCTTTAUAAGGG/3CholTEG/ | 126 |
| 5'-mG5mCAGAGGTGAAGp5mCGAAGUG5meC-3 | 127 |
| 5'-mG5mCAGAGGTGAAG5mCGAAGUG5mC-Cholesterol-3' | 128 |
| 5'-mG5mCAGAGGTGAAGp5mCGAAGUG5mC-TEG-Cholesterol-3' | 129 |
| 5'-mG5mCAGAGGTGAAG5mCGAAGUG5mC-Tocopherol-3' | 130 |
| 5'-mG5mCAGAGGTGAAG5mCGAAGUG5mC-TEG-Tocopherol-3' | 131 |
| 5'-mG5mCAGAGGTGAAG5mCGAAGUG5mC-GalNAc-3' | 132 |
| 5'-mG5meCAGAGGTGAAG5meCGAAGUG5meC-3' | 133 |
| 5'-mG5meCAGAGGTGAAG5meCGAAGUG5meC-po-Chol-3' | 134 |
| 5'-mG5meCAGAGGTGAAG5meCGAAGUG5meC-po-Tocopherol-3' | 135 |
| 5'-mG5meCAGAGGTGAAG5meCGAAGUG5meC-po-GalNAc-3' | 136 |
| 5'-mG5meCAGAGGTGAAG5meCGAAGUG5meC-3' | 137 |
| 5'-mG5meCAGAGGTGAAG5meCGAAGUG5meC-po-Chol-3' | 138 |
| 5'-mG5meCAGAGGTGAAG5meCGAAGUG5meC-po-Tocopherol-3' | 139 |
| 5'-mG5meCAGAGGTGAAG5meCGAAGUG5meC-po-GalNAc-3' | 140 |
| 5-mG5meCAGAGGTGAAG5meCGAAGUG5meC-3 | 141 |
| 5-mG5meCAGAGGTGAAG5meCGAAGUG5meC-Chol-3 | 142 |
| 5-mG5meCAGAGGTGAAG5meCGAAGUG5meC-Toco-3 | 143 |
| 5-mG5meCAGAGGTGAAG5meCGAAGUG5meC-GalNAc-3 | 144 |
| 5-G5meCAGAGGTGAAG5meCGAAGUG5meC-3 | 145 |
| 5-G5meCAGAGGTGAAG5meCGAAGUG5meC-Chol-3 | 146 |
| 5-G5meCAGAGGTGAAG5meCGAAGUG5meC-Toco-3 | 147 |
| 5-G5meCAGAGGTGAAG5meCGAAGUG5meC-GalNAc-3 | 148 |

TABLE H-continued

| Nucleobase Sequence (5'-3') | SEQ. ID NO. |
|---|---|
| 5-G5meCAGAGGTGAAG5meCGAAGUG5meC-3 | 149 |
| 5-dTGCAGAGGTGAAGCGAAGTG-3 | 150 |
| 5-dTGCAGAGGTGAAGCGAAGUG3' | 151 |
| 5-GCAGAGGTGAAGCGAAGUGC-3' | 152 |
| 5-GCAGAGGTGAAGCGAAGUGC-3' | 153 |
| 5'-GCAGAGGTGAAGCGAAGUGC-3' | 154 |
| 5'-dGCAGAGGTGAAGCGAAGUGC-3' | 155 |
| 5'-dGCAGAGGTGAAGCGAAGUGC-3' | 156 |
| 5'-dGCAGAGGTGAAGCGAAGUGC-3' | 157 |
| 5'-dGCAGAGGTGAAGCGAAGUGC-3' | 158 |

In embodiments, the disclosed oligonucleotides display an affinity for at least one of the six sequences of the HBV genome or its RNA equivalents and/or display stability complexed to at least one of the following six sequences of the HBV genome (Table E) or its RNA equivalents (Table F). In embodiments, the oligonucleotide complexed with a complementary HBV genome sequence has a melting temperature (Tm) of >37° C. The HBV genome may be an RNA sequence such as DR-1 and/or DR-2 RNA sequence. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with an HBV RNA under physiological conditions or nearly physiological conditions is >50° C.

In some aspects of the disclosure, the nucleobase sequence of the oligonucleotide of Formula (VIII) or (IX) comprises a sequence of 12-22 nucleotides, for example, 14-20 nucleotides or 16-19 nucleotides. In some embodiments, the nucleobase sequence of the oligonucleotide of Formula (VIII) or (IX) is 12, 13, 14, 15, 16, 17, 18, 19, 20, 21 or 22 nucleotides in length.

In another aspect of the disclosure, the oligonucleotides described herein are conjugated or modified at one or more end.

For example, in some embodiments, a terminal end of the oligonucleotide is protected from hydrolytic cleavage by at least one modified nucleotide at said terminal end. In some embodiments, the modified nucleotide is a modified nucleotide comprising a modified nucleotide comprising a 3'-N modification, and may include a thiophosphoramidate subunit linkage. In some embodiments, the oligonucleotides of Formulae (VIII) and (IX) further comprise at least one nucleotide (e.g. 1 or 2) at the 3' and/or 5' end that contains a thiophosphate intersubunit linkage and a thymine nucleobase. In some embodiments, the oligonucleotides of Formulae (VIII) and (IX) further comprise at least one nucleotide (e.g. 1 or 2) at the 3' and/or 5' end that contains a 2'-OMe modified nucleotide and a thymine nucleobase. In some embodiments, the oligonucleotides of Formulae (VIII) and (IX) further comprise at least one 2'-OMe modified nucleotide at the 3' and/or 5' end that contains a thiophosphate intersubunit linkage and a uracil nucleobase. In some embodiments, the an inverted dT can be incorporated at the 3'-end of the oligonucleotides of Formulae (VIII) and (IX), leading to a 3'-3' linkage which may inhibit degradation by 3' exonucleases and/or extension by DNA polymerases.

D. Conjugated Oligonucleotides

The present disclosure is also directed to additional components conjugated to the oligonucleotide such as targeting moieties and oligonucleotides modified at one or more ends.

In some embodiments, the oligonucleotides described herein are conjugated to one or more ligand targeting group or pharmacophore, optionally through a linking moiety, such as a HEG linker or a C6 or C7 amino linker. In some embodiments, oligonucleotides described herein further comprises a ligand targeting group or a pharmacophore conjugated at the 5' and/or 3' end through an optional linker. In preferred embodiments, the oligonucleotides described herein further comprise a ligand-targeting group conjugated at the 5' and/or 3' end through an optional linker. In some embodiments, the conjugation is at the 3'-end of the oligonucleotides described herein.

In some embodiments, the ligand-targeting group or a pharmacophore enhances the activity, cellular distribution or cellular uptake of the oligonucleotide by a particular type of cell such as hepatocytes.

In some embodiments, the ligand targeting group may be a lipid moiety such as a cholesterol moiety, tocopherols, cholic acid, a thioether, e.g., beryl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-phosphonate, a polyamine or a polyethylene glycol chain, or adamantane acetic acid, a palmitoyl moiety, or an octadecylamine or hexylaminocarbonyloxycholesterol moiety For example, in some embodiments, a terminal end of the oligonucleotide is protected from hydrolytic cleavage by at least one modified nucleotide at the terminal end. In some embodiments, the modified nucleotide is a modified nucleotide comprising a modified nucleotide comprising a 3'-N modification, and may include a thiophosphoramidate subunit linkage. In some embodiments, the oligonucleotide strand further comprises at least one nucleotide (e.g. 1 or 2) at the 3' and/or 5' end that contains a thiophosphate intersubunit linkage and a thymine nucleobase. In some embodiments, the oligonucleotide strand further comprises at least one nucleotide (e.g. 1 or 2) at the 3' and/or 5' end that contains a 2'-F, 2'-OMe, 2'-OEt, or 2'-MOE modified nucleotide. In some embodiments, the oligonucleotide strand further comprises at least one 2'-OMe modified nucleotide at the 3' and/or 5' end that contains a thiophosphate intersubunit linkage and a uracil nucleobase. In embodiments, the 3' end of the ASO is attached through an np or po linkage to a C6 amino linker further linked to GalNAc-6. For example, the following structures can exemplify this construct:

cholic acid, a thioether, e.g., beryl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-phosphonate, a polyamine or a polyethylene glycol chain, or adamantane acetic acid, a palmitoyl moiety, or an octadecylamine or hexylaminocarbonyloxycholesterol moiety.

3'-GalNAc-6-Conjugated ASO's

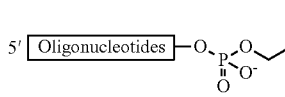
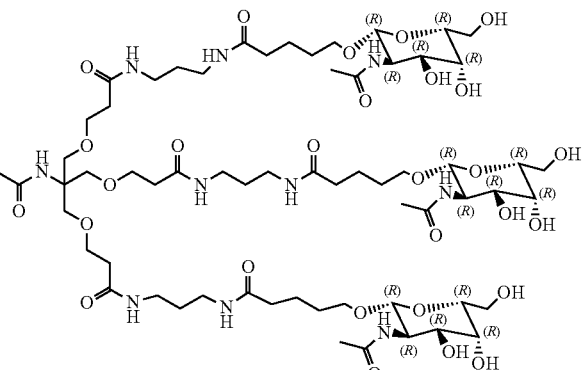

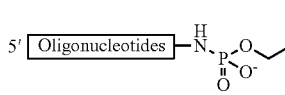
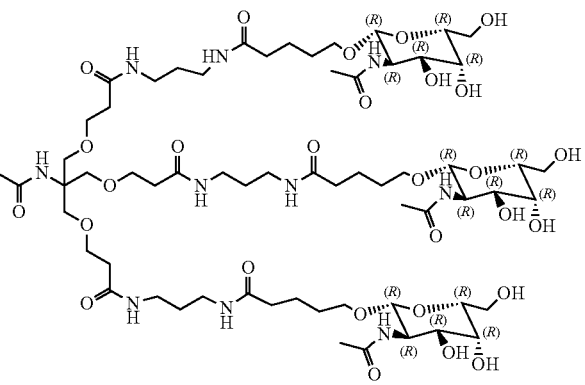

In some embodiments, an inverted dT can be incorporated at the 3'-end of the oligonucleotide strand, leading to a 3'-3' linkage that may inhibit degradation by 3' exonucleases and/or extension by DNA polymerases.

In some embodiments, the oligonucleotides described herein are conjugated to one or more ligand targeting group or pharmacophore, optionally through a linking moiety, such as a HEG linker or a C6 amino linker. In some embodiments, the oligonucleotide strand further comprises a ligand-targeting group or a pharmacophore conjugated at the 5' and/or 3' end through an optional linker. In some embodiments, the conjugation is at the 3'-end of the oligonucleotide strand.

In some embodiments, the ligand-targeting group or a pharmacophore enhances the activity, cellular distribution, or cellular uptake of the oligonucleotide by a particular type of cell such as hepatocytes.

In some embodiments, the ligand targeting group may be a lipid moiety such as a cholesterol moiety, tocopherols, In some embodiments, the ligand-targeting group may be a naturally occurring substance, such as a protein (e.g., human serum albumin (HSA), low-density lipoprotein (LDL), or globulin).

In some embodiments, the ligand-targeting group may be a carbohydrate (e.g., a dextran, pullulan, chitin, chitosan, inulin, cyclodextrin, N-acetylgalactosamine, or hyaluronic acid). Carbohydrates include monosaccharides such as N-acetylgalactosamine (GalNAc), disaccharides, trisaccharides, tetrasaccharides, oligosaccharides, and polysaccharides. In certain embodiments of the compositions and methods of the invention, a ligand is one or more GalNAc derivatives attached such as two or three GalNAc derivatives attached to the oligonucleotide through a bivalent or trivalent-branched linker, respectively.

In embodiments, the oligonucleotide is linked to the targeting moiety through a linker, such as an amino alkyl linker (e.g., C6-NH$_2$). For example, GAlNAc—1-6 may be linked to the oligonucleotide through this type of linker.

In some embodiments, the ligand-targeting group may be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-gly-colied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide. The ligand targeting group can also include targeting groups, e.g., a cell or tissue targeting agent, e.g., a lectin, glycoprotein, lipid or protein, e.g., an antibody, that binds to a specified cell type such as an hepatocyte.

In some embodiments, the ligand-targeting group is Gal-NAc or a derivative thereof. For example, the following GalNAc derivatives are included in some embodiments.

GalNAc-1

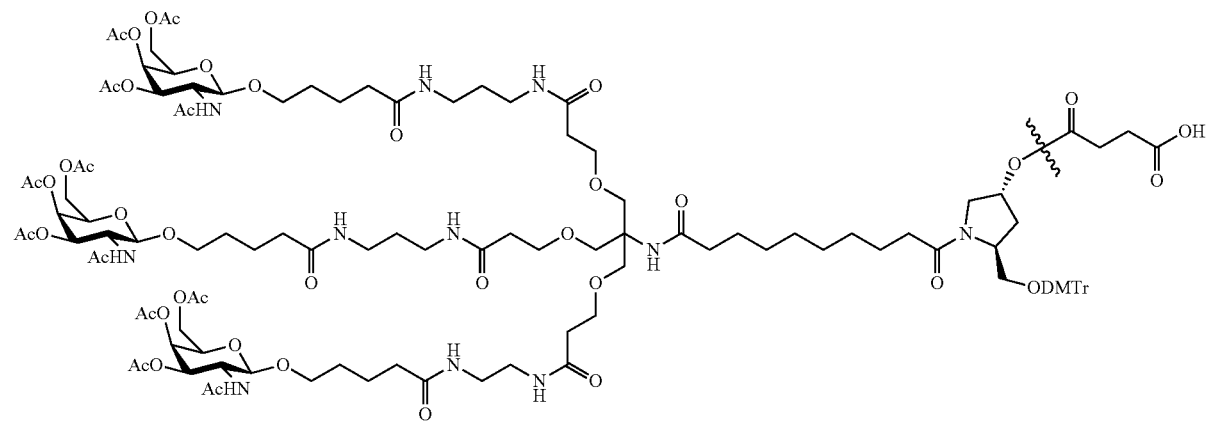

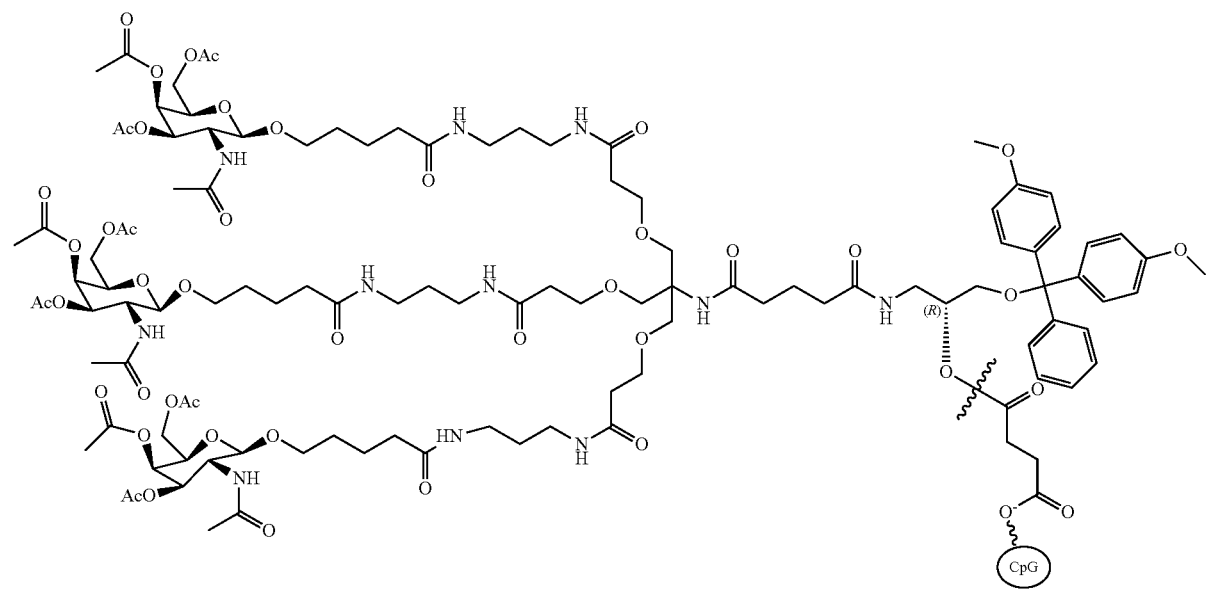

-continued
GalNAc-3
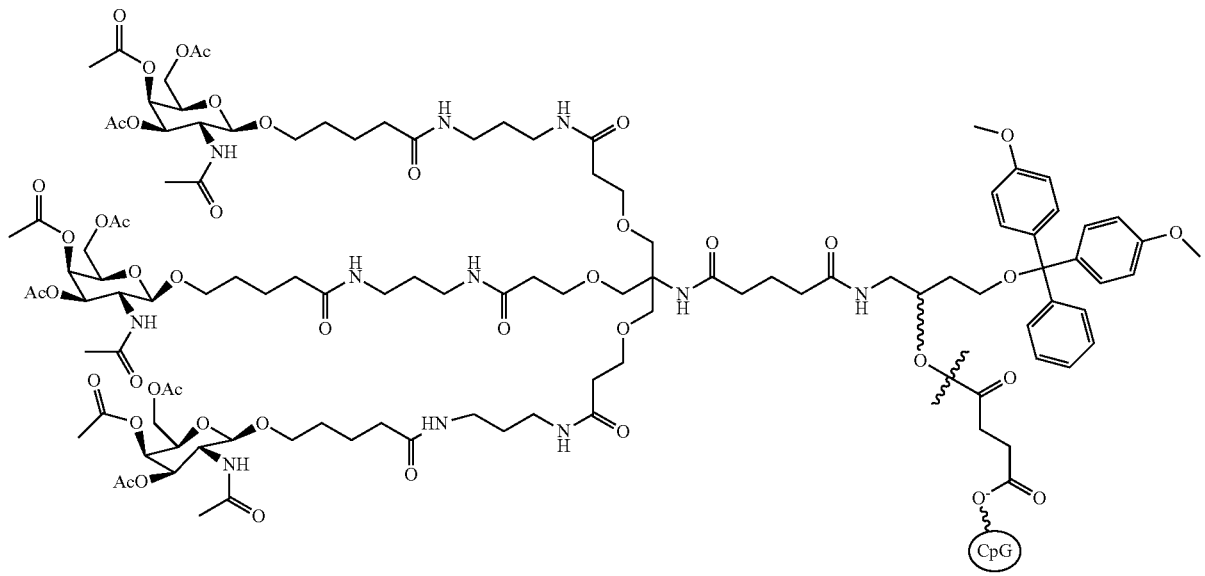
GalNAc-4
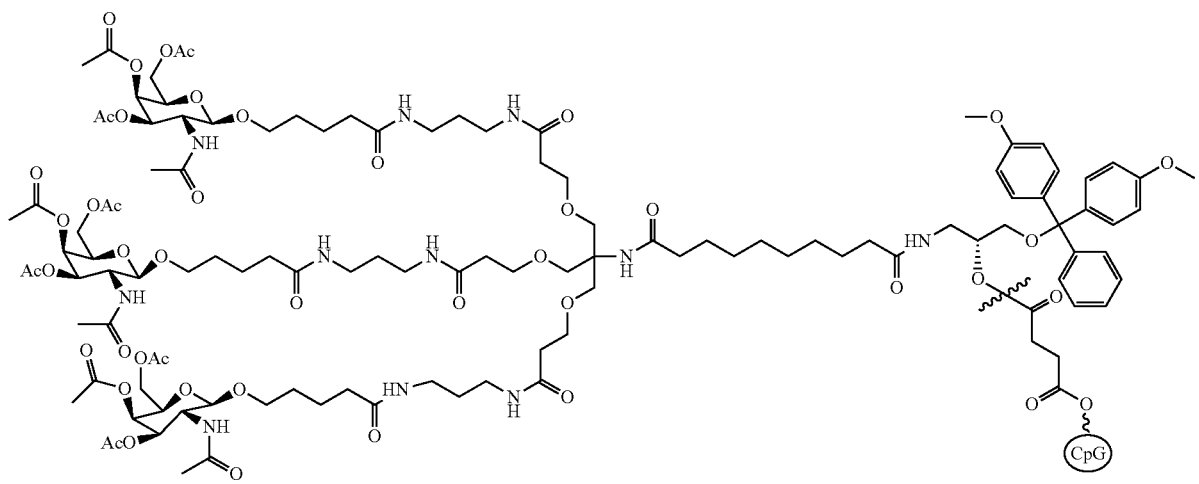
GalNAc-5
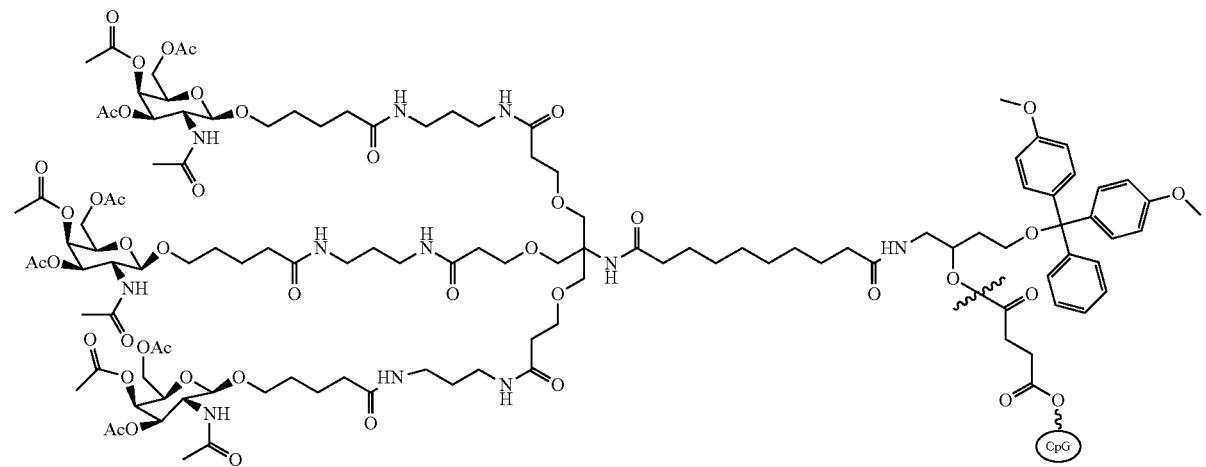

-continued
GalNAc-6
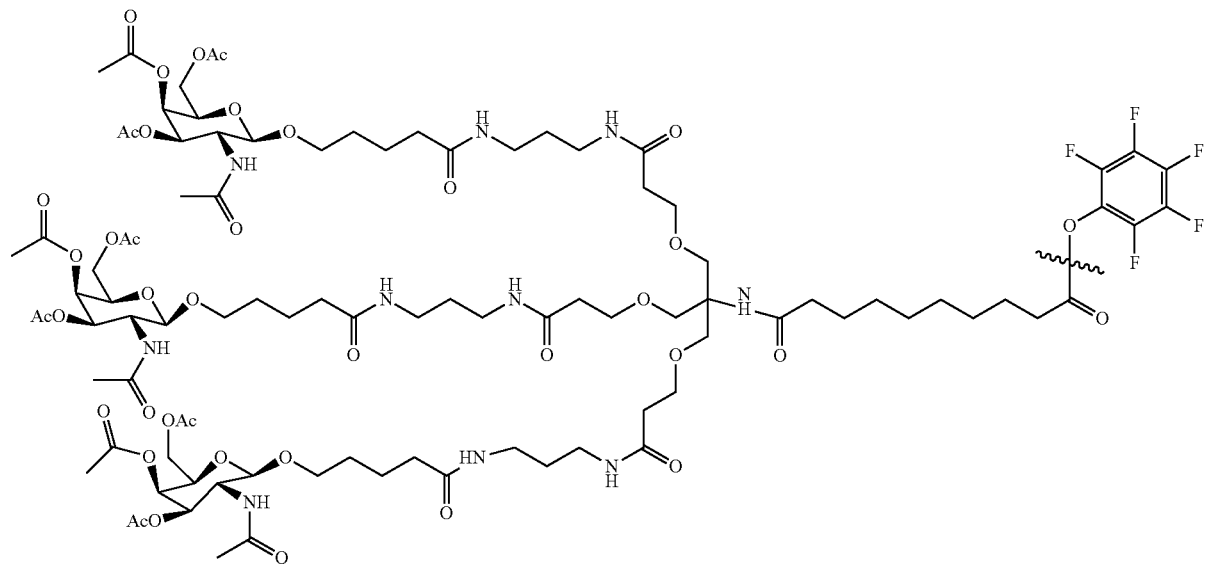
GalNAc-7
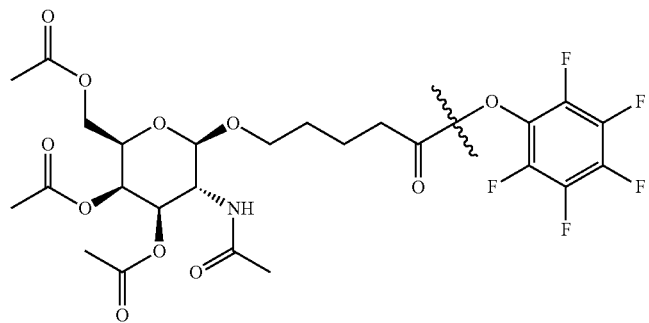
GalNAc-8
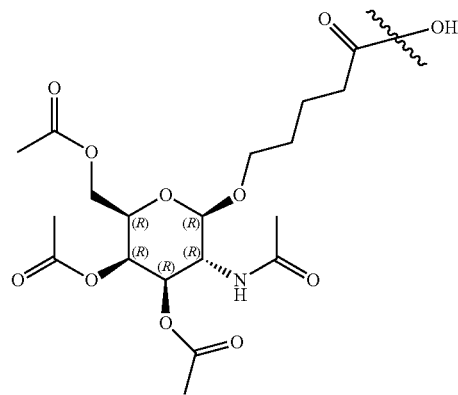

-continued
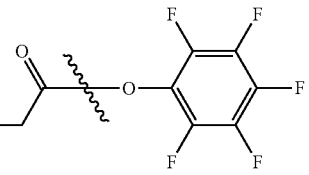
GalNAc-9
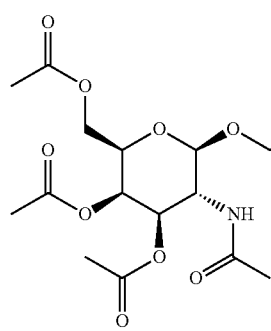
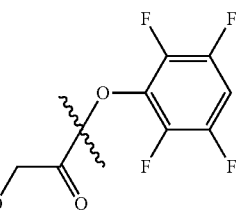
GalNAc-10
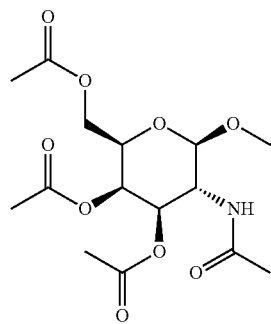
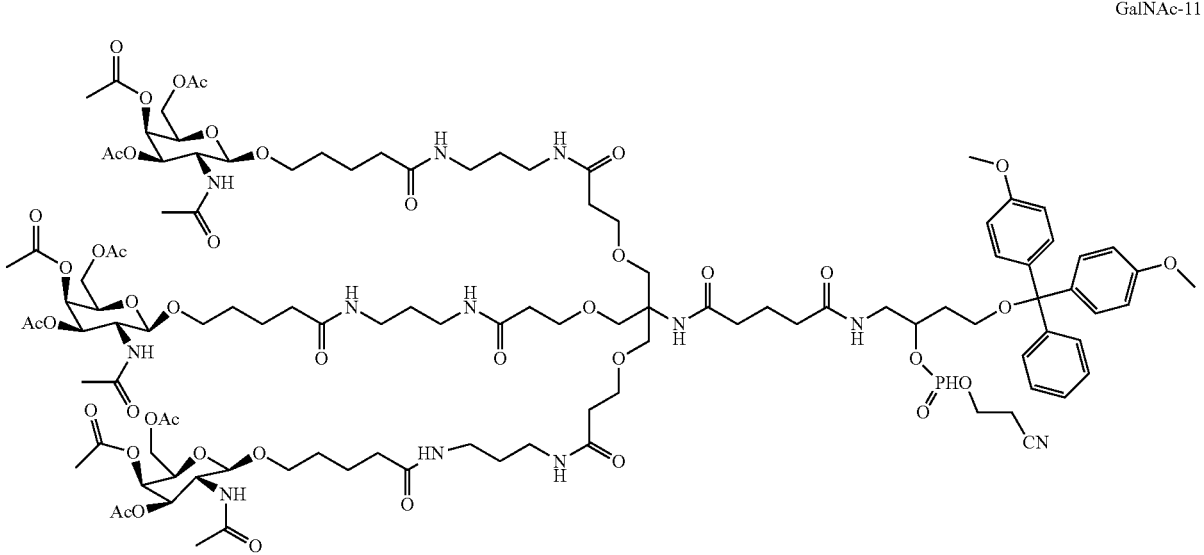
GalNAc-11

-continued

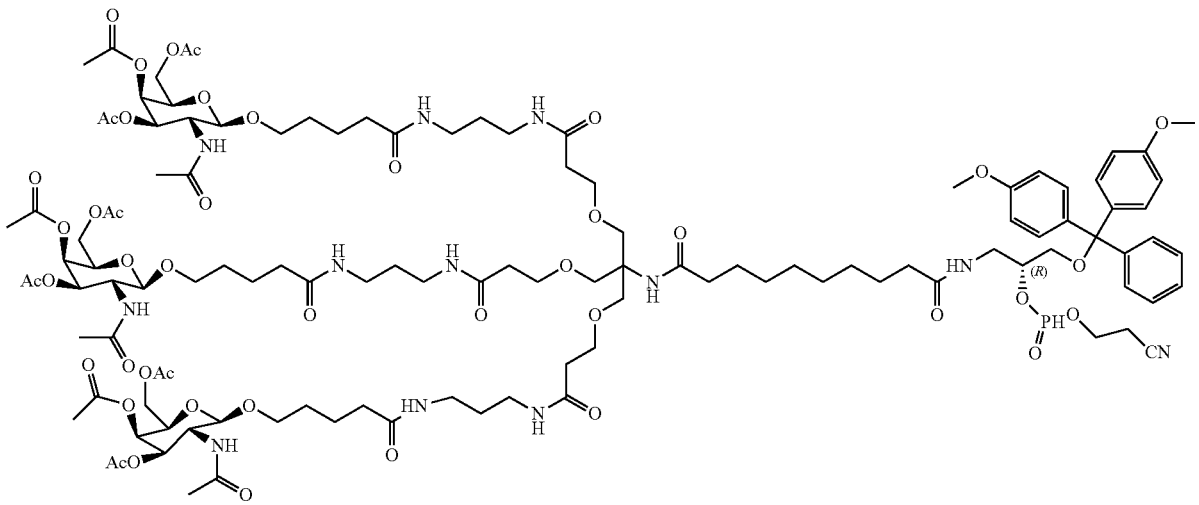

GalNAc-12

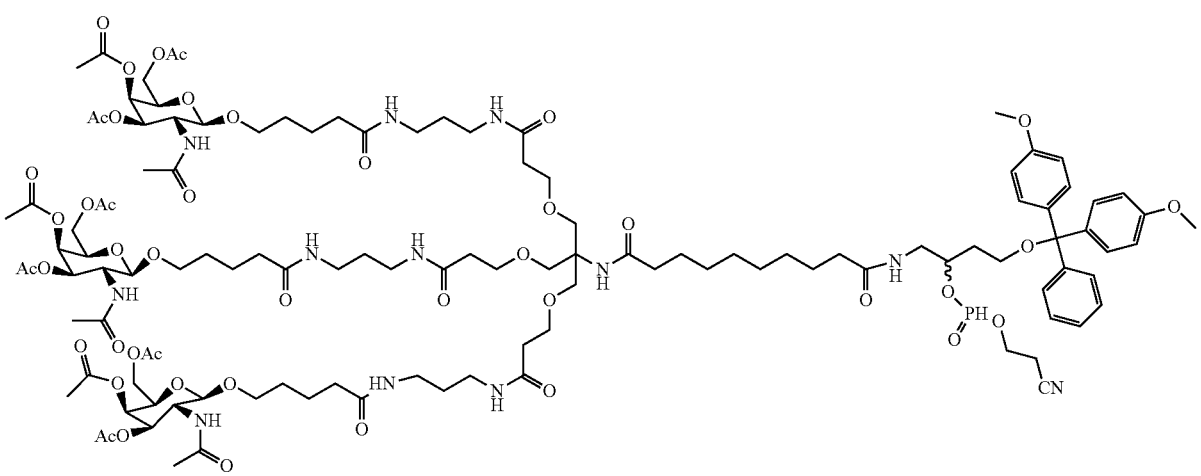

GalNAc-13

In some embodiments, the ligand-targeting group may be an aptamer. An "aptamer" refers to an oligonucleotide or peptide molecule that binds to a specific target molecule. For example, an aptamer can be selected to target a specific cell type in the body. When conjugated to the disclosed oligonucleotide, it can direct the oligonucleotide towards the targeted cells. In another example, an aptamer may target a viral protein, such as the core protein of HBV. See, e.g., Oncogene, 2001 Oct. 4; 20(45):6579-86; WO2011060557. The aptamer may specifically bind the reverse transcriptase primer or HBV reverse transcriptase or HBV Enhancer I core sequence, for example, as described in WO2002081494.

In some embodiments, the ligand targeting group may be selected from one or more of a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fructose, glycosylated polyaminoacids, multivalent galactose, transferrin, bisphosphonate, polyglutamate, polyaspartate, a lipid, cholesterol, a steroid, bile acid, folate, vitamin B 12, vitamin A, biotin, a RGD peptide, or a RGD peptide mimetic.

Additional ligand targeting groups are disclosed, e.g., in WO2016077321, which is incorporated herein by reference in its entirety.

2. Compositions

The present disclosure also encompasses pharmaceutical compositions comprising oligonucleotides of the present disclosure. One embodiment is a pharmaceutical composition comprising an oligonucleotide of Formula (I), (II), (III), (IV), (V), or (VI), or other oligonucleotide of the present disclosure and a pharmaceutically acceptable diluent or carrier.

In some embodiments, the pharmaceutical composition containing the oligonucleotide of the present disclosure is formulated for systemic administration via parenteral delivery. Parenteral administration includes intravenous, intra-arterial, subcutaneous, intraperitoneal or intramuscular injection or infusion; also subdermal administration, e.g., via an implanted device. In a preferred embodiment, the pharmaceutical composition containing the oligonucleotide of the present disclosure is formulated for subcutaneous (SC) or intravenous (IV) delivery. Formulations for parenteral administration may include sterile aqueous solutions, which may also contain buffers, diluents and other pharmaceutically acceptable additives as understood by the skilled artisan. For intravenous use, the total concentration of solutes may be controlled to render the preparation isotonic.

The pharmaceutical compositions containing the oligonucleotide of the present disclosure are useful for treating a disease or disorder, e.g., associated with the expression or activity of an HBV gene.

3. Methods of Use

One aspect of the present technology includes methods for treating a subject diagnosed as having, suspected as having, or at risk of having an HBV infection and/or an HBV-associated disorder. In therapeutic applications, compositions comprising the oligonucleotides of the present technology are administered to a subject suspected of, or already suffering from such a disease (such as, e.g., presence of an such as HBV antigen surface and envelope antigens (e.g., HBsAg and/or HBeAg) in the serum and/or liver of the subject, or elevated HBV DNA or HBV viral load levels), in an amount sufficient to cure, or at least partially arrest, the symptoms of the disease, including its complications and intermediate pathological phenotypes in development of the disease.

In some embodiments the oligonucleotides of the present technology show affinity to at least one of the following regions or HBV RNA transcripts in Table J.

TABLE J

| Region | Targeted HBV RNA transcripts | HBV Proteins affected |
| --- | --- | --- |
| Pol/S | Pre-Core, Pg, Pre-S1, Pre-S2 | HBeAg, HBcAg, Polymerase, Large HBsAg, Middle HBsAg, Small HBsAg |
| Pol | Pre-Core, Pg, Pre-S1, Pre-S2 | HBeAg, HBcAg, Polymerase, Large HBsAg, Middle HBsAg, Small HBsAg |
| Pol/X | Pre-Core, Pg, Pre-S1, Pre-S2, X | HBeAg, HBcAg, Polymerase, Large HBsAg, Middle HBsAg, Small HBsAg, HBxAg |
| DR1 | Pre-Core, Pg, Pre-S1, Pre-S2, X | HBeAg, HBcAg, Polymerase, Large HBsAg, Middle HBsAg, Small HBsAg, HBxAg |
| DR2 | Pre-Core, Pg, Pre-S1, Pre-S2, X | HBeAg, HBcAg, Polymerase, Large HBsAg, Middle HBsAg, Small HBsAg, HBxAg |
| Pre-PolyA | Pre-Core, Pg, Pre-S1, Pre-S2, X | HBeAg, HBcAg, Polymerase, Large HBsAg, Middle HBsAg, Small HBsAg, HBxAg |

Subjects suffering from an HBV infection and/or an HBV-associated disorder can be identified by any or a combination of diagnostic or prognostic assays known in the art. For example, typical symptoms of HBV infection and/or an HBV-associated disorder include, but are not limited to the presence of serum and/or liver HBV antigen (e.g., HBsAg and/or HBeAg), elevated ALT, elevated AST, the absence or low level of anti-HBV antibodies, liver injury, cirrhosis, delta hepatitis, acute hepatitis B, acute fulminant hepatitis B, chronic hepatitis B, liver fibrosis, end-stage liver disease, hepatocellular carcinoma, serum sickness-like syndrome, anorexia, nausea, vomiting, low-grade fever, myalgia, fatigability, disordered gustatory acuity and smell sensations (aversion to food and cigarettes), right upper quadrant and epigastric pain (intermittent, mild to moderate), hepatic encephalopathy, somnolence, disturbances in sleep pattern, mental confusion, coma, ascites, gastrointestinal bleeding, coagulopathy, jaundice, hepatomegaly (mildly enlarged, soft liver), splenomegaly, palmar erythema, spider nevi, muscle wasting, spider angiomas, vasculitis, variceal bleeding, peripheral edema, gynecomastia, testicular atrophy, abdominal collateral veins (caput medusa), high levels of alanine aminotransferase (ALT) and aspartate aminotransferase (AST) (within a range of 1000-2000 IU/mL), ALT levels higher than AST levels, elevated gamma-glutamyl transpeptidase (GGT) and/or alkaline phosphatase (ALP) levels, decreased albumin levels, elevated serum iron levels, leukopenia (i.e., granulocytopenia), lymphocytosis, increased erythrocyte sedimentation rate (ESR), shortened red blood cell survival, hemolysis, thrombocytopenia, a prolongation of the international normalized ratio (INR), the presence of serum HBV DNA, elevation of the aminotransferases (<5 times the ULN), increased bilirubin levels, prolonged prothrombin time (PT), hyperglobulinemia, the presence of tissue-nonspecific antibodies, such as anti-smooth muscle antibodies (ASMAs) or antinuclear antibodies (ANAs), the presence of tissue-specific antibodies, such as antibodies against the thyroid gland, elevated levels of rheumatoid factor (RF), hyperbilirubinemia, low platelet and white blood cell counts, AST levels higher than ALT levels, lobular inflammation accompanied by degenerative and regenerative hepatocellular changes, and predominantly centrilobular necrosis.

In some embodiments, subjects treated with the oligonucleotide composition of the present technology will show amelioration or elimination of one or more of the following conditions or symptoms: the presence of serum and/or liver HBV antigen (e.g., HBsAg and/or HBeAg), the absence or low level of anti-HBV antibodies, liver injury, cirrhosis, delta hepatitis, acute hepatitis B, acute fulminant hepatitis B, chronic hepatitis B, liver fibrosis, end-stage liver disease, hepatocellular carcinoma, serum sickness-like syndrome, anorexia, nausea, vomiting, low-grade fever, myalgia, fatigability, disordered gustatory acuity and smell sensations (aversion to food and cigarettes), right upper quadrant and epigastric pain (intermittent, mild to moderate), hepatic encephalopathy, somnolence, disturbances in sleep pattern, mental confusion, coma, ascites, gastrointestinal bleeding, coagulopathy, jaundice, hepatomegaly (mildly enlarged, soft liver), splenomegaly, palmar erythema, spider nevi, muscle wasting, spider angiomas, vasculitis, variceal bleeding, peripheral edema, gynecomastia, testicular atrophy, abdominal collateral veins (caput medusa), ALT levels higher than AST levels, leukopenia (i.e., granulocytopenia), decreased albumin levels, elevated serum iron levels, lymphocytosis, increased erythrocyte sedimentation rate (ESR), shortened red blood cell survival, hemolysis, thrombocytopenia, a prolongation of the international normalized ratio (INR), the presence of serum HBV DNA, prolonged prothrombin time (PT), hyperglobulinemia, the presence of tissue-nonspecific antibodies, such as anti-smooth muscle antibodies (ASMAs) or antinuclear antibodies (ANAs), the presence of tissue-specific antibodies, such as antibodies against the thyroid gland, hyperbilirubinemia, low platelet and white blood cell counts, AST levels higher than ALT levels, lobular inflammation accompanied by degenerative and regenerative hepatocellular changes, and predominantly centrilobular necrosis.

In some embodiments, subjects treated with the oligonucleotide composition of the present technology will show a reduction in the expression levels of one or more biomarkers selected from among alanine aminotransferase (ALT), aspartate aminotransferase (AST), gamma-glutamyl transpeptidase (GGT), alkaline phosphatase (ALP), bilirubin, and rheumatoid factor (RF), compared to untreated subjects suffering from an HBV infection and/or an HBV-associated disorder.

The present disclosure provides a method for treating a subject diagnosed as having, or suspected as having an HBV infection and/or an HBV-associated disorder comprising administering to the subject an effective amount of an oligonucleotide composition of the present technology.

The oligonucleotides and compositions of the present disclosure may be used in antisense therapy. For example, the oligonucleotide may contain a nucleobase sequence that is complementary or hybridizes to a target nucleic acid sequence of a known viral DNA or RNA sequence, for example, in HBV.

Some embodiments include a method of modulating expression of a target by contacting a target nucleic acid with an antisense compound comprising the oligonucleotide of the present disclosure. In some embodiments, the target nucleic acid is in a cell, for example, in an animal such as a human.

Some embodiments, include a method of inhibiting expression of a target RNA in an animal, comprising administering to the animal an antisense compound comprising the oligonucleotide of the present disclosure. The oligonucleotide may be complementary or hybridize to a portion of the target RNA.

Some embodiments include a method for reducing the viral load of a virus in a subject infected with the virus comprising administering a therapeutically effective amount of a oligonucleotide or a composition of the present disclosure to the subject in need thereof thereby reducing the viral load of the virus in the subject. The oligonucleotide may be complementary or hybridize to a portion of the target RNA in the virus.

Some embodiments include a method for inhibition of viral gene expression in a cell or subject comprising contacting the cell with a oligonucleotide or a composition of the present disclosure, or administering a therapeutically effective amount of a oligonucleotide or a composition of the present disclosure to a subject in need thereof. The oligonucleotide may be complementary or hybridize to a portion of the target RNA in the virus.

Other embodiments include a method of reducing the level of a virus antigen in a subject infected with the virus, comprising administering a therapeutically effective amount of a oligonucleotide or composition of the present disclosure to the subject in need thereof thereby reducing the level of the virus antigen in the subject. The oligonucleotide may be complementary or hybridize to a portion of the target RNA in the virus.

The oligonucleotides and compositions of the present disclosure may be used, e.g., to inhibit or reduce Hepatitis B virus (HBV) gene expression or inhibit replication of a HBV virus or for treatment of a subject having HBV or for reducing the viral load of Hepatitis B virus (HBV) in a subject infected with HBV. In embodiments, the disclosed chimeric oligonucleotides are used to induce RNase H activity at a target gene.

The oligonucleotides and compositions of the present disclosure may be used, e.g., to compete for a micro-RNA binding site to HCV RNA thereby inhibiting replication.

The present disclosure is also directed to methods of stabilizing an oligonucleotide for delivery to a subject. Stabilization of an oligonucleotide is characterized [quantified] herein as increasing the melting point or temperature, $T_m$, of an oligonucleotide.

The disclosed oligonucleotide constructs may be administered alone or in combination with one or more additional treatments for the targeted ailment. The disclosed oligonucleotide constructs may be administered alone or in combination with one or more additional treatments for HBV infection. In combination therapies, it is understood that the oligonucleotide constructs and one or more additional treatments for HBV infection may be administered simultaneously in the same or separate compositions, or administered separately, at the same time or sequentially.

In some embodiments, the disclosed oligonucleotide constructs are administered in combination with HBV replication inhibitors or immune modulator agents or in regimens that combine anti-HBV oligonucleotide agents with both HBV replication inhibitors and immune modulation agents. In embodiments, the disclosed oligonucleotide constructs are administered in combination with standard of care treatment for HBV infection. Standard of care treatment for HBV infection can include inhibitors of viral polymerase such as nucleotide/nucleotide analogs (e.g., Lamivudine, Telbivudine, Entecavir, Adefovir, Tenofovir, and Clevudine, Tenofovir alafenamide (TAF), CMX157, and AGX-1009) and Interferons (e.g., Peg-IFN-2a and IFN-α-2b, Interferon lambda). In embodiments, the disclosed oligonucleotide constructs are administered in combination with one or more oligonucleotides after either simultaneous (co-administration) or sequential dosing. Oligonucleotides can include siRNA such as ALN-HBV, ARB-1467, ARC-520 and ARC-521, antisense oligonucleotides such as RG6004 (LNA HBV), Ionis-HBVRx and Ionis-HBV-LRx, miRNA mimics or inhibitors, aptamers, steric blockers, saRNA, shRNA, immunomodulatory and/or HBsAg release inhibiting such as REP 2139 and REP 2165 oligonucleotides. In embodiments, the disclosed oligonucleotide constructs are administered in combination with one or more antiviral agents such as viral replication inhibitors. In embodiments, the disclosed oligonucleotide constructs are administered in combination with HBV Capsid inhibitors. HBV capsid inhibitors can include NVR 3-778, AB-423, GLS-4, Bayer 41-4109, HAP-1, and AT-1. In embodiments, the disclosed oligonucleotide constructs are administered in combination with one or more immunomodulators such as TLR agonists. TLR agonists can include GS-9620, ARB-1598, ANA975, RG7795(ANA773), MEDI9197, PF-3512676, and IMO-2055. In embodiments, the disclosed oligonucleotide constructs are administered in combination with HBV vaccines. HBV vaccines can include Heplislav, ABX203, and INO-1800. In embodiments, the disclosed oligonucleotide constructs are administered in combination Some embodiments include inhibition of HBV gene expression in a cell or subject comprising contacting the cell with an oligonucleotide or composition of the present disclosure, or administering a therapeutically effective amount of a oligonucleotide or composition of the present disclosure to a subject in need thereof.

Some embodiments include the treatment of a disease or disorder associated with the expression or activity of a HBV gene comprising administering a therapeutically effective amount of an oligonucleotide or composition of the present disclosure to a subject in need thereof.

Some embodiments include a method for reducing the viral load of Hepatitis B virus (HBV) in a subject infected with HBV comprising administering a therapeutically effective amount of an oligonucleotide or composition of the present disclosure to the subject in need thereof thereby reducing the viral load of HBV in the subject. Some embodiments also provide methods of reducing the viral load of Hepatitis D virus (HDV) in a subject infected with HDV.

Other embodiments include a method of reducing the level of a Hepatitis B virus (HBV) antigen in a subject infected with HBV comprising administering a therapeutically effective amount of an oligonucleotide or composition of the present disclosure to the subject in need thereof thereby reducing the level of the HBV antigen in the subject. Some embodiments also provide methods of reducing the level of a Hepatitis D virus (HDV) antigen in a subject infected with HDV. In some embodiments, the HBV antigen is HBsAg or HBeAg.

In one embodiment, an oligonucleotide or composition of the present disclosure targeting HBV is administered to a subject having an HBV infection or both and HBV and an HDV infection, and/or an HBV-associated disease such that the expression of one or more HBV genes, HBV ccc DNA levels, HBV antigen levels, HBV viral load levels, ALT, and/or AST, e.g., in a cell, tissue, blood or other tissue or fluid of the subject are reduced by at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more, or values between two of these numbers, upon administration to the subject of the oligonucleotide or composition of the present disclosure. In some embodiments, the HBV antigen levels are decreased by the previously recited amount. In some embodiments the antigen is HBsAg or HBeAg. In some embodiments, the HBV viral load levels are decreased by the previously recited amount.

In one embodiment, a oligonucleotide or composition of the present disclosure targeting HBV is administered to a subject having an HBV infection or both and HBV and an HDV infection, and/or an HBV-associated disease such that the level of anti-HBV antibodies, e.g., in a cell, tissue, blood or other tissue or fluid of the subject are increased by at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more, or values between two of these numbers, when the an oligonucleotide or composition of the present disclosure is administered to the subject.

Administration of the oligonucleotide or composition of the present disclosure according to the methods and uses of the disclosure may result in a reduction of the severity, signs, symptoms, and/or markers of such diseases or disorders in a patient with an HBV infection or both and HBV and an HDV infection, and/or HBV-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%, or values between two of these numbers.

The amount of an oligonucleotide or composition of the present disclosure may be determined by a medical professional. The daily dosage of the products may be varied over a wide range from 0.001 to 1,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day, or any range therein. Preferably, the range is from about 0.01 to about 50.0 mg/kg of body weight per day, or any range therein. More preferably, from about 0.01 to about 10.0 mg/kg of body weight per day, or any range therein. More preferably, from about 0.01 to about 1.0 mg/kg of body weight per day, or any range therein. The oligonucleotides may be administered on a regimen of 1 to 4 times per day. For example, the oligonucleotides of the present disclosure may be administered at one or more doses of from about 0.1 mg/kg to about 100 mg/kg. For example, the disclosed oligonucleotides may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, 50, 55, 60, 65, 70, 75, 80, 85, 90, 95 or about 100 mg/kg. Values and ranges intermediate to the recited values are also intended to be part of this disclosure. These values may apply to intravenous infusion and/or subcutaneous delivery. Other forms of delivery described herein may also be administered at these doses. The dosages may be varied depending upon the requirement of the patients, the severity of the condition being treated and the oligonucleotides being employed. The use of either daily administration or post-periodic dosing may be employed.

The oligonucleotides of the present disclosure can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months, or longer. After an initial treatment regimen, the treatments can be administered on a less frequent basis. For example, after administration weekly or biweekly for three months, administration can be repeated once per month, for six months or a year or longer.

The oligonucleotides of the present disclosure also can be administered by subcutaneous delivery. The administration may be repeated, for example, on a regular basis, such as weekly, biweekly (i.e., every two weeks) for one month, two months, three months, four months, or longer. After an initial treatment regimen, the treatments can be administered on a less frequent basis. For example, after administration weekly or biweekly for three months, administration can be repeated once per month, for six months or a year or longer.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of CHB may be assessed, for example, by periodic monitoring of viral load and transaminase levels. Compari-

4. Definitions

It is to be understood that the terminology used herein is for the purpose of describing particular embodiments only and is not intended to limit the scope of the present invention. The following definitions shall apply unless otherwise indicated.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5.'" Certain bases not commonly found in naturally occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition, and sequence of the oligonucleotide, ionic strength, and incidence of mismatched base pairs. A complement sequence can also be an RNA sequence complementary to the DNA sequence or its complement sequence, and can also be a cDNA.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically, and preferably, conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids, which differ over a stretch of 20 contiguous nucleotides by more than two bases.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

"Pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

"Constructs" of the oligonucleotides can refer to an oligonucleotide of the present disclosure and, e.g., (1) a conjugated moiety, such as those described herein (such as targeting moieties) or (2) domains of modified/unmodified nucleotides, such as in some chimeric oligonucleotides.

"Chimeric oligonucleotide" refers to an oligonucleotide having more than one domain, for example, as exemplified by Formulae (VI) and (VII). The chimeric oligonucleotide may include additional components, e.g., a ligand-targeting group or a pharmacophore or additional nucleotides, linkers, etc.

"Modified nucleoside" refers to a nucleoside having, independently, a modified sugar moiety and/or modified nucleobase. It is understood that nucleosides can be linked through intersubunit linkages, such as phosphodiester intersubunit linkages, thiophosphate intersubunit linkages, phosphoramidate intersubunit linkages, and thiophosphoramidate intersubunit linkages "Modified nucleotides" may refer to a nucleoside and intersubunit linkage together.

"Unmodified" or "natural" nucleobases include the purine bases adenine (A) and guanine (G), and the pyrimidine bases thymine (T), cytosine (C) and uracil (U). "Modified nucleobases" include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluorometltyl and other 5-substituted uracils and cytosines, 7-methylguanine and 7-methyladenine, 2-F- adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-am-oe1hoxy)-H-pyrimido[5,4-b][1,4]benzoxazin-2 (3H)-one), carbazole cytidine (2H-pyrimido[4,5-b]indol-2-one), pyridoindole cytidine (H-pyrido[3,2,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine, and 2-pyridone.

In some embodiments, the modified nucleobase is selected from the group consisting of 5-methylcytosine, 2,6-diaminopurine, 5-methyluracil, and a g-clamp. In some embodiments, the g-clamp is

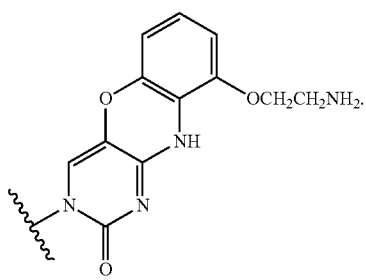

"Ligand targeting group" refers to a moiety that promotes delivery of the oligonucleotide to HBV infected hepatocytes through receptor binding. These groups include "receptor targeting ligands," such as GalNAc and Cholesterol, which target cell surface receptor ASGPR and LDL receptor on cell surfaces, respectively. Other receptor targeting ligands that target these receptors on cell surfaces are also within the scope of this term.

"Pharmacophore" refers to an oligonucleotide drug sequence that interacts HBV DNA or RNA molecules within HBV/HDV or HBV-infected cells and triggers antiviral responses.

"Conformationally restricted nucleoside" refers to nucleosides having a bridged or bicyclic sugar structure wherein the conformation of the nucleoside may be fixed in a particular configuration. For example, conformationally restricted nucleosides include those with fixed $C_3$'-endo sugar puckering. Exemplary embodiments include bridged nucleic acids (BNAs), e.g., 2', 4'-BNA nucleosides such as α-L-Methyleneoxy (4'-$CH_2$—O-2') LNA, β-D-Methyleneoxy (4'-$CH_2$—O-2') LNA, Ethyleneoxy (4'-$(CH_2)_2$—O-2') ENA, 2',4'-$BNA^{NC}$[NH], 2',4'-$BNA^{NC}$[NMe], 2',4'-$BNA^{NC}$[NBn], aminooxy (4'-$CH_2$—O—N(R)-2') BNA, and oxyamino (4'-$CH_2$—N(R)-0-2') BNA. Other exemplary BNA structures include but are not limited to, oligonucleotides having at least one bridge between the 4' and the 2' position of the sugar wherein each of the bridges independently comprises 1 or from 2 to 4 linked groups independently selected from —$[C(R_1)(R_2)]_n$—, —$C(R_1)$=$C(R_2)$—, —$C(R_1)$=N—, —C(=$NR_1$)—, —C(=O)—, —C(=S)—, —O—, —$Si(R_1)_2$—, —$S(=O)_x$—, and —$N(R_1)$—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=$O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group. Certain BNAs have been prepared and disclosed in the patent literature as well as in scientific literature (see for example: issued U.S. Pat. Nos. 7,053,207; 6,268,490; 6,770,748; 6,794,499; 7,034,133; 6,525,191; 7,696,345; 7,569,575; 7,314,923; 7,217,805; and 7,084,125, hereby incorporated by reference herein in their entirety. "Conformationally restricted nucleotide" refers to conformationally restricted nucleosides linked through an intersubunit linkage.

In some embodiments, the conformationally restricted nucleoside is selected from optionally substituted LNA or optionally substituted ENA. The optionally substituted LNA or ENA may be substituted by an alkyl moiety, for example a methyl or ethyl on one of the —$CH_2$— moieties.

"Inhibiting expression" refers to a reduction or blockade of the expression or activity and does not necessarily indicate a total elimination of expression or activity.

"Inhibiting replication of a virus" refers to reduction or blockade of the replication of a virus and does not necessarily indicate a total elimination of replication of the virus.

"Subject" refers to mammals and includes humans and non-human mammals. In some embodiments, the subject is a human, such as an adult human.

"Treating" or "treatment" of a disease in a subject refers to (1) preventing the disease from occurring in a subject that is predisposed or does not yet display symptoms of the disease; (2) inhibiting the disease or arresting its development; or (3) ameliorating or causing regression of the disease.

"Therapeutically effective amount" means an amount of a pharmaceutical agent that provides a therapeutic benefit to a subject.

"Pharmaceutically acceptable salt" means physiologically and pharmaceutically acceptable salts of the compounds of the present disclosure, i.e., salts that retain the desired biological activity of the parent oligonucleotide/compound and do not impart undesired toxicological effects thereto.

The following abbreviations are used in this disclosure. 2'-H (deoxyribose) nucleosides are referred to by an uppercase letter corresponding to the nucleobase, e.g., A, C, G, and T. 2'-OH (ribose) nucleosides are referred to by a lowercase r and an uppercase letter corresponding to the nucleobase, e.g., rA, rC, rG, and rU. 2'-O-Me nucleosides are referred to by a lowercase m and an uppercase letter corresponding to the nucleobase, e.g., mA, mC, mG and mU. 2'-MOE nucleosides are referred to by a lowercase "moe" and an uppercase letter corresponding to the nucleobase, e.g., moeA, moeC, moeG and moeU. 2'-ribo-F nucleosides are referred to by a lowercase "f" and an uppercase letter corresponding to the nucleobase, e.g., fA, fC, fG and fU. 2'-arabino-F nucleosides are referred to by a lowercase "af" and an uppercase letter corresponding to the nucleobase, e.g., afA, afC, afG and afU. mA* is 3'-amino-2'-OMe-2,6-Diaminopurine. A* is 3'-amino-2'-deoxy-2,6-Diaminopurine. fA* is 3'-amino-2'-F-2,6-Diaminopurine.

LNA nucleosides are referred to by an "L" and an uppercase letter corresponding to the nucleobase, e.g., LA, LC, LG, LT.

For the backbone or intersubunit linkages of the nucleotides, phosphodiester intersubunit linkages are referred to as "PO" or are generally not included in sequence details; thiophosphate intersubunit linkages are abbreviated as lowercase "ps"; phosphoramidate intersubunit linkages are abbreviated as lowercase "np"; and thiophosphoramidate intersubunit linkages are abbreviated as lowercase "nps."

N3'→P5' refers to modified nucleotides having intersubunit linkages where the 3' moiety contains N (e.g., NH) and is linked through a P. For example, the following structure has a N3'→P5' linkage:

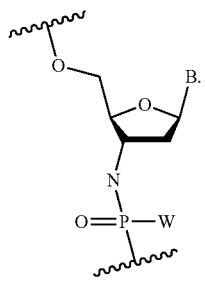

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

It is also to be appreciated that the various modes of treatment or prevention of the diseases or conditions described herein are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates that may need to be independently confirmed.

5. Examples

The following examples illustrate certain embodiments of the present disclosure to aid the skilled person in practicing the disclosure. Accordingly, the examples are in no way considered to limit the scope of the disclosure.

Methods of Making

All the monomers were dried in vacuum desiccator with desiccants (KOH and $P_2O_5$, RT 24 h). Synthesis solid supports (CPG) attached to the first 5' residue were obtained from commercially available sources. All other synthesis reagents and solvents were obtained from commercially available sources and used as such. The chemicals and solvents for post synthesis workflow were purchased from commercially available sources and used without any purification or treatment. Solvent (Acetonitrile) and solutions (amidite and activator) were stored over molecular sieves during synthesis.

The control, nuclease stabilized, 3'-cholesterol, 3'-Tocopherol and 3'-GalNAc conjugated antisense oligonucleotides used in this study are shown, e.g., in Tables 10-13. The antisense oligonucleotides were synthesized on an ABI-394 synthesizer using the standard 93-step cycle written by the manufacturer. The solid support was controlled pore glass and the monomers contained standard protecting groups. Each oligonucleotide was individually synthesized using commercially available 5'-O-(4,4'-dimethoxytrityl)-3'-O-(2-cyanoethyl-NN-diisopropyl) DNA and or 2'-O-Me phosphoramidite monomers of 6-N-benzoyladenosine ($A^{Bz}$), 4-N-acetylcytidine ($C^{Ac}$), 2-N-isobutyrylguanosine ($G^{iBu}$), and Thymidine (T), according to standard solid phase oligonucleotide synthesis protocols. The phosphoramidites were purchased from commercially available sources. The 2'-O-Me-2,6,diaminopurine phosphoramidite was purchased from commercially available sources. The DDTT ((dimethylamino-methylidene) amino)-3H-1,2,4-dithiazaoline-3-thione was used as the sulfur-transfer agent for the synthesis of oligoribonucleotide phosphorothioates. Modified oligonucleotides were obtained using an extended coupling of 0.1M solution of phosphoramidite in $CH_3CN$ in the presence of 5-(ethylthio)-1H-tetrazole activator to a solid bound oligonucleotide followed by standard capping, oxidation and deprotection. The stepwise coupling efficiency of all modified phosphoramidites was more than 98%. Oligonucleotide-bearing solid supports were heated with aqueous ammonia/ethanol (3:1) solution at 55° C. for 8 h to deprotect the base labile protecting groups.

The cholesterol and tocopherol conjugated oligonucleotides were obtained by starting solid phase synthesis on cholesterol and Tocopherol support attach on TEG linker and final coupling of the phosphoramidite to the support-bound oligonucleotide. The GalNAc conjugated ASOs were synthesized from a hydroxyprolinol-GalNAc solid support. GalNAc was tethered to trans-4-hydroxyprolinol via a 6-aminohexanoate linkage to obtain a hydroxyprolinol-GalNAc moiety that was subsequently attached to a functionalized control pore glass (CPG) to obtain the solid support.

The unconjugated and GalNAc modified oligonucleotides were purified by anion-exchange HPLC. The buffers were 20 mM sodium phosphate in 10% $CH_3CN$, pH 8.5 (buffer A) and 20 mM sodium phosphate in 10% $CH_3CN$, 1.8 M NaBr, pH 8.5 (buffer B). Fractions containing full-length oligonucleotides were pooled, desalted and lyophilized.

The cholesterol and tocopherol conjugated sequences were purified by high-performance liquid chromatography (HPLC) on an in-house packed RPC-Source15 reverse-phase column. The buffers were 20 mM NaOAc in 10% $CH_3CN$ (buffer A) and 20 mM NaOAc in 70% $CH_3CN$ (buffer B). Analytical HPLC and ES LC-MS established the integrity of the oligonucleotides.

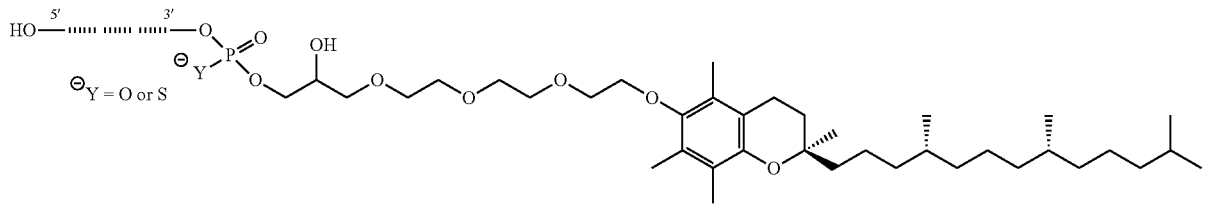

Vit E TEG linker

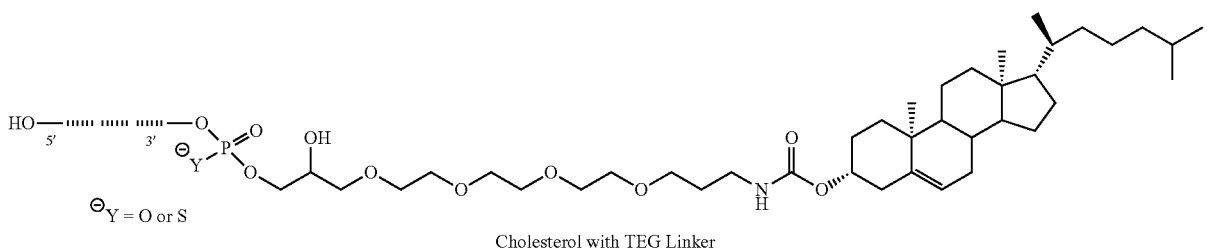

Cholesterol with TEG Linker

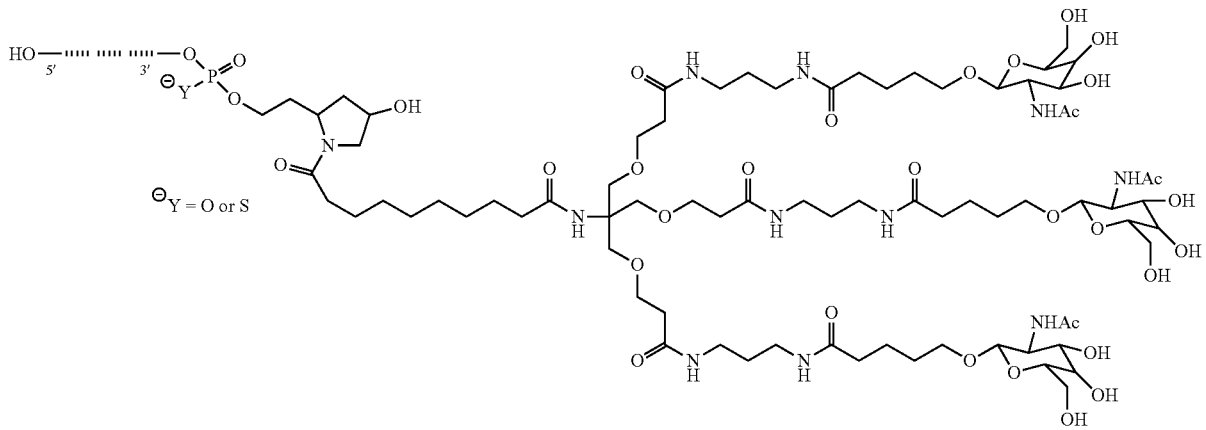

GalNac with Hyp-Linker

Synthesis of Phosphoramidate (NP) and Thiophosphoramidate (NPS) Modified Oligonucleotides The NP and NPS modified oligonucleotides were synthesized on an ABI-394 synthesizer using the 93-step cycle written with modifications to deblock, coupling and wait steps. The solid support was 3'-NHTr-5'-LCAA-CPG. Each oligonucleotide was individually synthesized using 3'-NH-Tr-5'-O-(2-cyanoethyl-N,N-diisopropyl) DNA phosphoramidite monomers of 6-N-benzoyladenosine ($A^{Bz}$), 4-N-Benzylcytidine ($C^{Bz}$), 2-N-isobutyrylguanosine ($G^{iBu}$), and Thymidine (T), according to standard solid phase phosphoramidite chemistry protocols by using the procedure described in *Nucleic Acids Research*, 1995, Vol. 23, No. 14 2661-2668.

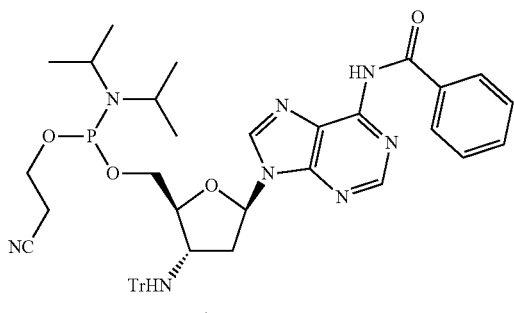

3'-NHTr-dA (Bz)

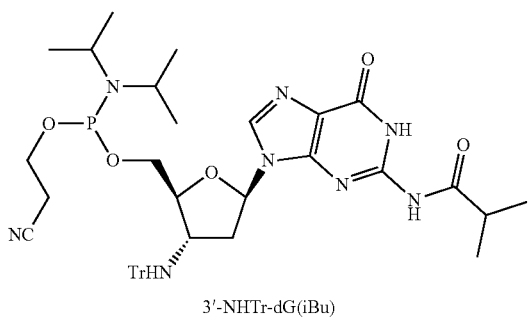

3'-NHTr-dG(iBu)

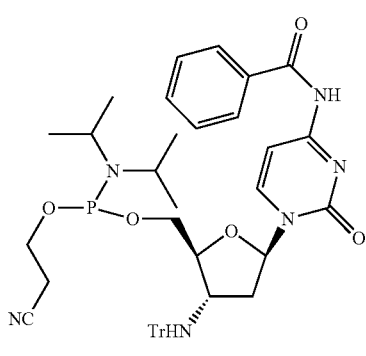

3'-NHTr-dC(Bz)

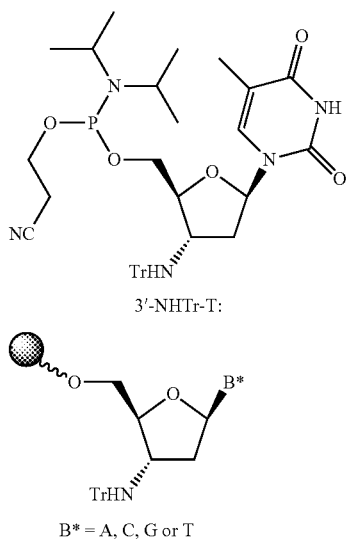

3'-NHTr-T:

B* = A, C, G or T

3'-NHTr-DNA Building Blocks for Oligomer Synthesis

The 2'-F 3'-NH-MMtr-5'-O-(2-cyanoethyl-N,N-diisopropyl) Uridine (U) and 4-N-benzoylcytidine ($C^{Bz}$) phosphoramidite monomers) were synthesized by using the procedure described in *Nucleic Acids Research*, 1996, Vol. 24, No. 15, 2966-2973

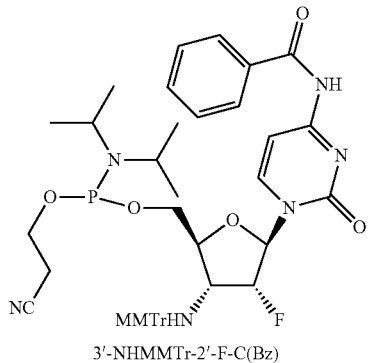

3'-NHMMTr-2'-F-C(Bz)

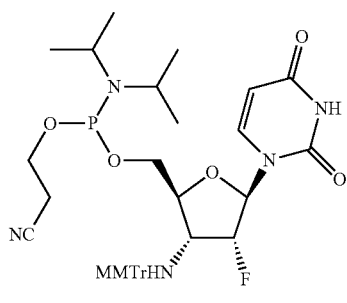

3'-NHMMTr-2'-F U:

2'-F 3'-NH-MMTr-5'-O-(2-cyanoethyl-N,N-diisopropyl) 6-N-benzoyladenosine ($A^{Bz}$), 2-N-isobutyrylguanosine ($G^{iBu}$), were synthesized as the procedure described below

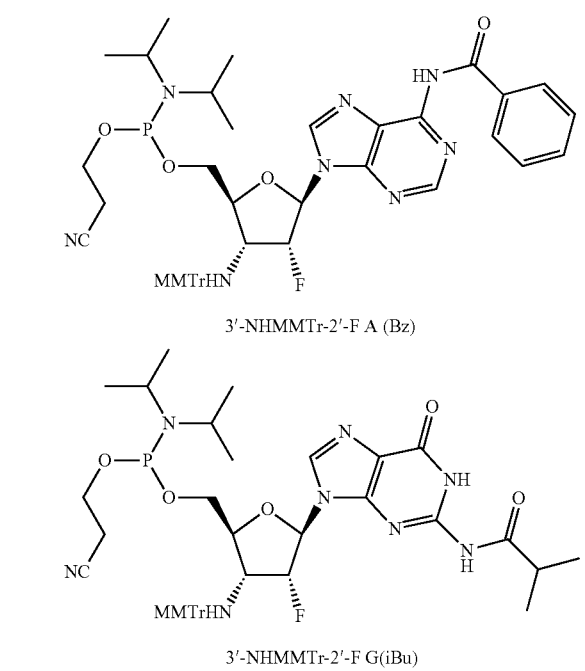
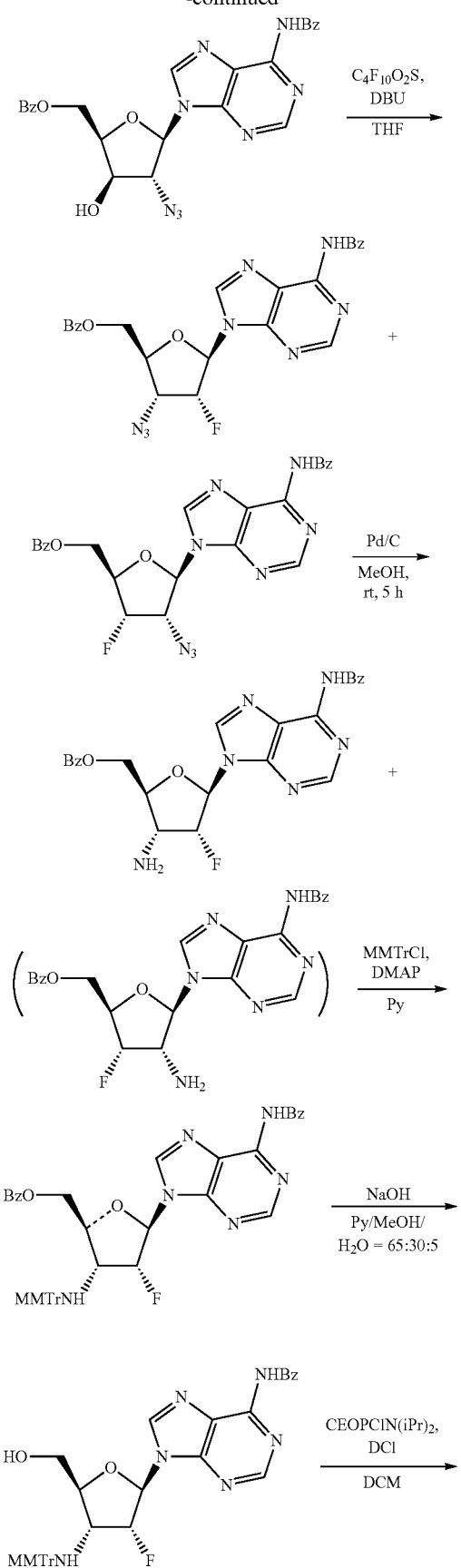

-continued

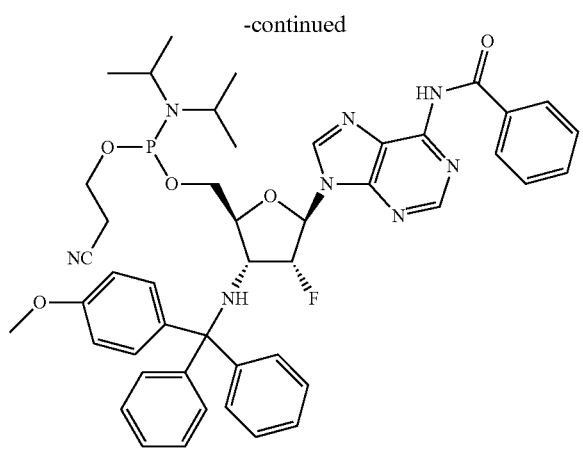

Preparation of PH-1

To a solution of (2R,3S,4S,5R)-2-(6-amino-9H-purin-9-yl)-5-(hydroxymethyl)oxolane-3,4-diol (300 g, 1.123 mol, 1.00 equiv) in N,N-dimethylformamide (7500 mL) with an inert atmosphere of nitrogen, was added triphenylphosphine (735 g, 2.802 mol, 2.50 equiv). The resulting solution was stirred for 15 min at 0° C. This was followed by the addition of a solution of diethyl azodicarboxylate (449.4 g, 2.581 mol, 2.54 equiv.) in N, N-dimethylformamide (7500 mL) dropwise with stirring at 0° C. in 60 min. The resulting solution was stirring, for 2 h at 25° C. The resulting mixture was concentrated under reduced pressure. The product was precipitated by the addition of ether. The solids were collected by filtration. The crude product was purified by re-crystallization from methanol. The solid was dried in an oven under reduced pressure. This resulted in 186 g (66%) of PH-1 as a white solid. 1H-NMR (DMSO-$d_6$, 400 MHz): 8.34-8.07 (m, 2H), 7.44-7.26 (m, 2H), 6.30-6.21 (m, 1H), 5.07-4.95 (m, 1H), 4.33-4.20 (m, 1H), 4.15-4.03 (m, 2H), 3.71-3.50 (m, 2H).

Preparation of PH-2

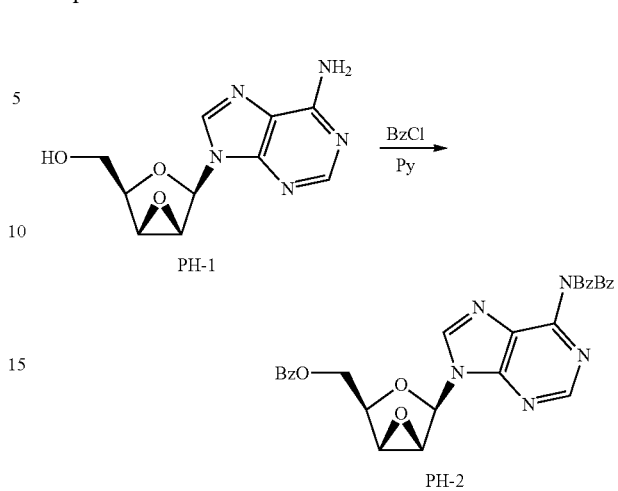

To a solution of PH-1 (100 g, 401.2 mmol, 1.00 equiv.) in pyridine (1000 mL) with an inert atmosphere of nitrogen, was added benzoyl chloride (175 g, 1.245 mol, 3.10 equiv.) dropwise with stirring at 0° C. in 30 min. The resulting solution was stirred for 3 h at 25° C. The resulting solution was diluted with 400 mL of ethyl acetate. The resulting mixture was washed with 3×300 mL of water and 2×300 mL of saturated sodium bicarbonate solution respectively. The resulting mixture was washed with 1×300 mL of saturated sodium chloride solution. The mixture was dried over anhydrous sodium sulfate, filtered, and concentrated under reduced pressure. The residue was applied onto a silica gel column with ethyl acetate/petroleum ether (2/1). This resulted in 157 g (70%) of PH-2 as a white solid.

Preparation of PH-3

To a solution of PH-2 (30 g, 53.42 mmol, 1.00 equiv) in N,N-dimethylformamide (300 mL) with an inert atmosphere of nitrogen, was added ammonium chloride (5.7 g, 106.56 mmol, 2.00 equiv) and sodium azide (34.8 g, 535.30 mmol, 10.00 equiv) in order. The resulting solution was stirred for 5 h at 50° C. The resulting solution was diluted with 2000 mL of dichloromethane. The resulting mixture was washed with 3×2000 mL of water, 1×2000 mL of saturated sodium bicarbonate solution and 1×2000 mL of saturated sodium chloride solution respectively. The mixture was dried over anhydrous sodium sulfate, filtered, and concentrated under reduced pressure. This resulted in 24 g (90%) of PH-3 and PH-3S (5:1) as a white solid.

Preparation of PH-4

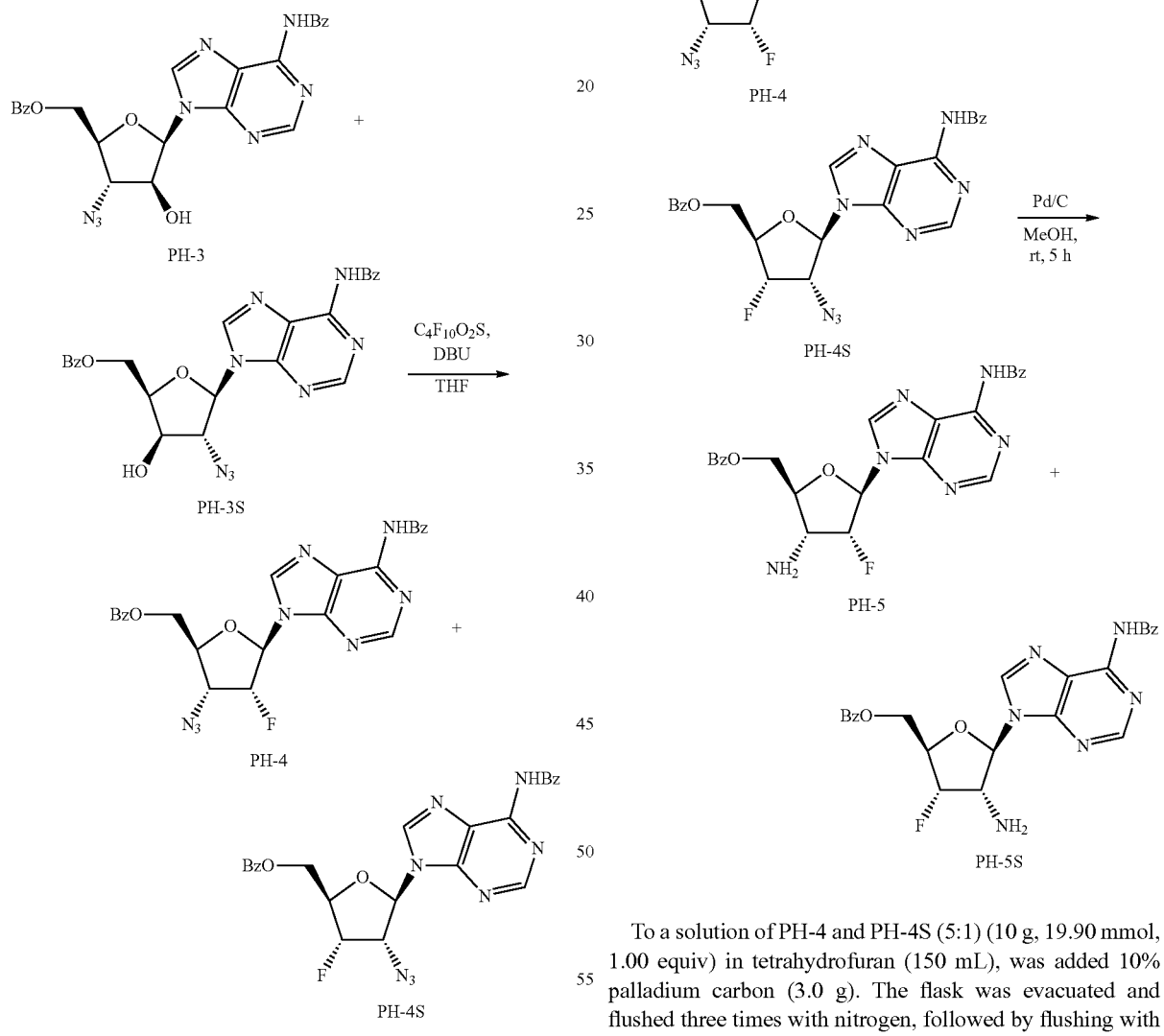

To a solution of PH-3 and PH-3S (5:1) (10 g, 19.98 mmol, 1.00 equiv) in tetrahydrofuran (100 mL) with an inert atmosphere of nitrogen, was added 1,8-Diazabicyclo [5.4.0] undec-7-ene (10.69 g, 70.22 mmol, 3.50 equiv). This was followed by the addition of perfluorobutylsulfonyl fluoride (12.69 g, 2.10 equiv) dropwise with stirring at 0° C. in 10 min. The resulting solution was stirred for 1.5 h at 0° C. The resulting solution was diluted with 200 mL of dichloromethane. The resulting mixture was washed with 3×200 mL of water, 1×200 mL of saturated sodium bicarbonate solution and 1×200 mL of saturated sodium chloride solution respectively. The mixture was dried over anhydrous sodium sulfate, filtered, and concentrated under reduced pressure. The crude product was re-crystallized from ethyl acetate/petroleum ether in the ratio of 1:1. This resulted in 6 g (60%) of PH-4 and PH-4S (5:1) as a white solid. MS m/z [M+H]+ (ESI): 503.

To a solution of PH-4 and PH-4S (5:1) (10 g, 19.90 mmol, 1.00 equiv) in tetrahydrofuran (150 mL), was added 10% palladium carbon (3.0 g). The flask was evacuated and flushed three times with nitrogen, followed by flushing with hydrogen. The resulting solution was stirred for 1 h at room temperature. The solids were filtered out. The resulting mixture was concentrated under reduced pressure. The crude product (10 g) was purified by Flash-Prep-HPLC with the following conditions (IntelFlash-1): Column, C18; mobile phase, waters and acetonitrile (30% acetonitrile up to 50% in 30 min); Detector, UV 254 nm. This resulted in 7 g (74%) of PH-5 as a white solid and 1.0 g of PH-5S as a white solid. MS m/z [M+H]+ (ESI): 477.

Preparation of PH-6

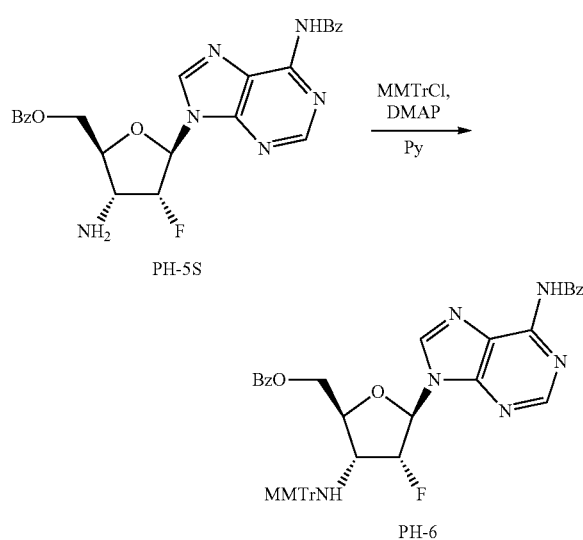

To a solution of PH-5 (4 g, 8.40 mmol, 1.00 equiv) in pyridine (40 mL) with an inert atmosphere of nitrogen, was added 4-dimethylaminopyridine (1.5 g, 12.28 mmol, 1.50 equiv) and 4-methoxytriphenylmethyl chloride (10.3 g, 4.00 equiv) in order. The resulting solution was stirred for 16 h at 25° C. The resulting solution was diluted with 300 mL of dichloromethane. The resulting mixture was washed with 1×300 mL of water and 3×300 mL of saturated sodium bicarbonate solution. The resulting mixture was washed with 1×300 mL of saturated sodium chloride solution respectively. The mixture was dried over anhydrous sodium sulfate, filtered, and concentrated under reduced pressure. The residue was applied onto a silica gel column with dichloromethane/methanol (100/1). This resulted in 5.7 g (91%) of PH-6 as a white solid.

Preparation of PH-7

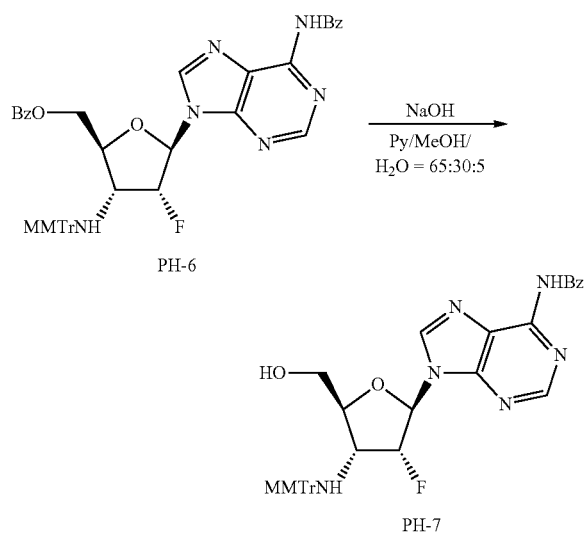

To a solution of PH-6 (5 g, 6.68 mmol, 1.00 equiv) in pyridine/methanol/water (32.2/14.7/2.4 mL), was added sodium hydroxide (2 mol/L) (7.2 mL, 1.10 equiv) dropwise with stirring at 0° C. in 5 min. The resulting solution was stirred for 20 min at 0° C. The reaction was then quenched by the addition of 200 mL of ice water. The resulting solution was extracted with 400 mL of dichloromethane and the organic layers combined. The resulting mixture was washed with 1×300 mL of water and 1×300 mL of saturated sodium chloride solution. The mixture was dried over anhydrous sodium sulfate, filtered, and concentrated under reduced pressure. The residue was applied onto a silica gel column with methanol/dichloromethane (1:100). This resulted in 4.3 g (100%) of PH-7 as a white solid. MS m/z [M+H]+ (ESI): 645.

Preparation of PH-8

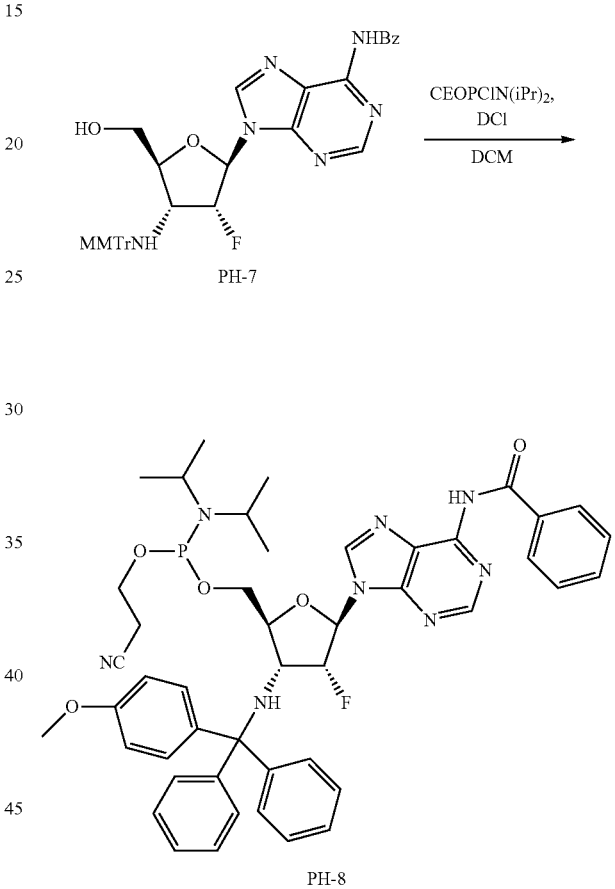

To a solution of PH-7 (19.4 g, 35.89 mmol, 1.00 equiv) in dichloromethane (200 mL) with an inert atmosphere of nitrogen, was added 3-([bis [bis (propan-2-yl) amino] phosphanyl] oxy) propanenitrile (11.79 g, 39.12 mmol, 1.30 equiv). This was followed by the addition of 4, 5-Dicyanoimidazole (4.26 g, 1.20 equiv) at 0° C. The resulting solution was stirred for 30 min at room temperature. The resulting solution was diluted with 1000 mL of dichloromethane. The resulting mixture was washed with 3×800 mL of saturated sodium bicarbonate solution and 1×800 mL of sodium chloride solution respectively. The mixture was dried over anhydrous sodium sulfate, filtered, and concentrated under reduced pressure. The crude product was purified by Flash-Prep-HPLC with the following conditions: Column, C18; mobile phase, waters and acetonitrile (40% acetonitrile up to 80% in 6 min); Detector, UV 254 nm. This resulted in 15.2 g (50%) of PH-8 as a white solid. MS m/z [M+H]+ (ESI): 845.

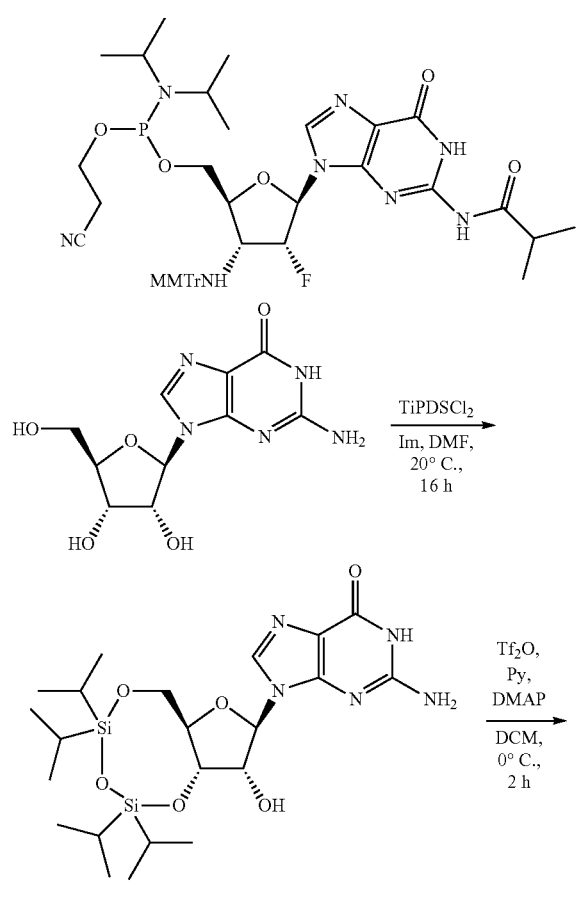
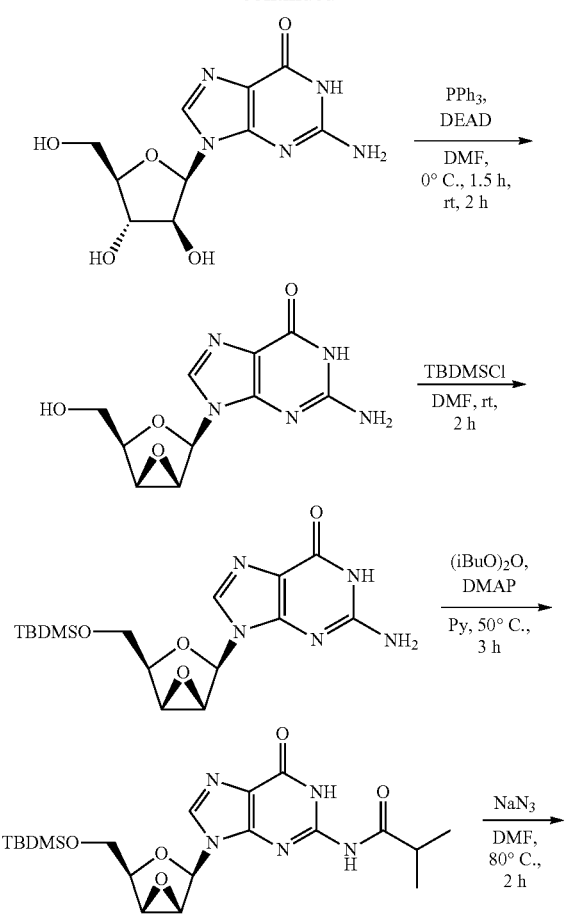

-continued

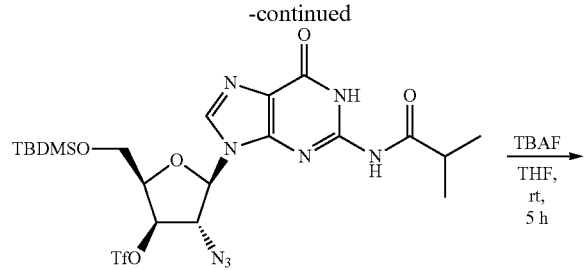

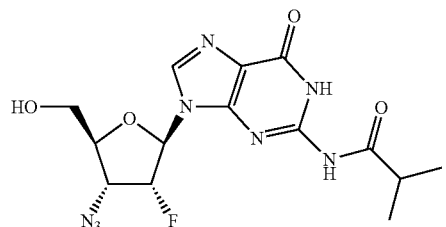

Pd/C H₂
MeOH,
rt, 1 h

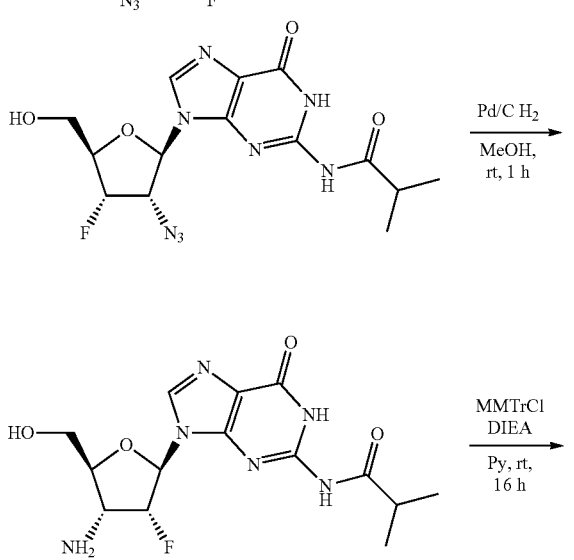

Preparation of PH-11

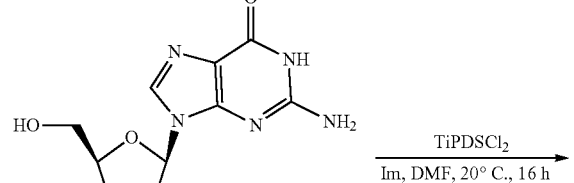

To a solution of 2-amino-9-[(2R,3R,4S,5R)-3,4-dihydroxy-5-(hydroxymethyl)oxolan-2-yl]-6,9-dihydro-1H-purin-6-one (700 g, 2.47 mol, 1.00 equiv) in N,N-dimethylformamide (7 L) with an inert atmosphere of nitrogen, was added imidazole (504 g, 7.41 mol, 3.00 equiv). This was followed by the addition of 1, 3-Dichloro-1, 1, 3, 3-tetraisopropyldisiloxane (770 g, 2.44 mol, 1.00 equiv) dropwise with stirring at 20° C. The resulting solution was stirred for 16 h at 20° C. The reaction solution was then poured into 70 L of water/ice. The solids were collected by filtration. This resulted in 1200 g (92%) of PH-11 as a white solid. MS m/z [M+H]+ (ESI): 526.

Preparation of PH-12

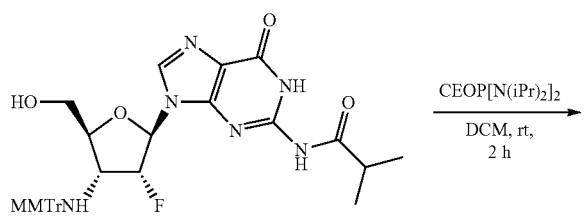

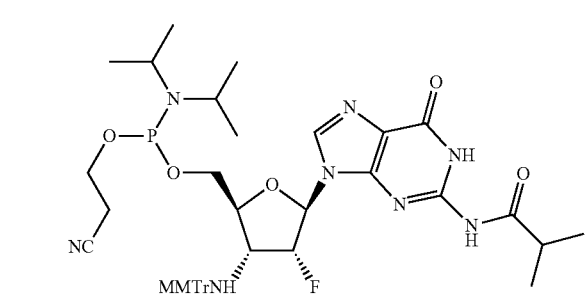

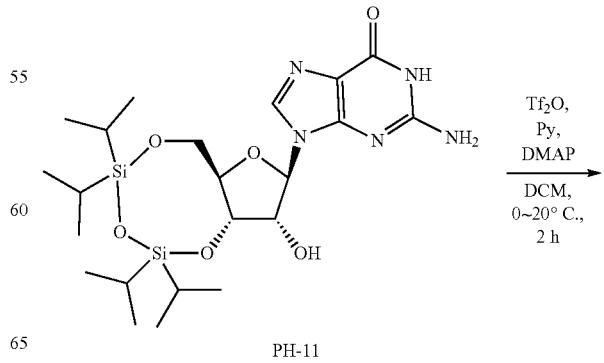

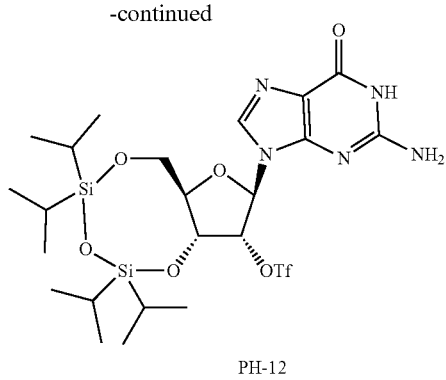

PH-12

To a solution of PH-11 (530 g, 1.01 mol, 1.00 equiv) in dichloromethane (5000 mL) with an inert atmosphere of nitrogen, was added pyridine (725 g, 9.17 mol, 9.00 equiv) and 4-dimethylaminopyridine (147 g, 1.20 mol, 1.20 equiv) in order. This was followed by the addition of trifluoromethanesulfonic anhydride (426 g, 1.51 mol, 1.20 equiv) dropwise with stirring at 0° C. The resulting solution was stirred for 15 min at 0° C. Then the resulting solution was allowed to react with stirring, for an additional 2 h at 20° C. The resulting solution was diluted with 5000 mL of dichloromethane. The resulting solution was washed with 2×3000 mL of saturated sodium bicarbonate and 1×3000 mL of saturated sodium chloride respectively. The solution was dried over anhydrous sodium sulfate, filtered, and concentrated under reduced pressure. This resulted in 600 g (90%) of PH-12 as a brown solid.

The product was used in the next step directly without further purification.

Preparation of PH-13

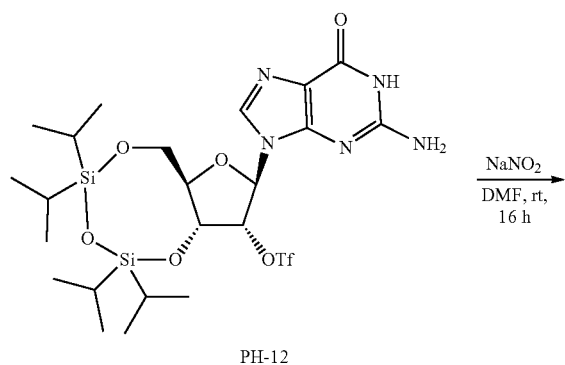

To a solution of PH-12 (200 g, 304.04 mmol, 1.00 equiv) in N,N-dimethylformamide (1000 mL) with an inert atmosphere of argon, was added sodium nitrite (115 g, 1.67 mol, 5.00 equiv). The resulting mixture was stirred for 16 h at 25° C. The resulting solution was poured into 5000 ml water/ice. The solids were collected by filtration. The crude product was re-crystallized from dichloromethane/acetonitrile in the ratio of ¼ (50 ml/g). This resulted in 78 g (49% over last two steps) of PH-13 as a solid. MS m/z [M+H]+ (ESI): 526.

Preparation of PH-14

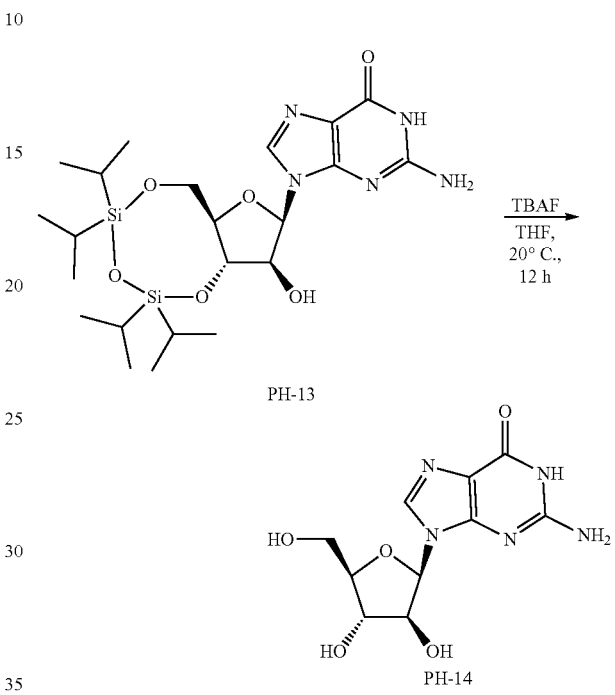

To a solution of PH-13 (50 g, 95.10 mmol, 1.00 equiv) in tetrahydrofuran (500 mL) with an inert atmosphere of nitrogen, was added tetrabutylammonium fluoride (95 mL, 1.00 equiv, 1N in tetrahydrofuran). The resulting mixture was stirred for 12 h at 20° C. The resulting mixture was concentrated under reduced pressure. The crude was re-crystallized from methanol/ethyl acetate in the ratio of ⅕ (20 ml/g) three times. The solids were collected by filtration, and then purified by Flash with the following conditions: Column, C18 silica gel; mobile phase, waters and acetonitrile (2% acetonitrile up to 10% in 10 min); Detector, UV 254 nm. This resulted in 16 g (59%) of PH-14 as a brown solid. 1H-NMR (DMSO-d$_6$, 400 MHz): 10.44 (s, 1H), 6.49 (s, 2H), 6.02 (s, 1H), 5.55-5.65 (m, 2H), 5.10 (s, 1H), 4.08 (m, 2H), 3.76 (m, 1H), 3.64 (m, 1H).

Preparation of PH-15

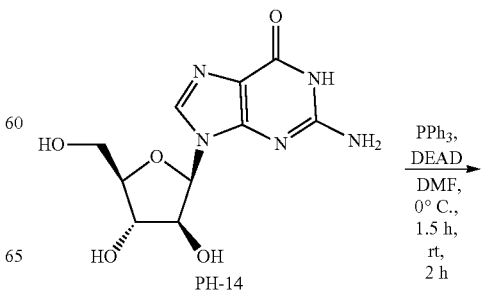

-continued

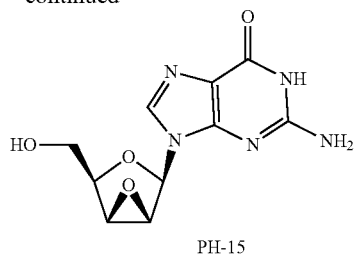
PH-15

To solution of PH-14 (220 g, 776.72 mmol, 1.00 equiv) in N,N-dimethylformamide (2000 mL) with an inert atmosphere of argon, was added triphenylphosphine (509 g, 1.94 mol, 2.50 equiv). The resulting solution was stirred for 1.5 h at 0° C. To this was added diethyl azodicarboxylate (338 g, 1.94 mol, 2.50 equiv) dropwise with stirring at 0° C. The resulting solution was stirred for 2 h at room temperature. The resulting mixture was poured into 20 L cold ethyl ether. The solids were collected by filtration, then re-crystallized from methanol/ethyl acetate in the ratio of ⅒ (10 ml/g). This resulted in 100 g (49%) of PH-15 as a brown solid. MS m/z [M+H]+ (ESI): 266.

Preparation of PH-16

To a solution of PH-15 (100 g, 377.0 mmol, 1.00 equiv) in N,N-dimethylformamide (1000 mL) with an inert atmosphere of nitrogen, was added imidazole (77 g, 1.131 mol, 3.00 equiv). This was followed by the addition of tert-butyldimethylsilyl chloride (142 g, 942 mmol, 1.50 equiv.) dropwise with stirring at 0° C. The resulting solution was stirred for 2 h at room temperature. The reaction was then quenched by the addition of methanol. The resulting mixture was concentrated under reduced pressure. The residue was applied onto a silica gel column with dichloromethane/methanol (100:115:1). This resulted in 80 g (85%) of PH-16 as a solid. MS m/z [M+H]+ (ESI): 380.

Preparation of PH-17

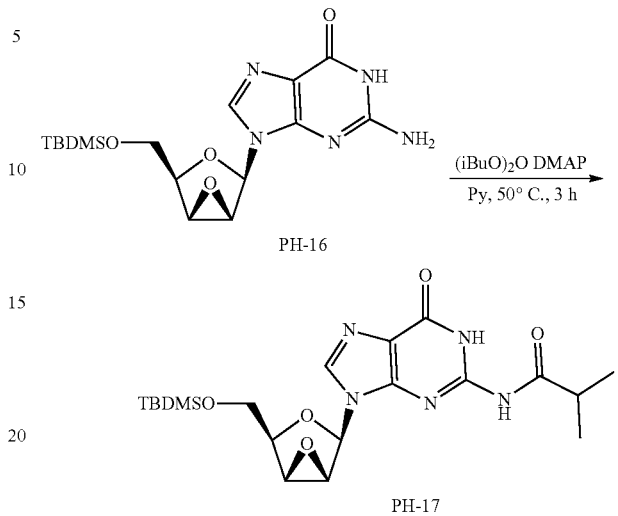

To a solution of PH-16 (73 g, 192.37 mmol, 1.00 equiv) in pyridine (730 mL) with an inert atmosphere of nitrogen, was added 4-dimethylaminopyridine (23.5 g, 192.35 mmol, 0.50 equiv). This was followed by the addition of isobutyric anhydride (213 g, 1.35 mol, 5.00 equiv) dropwise with stirring. The resulting solution was stirred for 3 h at 50° C. The reaction was then quenched by the addition of ice water. The resulting solution was extracted with 3×2000 mL of dichloromethane and the organic layers combined. The resulting mixture was washed with 3×2000 mL of saturated sodium bicarbonate, 3×2000 mL of water and 3×2000 mL of saturated sodium chloride respectively. The organic layers was dried over anhydrous sodium sulfate, filtered, and concentrated under reduced pressure. The residue was applied onto a silica gel column with dichloromethane/methanol (100:120:1). This resulted in 52 g (60%) of PH-17 as a yellow solid. MS m/z [M+H]+ (ESI): 450.

Preparation of PH-18

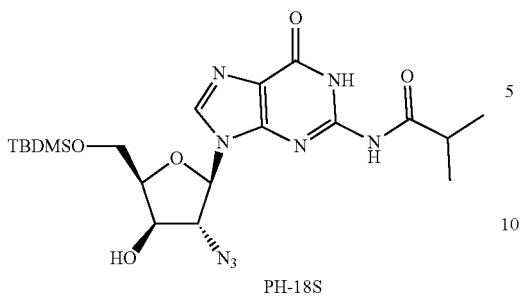

PH-18S

To a solution of PH-17 (20 g, 44.4 mmol, 1.00 equiv) in N, N-dimethylformamide (100 mL) with an inert atmosphere of nitrogen was added sodium azide (18 g, 267 mmol, 6.00 equiv). The resulting solution was stirred for 2 h at 80° C. The resulting mixture was diluted with 1000 mL of dichloromethane. The resulting solution was washed with 3×1000 mL of saturated sodium bicarbonate, 3×1000 mL of water and 3×1000 mL of saturated sodium chloride respectively. The solution was dried over anhydrous sodium sulfate and concentrated under reduced pressure. The residue was applied onto a silica gel column with dichloromethane/methanol (100/1-40/1). This resulted in 11 g (50%) of PH-18/PH-18S (5.2:1) as a yellow solid. MS m/z [M+H]+ (ESI): 493

Preparation of PH-19

To a solution of PH-18/PH-18S (5.2:1) (16 g, 37.87 mmol, 1.00 equiv) in dichloromethane (160 mL), was added pyridine (23 g, 290.77 mmol, 9.00 equiv) and dimethylaminopyridine (4.35 g, 35.66 mmol, 1.20 equiv). This was followed by the addition of 1, 3-bis (trifluoromethylsulfonyl) trioxidane (11.9 g, 37.88 mmol, 1.20 equiv) dropwise with stirring at 0° C. The resulting solution was stirred for 2 h at 20° C. The reaction was quenched by the addition of water/ice. The resulting mixture was extracted with 2×1000 mL of dichloromethane and the organic layers combined. The resulting solution was washed with 1×1000 mL of saturated sodium chloride. The resulting solution was concentrated under reduced pressure. This resulted in 16 g (68%) of PH-19/PH-19S as a brown solid. The product was used in the next step directly without further purification.

Preparation of PH-20

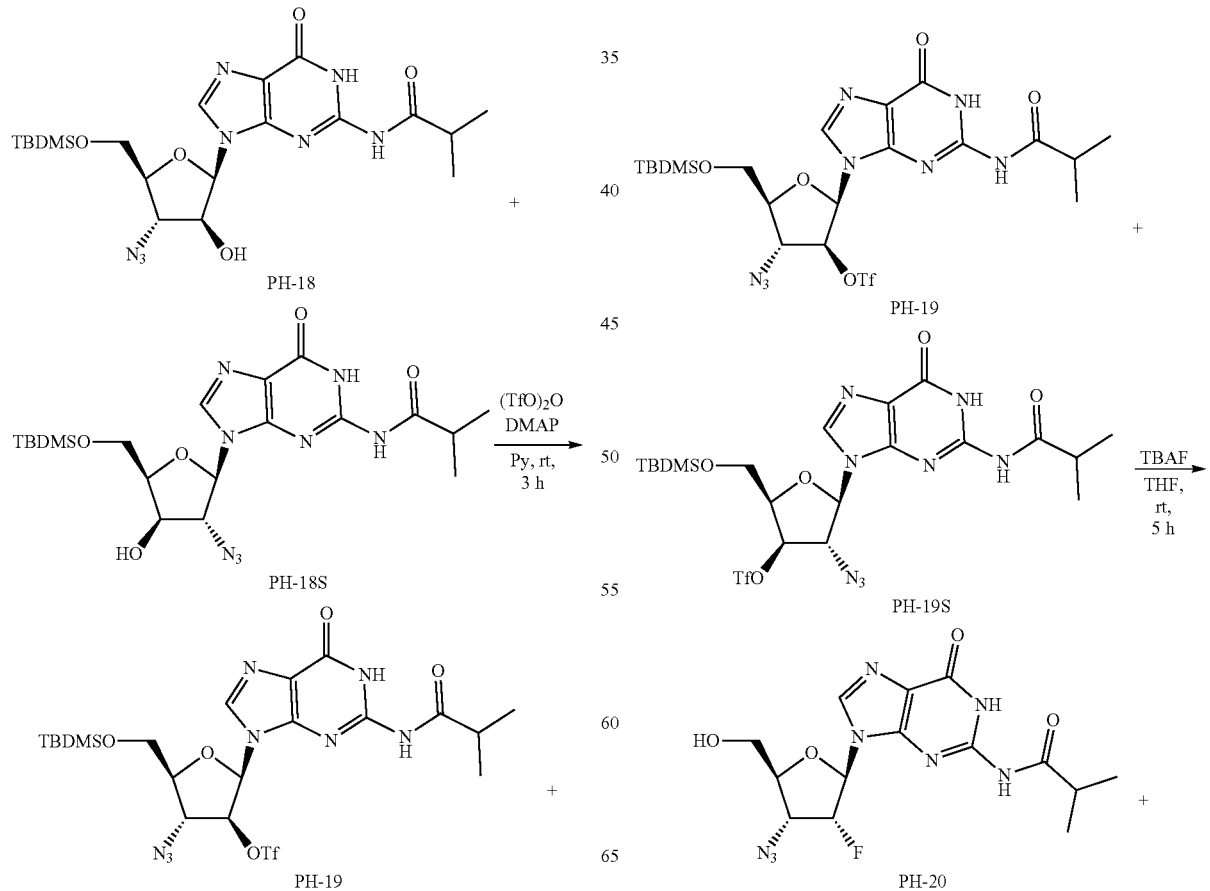

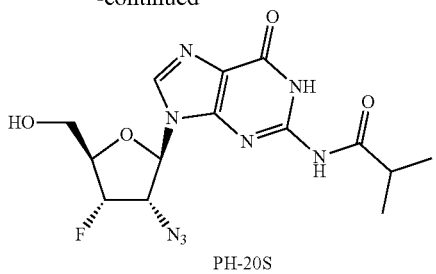

PH-20S

To a solution of PH-19/PH-19S (16 g, 25.61 mmol, 1.00 equiv) in tetrahydrofuran (160 mL) with an inert atmosphere of argon, was added tetrabutylammonium fluoride (100 mL, 5.00 equiv) dropwise with stirring at 0° C. The resulting solution was stirred for 5 h at room temperature. The resulting solution was diluted with 1000 mL of dichloromethane. The resulting solution was washed with 1×500 mL of water and 1×500 mL of saturated sodium chloride respectively. The resulting solution was concentrated under reduced pressure. The residue was applied onto a silica gel column with dichloromethane/methanol (100/120/1). This resulted in 8 g (85%) of PH-20/PH-20S (7:1) a yellow solid. MS m/z [M+H]+ (ESI): 381.

Preparation of PH-21

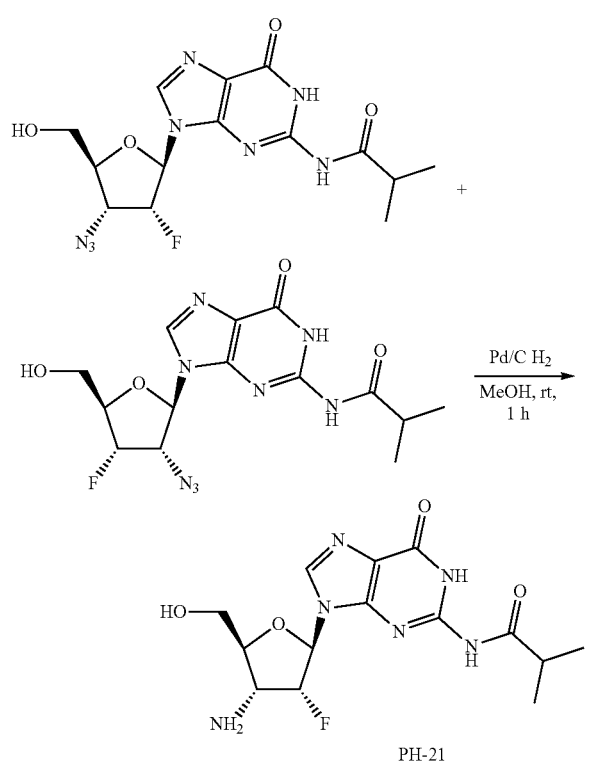

PH-21

To a solution of PH-20/PH-20S (3.4 g, 8.94 mmol, 1.00 equiv) in methanol (50 mL) was added 10% palladium carbon (1.7 g). The flask was evacuated and flushed three times with nitrogen, followed by flushing with hydrogen. The resulting solution was stirred for 1 h at room temperature. The resulting solution was diluted with 100 mL of methanol. The solids were filtered out. The resulting solution was concentrated under reduced pressure. The crude product was purified by Flash-Prep-HPLC with the following conditions: Column, C18 silica gel; mobile phase, waters and acetonitrile (5% acetonitrile up to 50% in 35 min); Detector, UV 254 nm. This resulted in 1.7 g (54%) of PH-21 as a white solid. 1H-NMR (DMSO-$d_6$, 400 MHz): 12.13 (s, 1H), 11.91 (s, 1H), 8.91 (s, 2H), 8.23 (s, 2H), 7.25 (m, 1H), 5.78 (m, 1H), 4.62-3.72 (m, 4H), 2.92 (m, 1H), 1.13 (s, 6H).

Preparation of PH-22

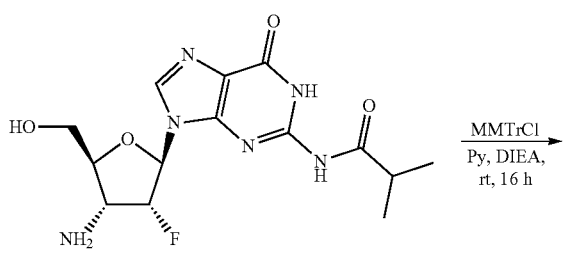

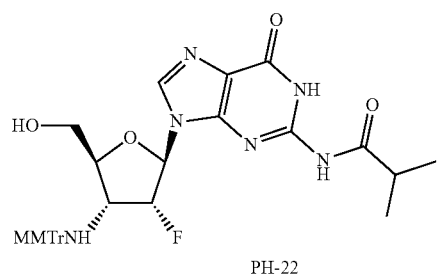

PH-22

To a solution of PH-21 (6.0 g, 16.95 mmol, 1.00 equiv) in pyridine/N,N-diisopropylethylamine (100/20 mL) with an inert atmosphere of argon, was added 1-(chlorodiphenylmethyl)-4-methoxybenzene (6.24 g, 20.34 mmol, 1.20 equiv). The resulting solution was stirred for 16 h at room temperature. The resulting solution was diluted with 1000 ml of dichloromethane. The resulting solution was washed with 1×250 mL of saturated sodium bicarbonate, 1×250 ml of water and 1×250 mL of saturated sodium chloride respectively. The residue was applied onto a silica gel column with dichloromethane/methanol (100/150/1). This resulted in 13 g (74%) of PH-22 as a white solid. 1H-NMR (DMSO-$d_6$, 400 MHz): 12.15 (s, 1H), 11.70 (s, 1H), 8.14 (s, 1H), 7.49 (m, 4H), 7.24 (m, 6H), 7.15 (m, 2H), 6.72 (m, 2H), 5.82 (m, 1H), 5.30 (m, 1H), 4.04 (m, 3H), 3.62 (s, 3H), 3.45 (m, 1H), 2.83-2.62 (m, 3H), 1.10 (m, 6H).

Preparation of PH-23

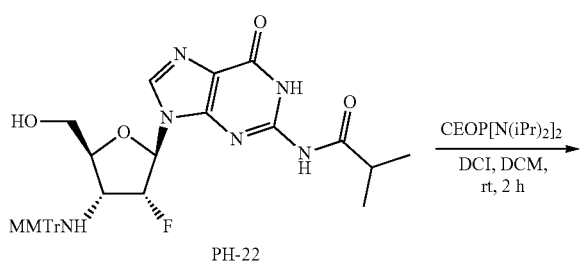

PH-22

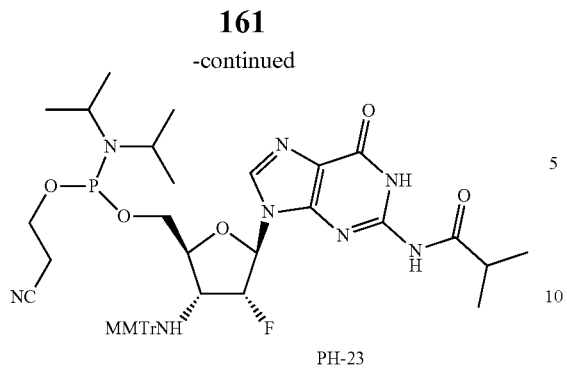

PH-23

To a solution of PH-22 (7.8 g, 12.45 mmol, 1.00 equiv.) in dichloromethane (80 mL) with an inert atmosphere of argon, was added 3-(bis[bis(propan-2-yl)amino]phosphanyloxy)propanenitrile (7.5 g, 24.92 mmol, 2.00 equiv.) and 4,5-dicyanoimidazole (2.2 g, 18.63 mmol, 1.50 equiv.) in order. The resulting solution was stirred for 2 h at room temperature. The resulting mixture was diluted with 1000 mL of dichloromethane. The resulting solution was washed with 3×250 mL of saturated sodium bicarbonate, 3×250 mL of water and 3×250 mL of saturated sodium chloride respectively. The resulting solution was concentrated under reduced pressure. The crude product was purified by Flash-Prep-HPLC with the following conditions: Column, C18 silica gel; mobile phase, waters and acetonitrile (40% acetonitrile up to 95% in 35 min); Detector, UV 254 nm. This resulted in 8.06 g (78%) of PH-23 as a white solid. MS m/z [M+H]+ (ESI): 827.

2'-F-3'-NHTr Building Blocks for Oligomer Synthesis

The 2'-O-Me 3'-NH-MMTr-5'-O-(2-cyanoethyl-N,N-diisopropyl) phosphoramidite monomers of 6-N-benzoyladenosine ($A^{Bz}$), 4-N-Benzylcytidine ($C^{Bz}$), 2-N-isobutyrylguanosine ($G^{iBu}$), and Uridine (U) as shown below were synthesized using the procedure described in WO 200118015 A1

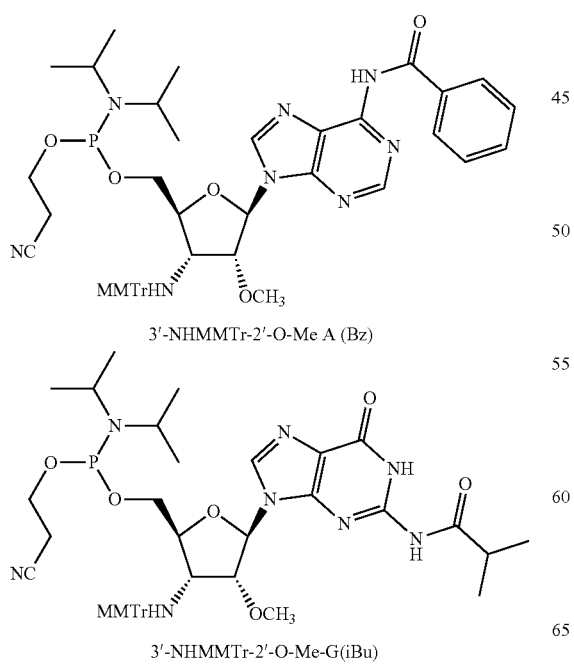

3'-NHMMTr-2'-O-Me A (Bz)

3'-NHMMTr-2'-O-Me-G(iBu)

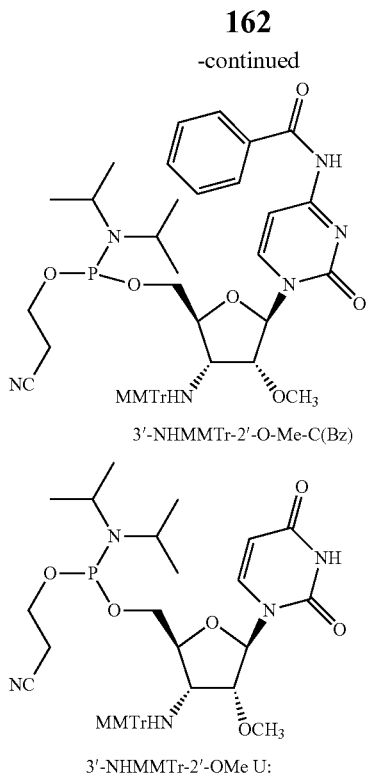

3'-NHMMTr-2'-O-Me-C(Bz)

3'-NHMMTr-2'-OMe U:

2'-O-Me-3'-NHTr Building Blocks for Oligomer Synthesis

Exemplary phosphoroamidates include:

| Raw material description |
| --- |
| 3'-NHTr-dA(Bz) |
| 3'-NHTr-dC(Bz) |
| 3'-NHTr-dG(iBu) |
| 3'-NHTr-T: |
| 3'-NHMMTr-2'-F-A(NH-Bz) |
| 3'-NHMMTr-2'-F-C(NH-Bz) |
| 3'-NHMMTr-2'-F-G(NH-iBu) |
| 3'-NHMMTr-2'-F-U: |
| 3'-NHMMTr-2'-OMe-A(NH-Bz) |
| 3'-NHMMTr-2'-OMe-C(NH-Bz) |
| 3'-NHMMTr-2'-OMe-G(NH-iBu) |
| 3'-NHMMTr-2'-OMe U: |
| 3'-NHTr (dA, dC, dG and dT)-CPG 500 Å: |
| Loading: 64-83 μmol/g |

The reverse phosphoramidite 3'-O-DMT-deoxy Adenosine (NH-Bz), 5'-O-(2-cyanoethyl-N,N-diisopropyl phosphoramidite, 3'-O-DMT-deoxy Guanonosine (NH-ibu), 5'-O-(2-cyanoethyl-N,N-diisopropyl phosphoramidite, 3'-O-DMT-deoxy Cytosine (NH-Bz), 5'-O-(2-cyanoethyl-N,N-diisopropyl phosphoramidite, 3'-O-DMT-deoxy Thymidine (NH-Bz), 5'-O-(2-cyanoethyl-N,N-diisopropyl phosphoramidite and reverse solid supports were purchased from commercially-available sources (Chemgenes).

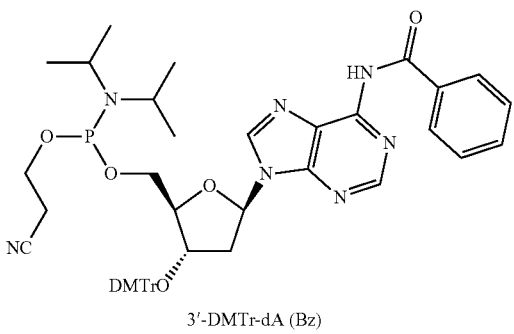

3'-DMTr-dA (Bz)

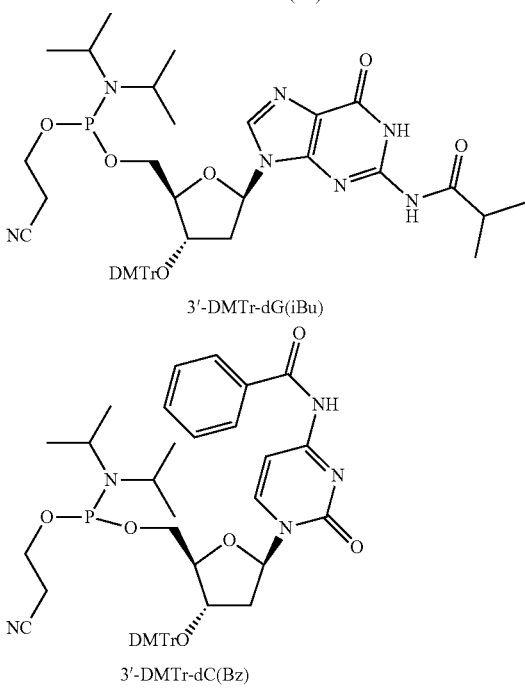

3'-DMTr-dG(iBu)

3'-DMTr-dC(Bz)

3'-DMTr-T:

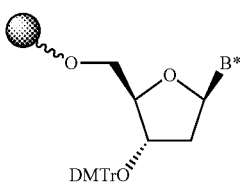

B* = A, C, G or T

Reverse DNA Building Blocks for Oligomer Synthesis

Exemplary reverse phosphoroamidites used for this disclosure include:

| Raw material description |
| --- |
| 3'-O-DMTr-2'-OMe-A(NH-Bz) |
| 3'-O-DMTr-2'-OMe-C(NH-Bz) |
| 3'-O-DMTr-2'-OMe-G(NH-iBu) |
| 3'-O-DMTr-2'-OMe-U: |
| 3'-ODMTr (dA, dC, dG and dT)-CPG 500 Å: |
| Loading: 64-83 µmol/g |

For making the oligomers with the following modifications: 2'-F—NPS-PS-2'-F-NPS; 2'-F—NP-PS-2'-F-NP; 2'-OMe-NP-PS-2'-OMe-NP; 2'-OMe-NPS-DNA-PS-2'-OMe-NPS, the synthesis was carried out on a 1 µM scale in a 5' to 3' direction with the 5'-phosphoramidite monomers diluted to a concentration of 0.1 M in anhydrous $CH_3CN$ in the presence of 5-(benzylthio)-1H-tetrazole activator (coupling time 2.0-4.0 min) to a solid bound oligonucleotide followed by standard capping, oxidation and deprotection afforded modified oligonucleotides. The stepwise coupling efficiency of all modified phosphoramidites was more than 98%. The DDTT (dimethylamino-methylidene) amino)-3H-1, 2, 4-dithiazaoline-3-thione was used as the sulfur-transfer agent for the synthesis of oligoribonucleotide phosphorothioates. Oligonucleotide-bearing solid supports were heated at room temperature with aqueous ammonia/Methylamine (1:1) solution for 3 h in shaker to cleavage from support and deprotect the base labile protecting groups.

Examples 1-4

Example 1

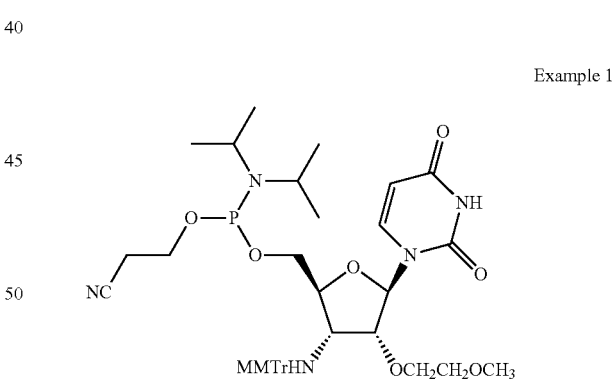

Example 2

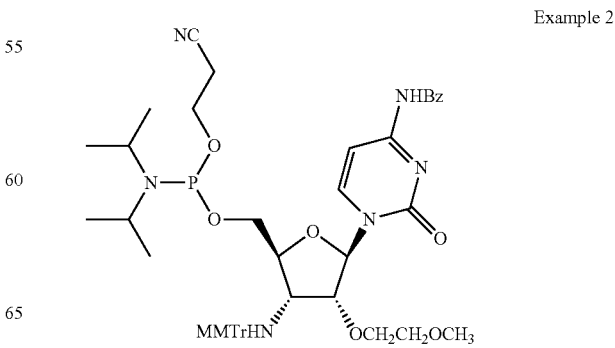

Example 3

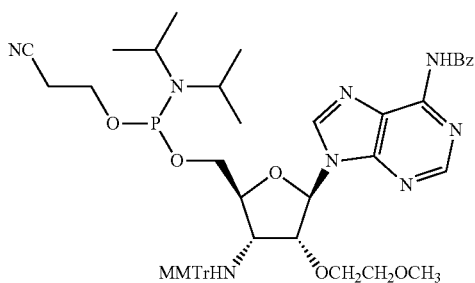

Example 4

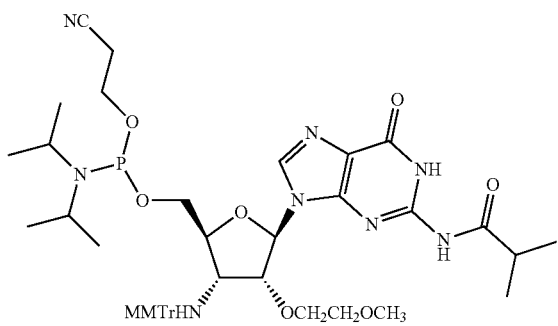

The appropriately protected 2'-O-methoxy ethyl-3'-aminonucleoside-5'-phosphoramidite building blocks (examples 1-4 were prepared after chemical transformations shown in Schemes 1-4.

First for synthesis of uracil based 3'-NH-MMTr-2'-O-methoxyethyl phosphoramidites example 5, key 3'-azido-2'-methoxyethyl intermediate 3 was obtained in low yields via an-hydro intermediate 2 as shown in scheme 1.

Due to low yielding alkylation, 3-1 was reacted with BOMCl/DBU to give N-3 protected intermediate 3-4, which was alkylated by using 2-bromoethyl methyl ether/Ag$_2$O/NaI/DMF to give 2'-O-methoxyethyl derivative 3-5 as shown below in scheme 1. Deprotection of N-3-BOM group using hydrogenation condition (Pd/C/H2) resulted in 10-20% desired 3'-amino intermediate 3-6a along with significant over reduced side product 3-6b.

Scheme 1

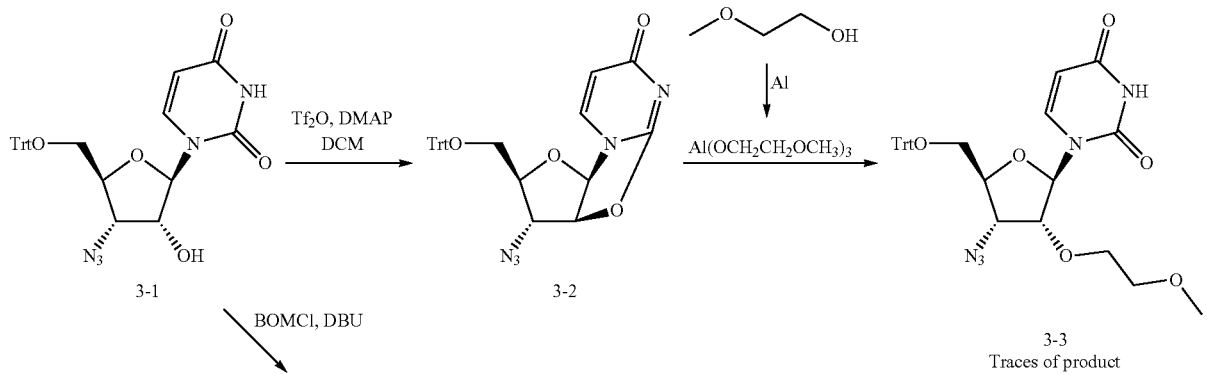

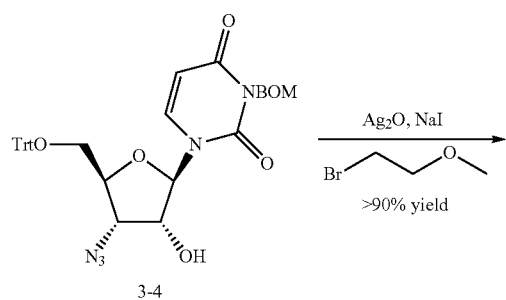

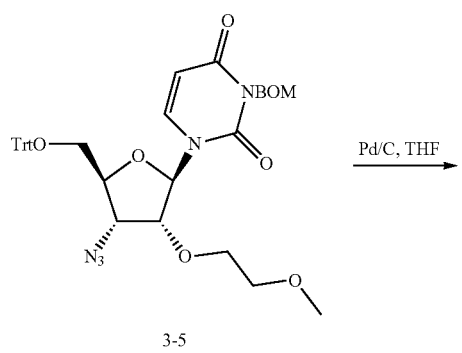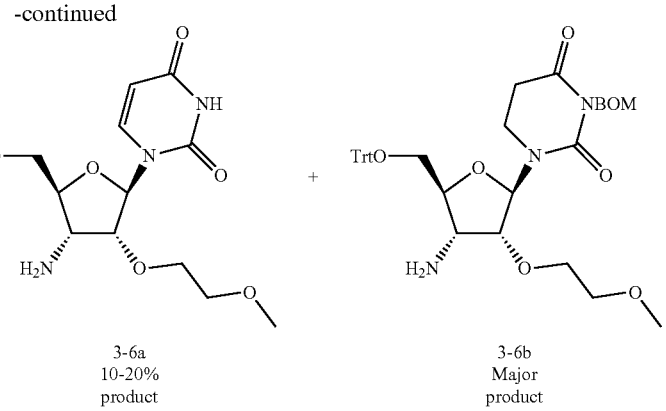

2'-O-alkylation in high yield is obtained as shown below in scheme 2. For this purpose, 3-1 was treated with PMBCl/DBU/DMF to give N-3 protected intermediate 4-2, which was subjected for 2'-O alkylation using 2-bromoethyl methyl ether/Ag$_2$O/NaI/DMF to give 2'-O-methoxyethyl derivative 4-3. Then, 5'-de-tritylation of 4-3 and re-protection of 5'-hydroxyl group using benzoyl chloride afforded 4-5.

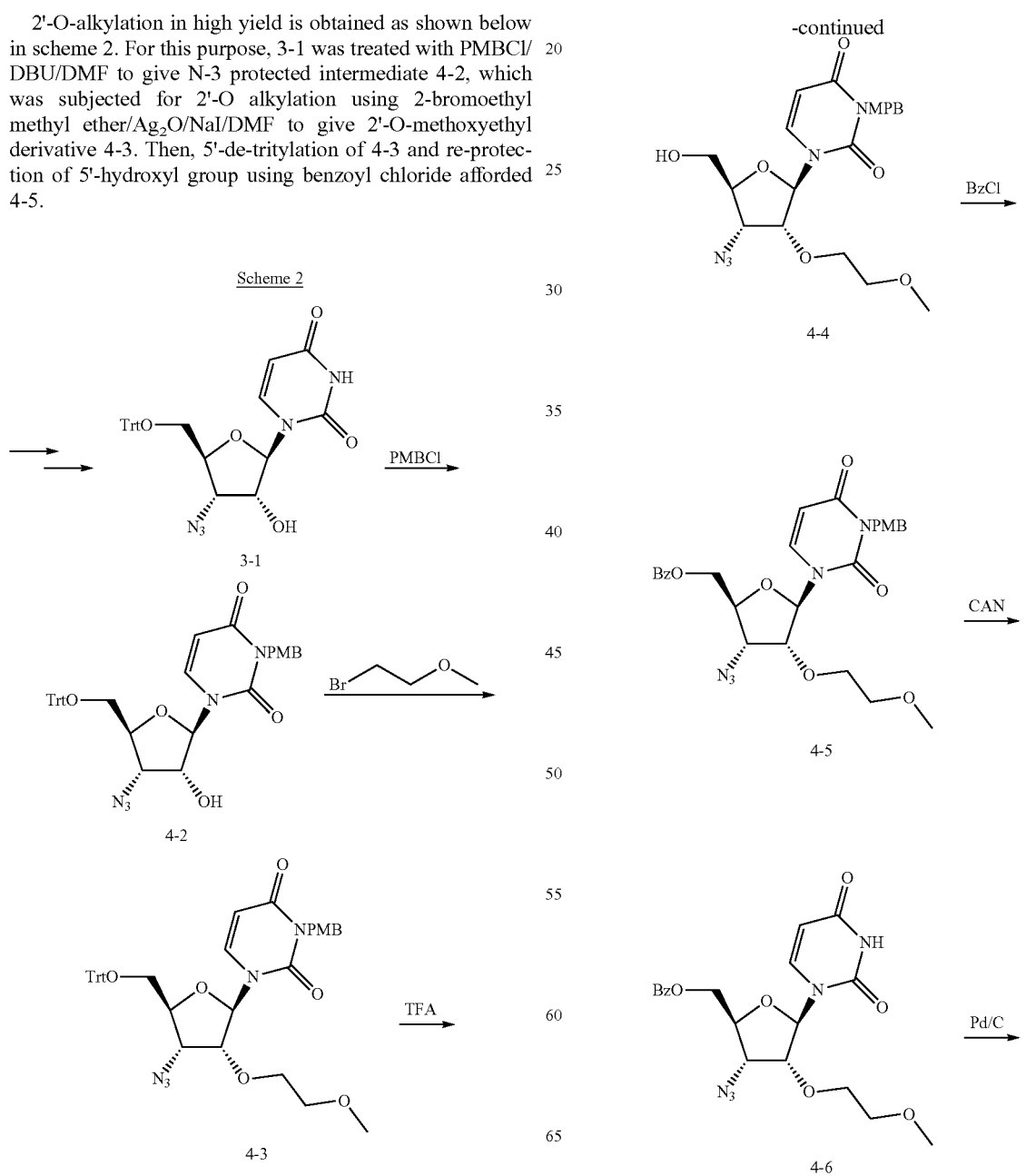

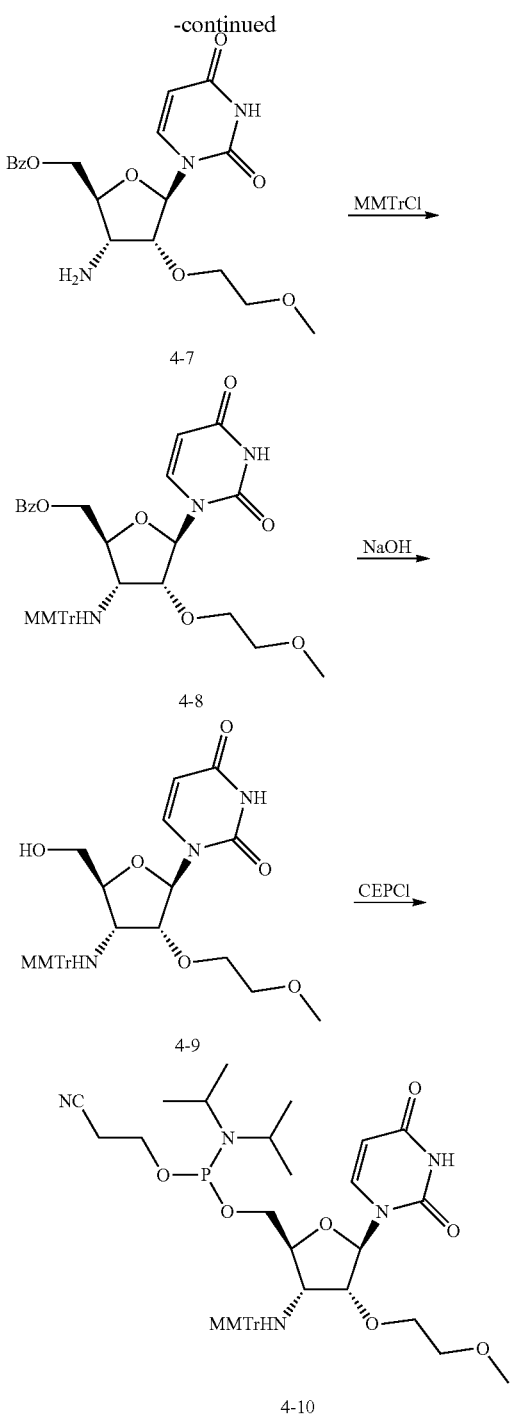

De-protection of PMB group of intermediate 4-5 in mild conditions gives 4-6. 3'-Azido group of intermediate 4-6 was reduced to an amine, which was then immediately protected, such as reaction with 4-monomethoxytritylchloride, to give 4-8. The 5'-benzyl ester was then cleaved using an alkaline solution, followed by phosphitylation using known protocols to give the desired 2'-O-methoxyethoxy uridine phosphoramidite monomer 4-10.

Preparation of (4-2): To a solution of 3-1 (45.30 g, 88.56 mmol) in DMF (120.00 mL) was added PMBCl (20.80 g, 132.84 mmol) and DBU (44.61 g, 177.12 mmol), the mixture was stirred at r.t. for 2 h. Water was added, extracted with EA. The organic layer was concentrated and purified by column to give 4-2 (52.00 g, 82.32 mmol) as a white solid. ESI-LCMS: m/z 632.3 [M+H]$^+$.

Preparation of (4-3): To a solution of 4-2 (50.00 g, 79.15 mmol) in DMF (120.00 mL) was added 2-Bromoethyl methyl ether (16.50 g, 118.73 mmol) and Ag$_2$O (18.34 g, 79.15 mmol, 2.57 mL), then NaI (5.93 g, 39.58 mmol) was added. The reaction mixture was stirred at r.t. for 12 h. LC-MS showed work well. Filtered and added water and EA, the organic layer was concentrated and purified by column to give 4-3 (52.00 g, 75.39 mmol) as a colorless oil. ESI-LCMS: m/z 690.4 [M+H]$^+$.

Preparation of (4-4): To a solution of 4-3 (52.00 g, 75.39 mmol) in DCM (200.00 mL) was added TFA (150.00 mL). The mixture was stirred at r.t. for 1 h. The reaction mixture was slowly added to cold NH$_4$OH, extracted with DCM. The organic layer was concentrated and purified to give 4-4 (31.00 g, 69.28 mmol) as a colorless oil. ESI-LCMS: m/z 448.2 [M+H]$^+$. $^1$H-NMR (DMSO-d$_6$, 400 MHz): δ ppm 8.02 (d, J=8.12 Hz, 1H), 7.26-7.23 (m, 2H), 6.87-6.84 (m, 2H), 5.87-5.81 (m, 2H), 5.38 (t, J=5.0 Hz, 1H), 4.96-4.85 (m, 2H), 4.36-4.34 (m, 1H), 4.17-4.14 (m, 1H), 4.00-3.97 (m, 1H), 3.83-3.77 (m, 1H), 3.75-3.72 (m, 1H), 3.71 (s, 3H), 3.70-3.68 (m, 1H), 3.61-3.56 (m, 1H), 3.45-3.43 (m, 2H), 3.18 (s, 3H).

Preparation of (4-5): To a solution of 4-4 (31.00 g, 69.28 mmol) in Pyridine (200.00 mL) was added BzCl (13.14 g, 93.87 mmol), the reaction mixture was stirred at r.t. for 15 min and concentrated and purified by column to give 4-5 (35.10 g, 63.8 mmol) as a white solid. ESI-LCMS: m/z 552.2 [M+H]$^+$.

Preparation of (4-6): To a solution of 4-5 (35.10 g, 63.8 mmol) in acetonitrile (300.00 mL) and water (100.00 mL) was added Ceric ammonium nitrate (105 g, 191.40 mmol), the reaction mixture was stirred at r.t. for 12 h and concentrated and extracted with EA. The organic layer was concentrated and purified by column to give 4-6 (27.5 g, 63.75 mmol) as a yellow solid. ESI-LCMS: m/z 432.2 [M+H]$^+$.

Preparation of (4-7): To a solution of 4-6 (27.50 g, 63.75 mmol) in THF (500.00 mL) was added Pd/C (3.00 g), the reaction mixture was stirred at r.t. for 12 h and filtered and concentrated to give 4-7 (25.00 g, 61.67 mmol) as a yellow solid. ESI-LCMS: m/z 406.2 [M+H]$^+$.

Preparation of (4-8): To a solution of 4-7 (25.00 g, 61.67 mmol) in DCM (300.00 mL) was added MMTrCl (28.49 g, 92.51 mmol) and Collidine (14.95 g, 123.34 mmol), then AgNO$_3$ (15.7 g, 92.5 mmol) was added. The reaction mixture was stirred at r.t. for 1 h., and filtered and the organic layer was washed water, dried over Na$_2$SO$_4$ and purified by silica gel column to give 4-8 (33.00 g, 48.69 mmol) as a yellow solid.

Preparation of (4-9): To a solution of 4-8 (14.50 g, 21.39 mmol) was added 1 N NaOH in methanol (200 mL) in water (20 mL), the reaction mixture was stirred at r.t. for 1 h. and concentrated and extracted with DCM, the organic layer was concentrated and purified by silica gel column to give 4-9 (11.50 g, 20.05 mmol) as a white solid. $^1$H-NMR (DMSO-d$_6$, 400 MHz): δ ppm 11.26 (s, 1H), 7.95 (d, J=8.4 Hz, 1H), 7.47-7.44 (m, 4H), 7.34-7.17 (m, 8H), 6.82 (d, J=8.8 Hz, 2H), 5.50-5.48 (m, 2H), 5.13 (t, J=3.6 Hz, 1H), 4.05-3.98 (m, 3H), 3.78 (s, 3H), 3.52-3.49 (m, 1H), 3.34-3.32 (m, 2H), 3.14 (s, 3H), 3.08-3.04 (m, 1H), 2.89-2.86 (m, 1H), 2.70 (d, J=10.0 Hz, 1H), 1.51 (d, J=4.4 Hz, 1H).

Preparation of (4-10): To a solution of 4-9 (11.50 g, 20.05 mmol) in DCM (100.00 mL) was added DMAP (489.85 mg, 4.01 mmol) and DIPEA (10.36 g, 80.19 mmol, 14.01 mL). Then CEPCl (5.70 g, 24.06 mmol) was added to the solution.

The mixture was stirred at r.t. for 30 min. The reaction was quenched with saturated NaHCO$_3$. The organic layer was washed with brine, dried over Na$_2$SO$_4$, concentrated to give the crude product. The crude product was purified by Flash-Prep-HPLC. The product was dissolved in anhydrous toluene and concentrated for three times. Then the product was dissolved anhydrous acetonitrile and concentrated for three times. This resulted in 13 g to give 4-10 as a white solid. MS m/z [M–H]$^-$ (ESI): 772.3; $^1$H-NMR (CDCl$_3$, 400 MHz): 9.01 (s, 1H), 8.07-7.61 (m, 1H), 7.53-7.41 (m, 6H), 7.29-7.15 (m, 5H), 6.79-6.76 (m, 2H), 5.63-5.57 (m, 2H), 4.27-4.15 (m, 2H), 4.06-3.95 (m, 1H), 3.85-3.77 (m, 1H), 3.75 (s, 3H), 3.69-3.35 (m, 7H), 3.23 (d, J=4 Hz, 1H), 2.26-2.91 (m, 3H), 2.59 (t, J=6.4 Hz, 1H), 1.75-1.39 (m, 1H), 1.21-1.11 (m, 12H). $^{31}$PNMR (162 MHz, CDCl$_3$): 149.10, 148.26.

Example 5

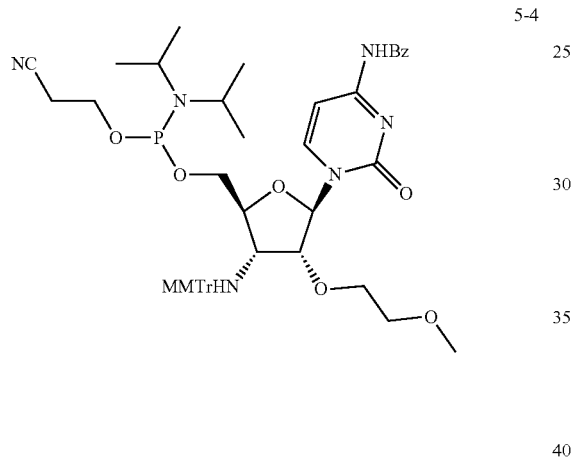

5-4

The 2'-O-methoxyethoxy-NH-benzoyl-cytosine phosphoramidite compound 5-4 was obtained by conversion of uridine intermediate 4-8 into 3'-amino cytidine analogue 5-1 followed by phosphitylation using known protocols to give the desired 2'-O-methoxyethoxy cytidine phosphoramidite monomer 5-4 as shown below in scheme 3.

Scheme 3

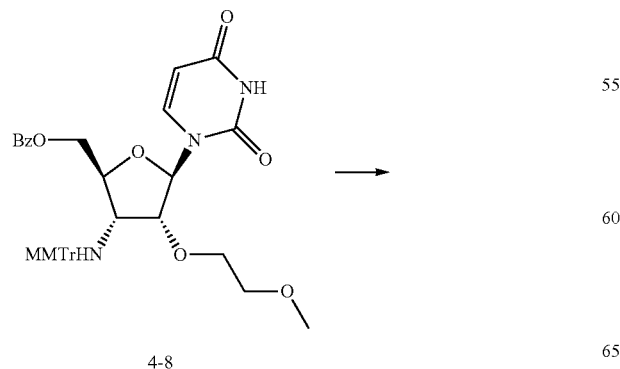

4-8

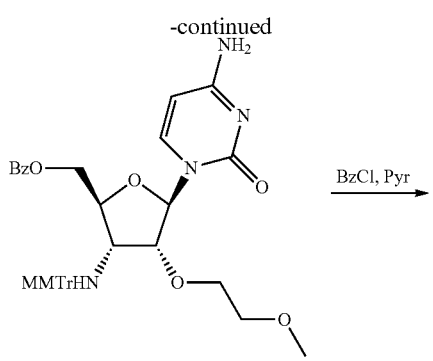

5-1

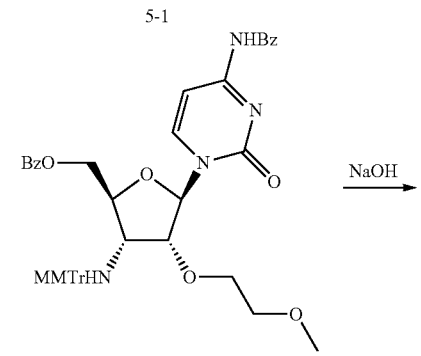

5-2

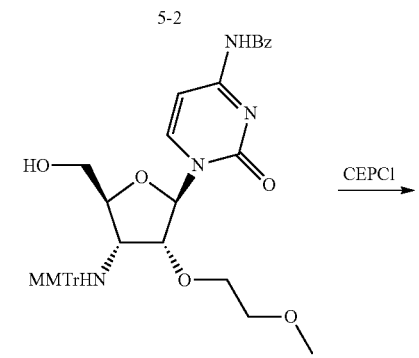

5-3

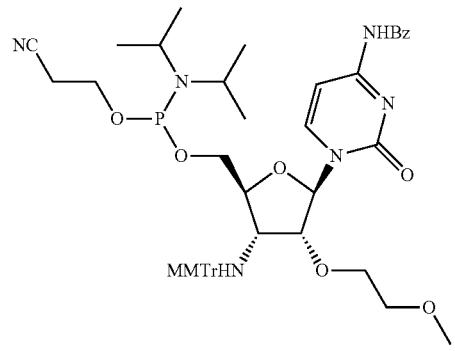

5-4

Preparation of (5-1): To a solution of 4-8 (18.50 g, 27.30 mmol) in acetonitrile (250.00 mL) was added TPSCl (16.49 g, 54.60 mmol) and DMAP (6.67 g, 54.60 mmol), then TEA (5.52 g, 54.60 mmol, 7.56 mL) was added to the solution. The reaction mixture was stirred at r.t. for 5 h under N$_2$. NH$_4$OH (50.00 mL) was added to the reaction mixture. The mixture was stirred at r.t. for 12 h. The solution was concentrated and extracted with EA. The organic layer was washed by brine and dried over Na$_2$SO$_4$. The organic layer was concentrated and purified by silica gel column to give 5-1 (16.00 g, 23.64 mmol) as a yellow solid.

Preparation of (5-2): To a solution of 5-1 (16.00 g, 23.64 mmol) in Pyridine (100.00 mL) was added BzCl (4.96 g, 35.46 mmol) at 0° C. The mixture was stirred at r.t. for 1 h. The solution was concentrated and purified by silica gel column to give 5-2 (17.40 g, 22.28 mmol) as a white solid.

Preparation of (5-3): Compound 5-2 (17.40 g, 22.28 mmol) was added to 180 mL of 1 N NaOH solution in Pyridine/MeOH/H$_2$O (65/30/5) at 0° C. The suspension was stirred at 0° C. for 15 min. The reaction mixture was quenched by addition of sat. NH$_4$Cl solution. The solution was extracted with EA and the combined organic layers were washed with sat. NaHCO$_3$ solution, brine, dried over Na$_2$SO$_4$, filtered, and concentrated. The residue was purified by column to give 5-3 (12.50 g, 18.47 mmol) as white solid. $^1$H-NMR (DMSO-d$_6$, 400 MHz): δ ppm 12.25 (s, 1H), 8.53 (d, J=7.6 Hz, 1H), 8.01 (d, J=5.2 Hz, 2H), 7.64-7.60 (m, 1H), 7.52-7.42 (m, 6H), 7.31 (d, J=8.8 Hz, 2H), 7.26-7.14 (m, 7H), 6.79 (d, J=8.8 Hz, 2H), 5.55 (s, 1H), 5.23 (t, J=3.6 Hz, 1H), 4.09-3.97 (m, 3H), 3.73 (s, 3H), 3.70-3.66 (m, 1H), 3.38-3.34 (m, 2H), 3.17 (s, 3H), 3.11-3.05 (m, 1H), 2.96-2.91 (m, 1H), 2.68 (d, J=10.8 Hz, 1H), 1.49 (d, J=4 Hz, 1H).

Preparation of (5-4): To a solution of 5-3 (12.50 g, 18.47 mmol) in DCM (100.00 mL) was added DMAP (451.30 mg, 3.69 mmol) and DIPEA (9.55 g, 73.88 mmol, 12.90 mL), then CEPCl (5.25 g, 22.16 mmol) was added. The mixture was stirred at r.t. for 30 min. The reaction was quenched with saturated NaHCO$_3$. The organic layer was washed with brine, dried over Na$_2$SO$_4$, concentrated to give the crude product. The crude was by Flash-Prep-HPLC. The product was dissolved in anhydrous toluene and concentrated for three times. Then the product was dissolved anhydrous acetonitrile and concentrated for three times. This resulted in 13 g to give 5-4 as a white solid. MS m/z [M−H]$^-$ (ESI): 875.4. $^1$H-NMR (400 MHz, CDCl$_3$): δ ppm 8.64-8.20 (m, 2H), 7.90-7.88 (m, 2H), 7.62-7.58 (m, 1H), 7.53-7.39 (m, 8H), 7.25-7.15 (m, 6H), 6.78-6.74 (m, 2H), 5.69 (d, J=1.72 Hz, 1H), 4.37-4.21 (m, 2H), 4.10-4.03 (m, 1H), 3.90-3.79 (m, 2H), 3.75 (d, J=1.64 Hz, 3H), 3.68-3.52 (m, 3H), 3.46-3.42 (m, 2H), 3.26 (d, J=1.2 Hz, 3H), 3.17-2.97 (m, 2H), 2.94-2.87 (m, 1H), 2.67-2.48 (m, 2H), 1.79-1.51 (m, 1H), 1.26-1.18 (m, 12H). $^{31}$PNMR (162 MHz, CDCl$_3$): 148.93, 148.03

Example 6

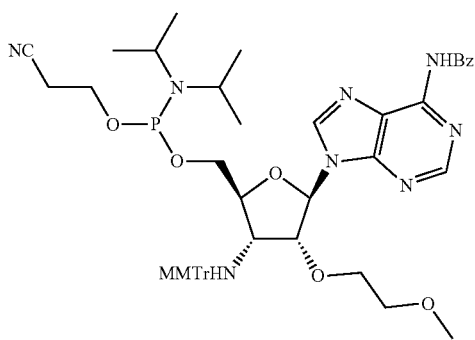

6-10

The synthesis of the 2'-O-methoxyethyl adenosine analogue 6-10 was achieved as shown below in scheme 6. The intermediate 6-2 under basic condition (NH$_3$/MeOH) resulted in diol 6-3, which then upon protection of 5'-hydroxy group using TBDPSCl to give 6-4 Intermediate 6-4. Then, 2'-O alkylation of 6-4 using 2-bromoethyl methyl ether/NaH/DMF to give 2'-O-methoxyethyl derivative 6-5 without the protection of C-6-exocyclic amine of 6-4. In an inventive way selective alkylation of 2'-OH group of intermediate 6-4 was achieved.

Scheme 4

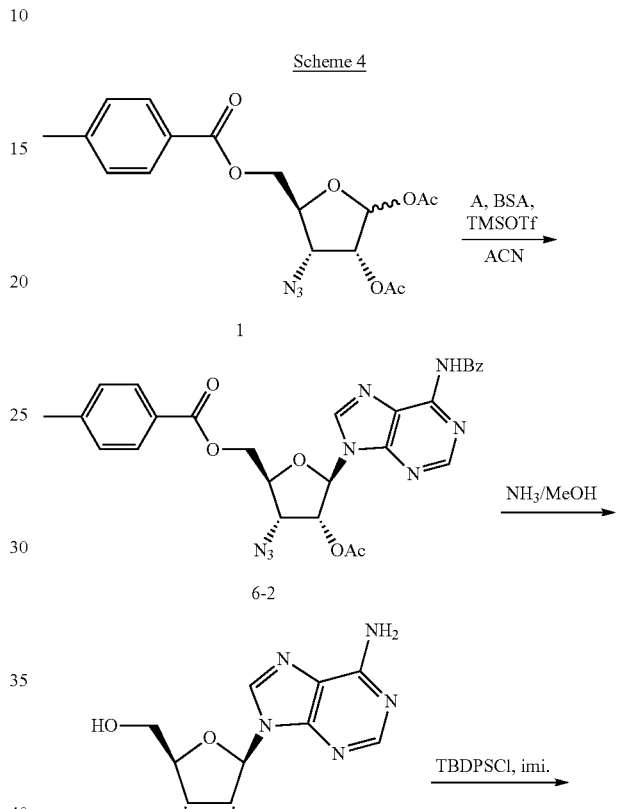

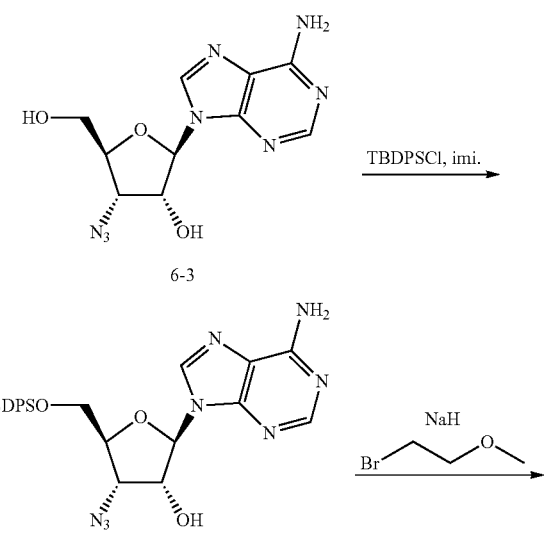

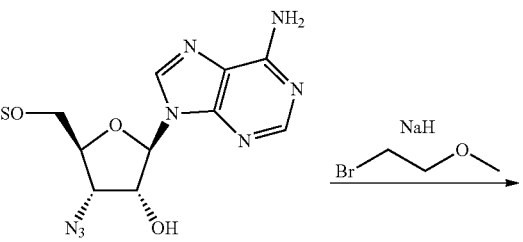

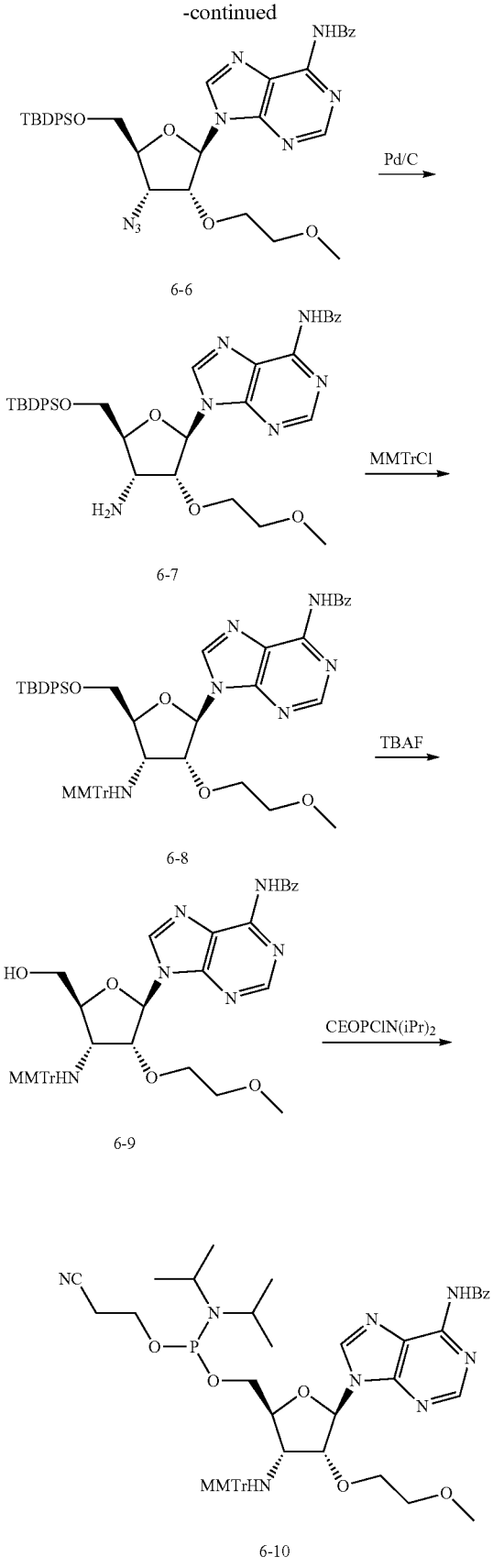

3'-Azido group of intermediate 6-5 was reduced to the amine 6-7, which was then immediately protected, such as reaction with 4-monomethoxytritylchloride, to give the precursor 6-8 after de-protection of 5'-OTBDPS group using TBAF/THF. The phosphitylation of 6-9 using known protocols is performed to give the desired 2'-O-methoxyethoxy adenine-NH-benzoyl phosphoramidite monomer 6-10.

Preparation of (6-2): To a solution of compound 1 (79.50 g, 210.68 mmol) in dry ACN (1.20 L) was added N-(5H-Purin-6-yl)benzamide (100.80 g, 421.36 mmol) and BSA (180.07 g, 884.86 mmol). The resulting suspension was stirred at 50° C. until clear. Then the mixture was cooled at −20° C. and TMSOTf (93.54 g, 421.36 mmol) was added by syringe. Then the mixture was stirred at 70° C. for 72 h under N2, and quenched with sat NaHCO$_3$ and extracted with DCM. The organic layer was dried over Na$_2$SO$_4$, then solvent was evaporated, and the residue was purified on silica gel to afford compound 6-2 (107.50 g, 192.26 mmol, 91.26% yield) as a yellow solid. $^1$H-NMR (400 MHz, DMSO): δ=11.28 (s, 1H), 8.64 (d, J=6.4 Hz, 2H), 8.05 (d, J=8.0 Hz, 2H), 7.84 (d, J=8.0 Hz, 2H), 7.66 (t, J=7.6 Hz, 1H), 7.56 (t, J=8.0 Hz, 2H), 7.33 (d, J=8.0 Hz, 2H), 6.37 (d, J=3.6 Hz, 1H), 6.17 (dd, J=6.0 Hz, 1H), 5.09 (t, J=6.8 Hz, 1H), 4.69-4.56 (m, 2H), 4.40-4.38 (m, 1H), 2.39 (s, 3H), 2.17 (s, 3H). ESI-LCMS: m/z 557.2 [M+H]$^+$.

Preparation of (6-3): To a solution of compound 6-2 (107.50 g, 192.26 mmol) dissolved in 33 wt. % methylamine in ethanol (600.00 mL), then the mixture were stirred at 20° C. for 16 h, then solvent was evaporated, washed with 50% EtOAc in petroleum ether (1.5 L), filtered to afford compound 6-3 (52.50 g, 179.64 mmol, 93.44% yield) as a slightly yellow solid. ESI-LCMS: m/z 293.1 [M+H]$^+$.

Preparation of (6-4): A solution of compound 6-3 (52.50 g, 179.64 mmol), imidazole (18.32 g, 269.46 mmol) and TBDPS-Cl (54.34 g, 197.60 mmol) in pyridine (500.00 mL) was stirred at 20° C. for 2 h, LC-MS showed 6-3 was consumed. Then quenched with MeOH (30 mL), concentrated to give the crude product which was purified on silica gel with to afford compound 6-4 (72.60 g, 136.81 mmol, 76.16% yield) as a white solid. $^1$H-NMR (400 MHz, DMSO): δ=8.29 (s, 1H), 8.10 (s, 1H), 7.63-7.59 (m, 4H), 7.48-7.33 (m, 8H), 6.36 (d, J=5.6 Hz, 1H), 5.97 (d, J=4.4 Hz, 1H), 5.10-5.06 (m, 1H), 4.47 (t, J=5.6 Hz, 1H), 4.14-4.11 (m, 1H), 3.94 (dd, J=11.2 Hz, 1H), 3.83 (dd, J=11.6 Hz, 1H), 0.99 (s, 9H). ESI-LCMS: m/z 531.3 [M+H]$^+$.

Preparation of (6-5): A solution of 6-4 (35.00 g, 65.96 mmol) and 1-Bromo-2-methoxyethane (18.33 g, 131.91 mmol) in dry DMF (400.00 mL), was added NaI (19.77 g, 131.91 mmol) and Ag$_2$O (15.29 g, 65.96 mmol), the mixture was stirred at room temperature for 5 h. Then the reaction was poured into ice water, extracted with EA, washed with brine and dried over anhydrous Na$_2$SO$_4$. The solvent was evaporated, and the residue was purified on silica gel to give 6-5 (23.70 g, 40.26 mmol, 61.04% yield) as a white solid and by-product of TBDPS lost 5.20 g, 9.81 mmol, 14.87% yield) as a white solid. $^1$H-NMR (400 MHz, DMSO): δ=8.31 (s, 1H), 8.11 (s, 1H), 7.63-7.60 (m, 4H), 7.47-7.44 (m, 2H), 7.40-7.36 (m, 6H), 6.10 (d, J=4.4 Hz, 1H), 5.02 (t, J=4.8 Hz, 1H), 4.69 (t, J=5.6 Hz, 1H), 4.18-4.14 (m, 1H), 3.95 (dd, J=11.6 Hz, 1H), 3.84 (dd, J=11.6 Hz, 1H), 3.78-3.75 (m, 2H), 3.45 (t, J=4.8 Hz, 1H), 3.16 (s, 3H), 0.99 (s, 9H). ESI-LCMS: m/z 589.5 [M+H]$^+$.

Preparation of (6-6): To a solution of 6-5 (31.23 g, 53.04 mmol) in pyridine (300.00 mL) at 0° C., was added BzCl (11.22 g, 79.56 mmol) dropwise. The mixture was stirred at r.t. for 2 h. Then the solution was cooled to 0° C., and ammonium hydroxide (20 mL, 30%) was added and the mixture was allowed to warm to r.t., then the solvent was evaporated, 300 mL H₂O and 600 mL EA were added into separate the solution, the aqueous was extracted by EA, combined the organic and washed with brine, dried over anhydrous Na₂SO₄, the solvent was removed and the residue was purified on silica gel to give 6-6 (28.70 g, 41.42 mmol, 78.09% yield) as a white solid. ESI-LCMS: m/z 693.4 [M+H]⁺.

Preparation of (6-7): A solution of 6-6 (28.70 g, 41.42 mmol) in EA (150.00 mL) was added Pd/C (3.00 g) and MeOH (150.00 mL) under H₂. The mixture was stirred at r.t. for 5 h. Then the reaction was filtered and the filtrate concentrated to give 6-7 (25.49 g, 38.22 mmol, 92.27% yield) as a gray solid. ESI-LCMS: m/z 667.3 [M+H]⁺.

Preparation of (6-8): To a solution of 6-7 (25.49 g, 38.22 mmol) and AgNO₃ (12.98 g, 76.44 mmol) in DCM (300.00 mL) was added collidine (13.89 g, 114.66 mmol) and MMTrCl (19.43 g, 57.33 mmol), the mixture was stirred at r.t. for 2 h. Then the reaction was poured into ice water, the organic layer extracted with DCM, washed with brine and dried over anhydrous Na₂SO₄, the solvent was removed and the residue was purified on silica gel to give 6-8 (32.79 g, 34.92 mmol, 91.36% yield) as a gray solid.

Preparation of (6-9): A solution of 6-8 (32.79 g, 34.92 mmol) in THF (300.00 mL) was added TBAF (1M, 35.00 mL), the mixture was stirred at room temperature for 15 h. Then the solvent was removed and the residue was purified on silica gel with EA to give 6-9 (22.22 g, 31.71 mmol, 90.82% yield) as a white solid. ¹H-NMR (400 MHz, CDCl₃): δ=8.68 (s, 1H), 8.32 (s, 1H), 8.04 (d, J=7.2 Hz, 2H), 7.61-7.57 (m, 1H), 7.53-7.48 (m, 6H), 7.40 (d, J=8.8 Hz, 2H), 7.21-7.12 (m, 6H), 6.73 (d, J=8.8 Hz, 2H), 6.09 (d, J=2.4 Hz, 2H), 4.08-4.02 (m, 2H), 3.93-3.87 (m, 1H), 3.72 (s, 3H), 3.58-3.53 (m, 1H), 3.43-3.39 (m, 3H), 3.24-3.19 (m, 4H), 2.19 (br, 1H).

Preparation of (6-10): To a solution of 6-9 (14.00 g, 19.98 mmol), DMAP (488.19 mg, 4.00 mmol) and DIPEA (6.46 g, 49.95 mmol, 8.73 mL) in dry DCM (100.00 mL) was added CEPCl (5.68 g, 23.98 mmol) dropwise under Ar. The mixture was stirred at room temperature for 1 h. Then the reaction was wished with 10% NaHCO₃(aq) and brine, dried over Na₂SO₄, the solvent was removed and the residue was purified by c.c. with the PE/EA mixture, then concentrated to give the crude product. The crude product (10 g, dissolved in 10 mL of ACN) was purified by Flash-Prep-HPLC to obtain 6-10 (12.60 g, 13.98 mmol, 69.99% yield) as a white solid. Then the product was dissolved in dry toluene (15 mL) and concentrated three times, and with dry ACN three times. ¹H-NMR (400 MHz, CDCl₃): δ=9.12 (d, J=46.8 Hz, 1H), δ=8.71 (d, J=11.6 Hz, 1H), 8.50 (s, 0.6H), 8.22 (s, 0.4H), 8.04 (t, J=7.2 Hz, 2H), 7.63-7.59 (m, 1H), 7.55-7.46 (m, 6H), 7.40-7.37 (m, 2H), 7.19-7.06 (m, 6H), 6.69 (dd, J=8.8 Hz, 2H), 6.03 (d, J=3.2 Hz, 1H), 4.36-4.24 (m, 2H), 3.92-3.78 (m, 2H), 3.71 (d, J=11.6 Hz, 3H), 3.67-3.33 (m, 7H), 3.29 (d, J=11.2 Hz, 3H), 3.17-3.10 (m, 1H), 2.88 (dd, J=27.2 Hz, 1H), 2.65-2.50 (m, 2H), 2.38 (d, J=4.4 Hz, 0.4H), 1.80 (d, J=4.0 Hz, 0.6H), 1.23-1.15 (m, 12H). ³¹PNMR (400 MHz, CDCl₃): 148.86, 148.22. ESI-LCMS: m/z 901.3 [M+H]⁺.

Example 7

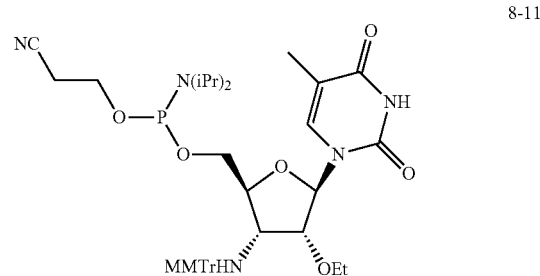

8-11

The appropriately protected 2'-O-ethyl-3'-amino-5'-phosphoramidite (example 9, 10, 11, 12), were prepared after chemical transformations shown in Schemes 8-12.

First for the synthesis of thymine based 3'-NH-MMtr-2'-O-ethyl phosphoramidites example 9, intermediate 2 was protected such as methyl propyolate in the presence of dimethylaminopyridine (Scheme 8) to give base N-3 protected intermediate 8-4 to facilitate the 2'-O-alkylation in higher yield. Further deacetylation of 8-4 to give C-2'-hydroxy intermediate 8-5.

Scheme 5

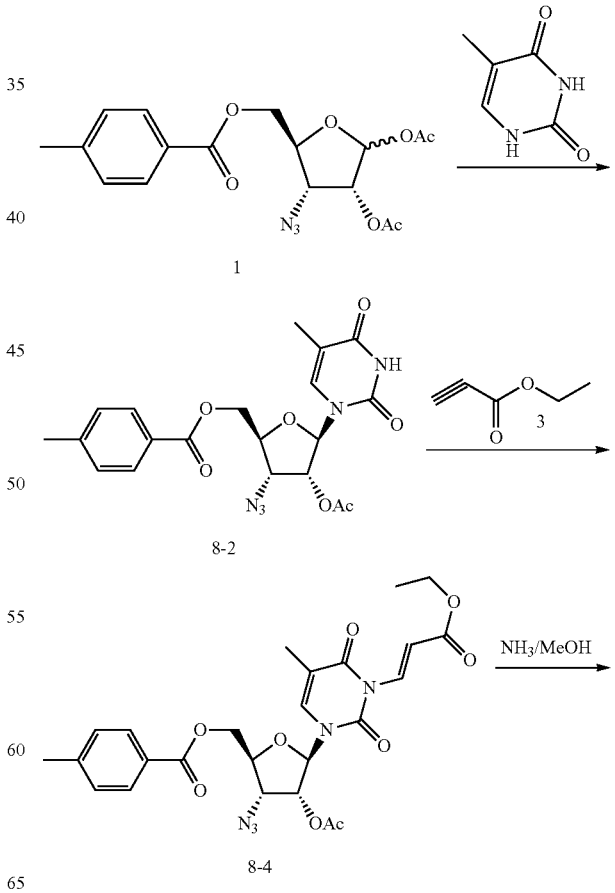

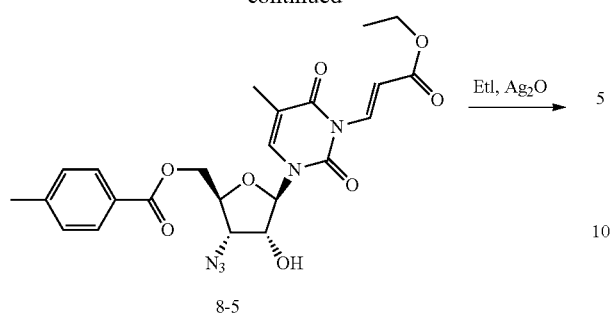

8-5

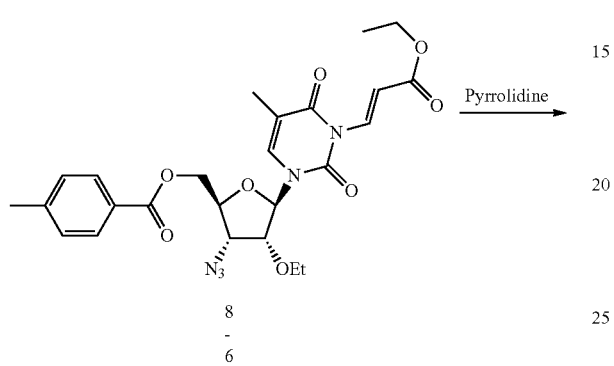

8-6

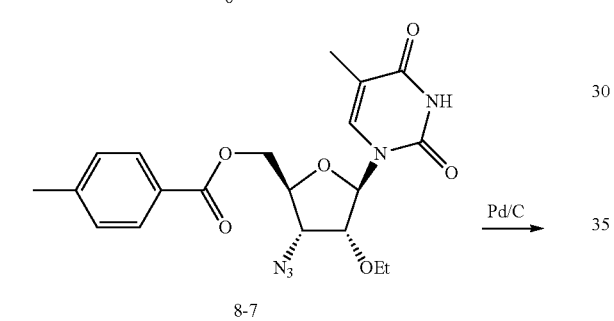

8-7

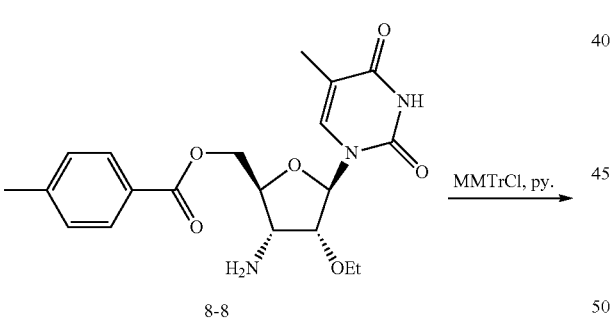

8-8

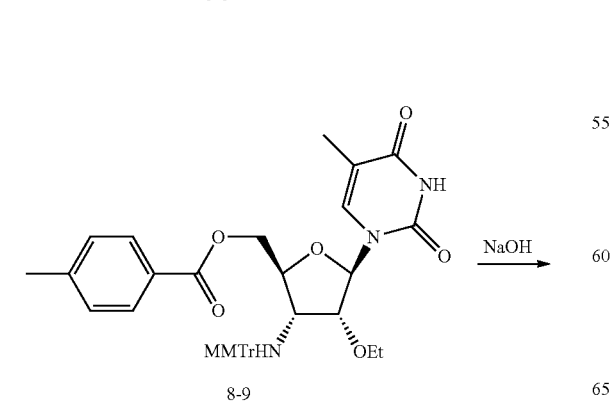

8-9

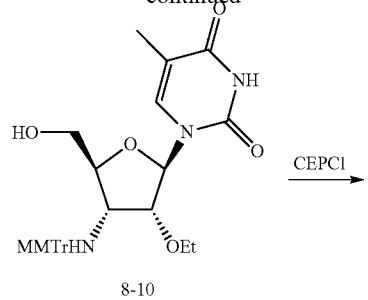

8-10

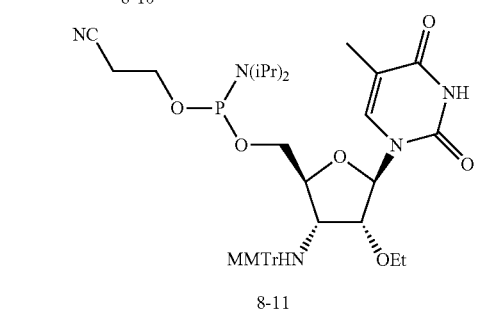

8-11

Further alkylation using iodoethane afforded 2'O-ethyl nucleoside 8-6. Intermediate 8-6 was converted to thymine base 2'-O-ethyl-3'-amino-5'-phosphoramidite 8-11 by following the similar chemistry for compound 4-10 shown in previous Scheme 4.

Preparation of (8-4): To a solution of 8-2 (22.0 g, 49.62 mmol) in MeCN (400 mL) was added DMAP (1.2 g, 9.92 mmol). Then 3 (5.8 g, 419.5 mmol) was added, the mixture was stirred at r.t. for 2 h under N2, TLC showed 8-2 was consumed. Concentrated and purified by a silica gel column by (PE:EA=6:1) to afford 8-4 (22.0 g, 40.63 mmol, 81.9% yield) as a yellow oil. ESI-LCMS: m/z 564 [M+Na]$^+$.

Preparation of (8-5): To a solution of 8-4 (28.0 g, 51.71 mmol) in MeOH (400 mL) was added con. NH$_4$OH aqueous solution (28 mL) at 0° C. The reaction mixture was stirred at 0° C. for 1.5 h, TLC showed 8-4 was consumed. Concentrated and purified by a silica gel column by (PE:EA=10:1-2:1) to afford 8-5 (21.0 g, 42.04 mmol, 81.3% yield) as a yellow oil. ESI-LCMS: m/z 522 [M+Na]$^+$.

Preparation of (8-6): To a solution of 8-5 (20.0 g, 40.04 mmol) in iodoethane (100 mL) was added Ag$_2$O (18.6 g, 80.08 mmol,). The reaction mixture was stirred at 50° C. for 5 h, after LC-MS show totally consumed of 8-5 filtered with diatomite and concentrated to afford 8-6 (16.0, 30.33 mmol, 75.7% yield) as a yellow oil which was used directly in next step. ESI-LCMS: m/z 528 [M+H]$^+$.

Preparation of (8-7): To a solution of 8-6 (16.0 g, 30.33 mmol) in MeCN (400 mL) was added pyrrolidine (8.63 g, 121.32 mol, 12 mL), the reaction mixture was stirred at r.t. overnight, TLC showed 8-6 was totally consumed. Concentrated and purified by a silica gel column by (DCM:MeOH=100:1-50:1) to afford 7 (12.0 g, 27.94 mmol, 92.1% yield) as a yellow oil. ESI-LCMS: m/z 430 [M+H]$^+$.

Preparation of (8-8): To a solution of 8-7 (12.0 g, 27.94 mmol) in THF (200 mL) was added Pd/C (1.2 g), the mixture was stirred at r.t. under H$_2$ overnight. LC-MS showed 7 was totally consumed. Filtered and washed with DCM (100 mL*3), then concentrated to afford 8-8 (11.0 g, 27.27 mmol, 97.6% yield) as a gray solid which was used directly in next step. ESI-LCMS: m/z 404 [M+H]$^+$.

Preparation of (8-9): To a solution of 8-8 (10.0 g, 24.79 mmol) in DCM (80 mL) was added MMTrCl (11.4 g, 37.18 mmol), 2,4,6-collidine (2.0 g, 16.61 mmol, 6.5 mL) and AgNO$_3$ (6.3 g, 37.18 mmol), the mixture was stirred at r.t. for 1.5 h. TLC showed 8-8 was totally consumed. Filtered and the organic layer was washed with water and dried over Na$_2$SO$_4$, then concentrated and purified by a silica gel column by (PE:EA=5:11:1) to afford 8-9 (16.0 g, 23.68 mmol, 95.5% yield) as a light-yellow solid.

Preparation of (8-10): 8-9 (4.0 g, 5.92 mmol) was added to the solution of 1.0 N NaOH solution (20 mL, MeOH/H$_2$O=9:1). The reaction mixture was stirred at 40° C. for 2 h, TLC showed 8-9 was consumed, concentrated and extracted with DCM (20 mL*2), the organic layer was dried over Na$_2$SO$_4$ and concentrated, the residue was purified by a silica gel column by (DCM:MeOH=200:150:1) to afford 8-10 (3.0 g, 53.8 mmol, 90.9 yield) as a white solid.

Preparation of (8-11): To a solution of 8-10 (2.36 g, 4.23 mmol) in DCM (2.0 mL) was added DMAP (103 mg, 0.8 mmol) and DIPEA (2.2 g, 16.92 mmol, 2.96 mL). Then CEPCl (1.0 g, 4.23 mmol) was added. The reaction mixture was stirred at r.t. for 1 h. TLC showed 8-10 was consumed, washed with saturated NaHCO$_3$ (5 mL), separated the organic layer and washed the water layer with DCM (10 mL*2). The combined organic layer was washed with brine, dried over Na$_2$SO$_4$, concentrated, and purified by Flash-Prep-HPLC to afford 8-11 (2.45 g, 3.23 mmol, 76.36% yield) as a white solid. $^1$H NMR (400 MHz, CDCl$_3$) δ 8.62 (s, 1H), 7.74 (dd, J=1.4 Hz, 0.5H), 7.60-7.50 (m, 4H), 7.51-7.41 (m, 2H), 7.34-7.16 (m, 7H), 7.12 (d, J=1.4 Hz, 0.5H), 6.88-6.76 (m, 2H), 5.66 (s, 1H), 4.37-4.23 (m, 1H), 4.16-4.05 (m, 1H), 4.05-3.94 (m, 0.5H), 3.88-3.74 (m, 4.5H), 3.72-3.35 (m, 3H), 3.22 (td, J=10.3, 4.7 Hz, 0.5H), 3.03-2.89 (m, 1.5H), 2.80-2.69 (m, 1H), 2.61 (t, J=6.5 Hz, 1H), 2.37 (td, J=6.6, 1.3 Hz, 1H), 1.97 (d, J=3.5 Hz, 0.5H), 1.91 (dd, J=11.4, 1.2 Hz, 3H), 1.52 (d, J=4.7 Hz, 0.5H), 1.29-1.17 (m, 12H), 1.08 (td, J=7.0, 4.9 Hz, 3H). $^{31}$P NMR (162 MHz, CDCl$_3$) δ 149.31, 147.14. ESI-LCMS: m/z 576 [M+H]$^+$.

GalNAc Synthesis

Synthesis of G-1

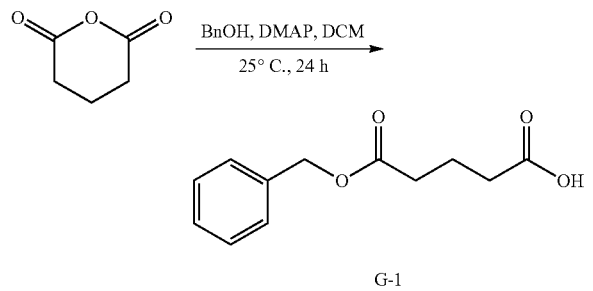

To a solution of oxane-2, 6-dione (1000 g, 8.76 mol, 1.00 equiv.), 4-dimethylaminopyridine (53.5 g, 437.9 mmol, 0.05 equiv.) in dichloromethane (10000 mL) with an inert atmosphere of nitrogen was added phenylmethanol (900 g, 8.32 mol, 0.95 equiv.) dropwise with stirring at room temperature. The resulting solution was stirred overnight at room temperature. The resulting mixture was washed with saturated sodium bicarbonate solution. The pH value of the aqueous layers was adjusted to 1 with 10% hydrochloric acid. The resulting solution was extracted with 3×2000 mL of ethyl acetate and the organic layers combined. The resulting mixture was washed with 2×3000 mL of saturated sodium chloride. The organic layer was dried over anhydrous sodium sulfate, filtered, and concentrated under reduced pressure. This resulted in 1240 g (64%) of G-1 as colorless oil. MS m/z [M+H]+ (ESI): 223.

Synthesis of G-2

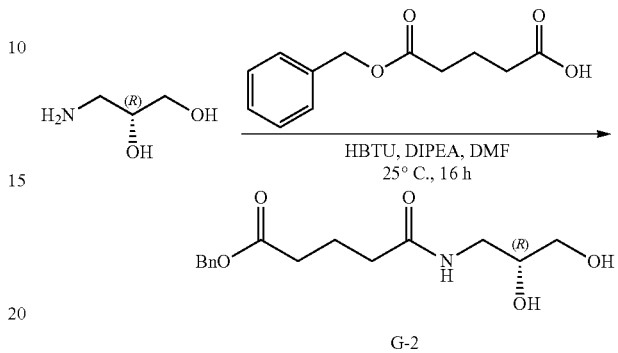

To a solution of G-1 (58.5 g, 263.23 mmol, 1.20 equiv.), N, N-diisopropylethylamine (34 g, 263.57 mmol, 1.20 equiv.) in N, N-dimethylformamide (600 mL) with an inert atmosphere of nitrogen was added O-Benzotriazole-N, N, N', N'-tetramethyl-uronium-hexafluorophosphate (100 g, 263.69 mmol, 1.20 equiv.) at room temperature. The resulting solution was stirred for 1 h at room temperature. This was followed addition of (2R)-3-aminopropane-1, 2-diol (20 g, 219.52 mmol, 1.00 equiv.) at room temperature. The resulting solution was allowed to react, with stirring, overnight at room temperature. The resulting solution was diluted with 2000 mL of ethyl acetate. The resulting mixture was washed with 2×1000 mL of saturated sodium bicarbonate solution. The mixture was dried over anhydrous sodium sulfate and concentrated under reduced pressure. The residue was applied onto a silica gel column with dichloromethane/methanol (1:100-1:10). This resulted in 38.7 g (60%) of G-2 as a light yellow solid. MS m/z [M+H]+ (ESI): 296.

Synthesis of G-3

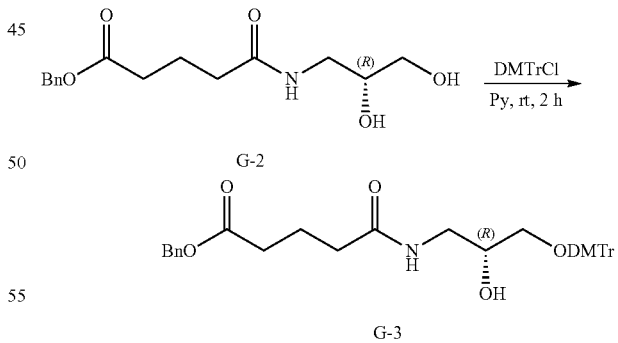

To a solution of G-2 (10 g, 33.86 mmol, 1.00 equiv.) in pyridine (100 mL) with an inert atmosphere of nitrogen was added 1-[chloro(4-methoxyphenyl)benzyl]-4-methoxybenzene (12.63 g, 37.28 mmol, 1.10 equiv.) at room temperature. The resulting solution was stirred overnight at room temperature. The reaction was then quenched by the addition of methanol (10 mL). The resulting mixture was concentrated under reduced pressure. The resulting solution was diluted with 1000 mL of ethyl acetate. The resulting mixture was washed with 2×500 mL of saturated sodium bicarbonate solution. The mixture was dried over anhydrous sodium sulfate and concentrated under reduced pressure. The residue was applied onto a silica gel column with dichloromethane/methanol (1:100-1:50). This resulted in 10.2 g (50%) of G-3 as light yellow oil. MS m/z [M+Na]+ (ESI): 620.

Synthesis of G-4

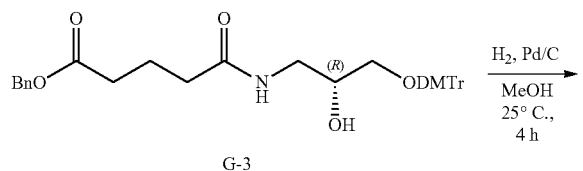

To a solution of G-3 (10 g, 16.73 mmol, 1.00 equiv.) in methanol (100 mL) was added 10% Palladium on activated carbon (1 g) at room temperature. The flask was evacuated and flushed five times with hydrogen. The resulting solution was stirred for 4 h at room temperature. The solids were filtered out. The resulting mixture was concentrated under reduced pressure. This resulted in 7.6 g (89%) of G-4 as a white solid. MS m/z [M+Na]+ (ESI): 530.

Synthesis of G-5

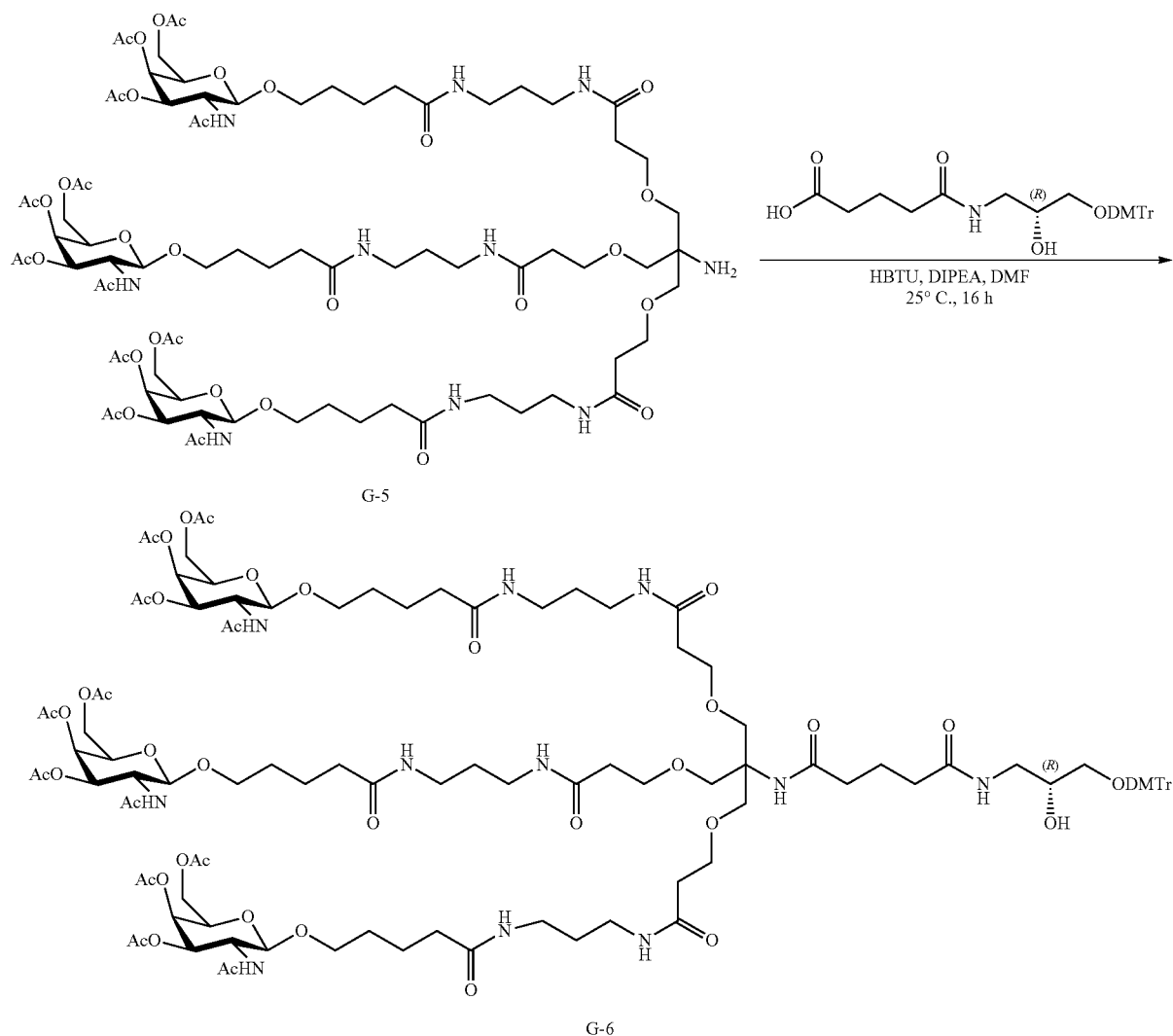

To a solution of G-4 (8.90 g, 17.53 mmol, 1.05 equiv.) in N, N-dimethylformamide (300 mL) with an inert atmosphere of nitrogen, was added N, N-diisopropylethylamine (6.47 g, 50.16 mmol, 3.00 equiv.) at room temperature. To this was added O-Benzotriazole-N, N, N-etramethyl-uronium-hexafluorophosphate (7.10 g, 18.73 mmol, 1.12 equiv.) at room temperature. The resulting solution was stirred for 15 min at room temperature. To the mixture was added G-5 Ref (*Nucleic Acids Research,* 2014, 42, (13) 8796-8807), (30 g, 16.72 mmol, 1.00 equiv.) at room temperature. The resulting solution was allowed to react, with stirring, overnight at room temperature. The resulting mixture was concentrated under reduced pressure. The crude product was purified by Flash-Prep-HPLC with the following conditions (IntelFlash-1): Column, C18 silica gel; mobile phase, acetonitrile/water with 0.04% NH$_4$HCO$_3$ (20% acetonitrile up to 70% in 15 min); Detector, UV 210 nm. This resulted in 20.1 g (53%) of G-6 as a white solid. MS m/z [M+H]$^+$ (ESI): 2283.
Synthesis of G-7
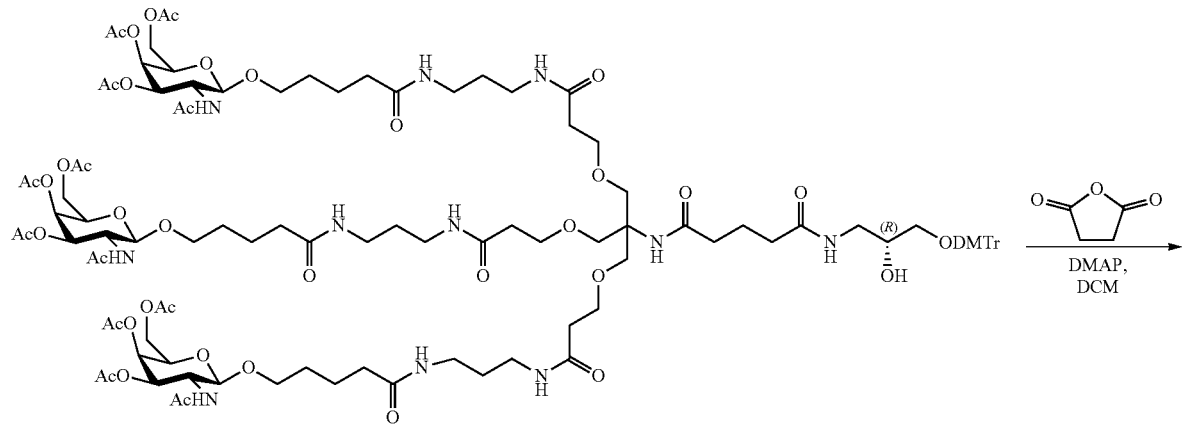
G-6
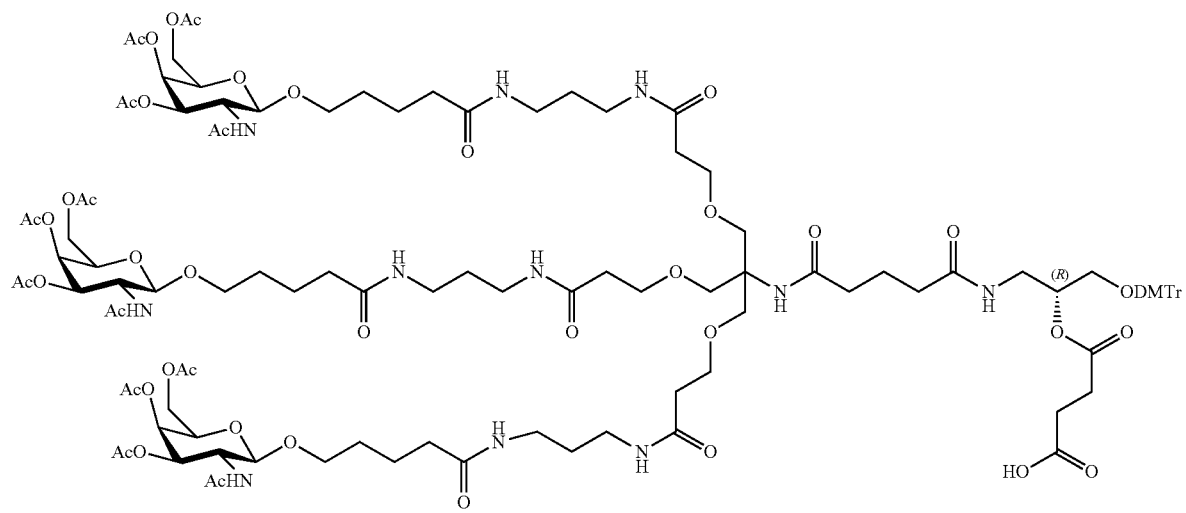
G-7

To a solution of G-6 (25 g, 10.96 mmol, 1.00 equiv.) in dichloromethane (750 mL) with an inert atmosphere of nitrogen, was added triethylamine (4.98 g, 49.21 mmol, 4.49 equiv.) at room temperature. To this was added 4-dimethylaminopyridine (1.33 g, 10.89 mmol, 0.99 equiv.) at room temperature. To the mixture was added oxolane-2, 5-dione (3.29 g, 32.88 mmol, 3.00 equiv.) at room temperature. The resulting solution was stirred overnight at room temperature. The resulting mixture was concentrated under reduced pressure. The crude product was purified by Flash-Prep-HPLC with the following conditions: Column, C18 silica gel; mobile phase, acetonitrile/water with 0.04% NH$_4$HCO$_3$ (20% acetonitrile up to 50% in 20 min); Detector, UV 230 nm. This resulted in 15.83 g (61%) of G-7 as a white solid as ammonium salt. MS m/z [M/2+NH$_4$]+ (ESI): 1210.

Synthesis of GalNAc-2-solid support-GPG

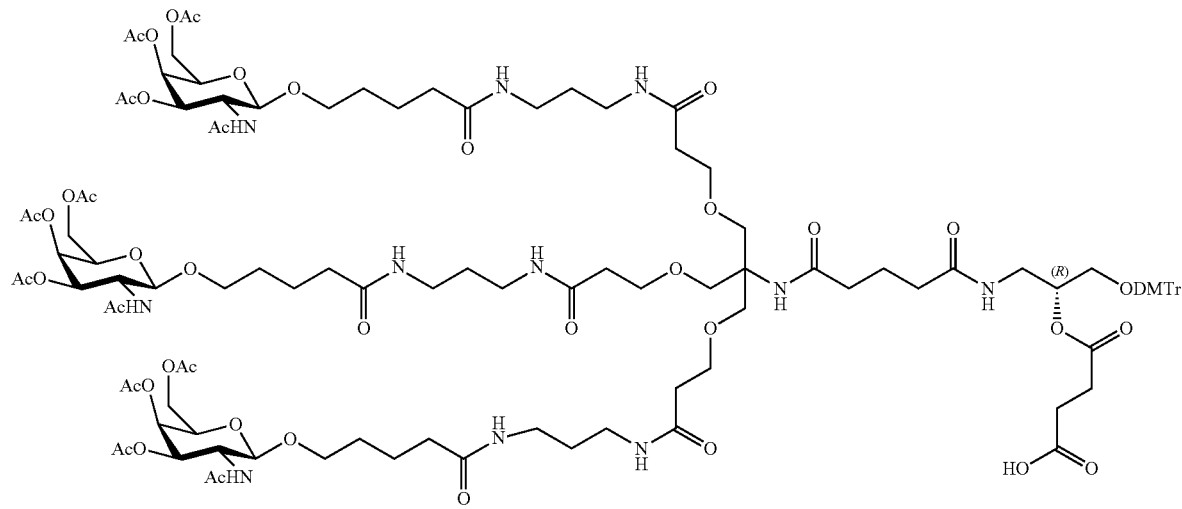

G-7

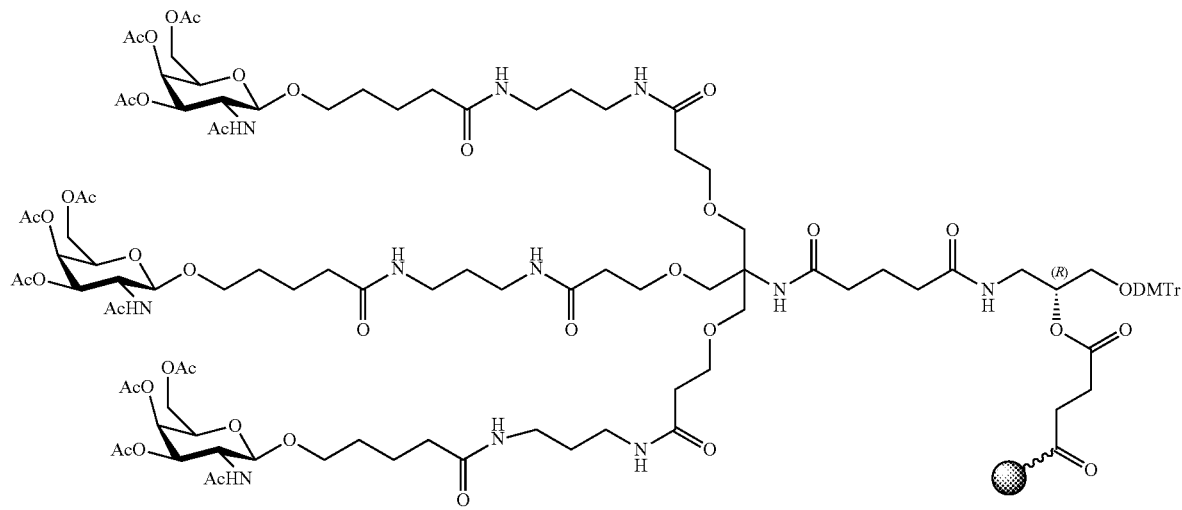

The G-7 was loaded onto the CPG by following the procedures described in Biotechniques., 1988 September; 6(8):768-75 using HBTU/TEA to give GalNAc-2-CPG (53 µmol/g).
Synthesis of GalNAc-6
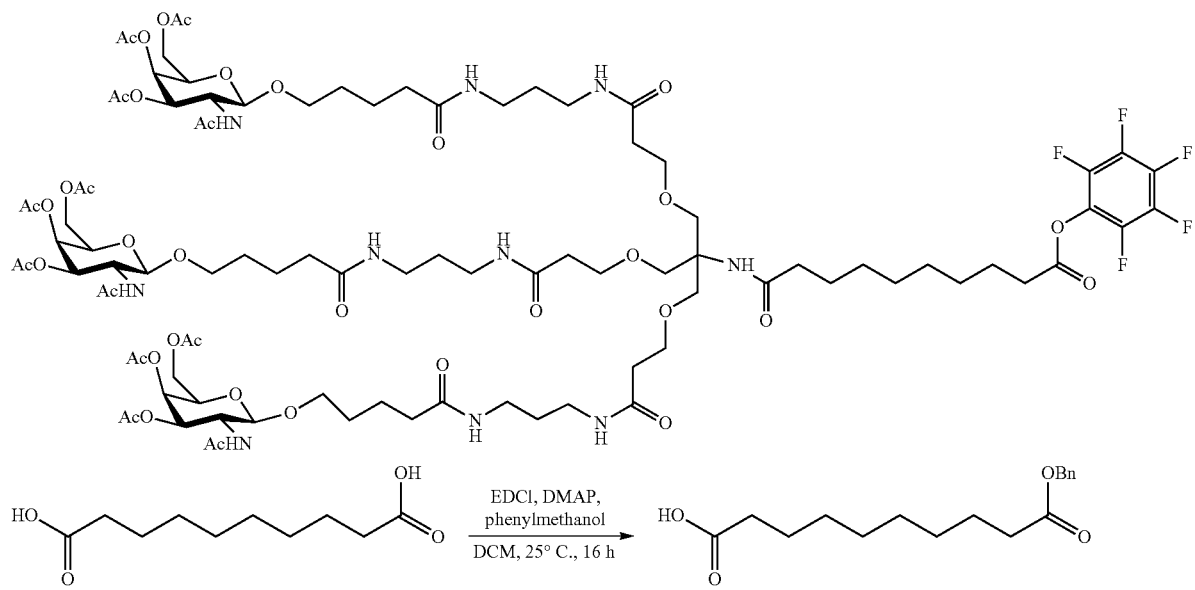
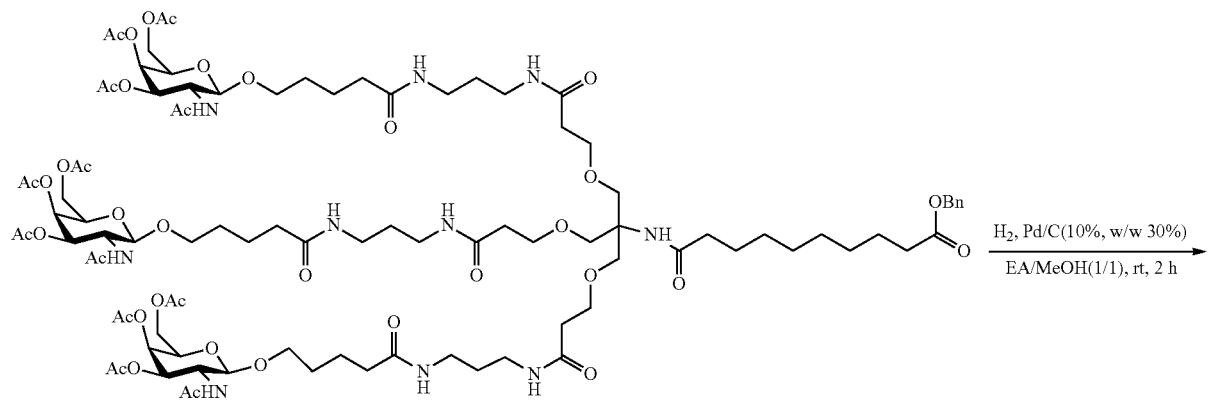
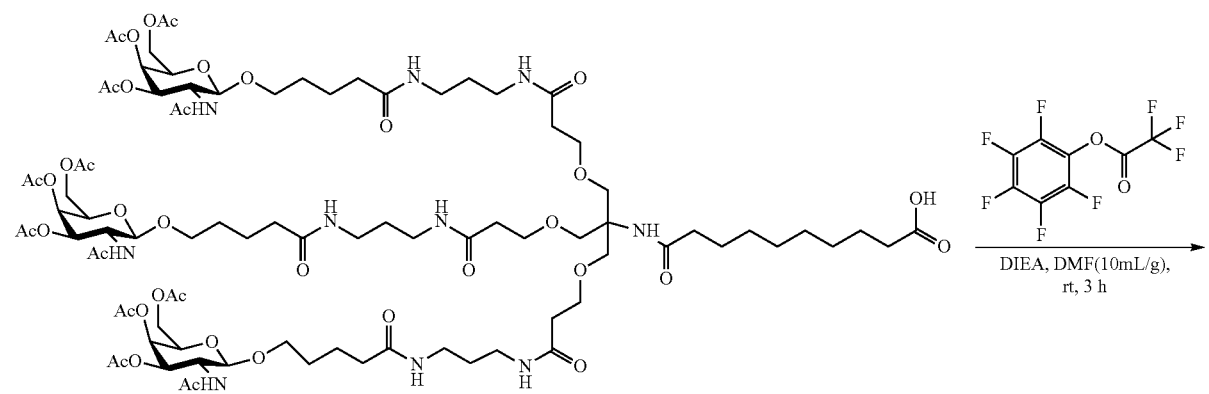

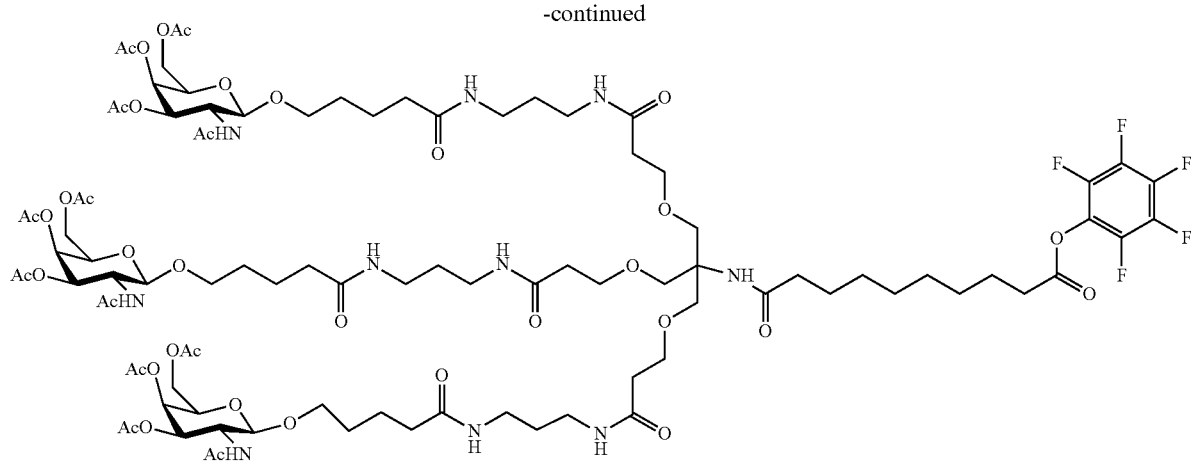

PH-ALP-015-RS2-200

Synthesis of G-8

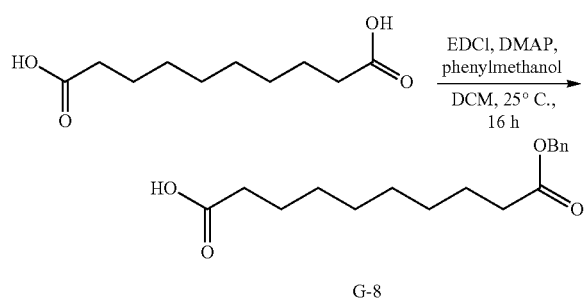

To a solution of decanedioic acid (100 g, 494.4 mmol, 1.00 equiv.) in dichloromethane (2000 mL), was added 4-dimethylaminopyridine (18.1 g, 148.2 mmol, 0.30 equiv.) at room temperature. To this was added N-(3-dimethylaminopropyl)-N'-ethylcarbodiimide hydrochloride (114 g, 594.7 mmol, 1.20 equiv.) at room temperature. The resulting solution was stirred for 1 h at room temperature. To the mixture was added Benzyl alcohol (64.1 g) dropwise with stirring at 0° C. The resulting solution was allowed to react, with stirring, overnight at room temperature. The resulting mixture was washed with saturated aqueous sodium chloride. The mixture was dried over anhydrous sodium sulfate and concentrated under reduced pressure. The crude product (100 g) was purified by Flash-Prep-HPLC with the following conditions (IntelFlash-1): Column, C18 silica gel; mobile phase, water and acetonitrile (60% acetonitrile up to 100% in 12 min and hold 100% for 5 min); Detector, UV 210 nm. This resulted in 60.7 g (42%) of G-8 as a white solid. MS m/z [M+H]+ (ESI): 293.

Synthesis of G-10

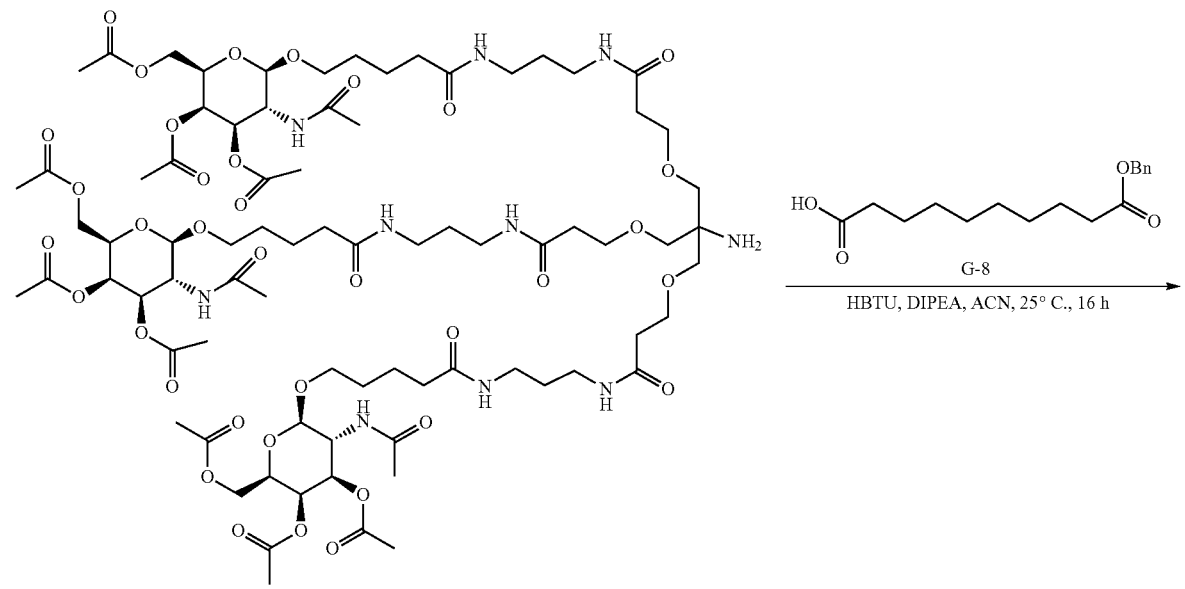

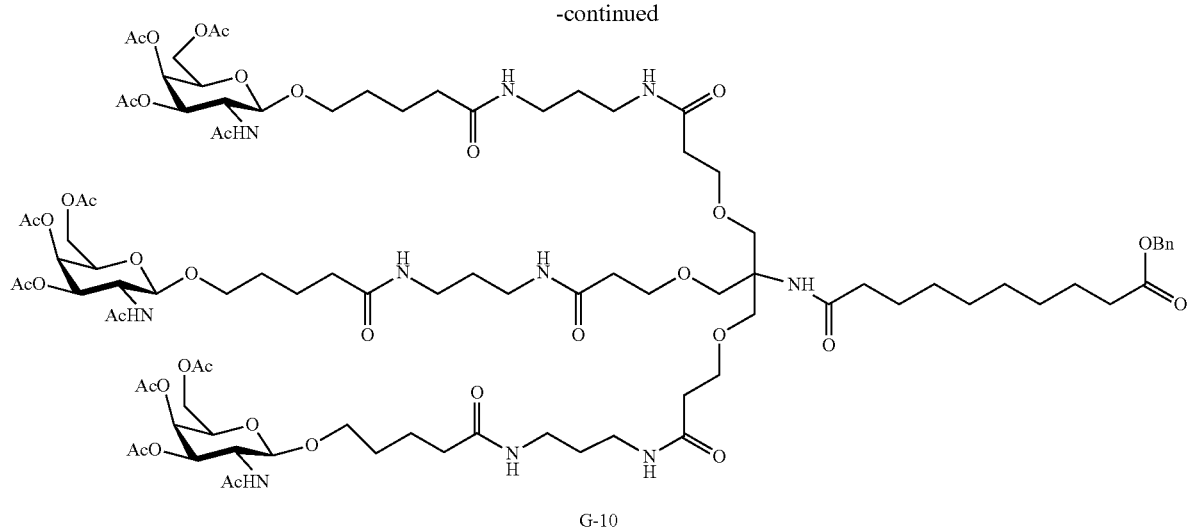

G-10

To a solution of G-8 (4.48 g, 15.32 mmol, 1.50 equiv.) in acetonitrile (320 mL) was added O-Benzotriazole-N,N,N-etramethyl-uronium-hexafluorophosphate (5.84 g, 15.40 mmol, 1.50 equiv.), N,N-Diisopropylethylamine (3.96 g, 30.64 mmol, 3.00 equiv.). The resulting solution was stirred for 1 h at 25° C. This was followed by the addition of G-9 (18.4 g, 10.26 mmol, 1.00 equiv.). The resulting solution was stirred for 16 h at 25° C., and then concentrated under vacuum. The crude product was purified by Flash with the following conditions: Column, C18 silica gel; mobile phase, acetonitrile in water=10% increasing to 70% within 15 min; Detector, UV 210 nm. This resulted in 12 g (57%) of G-10 as a white solid. H-NMR (DMSO, 400 MHz, ppm): 7.74-7.83 (m, 9H), 7.31-7.37 (m, 5H), 6.97 (s, 1H), 5.21 (d, J=3.3 Hz, 3H), 5.07 (s, 2H), 4.98 (dd, J=11.2 Hz, 3.4 Hz, 3H), 4.49 (d, J=8.4 Hz, 3H), 4.04 (s, 9H), 3.83-3.99 (m, 3H), 3.67-3.72 (m, 3H), 3.52-3.55 (m, 12H), 3.37-3.43 (m, 3H), 2.99-3.05 (m, 12H), 2.25-2.35 (m, 8H), 2.12 (s, 9H), 1.99-2.11 (m, 17H), 1.92 (s, 9H), 1.77 (s, 9H), 1.40-1.53 (m, 22H), 1.19-1.25 (m, 8H).

Synthesis of G-11

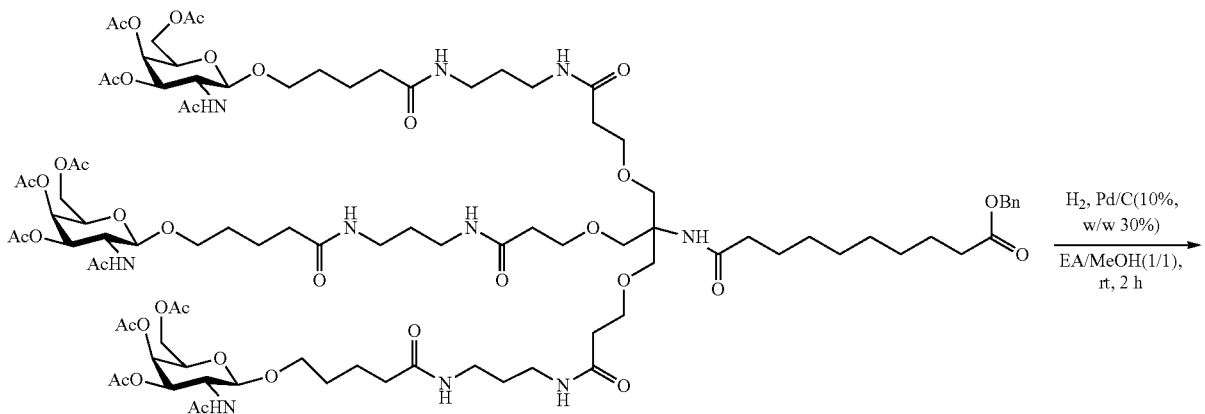

G-10

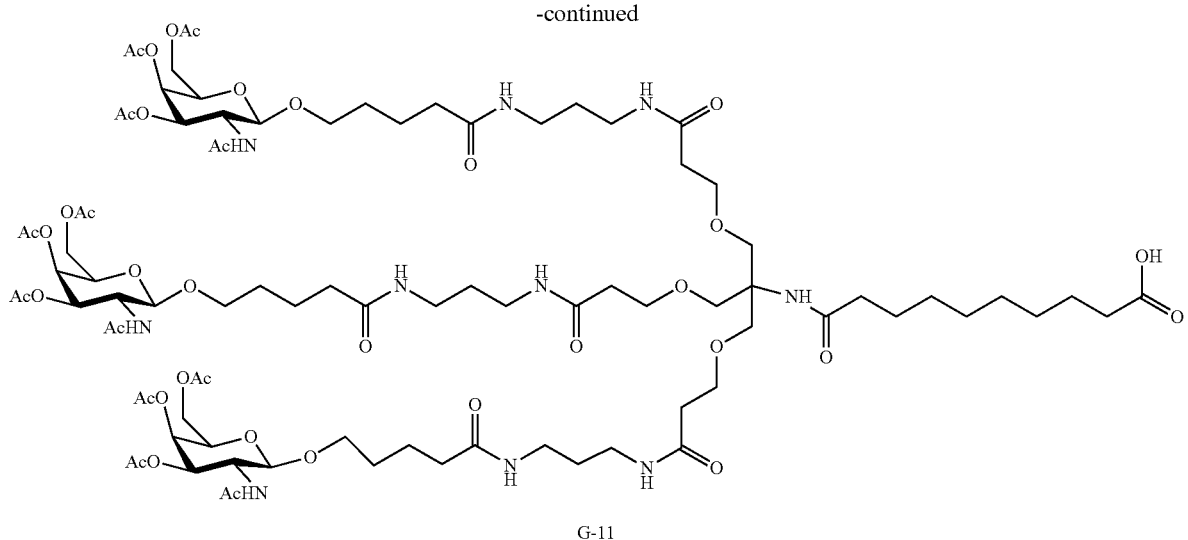

G-11

To a solution of G-10 (5 g, 2.45 mmol, 1.00 equiv.) in methanol/ethyl acetate (100 mL, v/v=1:1) was added 10% palladium carbon (1.5 g, 10%). The flask was evacuated and flushed five times with hydrogen. The mixture was stirred 2 h at room temperature under an atmosphere of hydrogen. The solids were filtered out. The resulting mixture was concentrated under vacuum. This resulted in 4 g (82%) of G-11 as a white solid.

Synthesis of GalNAc-6

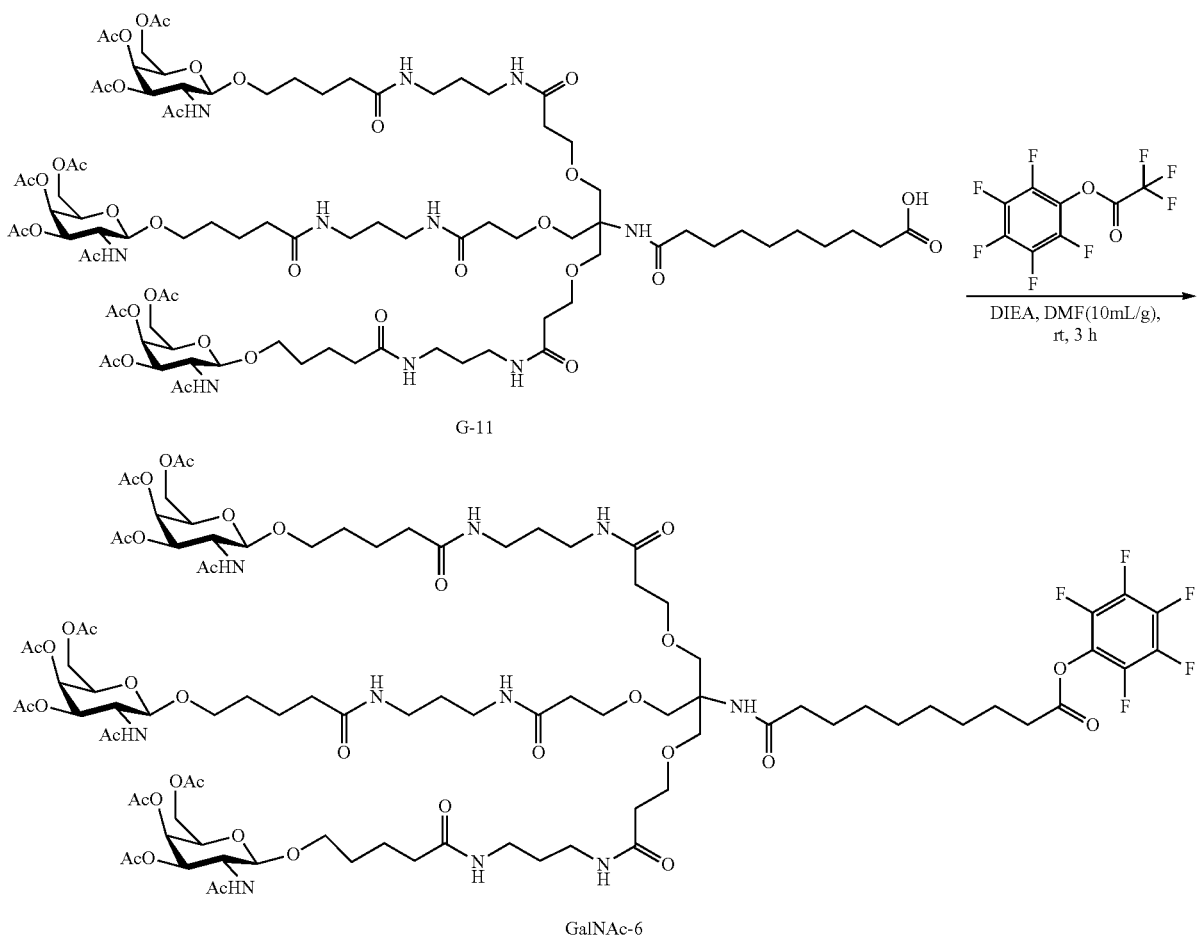

To a solution of G-11 (6.3 g, 3.18 mmol, 1.00 equiv.) in N,N-dimethylformamide (63 mL) was added N,N-diisopropylethylamine (1.0 g, 7.95 mmol, 2.50 equiv.). This was followed by the addition of pentafluorophenyl 2,2,2-trifluoroacetate (1.33 g, 4.77 mmol, 1.50 equiv.) dropwise with stirring at 0° C. The resulting solution was stirred for 3 h at 25° C. The resulting mixture was concentrated under vacuum. The crude product was purified by Flash with the following conditions: C18 gel column, eluent A water, eluent B acetonitrile; gradient: 20% up to 80% within 15 min, 100% maintained 3 min; Detector, UV 210 nm. This resulted in 5 g (73%) of GalNAc-6 as a white solid. MS m/z [M/2+H]$^+$ (ESI): 1073; H-NMR (DMSO, 300 MHz, ppm): 7.71-7.80 (m, 9H), 6.98 (s, 1H), 5.22 (d, J=3.3 Hz, 3H), 4.99 (dd, J=11.1 Hz, 3.3 Hz, 3H), 4.50 (d, J=8.4 Hz, 3H), 4.02 (s, 9H), 3.82-3.92 (m, 3H), 3.69-3.74 (m, 3H), 3.52-3.56 (m, 12H), 3.39-3.44 (m, 3H), 3.03 (s, 12H), 2.75-2.79 (m, 2H), 2.28 (t, J=6.3 Hz, 6H), 2.00-2.10 (m, 26H), 1.89 (s, 9H), 1.77 (s, 9H), 1.64-1.68 (m, 2H), 1.25-1.53 (m, 28H); F-NMR (DMSO, 162 MHz, ppm): −153.60, 153.67, 153.68, 153.69, 158.05, 158.14, 158.22, 162.53, 162.60, −162.62, 162.69, 162.70.

GalNAc Conjugation

For making the 5' GalNAc Conjugated oligomer with the following modifications: 2'-F—NPS-PS-2'-F-NPS; 2'-F—NP-PS-2'-F-NP; 2'-OMe-NP-PS-2'-OMe-NP; 2'-OMe-NPS-DNA-PS-2'-OMe-NPS, 2'-OEt-NPS-DNA-PS-2'-OEt-NPS and 2'-MOE-NPS-DNA-PS-2'-MOE-NPS the synthesis was carried out on a 10 to 200 µM scale in a 5' to 3' direction with the 5'-phosphoramidite monomers diluted to a concentration of 0.1 M in anhydrous CH$_3$CN in the presence of 5-(benzylthio)-1H-tetrazole activator (coupling time 2.0-4.0 min) to a GalNAc 2-CPG. The coupling cycle with modified protocols followed by standard capping, oxidation, and deprotection afforded modified oligonucleotides. The stepwise coupling efficiency was more than 98%. The DDTT (dimethylamino-methylidene) amino)-3H-1, 2, 4-dithiazaoline-3-thione was used as the sulfur-transfer agent for the synthesis of oligoribonucleotide phosphorothioates. The 0.2 M Phenyls acetyl disulfide (PADS) in Lutidine:Acetonitrile (1:1) was used as sulfurizing agent in large-scale synthesis (Akta OP-100). Oligonucleotide-bearing solid supports were heated at room temperature with aqueous ammonia/Methylamine (1:1) solution for 3 h in shaker to cleavage from support and deprotect the base labile protecting groups.

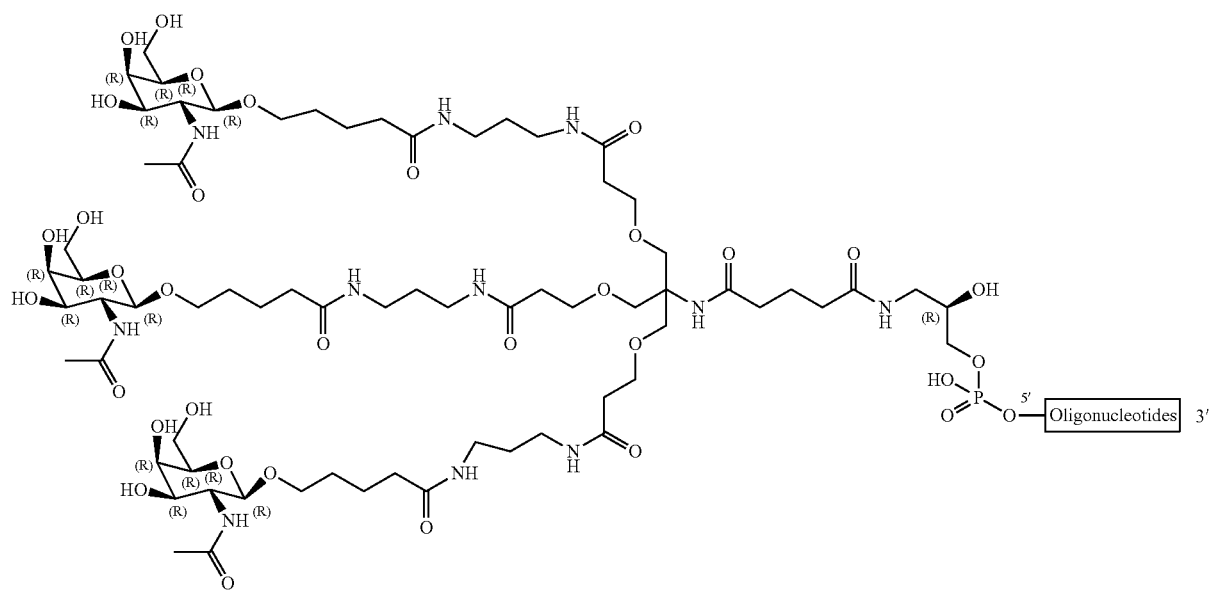

5'-GalNAc-2 Conjugated ASO's

3'-C6NH$_2$-NPS-PS-NPS-(Precursor) Synthesis

For making the 3' GalNAc Conjugated oligomers with the following modifications: 2'-F—NPS-PS-2'-F-NPS; 2'-F—NP-PS-2'-F-NP; 2'-OMe-NP-PS-2'-OMe-NP; 2'-OMe-NPS-DNA-PS-2'-OMe-NPS, 2'-OEt-NPS-DNA-PS-2'-OEt-NPS and 2'-MOE-NPS-DNA-PS-2'-MOE-NPS ASOs were synthesized at 10 µmol scale using universal support (Loading 65 µmol/g). The synthesis procedure is same as described above. At the 3'-terminal to introduce C6-NH$_2$ linker the 6-(4-Monomethoxytritylamino)hexyl-(2-cyanoethyl)-(N,N-diisopropyl)-phosphoramidite in 0.1 M Acetonitrile was used with coupling time 10 min. The Oligonucleotide-bearing solid supports were heated at room temperature with aqueous ammonia/Methylamine (1:1) solution for 3 h in shaker to cleavage from support and deprotect the base labile protecting groups. After IEX purification and desalting the C6-NH$_2$ modified ASO's can be used to perform post synthesis conjugation.

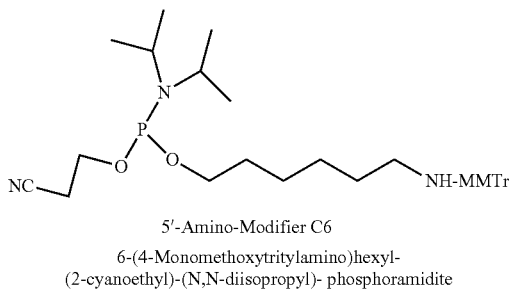

5'-Amino-Modifier C6
6-(4-Monomethoxytritylamino)hexyl-
(2-cyanoethyl)-(N,N-diisopropyl)- phosphoramidite 3'-GalNAc NPS-PS-NPS-ASO synthesis (Post Synthesis Conjugation)

The 3'-C6-NH$_2$ modified ASOs were dissolved in 0.2 M Sodium bicarbonate buffer, pH 8.5 (0.015 mM) and 5-7 mol equivalent of GalNAc-6 ester dissolved in DMSO was added. The reaction mixture was stirred at room temperature for 4 h. The sample was analyzed to confirm if any unreacted amino modified ASO's is present. To this aqueous ammonia (28 wt. %) was added (5× reaction volume) and stirred at room temperature for 2-3 h. Reaction mixture concentrated under reduced pressure and residue dissolved in water and purified by HPLC on a strong anion exchange column.

3'-GalNAc6 Conjugation

| Conc. Of Oligo's | Equivalent of GalNAc 6 PFP ester | Temp (° C.) | % Conversion to 3' GalNAc ASO |
|---|---|---|---|
| 0.015 mM | 5 | 25 | 75 |
| 0.0076 mM | 7 | 25 | 80 |
| 0.0076 mM | 4 | 25 | 65 |

Quantitation of Crude Oligomer or Raw Analysis

Samples were dissolved in deionized water (1.0 mL) and quantitated as follows: Blanking was first performed with water alone (1.0 mL) 20 ul of sample and 980 µL of water were mixed well in a microfuge tube, transferred to cuvette and absorbance reading obtained at 260 nm. The crude material is dried down and stored at −20° C.

Crude HPLC/LC-MS Analysis

The 0.1 OD of the crude samples were submitted for crude MS analysis. After Confirming the crude LC-MS data then purification step was performed.

HPLC Purification

The Phosphoramidate (NP) and Thiophosphoramidate (NPS) modified oligonucleotides with and without GalNAc conjugates were purified by anion-exchange HPLC. The buffers were 20 mM sodium phosphate in 10% CH$_3$CN, pH 8.5 (buffer A) and 20 mM sodium phosphate in 10% CH$_3$CN, 1.8 M NaBr, pH 8.5 (buffer B). Fractions containing full-length oligonucleotides were pooled, desalted, and lyophilized.

Desalting of Purified Oligomer

The purified dry oligomer was then desalted using Sephadex G-25 M (Amersham Biosciences). The cartridge was conditioned with 10 mL of deionized water thrice. Finally the purified oligomer dissolved thoroughly in 2.5 mL RNAse free water was applied to the cartridge with very slow drop wise elution. The salt free oligomer was eluted with 3.5 ml deionized water directly into a screw cap vial.

IEX HPLC and Electrospray LC/MS Analysis

Approximately 0.10 OD of oligomer is dissolved in water and then pipetted in special vials for IEX-HPLC and LC/MS analysis. Analytical HPLC and ES LC-MS established the integrity of the oligonucleotides. The purity and molecular weight were determined by HPLC analysis (60° C., IEX—Thermo DNAPac PA-100, A—25 mM sodium phosphate

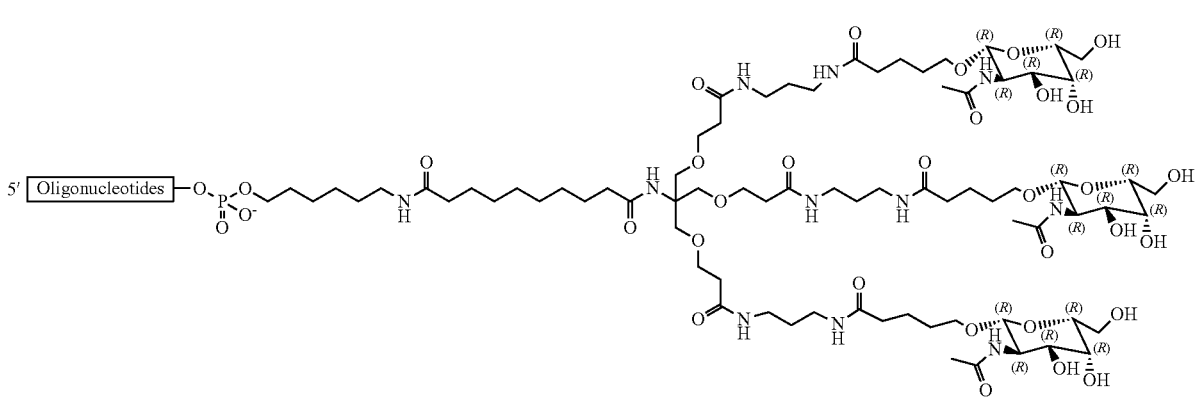

3'-GalNAc-6-Conjugated ASO's

10% acetonitrile pH 11, B—1.8 M NaBr 25 mM sodium phosphate 10% acetonitrile pH 11; RPIP—Waters XBridge OST C18, A—100 mM HFIP 7 mM TEA B—7:3 methanol/acetonitrile) and ESI-MS analysis using Promass Deconvolution for Xcalibur (Novatia, Newtown, Pa.). All oligonucleotides in the following tables were synthesized, and reference to molecular weights in the tables are actual measured weights that may have an error of MW, amu+/−2.

Stability Testing of Complexed Oligonucleotides

In embodiments, the disclosed oligonucleotides display an increased affinity for a target nucleic acid sequence compared to an unmodified oligonucleotide of the same sequence. For example, in some sequences the disclosed oligonucleotides has a nucleobase sequence that is complementary or hybridizes to a target nucleic acid sequence at a higher affinity than an unmodified oligonucleotide of the same sequence. In embodiments, the disclosed oligonucleotide complexed with a complementary target nucleic acid sequence has a melting temperature Tm of >37° C. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with a target nucleic acid sequence under physiological conditions or nearly physiological conditions is >50° C.

In certain embodiments, the target nucleic acid sequence may be selected from a nucleic acid sequence of a known viral DNA or RNA sequence such as the HBV genome.

In embodiments, the disclosed oligonucleotides display an affinity for at least one of the following six sequences of the HBV genome or its RNA equivalents and/or display stability complexed to at least one of the following six sequences of the HBV genome (Table E) or its RNA equivalents (Table F). In embodiments, the oligonucleotide complexed with a complementary HBV genome sequence has a melting temperature (Tm) of >37° C. The HBV genome may be an RNA sequence such as DR-1 and/or DR-2 RNA sequence. The complex may be formed under physiological conditions or nearly physiological conditions such as in phosphate-buffered saline (PBS). In embodiments, the Tm of the complex is >50° C. In embodiments, the Tm of the complex is 50-100° C. In embodiments, the Tm of a disclosed oligonucleotide duplexed with an HBV RNA under physiological conditions or nearly physiological conditions is >50° C.

In Vitro Testing of Oligonucleotides

Two HBV cell lines were used to assess the in vitro potency of oligonucleotides: HepG2.2.15 (2215) and HepG2.117 (2117). HBsAg reduction in tissue culture supernatant (sup) as well as cytotoxicity was measured using HepG2.2.15 cell. HBV DNA reduction in the sup as well as intracellular fraction was measured in HepG2.117 cell.

HepG2.2.15 cell line is a stable cell line with four integrated HBV genomes. The cells were grown at 37° C. in an atmosphere of 5% $CO_2$ in Dulbecco's modified Eagle's medium supplemented with 10% FCS, 100 IU/ml penicillin, 100 μg/ml streptomycin, and 2% glutamine. The day before the dosing, $2.5 \times 10^4$ cells/well were plated in collagen coated 96 well plates and incubated overnight. On the day of dosing, serially diluted oligomers were transfected into the cells with Lipofectamine RNAiMax (Thermo Fisher, Waltham, Mass.) following manufacturer's protocol. Duplicates were made for each drug concentration and each oligo was set up for both EC50 measurement and CC50 measurement. Three days after transfection, the supernatant (sup) was collected and used in HBsAg ELISA (AutoBio, China) for EC50 calculation. For CC50 measurement, CellTiter-Glo® (Promega, Madison, Wis.) was used in the assay following manufacturer's instruction.

HepG2.117 is a stable hepatoma cell line harboring an integrated 1.05 copy of the HBV genome (subtype ayw) under regulation of TetOFF (induction of transcription in the absence of tetracycline or its homolog doxycycline). The cells were grown at 37° C. in an atmosphere of 5% $CO_2$ in DMEM/F12 media supplemented with 10% FCS, 100 IU/ml penicillin, 100 μg/ml streptomycin, 2% glutamine, 250 μg/ml G418, and 2 μg/ml Tetracycline. The day before the dosing, the cell media-containing Tetracycline was removed, the cells washed to remove the residual Tetracycline and plated at $2.5 \times 10^4$ cells/well with treatment media (DMEM/F12 containing 2% Tet-system approved FBS 100 IU/ml penicillin, 100 μg/ml streptomycin, and 2% glutamine) in collagen coated 96 well plates. The cells were then incubated overnight. On the day of experiment, serially diluted oligomers were transfected into the cells with Lipofectamine RNAiMax (Thermo Fisher, Waltham, Mass.) following manufacturer's protocol. Duplicates were made for each drug concentration and each oligo was set up for both EC50 measurement and CC50 measurement. Four days after the transfection, the sup was collected to be used in HBV DNA qPCR directly. The HBV DNA from the cells was isolated with MagMAX™ Total Nucleic Acid Isolation Kit (Thermo Fisher) and then applied in qPCR as template. HBV subtype ayw DNA (accession number V01460) sequence was used to design (Primer Express, Thermo Fisher) the forward primer (5'-TTG CCT TCT GAC TTC TTT CCT TCT-3' (SEQ ID NO: 378)), reverse primer (5'-TGC CTG AGT GCT GTA TGG TGA G-3' (SEQ ID NO: 379)) and the fluorogenic TaqMan® probe (5'-TCG GGA AGC CTT AGA GTC TCC TGA-3' (SEQ ID NO: 380)) labelled with FAM (6-carboxyfluoresceine) in 5' and with TAMRA (6-carboxytetramethylrhodamine) in 3'. These primers and probe were used to carry out quantitative real-time PCR with AmpliTaq Gold DNA polymerase (Perkin-Elmer Life Science, Waltham, Mass.). The conditions for this reaction were as follows: 1 cycle, hot-start at 95° C. for 10 min followed by 50 cycles of denaturation (95° C. for 15 s) and annealing/polymerization (59° C. for 1 min).

Infectious HBV System in Primary Human Hepatocyte

Cryopreserved primary human hepatocytes (PHH) were thawed and plated in 24 well plates at 200,000 cells/well. The cells were allowed to recover overnight at 37° C. 5% $CO_2$. The cells were infected 0/N (37° C./5% $CO_2$) with HBV at moi 50-100. After infection for overnight, the viral inoculum is removed and the cells are washed three times with prewarmed wash medium. Then refill with fresh PHH culturing medium. The medium is replaced with 450 μl fresh medium. Add 50 ul transfect mixture. Dilute oligomers in Opti-MEM I (Life Technology, Cat #: 31985-070) to 20× of final concentration, mix with equal volume Opti-MEM I containing Lipofectamine RNAiMAX (Invitrogen, Cat #: 13778-150), pipet 3 times and incubate for 10-20 min at room temperature. Add 50 ul oligo:RNAiMAX mixture into the wells, tap the plates a few times with hands. Put the plates back to incubator. On the day of assay, Harvest supernatant for HBsAg and HBeAg ELISA, cell for cell viability. HBsAg ELISA was described in above section. For HBeAg, method from Autobio Diagnostics (CL0312-2) was used.

In Vivo Testing of Oligonucleotides

AAV/HBV is a recombinant AAV carrying replicable HBV genome. Taking advantage of the highly hepatotropic feature of genotype 8 AAV, the HBV genome can be efficiently delivered to the mouse liver cells. Infection of immune competent mouse with AAV/HBV can result in long-term HBV viremia, which mimics chronic HBV infection in patients. The AAV/HBV model can be used to evaluate the in vivo activity of various types of anti-HBV agents. Mice were infected with AAV-HBV on day −28 of the study. The test articles or negative control (PBS) were dosed subcutaneously (unless specified otherwise) three times on days 0, 2 and 4 at the specified dose levels. Or they can be injected as single dose at specified dose levels on day 0. The positive control, entecavir (ETV), for HBV DNA, but not for HBV antigens, was dosed orally every day. Serum HBV S antigen (HBsAg) and E antigen (HBeAg) were assayed through ELISA and HBV DNA through real time PCR. ELISA methods and qPCR method have been described in the in vitro assay sections above.

The following statements describe how the data in Table 1-43 were generated. For all of the in vitro HBsAg Cell line EC50 and CC50 data, the method for HepG2.2.15 was used and accordingly, "2215" was labeled in the columns or rows where the data was shown. For all of the in vitro HBV DNA Cell line EC50 and CC50 data, the method for HepG2.117 was used and accordingly, "2117" was labeled in the columns or rows where the data was shown. For all in vitro HBsAg as well as HBeAg EC50 data tested in HBV/PHH infectious system, PHH method was used and accordingly "PHH" was labeled in the columns or rows where the data was shown. For in vivo AAV-HBV mouse model results, method in in vivo section above was applied. The Maximum HBsAg (or HBeAg) reduction was described as nadir (unit Log reduction) and the nadir was labeled in the columns or rows where the data was shown. Two ASOs were often compared for their nadir. If value other than nadir was compared, they will be indicated in the text.

Method of Treatment

An adult human suffering from HBV infection is administered intravenously a therapeutically effective compound of the present disclosure, for example, a compound selected from Table 1-43. Treatment is continued until one or more symptom of HBV is ameliorated, or for example, serum HBV S antigen (HBsAg) and/or E antigen (HBeAg) levels are reduced.

An adult human suffering from HBV infection is administered subcutaneously a therapeutically effective compound of the present disclosure, for example, a compound selected from Table 1-43. Treatment is continued until one or more symptom of HBV is ameliorated, or for example, serum HBV S antigen (HBsAg) and/or E antigen (HBeAg) levels are reduced.

In the following tables, A through J corresponds to the following:
A) 0.05-10 nM;
B) 10-100 nM;
C) above 100 nM;
D) 0.1-5.0 nM;
E) 5.1-10.0 nM;
F) 10.1-21 nM;
G) 20-100
H) 10-1000
I) >1,000
J) >10,000.

TABLE 1

Chimeric oligonucleotide with PS and 2'-O-Me Modifications

| SEQ ID NO: | Sequence (5'-3') | 2215 HBsAg EC50 (nM) | 2215 CC50 (nM) | MaxHBsAg Log reduction* (nadir) | Molecular Weight (MW) |
|---|---|---|---|---|---|
| 101 | 3815 'mGpsmCpsmApsmGpsmApsmGps GpsTpsGnsApsApsGpsmCpsmGps mApsmApsmGpsmUpsmGpsmC-3' | A | J | | 6967.66 |
| 102 | 3825 'mGpsmCpsmApsmGpsmAnsmGps GpsTpsGpSApsApsGpsmCpsmGps mApsmApsmGpsmUpsmGpsmCps-Chol-3' | B | J | | 7739.69 |
| 103 | 3835 'mGpsmCpsmApsmGpsmApsmGps GpsTpsGpSApsApsGpsmCpsmGps mApsmApSmGpsmUpsmGpsmC-GalNAc-3' | B | J | 2 | 8728.57 |

*Log Reduction post 3 × 30 mg/kg SC

Figure 1B:
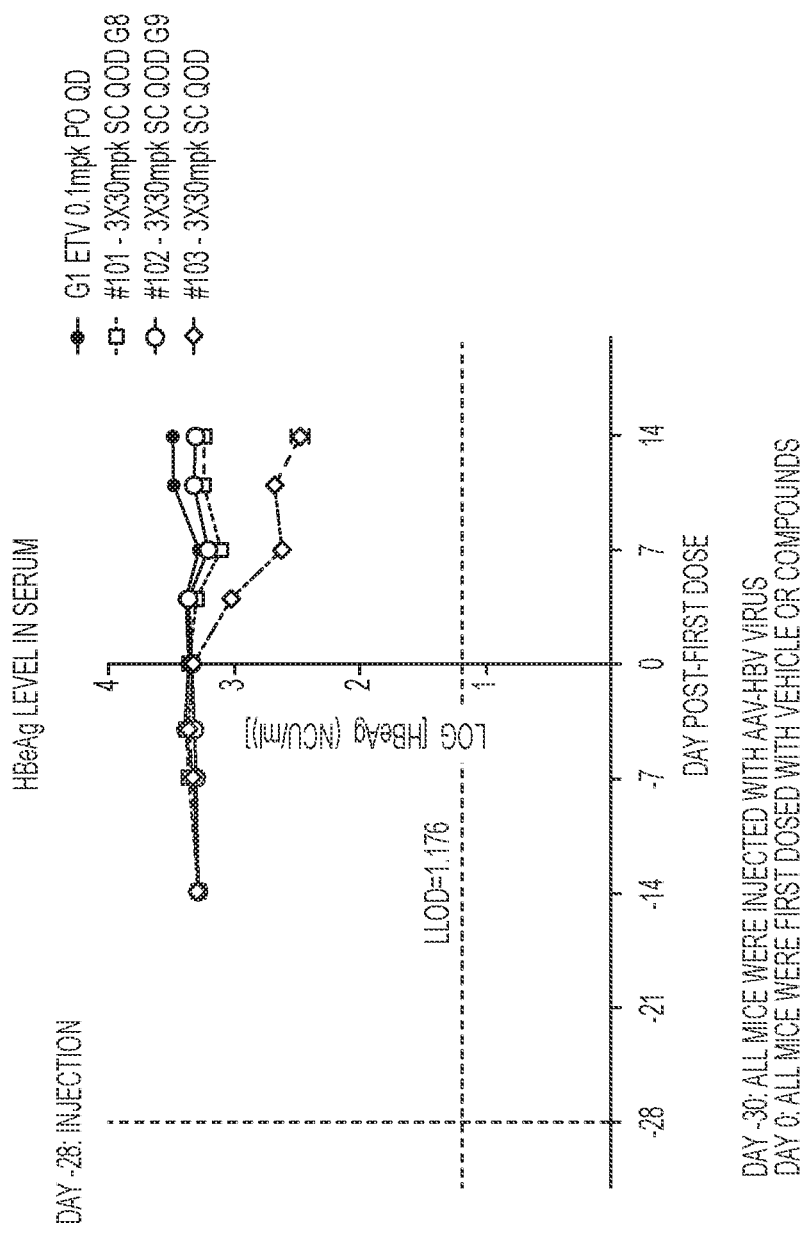
FIG. 1B shows HBeAg serum levels.
Figure 1C:
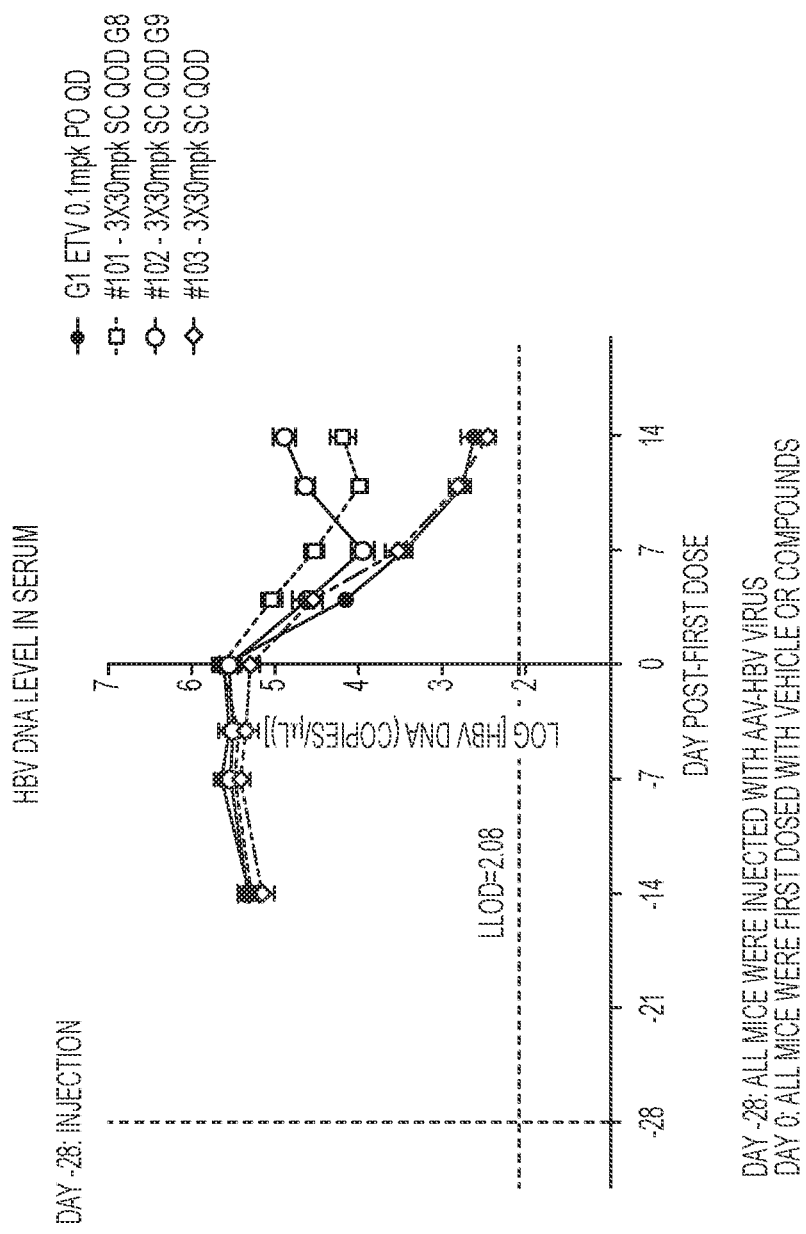
FIG. 1C shows DNA serum levels.

FIGS. 1A-C show results of 2-week testing of a compound of the present disclosure in vivo in an AAV/HBV mouse model. AAV/HBV is a recombinant Adeno-associated virus (AAV) carrying replicable HBV genome. Taking advantage of the highly hepatotropic feature of genotype 8 AAV, the HBV genome can be efficiently delivered to the mouse liver cells. Infection of immune competent mouse with AAV/HBV can result in long-term HBV viremia, which mimics chronic HBV infection in patients. The AAV/HBV model can be used to evaluate the in vivo activity of various types of anti-HBV agents. Mice were infected with AAV-HBV on day-28 of the study. The test articles or negative control (PBS) were dosed subcutaneously (unless specified otherwise) three times on days 0, 2 and 4 at the specified dose levels. The positive control entecavir (ETV, for HBV DNA, but not for HBV antigens) was dosed orally every day. Serial blood collections were carried out on the days shown in the figures. Serum HBV S antigen (HBsAg) and E antigen (HBeAg) were assayed through ELISA and HBV DNA through real time PCR. In FIGS. 1A-1C, three test articles #101, #102 (3' Cholesterol conjugated form of #101) and #103 (3' GalNAc conjugated form of #101) were tested along with ETV.

FIG. 1A shows HBsAg serum levels. ETV is known to reduce HBV DNA but has no effects on either HBsAg or HBeAg. GalNAc conjugated #101 reduced HBsAg ~2 log while unconjugated #101 and Cholesterol conjugated #102 had very little effect.

FIG. 1B shows HBeAg serum levels; and FIG. 1C shows DNA serum levels. The patterns for these three oligomers on HBeAg were very similar to that of HBsAg. The max HBeAg drop for #103 was ~0.7 log.

FIG. 1C shows DNA serum levels. All three oligomers reduced HBV DNA in mouse serum with GalNAc conjugated #103 being the most potent compound (max HBV DNA reduction on day 14 was ~3 log comparing with day 0 baseline). The positive control ETV also showed max 3 log drop in HBV DNA.

Figure 2A:
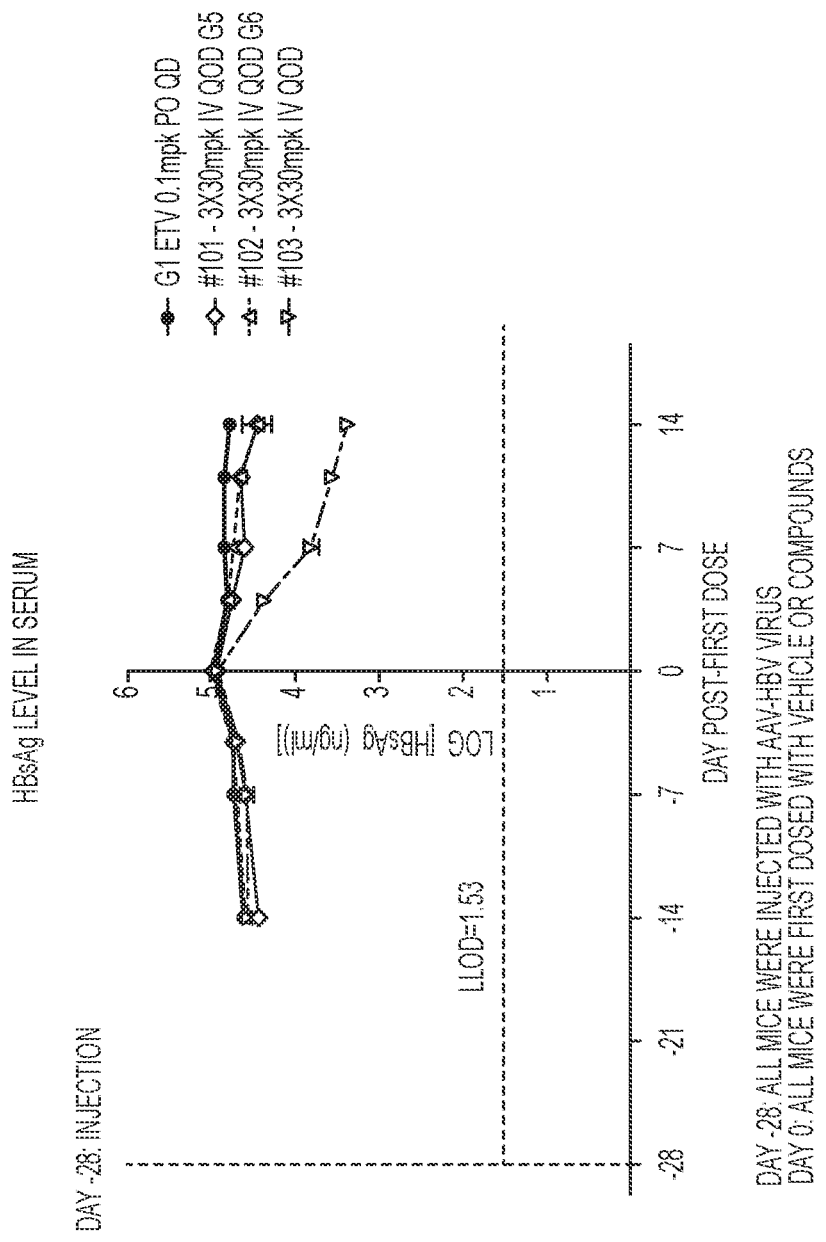
FIG. 2A show results HBsAg serum levels for a GalNAc conjugated compound of the present disclosure for IV administration.
Figure 2B:
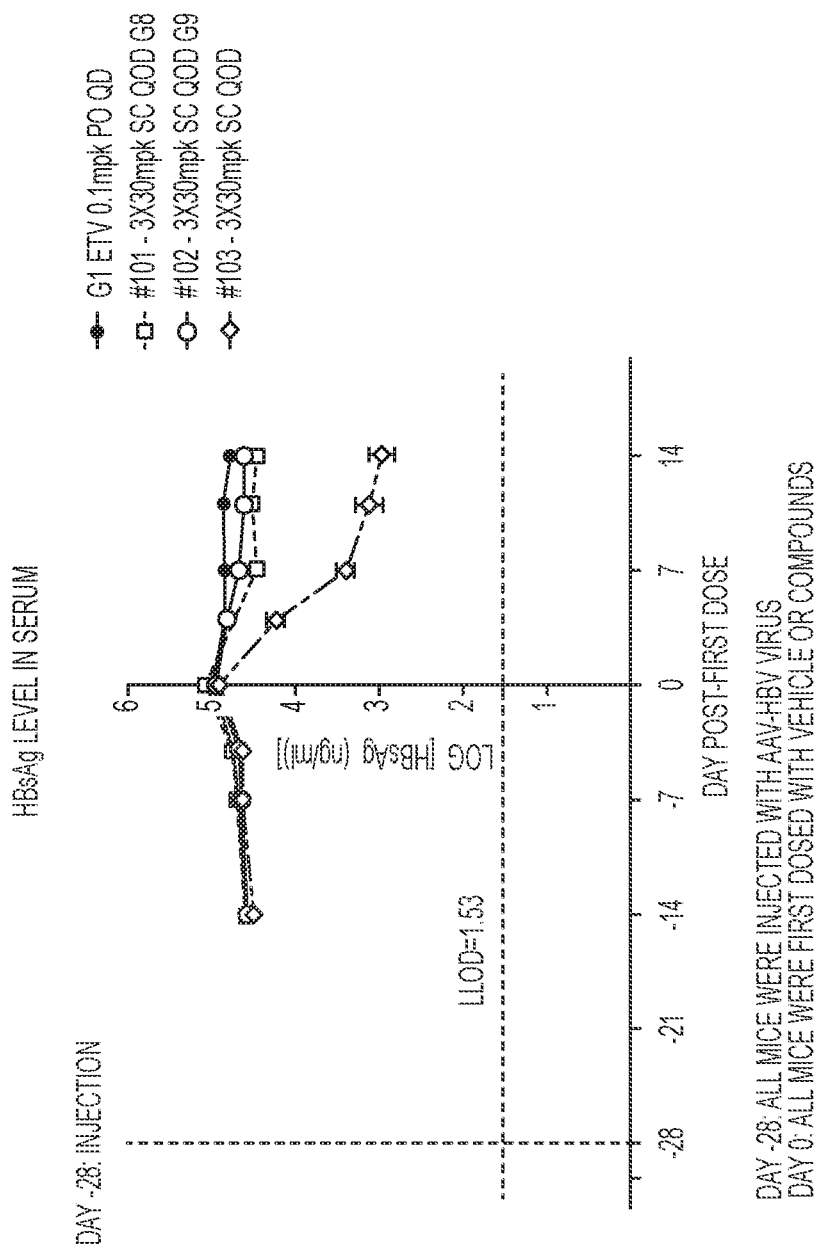
FIG. 2B shows HBsAg serum levels for a GalNAc conjugated compound of the present disclosure for SC administration.

FIGS. 2A-B show HBsAg serum levels for a GalNAc conjugated compound of the present disclosure as a SC and an IV administration in an in vivo mouse model. FIG. 2A show results for IV administration; FIG. 2B shows results for SC administration. The SC delivery showed slightly higher degree of HBsAg than the IV delivery with the same dosage

TABLE 2

| SEQ ID NO: | Sequence (5'-3') | 2215 EC50 (nM) | 2215 CC50 (nM) | MaxHBsAg Log reduction (nadir)* | MW |
|---|---|---|---|---|---|
| 104 384 | 5'mGpsmApsmUpsmUpsmApsmGps GpsCpsApsGpSApsGosGosTpsm GpsmApsmApsmApsmApsmApsmG3' | B | J | | 7275.92 |
| 105 385 | 5'mGpsmApsmUpsmUpsmApsmGps GpsCpsApSGnsApsGpsGpsTpsm GpsmApsmApsmApsmApsmApsmG-Chol-3 | A | J | | 8031.88 |
| 106 386 | 5'mGpsmApsmUpsmUpsmApsmGps GpsCpsApSGpsApsGpsGpsTpsm GpsmApsmApsmApsmApsmApsmG-GalNAc-3 | C | J | 0.8 | 9036.82 |

*Log Reduction post 3 x 30 mg/kg SC

Figure 3:
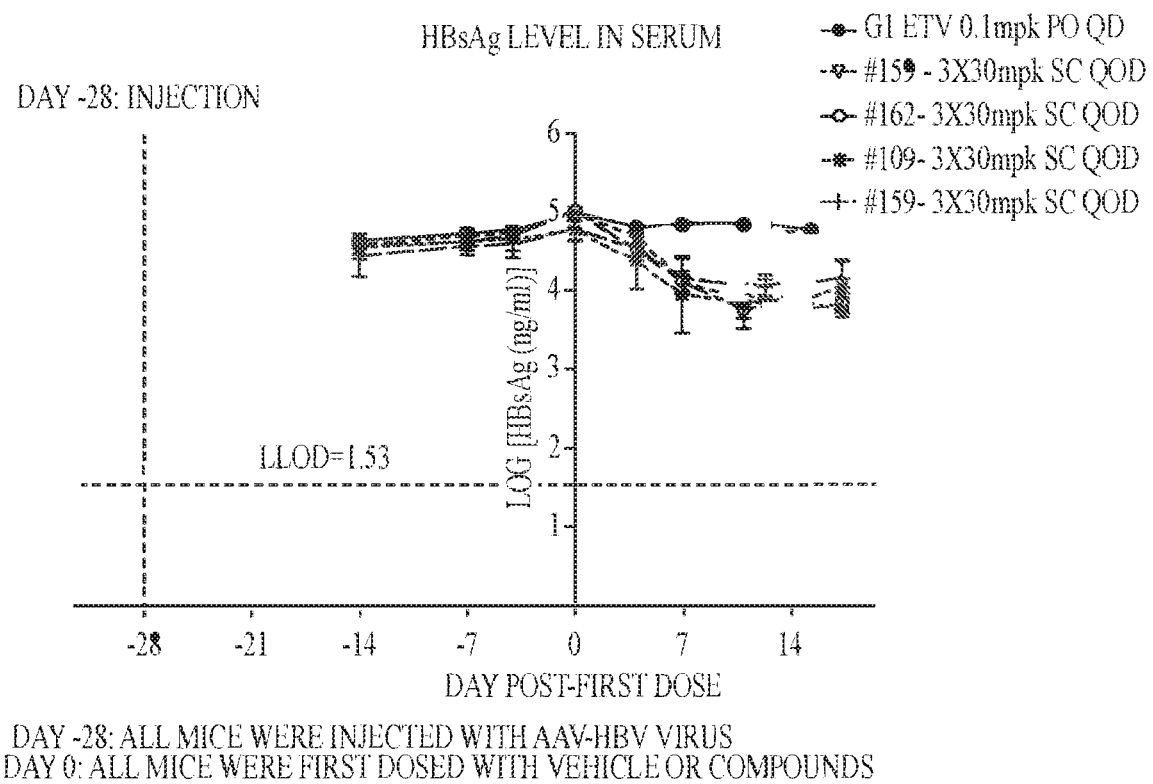
FIG. 3 shows HBsAg reduction levels for GalNAc conjugated compounds of the present disclosure.

FIG. 3 shows HBsAg reduction levels for GalNAc conjugated compounds of the present disclosure (#106, #109, #162 and #159) via subcutaneous delivery in an in vivo AAV-HBV mouse model. The max HBsAg reductions for these ASO were similarly ~1 Log.

TABLE 3

| SEQ ID NO: | Sequence (5'-3') | 2215 EC50 (nM) | 2215 CC50 (nM) | MaxHBsAg Log reduction (nadir)* | MW |
|---|---|---|---|---|---|
| 107 387 | 5'mGpsmApsmUpsmUnsmApsGpsGpsCps ApsGpSAnsGpsGpsTpsmGpsmApsmAnsm AnsmApsmApsmG3' | B | J | | 7245.89 |
| 108 388 | 5'mGpsmApsmUpsmUpsmApsGpsGpsCps ApsGnsApsGpsGpsTpsmGpsmApsmApsm ApSmApsmApsmG-Chpl-3 | A | J | | 8001.85 |
| 109 389 | 5'mGpsmApsmUpsmUpsmApsGpsGpsCps ApsGpsApsGpsGpsTpsmGpsmApsmApsm ApsmApsmApsmG-GalNAc-3 | C | J | 1 | 9006.80 |

*Log Reduction post 3 x 30 mg/kg SC

TABLE 4

| #ID | 2215 HBsAg EC50 (nM) | 2117 sup HBVDNA (EC50 nM) | 2117 Intra HBVDNA EC50(nM) | 2215 CC50 (nM) | MW |
|---|---|---|---|---|---|
| 110 | B | F | F | J | 7305.95 |
| 111 | B | E | E | J | 7320.96 |
| 112 | B | D | D | J | 7350.99 |
| 113 | B | D | D | J | 7350.99 |
| 114 | A | D | D | J | 7381.02 |
| 115 | B | D | E | J | 7275.92 |
| 116 | B | F | E | J | 7290.94 |
| 117 | A | D | D | J | 7320.97 |
| 118 | B | E | D | J | 7320.97 |
| 119 | A | D | D | J | 7351.00 |

| #ID | SEQ ID NO: | Sequence (5'-3') |
|---|---|---|
| 110 | 390 | 5'mGpsmDAPpsmUpsmUpsmDAPpsmGpsGpsCpsApsGpsApsGpsGpsTpsmGpsmApsmApsmApsmApsmApsmG3' |
| 111 | 391 | 5'mGpsmApsmUpsmUpsmApsmGpsGpsCpsApsGpsApsGpsGpsTpsmGpsmApsmApsmDAPpsmDAPpsmmDAPpsmG3' |
| 112 | 392 | 5'mGpsmApsmUpsmUpsmApsmGpsGpsCpsApsGpsApsGpsGpsTpsmGpsmDAPpsmDAPpsmDAPpsmDAPpsmDAPpsmG3' |
| 113 | 393 | 5'mGpsmDAPpsmUpsmUpsmDAPpsmGpsGpsCpsApsGpsApsGpsGpsTpsmGpsmApsmDAPpsmDAPpsmDAPpsmG3' |
| 114 | 394 | 5'mGpsmDAPpsmUpsmUpsmDAPpsmGpsGpsCpsApsGpsApsGpsGpsTpsmGpsmDAPpsmDAPpsmDAPpsmDAPpsmDAPpsmG3' |
| 115 | 395 | 5'mGpsmDAPpsmUpsmUpsmDAPpsGpsGpsCpsApsGpsApsGpsGpsTpsmGpsmApsmApsmApsmApsmApsmG3' |
| 116 | 396 | 5'mGpsmApsmUpsmUpsmApsmGpsGpsCpsApsGpsApsGpsGpsTpsmGpsmApsmApsmDAPpsmDAPpsmDAPpsmG3' |
| 117 | 397 | 5'mGpsmApsmUpsmUpsmApsmGpsGpsCpsApsGpsApsGpsGpsTpsmGpsmDAPpsmDAPpsmDAPpsmDAPpsmDAPpsmG3' |
| 118 | 398 | 5'mGpsmDAPpsmUpsmUpsmDAPpsGpsGpsCpsApsGpsApsGpsGpsTpsmGpsmApsmApsmDAPpsmDAPpsmDAPpsmG3' |
| 119 | 399 | 5'mGpsmDAPpsmUpsmUpsmDAPpsGpsGpsCpsApsGpsApsGpsGpsTpsmGpsmDAPpsmDAPpsmDAPpsmDAPpsmG3' |

TABLE 5

| #ID | SEQ ID NO: | Sequence (5'-3') | 2215 EC50 (nM) | 2215 CC50 (nM) | MW |
|---|---|---|---|---|---|
| 120 | 4005 | 5'mGpsmCpsmApsmGpsmApsmGpsGpsTpsGpsApsApsGpsmCpsmGpsmApsmDAPpsmGpsmUpsmGpsmC-3 | A | J | 6982.68 |
| 121 | 4015 | 5'mGpsmCpsmApsmGpsmApsmGpsGpsTpsGpsApsAgsGgsmCpsmGpsmDAPpsmDAPpsmGpsmUpsmGpsmC-3 | A | J | 6997.69 |
| 122 | 4025 | 5'mGpsmCpsmApsmGpsmDAPpsmGpsGpsTpsGpsApsApsGpsmCpsmGpsmDAPpsmDAPpsmGpsmUpsGpsmC-3 | A | J | 7012.71 |
| 123 | 4035 | 5'mGpsmCpsmApsmGpsmDAPpsmGpSmDAPpsmGpsGpsTpsGpsApsApsGpsmCpsmGpsmDAPpsmDAPpsmGpsmUpSmGpsmC-3 | A | C | 7027.72 |

TABLE 6

| #ID | HBsAg EC50 (nM) | CC50 (nM) | SEQ ID NO: | Sequence (5'-3') | MaxHBsAg Log reduction (nadir)* | MW |
|---|---|---|---|---|---|---|
| 159 | B | J | 404 | 5'mApsmApsmGpsmApsmGpsApsGpsGpsTpsGpsTps5meCpsGps5meCps5meCps5meCps5memCpsmGpsmUDSmGpsmG-GalNAc3' | 1 | 8630.55 |
| 160 | B | J | 405 | 5'mGpsmGpsmUpsmGpsmApsApsGps5meCpsGpsApsApsGpsTpsGps5mCpsmAps5memCpsmAps5memeCpsmG-GalNAc3' | 1.9 | 8624.54 |
| 161 | B | J | 406 | 5'mUpsmGpsmGps5memCpsmAps5meCpsTpsApsGpsTpsApsApsAps5meCpsTpsmGpsmApsmGps5memCps5memC-GalNAc3' | 1.9 | 8548.52 |
| 162 | B | J | 407 | 5'5memCpsmUpsmApsmGmGpsApsGpsTpsTps5meCps5meCpsGps5meCpsApsGpsmUpsmApsmUpsmGDSmG-GalNAc3' | 1 | 8553.45 |
| 163 | B | J | 408 | 5'mApsmGpsmApsmGpsmGpsTpsGps5meCpsGps5meCps5meCps5meCps5meCpsGpsTpsmGpsmGpsmUps5memCpsmG-GalNAc3' | 0.8 | 8611.53 |

TABLE 6-continued

| HBsAg #ID | EC50 (nM) | CC50 (nM) | SEQ ID NO: | Sequence (5'-3') | MaxHBsAg Log reduction (nadir)* | MW |
|---|---|---|---|---|---|---|
| 164 | B | J | 409 | 5'mUps5memCps5memCpsmGps5memCpsAps GpsTpsApsTpsGpsGpsApsTps5meCpsmGps mGps5memCpsmApsmG-GalNAc3' | 1.9 | 8610.55 |
| 165 | B | J | 410 | 5'mUpsmGps5memCpsmApsmGpsApsGpsGps TpsGpsApsApsGps5meCpsGpsmApsmApsm GpsmUpsmG-GalNAc3' | 2.8 | 8637.50 |
| 166 | B | J | 411 | 5'mApsGpsmUps5memCps5memCpsAps5me Cps5meCAps5meCpsGpsApsGpsTps5meCps mUpsmApsmGpsmAps5memC-GalNAc3' | 0.3 | 8507.51 |

*Log Reduction post 3 x 30 mg/kg SC

FIG. 3 shows HBsAg reduction levels for GalNAc conjugated compounds of the present disclosure (#106, #109, #162 and #159) via subcutaneous delivery in an in vivo AAV-HBV mouse model. The max HBsAg reductions for these ASO were similarly ~1 Log.

Figure 4A:
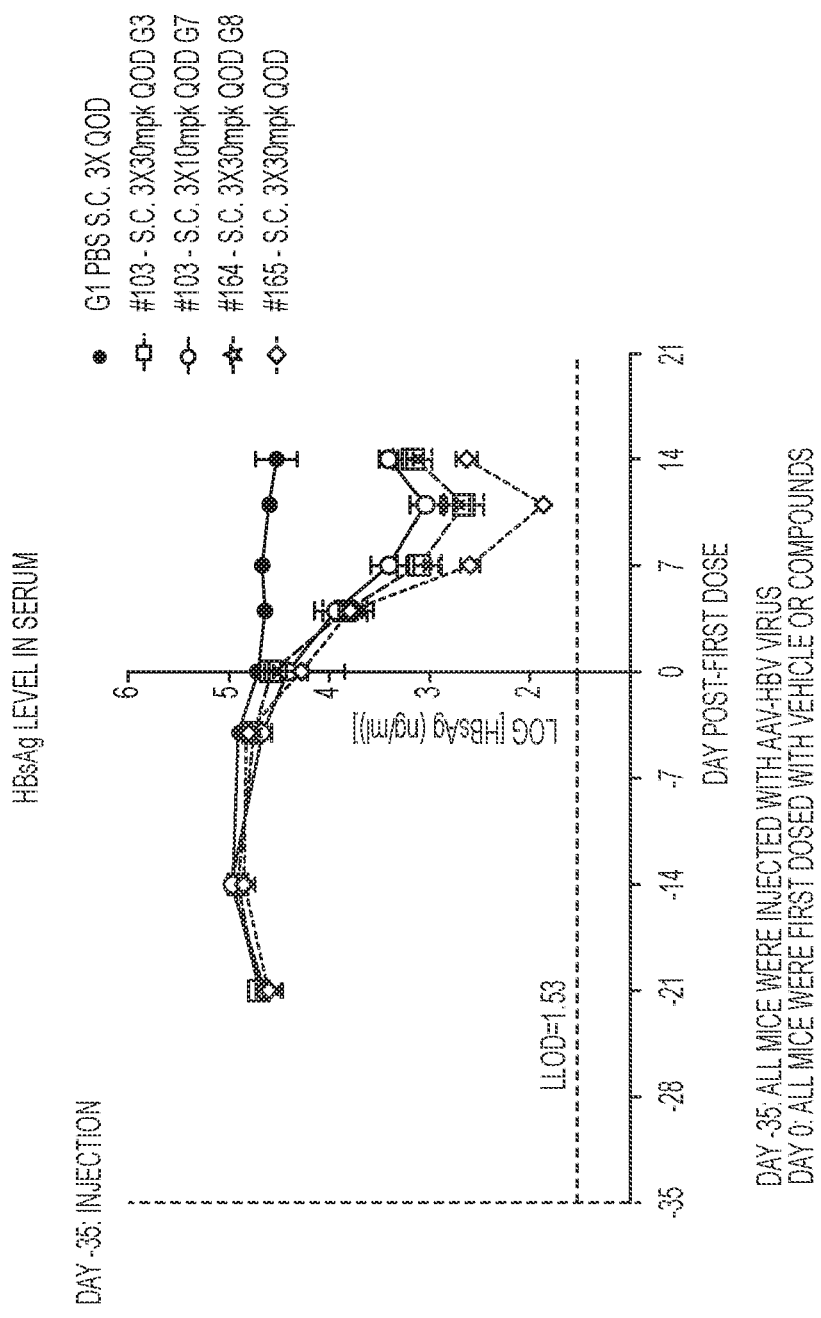
FIGS. 4A-4C show in vivo HBsAg, HBeAg and Serum HBV DNA data in an AAV-HBV mouse model for compounds of the present disclosure.
Figure 4B:
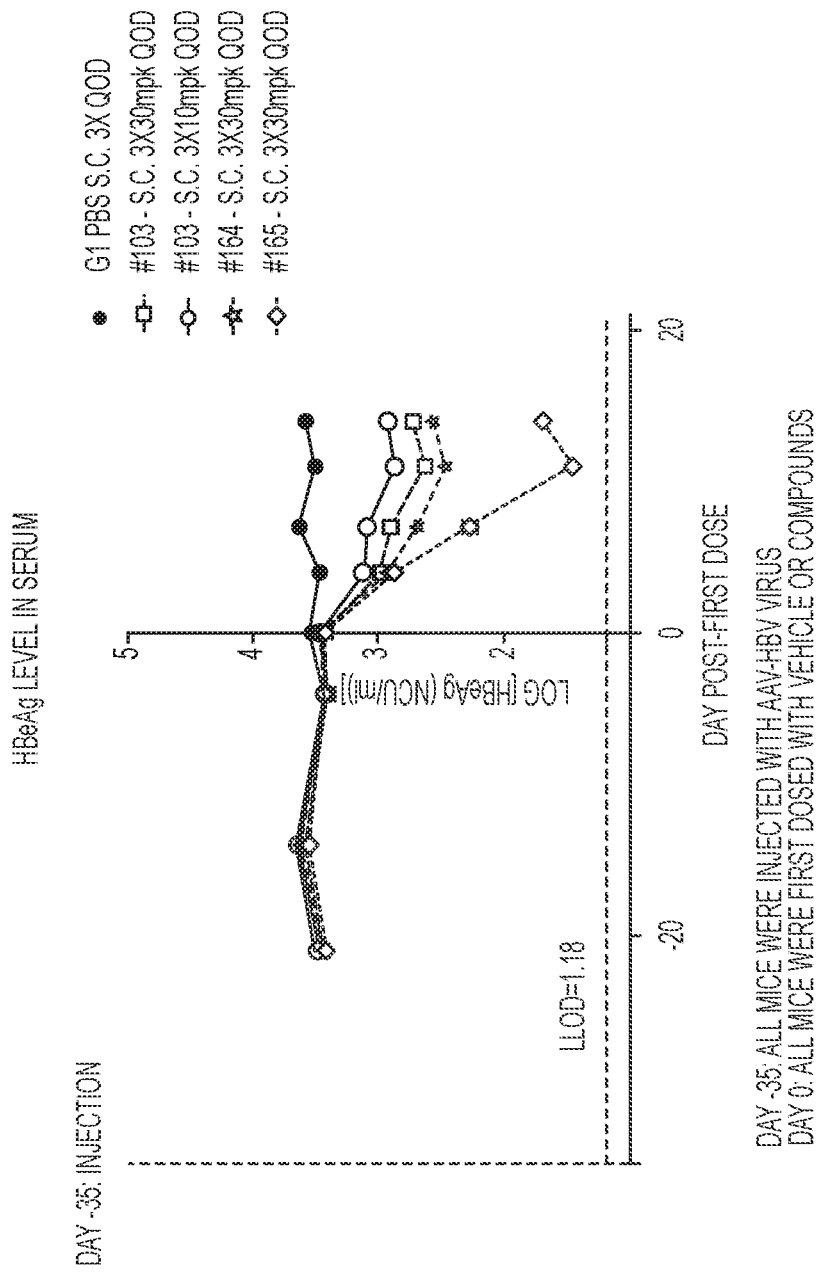
Figure 4C:
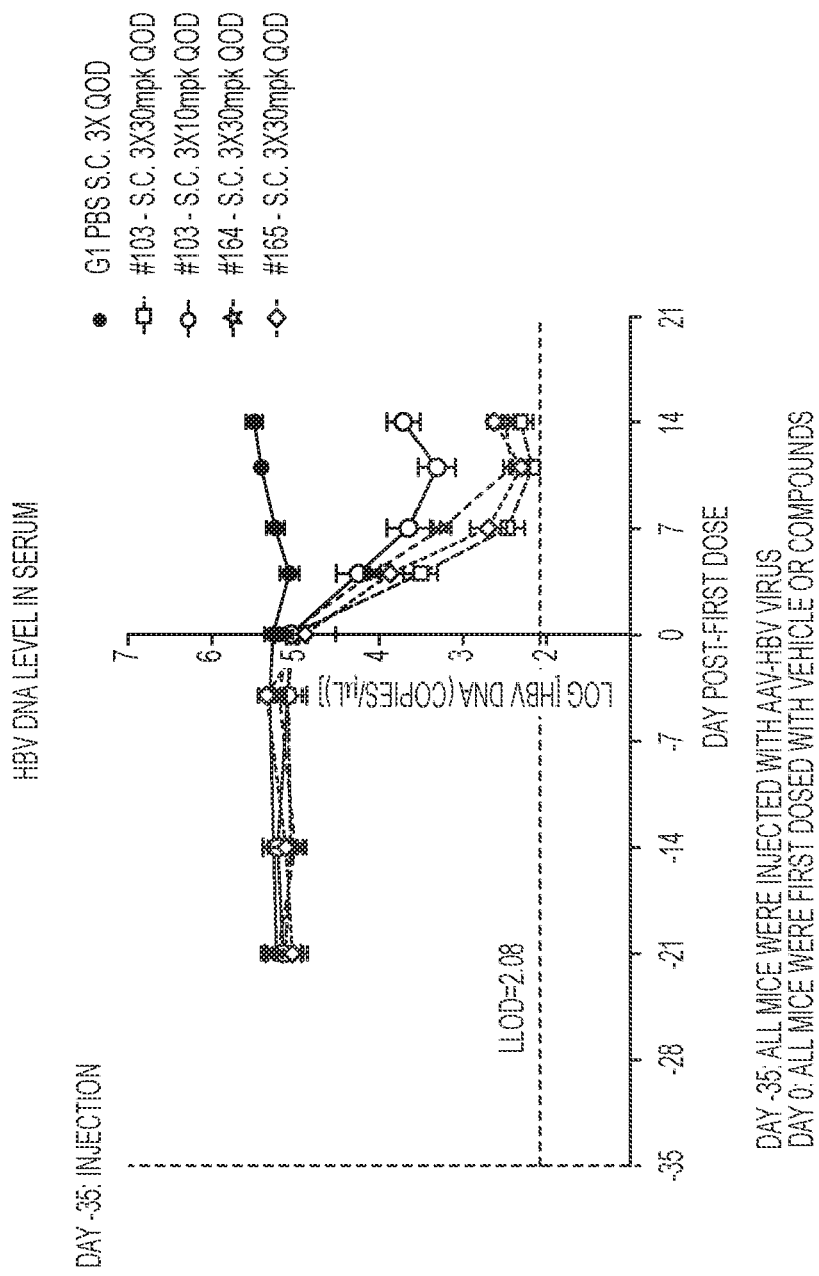

FIGS. 4A-C show in vivo HBsAg, HBeAg and Serum HBV DNA data in an AAV-HBV mouse model for compounds of the present disclosure. #103, #164 and #165 when delivered SC, showed significant reductions in HBsAg, HBeAg and Serum HBV DNA in AAV-HBV mouse model. #103 also demonstrated dose response when dosed at two different dose levels. FIG. 4A shows HBsAg serum levels. FIG. 4B shows HBeAg serum levels. FIG. 4C shows HBV DNA levels.

FIGS. 4A-C show in vivo HBsAg, HBeAg and Serum HBV DNA data in an AAV-HBV mouse model for compounds of the present disclosure. FIG. 4A shows HBsAg serum levels. FIG. 4B shows HBeAg serum levels. FIG. 4C shows HBV DNA levels.

Figure 5A:
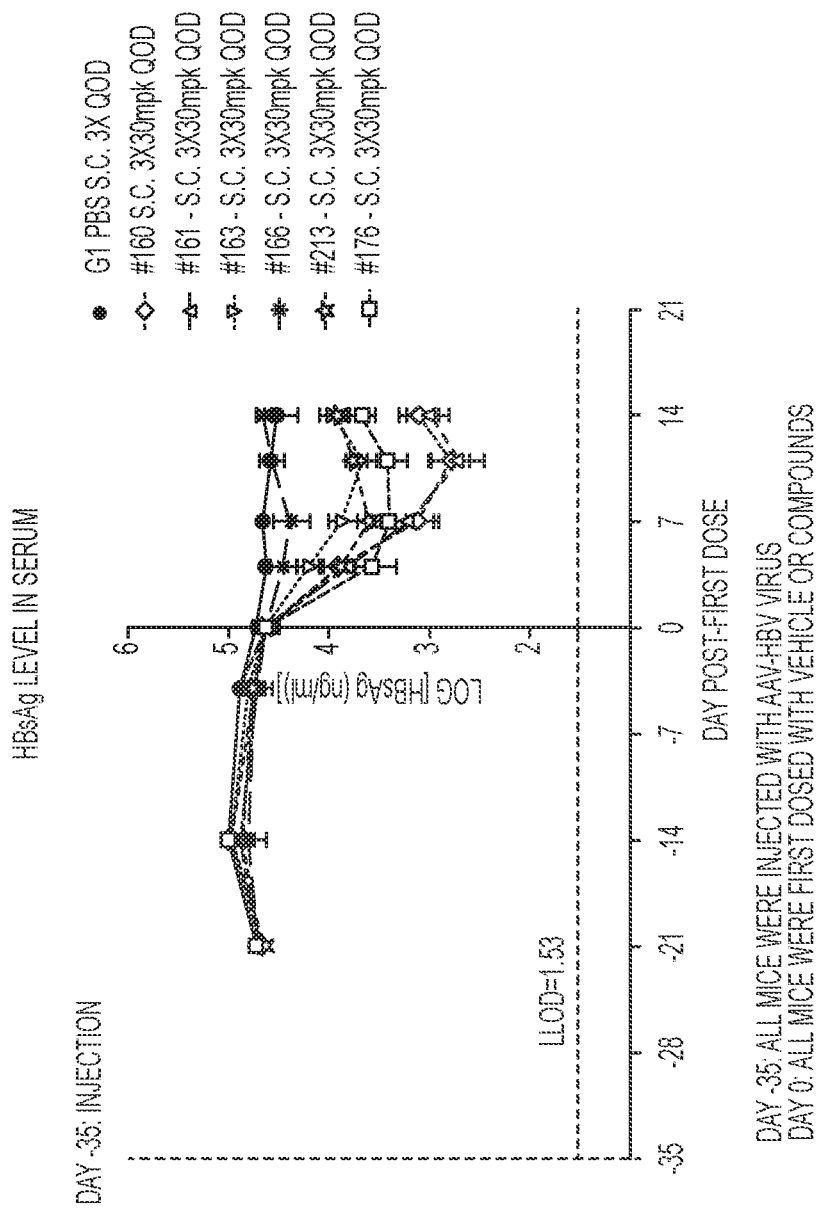
FIGS. 5A-5C show in vivo HBsAg, HBeAg and serum HBV DNA data in an AAV-HBV mouse model for compounds of the present disclosure.
Figure 5B:
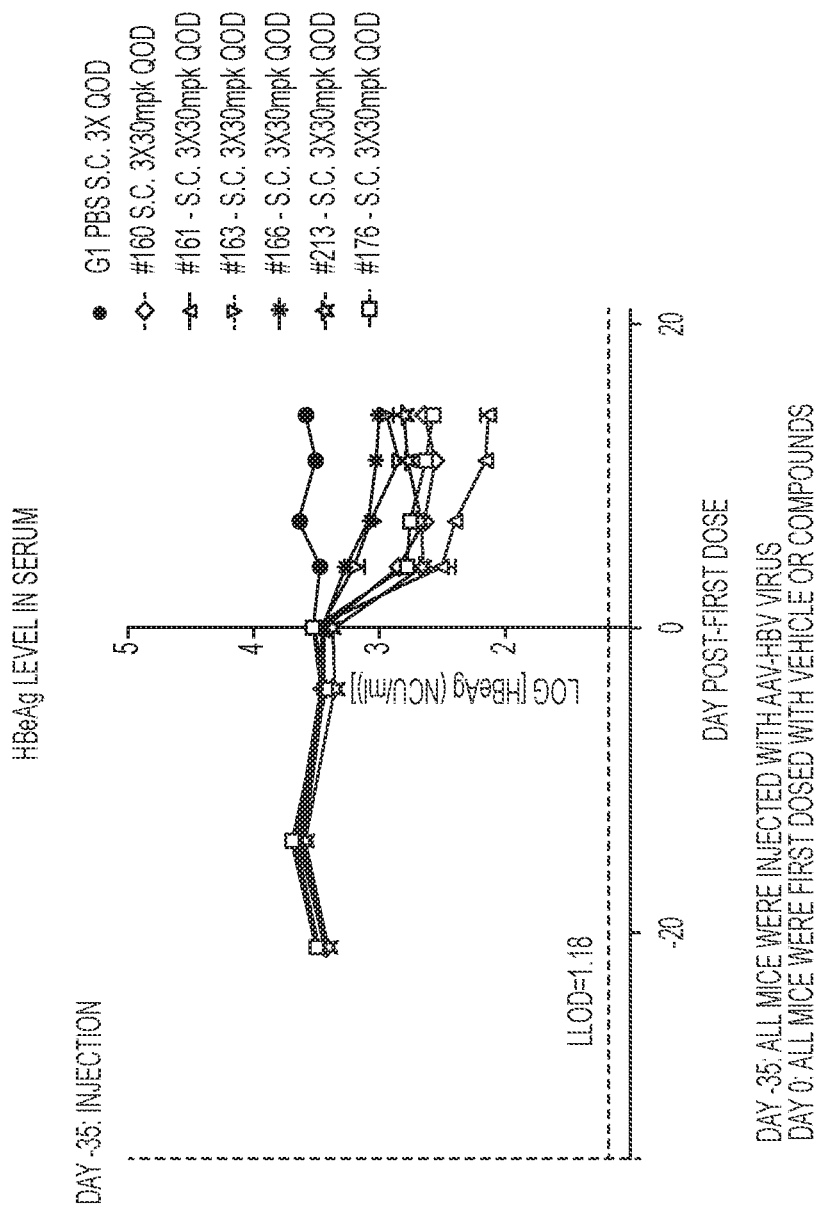
Figure 5C:
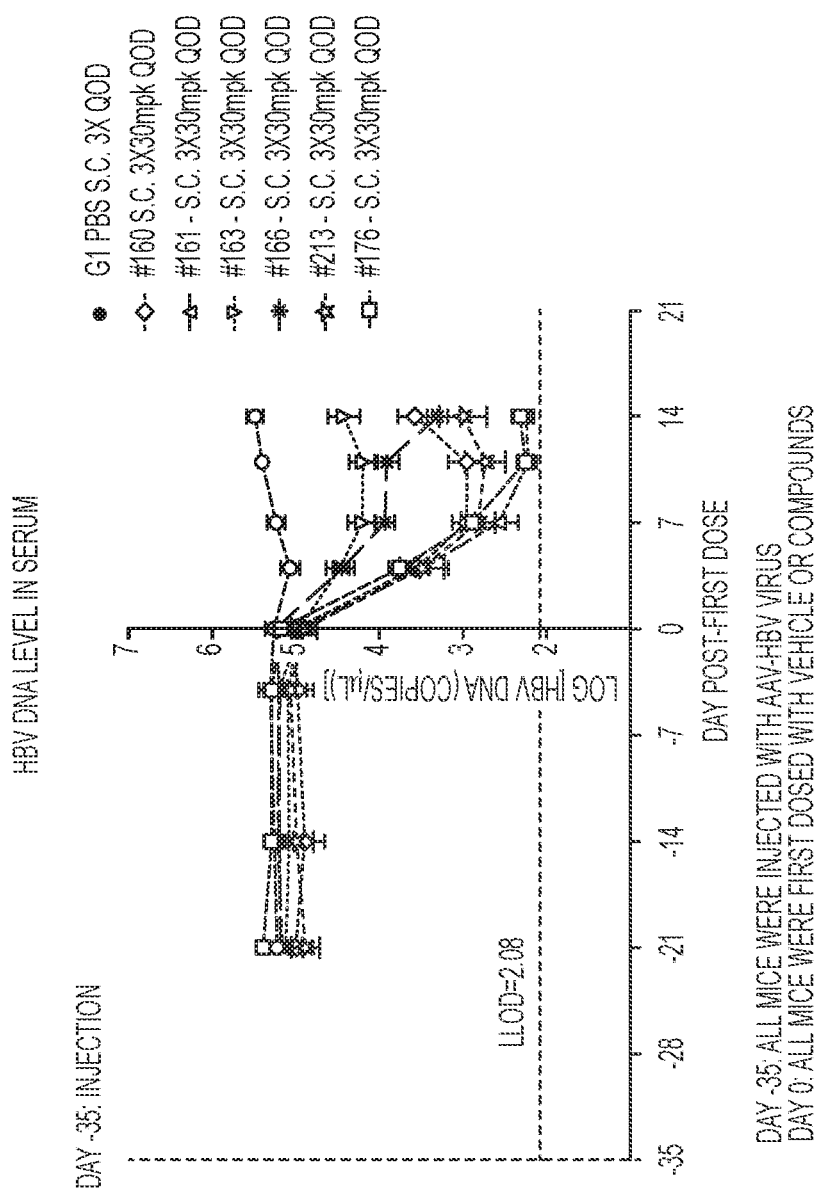

FIGS. 5A-C show in vivo HBsAg, HBeAg and serum HBV DNA data in an AAV-HBV mouse model for compounds of the present disclosure. #160, #161, #163, #166, #213 and #176 significantly reduced HBsAg, HBeAg and serum HBV DNA in AAV-HBV Mouse model. FIG. 5A shows HBsAg serum levels. FIG. 5B shows HBeAg serum levels. FIG. 5C shows HBV DNA levels.

TABLE 7

| #ID | HBsAg 2215 EC50 (nM) | 2215 CC50 (nM) | SEQBase ID Sequence NO:(5'-3') | SEQ ID NO: | Modified Sequence (5'-3') | MW |
|---|---|---|---|---|---|---|
| 167 | A | J | 412 GCAGAGGTGA AGCGAAGTGC | 415 | 5'fGnpsfCnpsfAnpsfGnpsfAnpsfGnps GpsTpsGpsApsApsGpsfCnpsfGnpsf AnpsfAnpsfGnpsfUnpsfGnps-3-NH$_2$-fC | 6785.38 |
| 168 | A | J | 413 GCAGAGGTGA AGCGAAGTGC | 416 | 5'fGnpsfCnpsfAnpsfGnpsfAnpsfGnps GpsTpsGpsApsApsGpsCpsfGnpsfAnpsf AnpsfGnpsfUnpsfGnps-3-NH$_2$-fC | 6768.37 |
| 169 | A | J | 414 GCAGAGGTGA AGCGAAGTGC | 417 | 5'fGnpsfCnpsfAnpsfGnpsfAnpsfGnps GpsTpsGpsApsApsGpsCpsGpsfAnpsf AnpsfGnpsfUnpsfGnps-3-NH$_2$-fC | 6751.37 |

TABLE 8

| #ID | SEQ ID NO: | Sequence (5'-3') | HBsAg 2215 EC50 (µM) | HBsAg 2215 CC50 (µM) | MW |
|---|---|---|---|---|---|
| 170 | 418 | 5'GnpCnpAnpGnpAnpGnpGpsTpsGps AnsAnsGpsCnpGnpAnpApsAnpGnpTnp Gnp-3NH$_2$-C | A | H-I | 6339.66 |
| 171 | 419 | 5'GnpsfCnpsfAnpsGnpsfAnpsGnps GpsTpsGpsApsApsGpsfCnpsGnpsf AnpsfAnpsGnpsfTnpsGnpS-3NH$_2$- fC | A | H-I | 6692.45 |

TABLE 8-continued

| #ID | SEQ ID NO: | Sequence (5'-3') | HBsAg 2215 EC50 (μM) | HBsAg 2215 CC50 (μM) | MW |
|---|---|---|---|---|---|
| 172 | 420 | 5'GnpfCnpfAnpGnpfAnpGnpGpsTps GpsApsApsGpsfCnpGnpfAnpfAnp GnpfTnpGnp-3NH$_2$-fC | A | H-I | 6483.58 |

TABLE 9

| #ID | SEQ ID NO: | Sequence (5'-3') | HBsAg 2215 EC50 (nM) | HBsAg 2215 CC50 (nM) | MW |
|---|---|---|---|---|---|
| 173 | 421 | 5'GnpsafCnpsafAnpsGpspafAnps GnpsGpsTpsGpsApsApsGpsafCnps GnpsafAnpsafAnpsGnpsafUnps GnpsafC | A | J | 6677.43 |
| 174 | 422 | 5'GnpafCnpafAnpGnpafAnpGnp GpsTpsGpsApsApsGpsafCnpGnpa fAnpafAnpGnpafUnpGnpafC | A | J | 6468.57 |
| 175 | 423 | 5'GnpafCnpafAnpGnpafAnpGnp GpsTpsGpsApsApsGpsCpsGnpaf AnpafAnpGnpafUnpGnpafC | A | J | 6466.65 |

TABLE 10

Gapmer (2'Ome, 5MeC) with 5'GalNAc

| SEQ ID NO: | Sequence(5'-3') | 2215 HBsAg EC50 (nM) | Max HBsAg Log Reduction (nadir)* |
|---|---|---|---|
| 204 | 424 | 5'-GalNAc-NHC6-psmUpsm5meCps m5meCpsmGpsm5meCpsApsGpsTps ApsTpsGpsGpsApsTps5meCpsmGps mGpsm5meCpsmApsmG3' | C | 1 |
| 205 | 425 | 5'-GalNAc-NHC6-psm5meCpsmUps mApsmGpsmGpsApsGpsTpsTps5me Cps5meCpsGps5meCpsGpsApsGpsmUps mApsmUpsmGpsmG3' | B | 1 |
| 206 | 426 | 5'-GalNAc-NHC6-psmApsmApsm GpsmApsmGpsApsGpsGpsTpsGps 5meCpsGps5meCps5meCps5meCps m5meCpsmGpsmUpsmGpsmG3' | B | 1 |
| 207 | 427 | 5'GalNAc-NHC6-psmApsmGpsmAps mGpsmGpsTpsGps5meCpsGns5me Cps5meCps5meCps5meCpsGpsTpsm GpsmGpsmUpsm5meCpsmG3' | B | 0.5 |
| 208 | 428 | 5'GalNAc-NHC6-psmUpsmGpsm5me CpsmApsmGpsApsGpsGpsTpsGps ApsAnsGpsSmeCpsGpsmApsmApsm GpsmUpsmG3' | | 1.4 |

*Log Reduction post 3 x 30 mg/kg SC

Figure 6A:
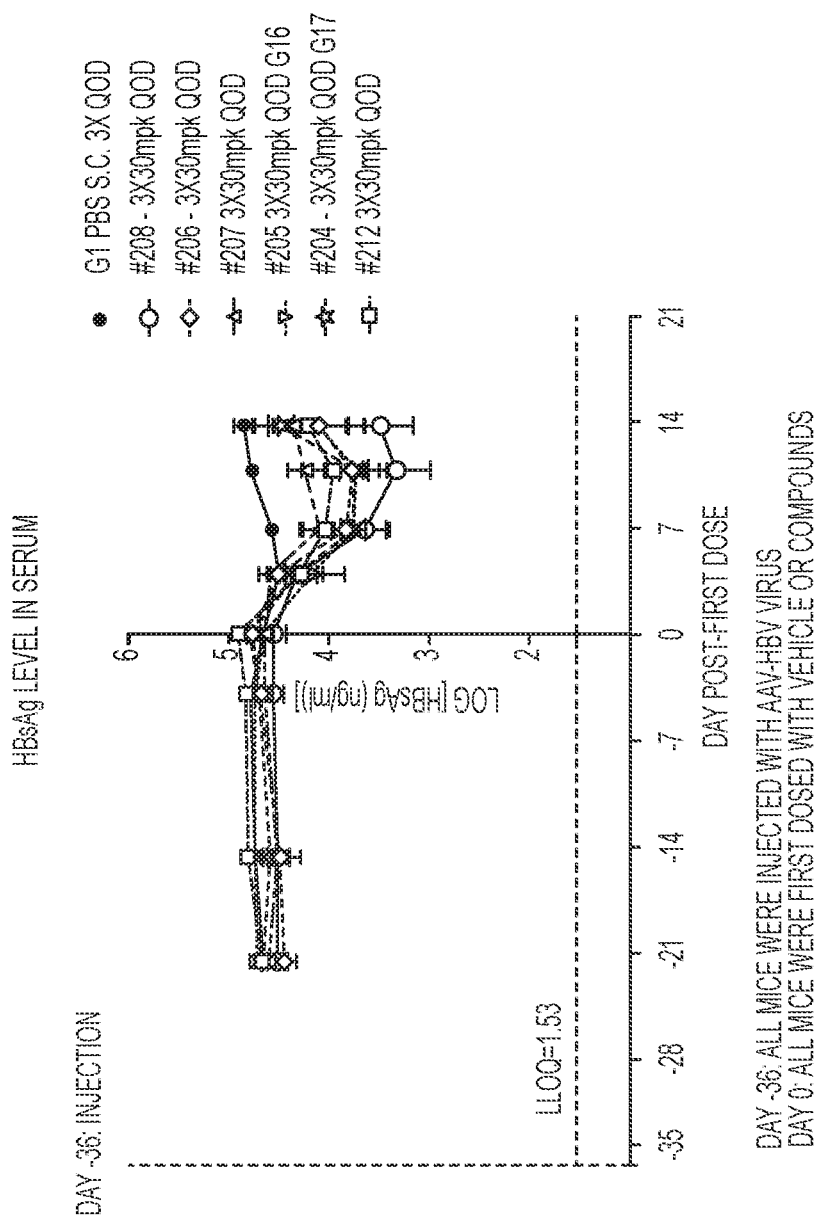
FIGS. 6A-6C show in vivo HBsAg, HBeAg and serum HBV DNA data in an AAV-HBV mouse model for compounds of the present disclosure.
Figure 6B:
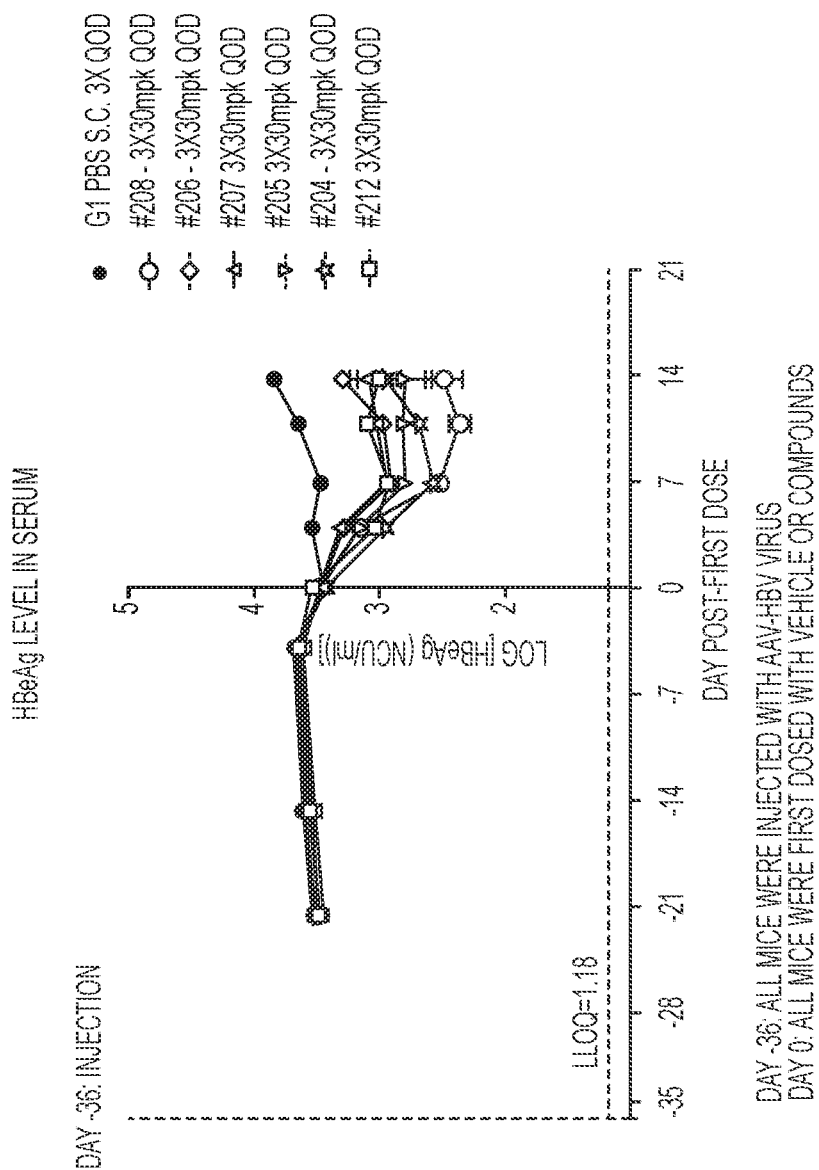
Figure 6C:
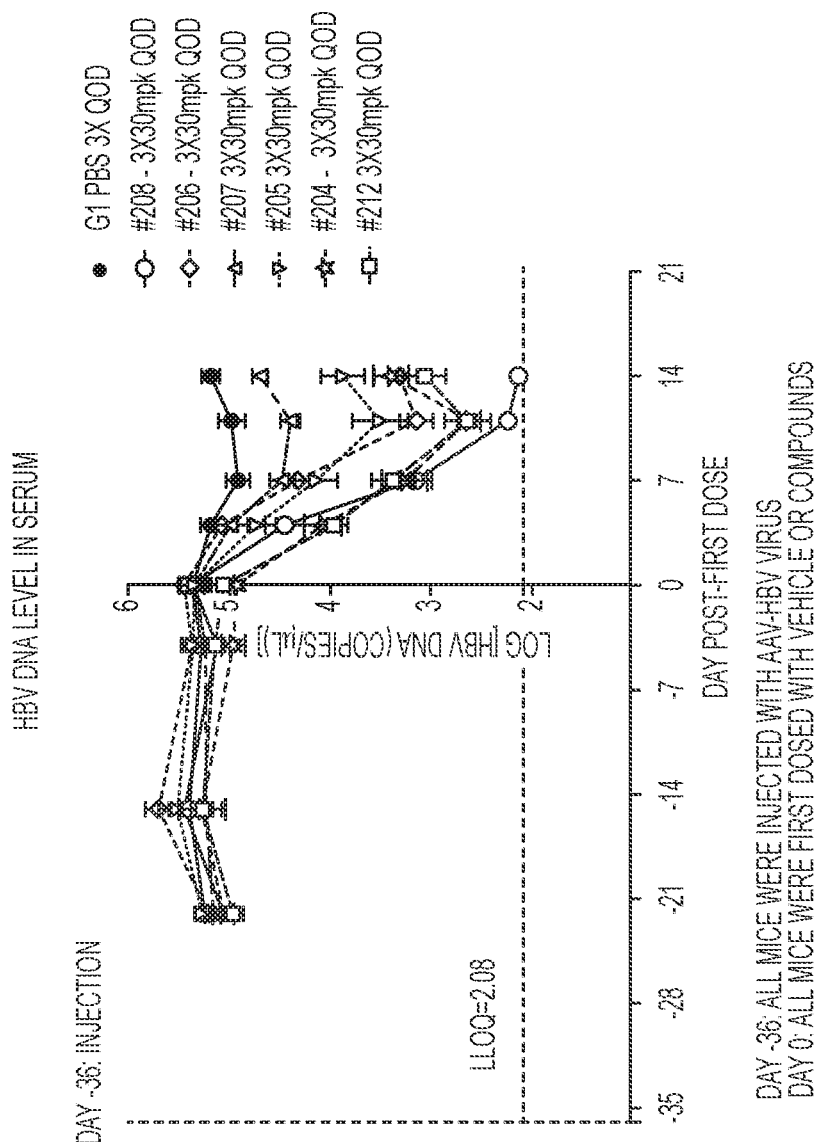
Figure 7A:
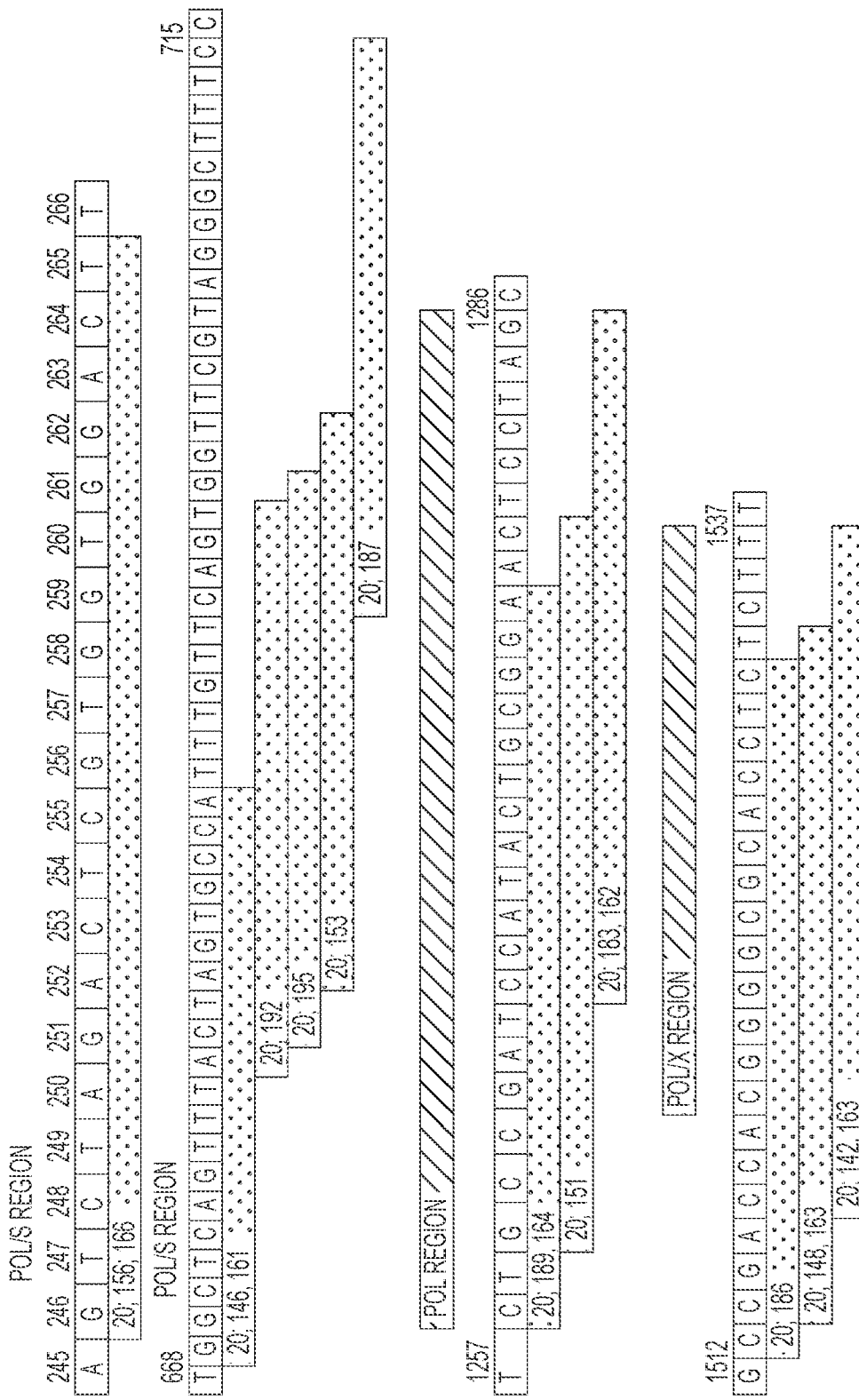

FIGS. 6A-6C show in vivo HBsAg, HBeAg and serum HBV DNA data in an AAV-HBV mouse model for compounds of the present disclosure. #204, #205, #206, #207, #208 and #212 significantly reduced HBsAg, HBeAg and serum HBV DNA in AAV-HBV Mouse model. FIG. 6A shows HBsAg serum levels. FIG. 6B shows HBeAg serum levels. FIG. 6C shows HBV DNA levels.

TABLE 11

Pre-Poly-A

| #ID | SEQ ID NO: | Sequence (5'-3') | 2215 HBsAg EC50 (nM) | 2215 CC50 (nM) | Max HBsAg Log Reduction (nadir)* | MW |
|---|---|---|---|---|---|---|
| 209 | 429 | mGpsmCpsmUpsmCpsmCpsmApsApsApsTpsTps CpsTpsTpsTpsmApsmUpsmApsmApsmGpsmG | A | J | | 6758.52 |
| 210 | 430 | mGpsmCpsmUpsmCpsmCpsmApsApsApsTpsTpsC psTpsTpsTpsmApsmUpsmApsmApsmGpsmG | A | J | | 6728.49 |

TABLE 11-continued

Pre-Poly-A

| #ID | SEQ ID NO: | Sequence (5'-3') | 2215 HBsAg EC50 (nM) | 2215 CC50 (nM) | Max HBsAg Log Reduction (nadir)* | MW |
|---|---|---|---|---|---|---|
| 211 | 431 | mGpsmCpsmUpsmCpsmCpsmApsApsApsTpsTpsCpsTpsTpsTpsApsmUpsmApsmApsmGpsmGpsmG | A | J | | 7073.77 |
| 212 | 432 | mGpsmCpsmUpsmCpsmCpsmApsmApsApsTpsTpsCpsTpsTpsTpsmApsmUpsmApsmApsmGpsmG/GalNAc/ | | | 0.8 | 8519.43 |
| 213 | 433 | mGpsmCpsmUpsmCpsmCpsmApsApsApsTpsTpsCpsTpsTpsTpsmApsmUpsmApsmApsmGpsmG/GalNAc/ | | | 1 | 8489.40 |
| 176 | 434 | mGpsmCpsmUpsmCpsmCpsmApsApsApsTpsTpsCpsTpsTpsTpsApsmUpsmApsmApsmGpsmGpsmG/GalNAc/ | B | I | 1.2 | 8834.67 |
| 214 | 435 | mGpsmCpsmUpsmCpsmCpsmApsmApsApsTpsTpsCpsTpsTpsTpsmApsmUpsmApsmApsmGpsmG/3CholTEG/ | | | | 7514.48 |
| 215 | 436 | mGpsmCpsmUpsmCpsmCpsmApsApsApsTpsTpsCpsTpsTpsTpsmApsmUpsmApsmApsmGpsmG/3CholTEG/ | | | | 7484.85 |
| 216 | 437 | mGpsmCpsmUpsmCpsmCpsmApsApsApsTpsTpsCpsTpsTpsTpsApsmUpsmApsmApsmGpsmGpsmG/3CholTEG/ | | | | 7829.72 |

*Log Reduction post 3 x 30mg/kg SC

TABLE 12

| #ID | SEQ ID NO: | Sequence (5'-3') | 2215 HBsAg EC50 (nM) | 2215 CC50 (nM) | MW |
|---|---|---|---|---|---|
| 217 | 438 | 5'-mGps5mmCpsmApsmGpsmApsmGpsGpsTpsGpsApsApsGp5mmCpsmGpsmApsmApsmGpsmUpsmGpsm5meC-3 | A | I | 7009.74 |
| 218 | 439 | 5'-mGps5mmCpsmApsmGpsmApsmGpsGpsTpsGpsApsApsGps5mmCpsmGpsmApsmApsmGpsmUpsmGps5mmC-Cholesterol-3' | B | I | 7764.7 |
| 219 | 440 | 5'-mGps5mmCpsmApsmGpsmApsmGpsGpsTpsGpsApsApsGp5mmCpsmGpsmApsmApsmGpsmUpsmGps5mmC-TEG-Cholesterol-3' | B | I | 7977.84 |
| 220 | 441 | 5'-mGps5mmCpsmApsmGpsmApsmGpsGpsTpsGpsApsApsGps5mmCpsmGpsmApsmApsmGpsmUpsmGps5mmC-Tocopherol-3' | B | I | 7708.65 |
| 221 | 442 | 5'-mGps5mmCpsmApsmGpsmApsmGpsGpsTpsGpsApsApsGps5mmCpsmGpsmApsmApsmGpsmUpsmGps5mmC-TEG-Tocopherol-3' | | 7920.79 | |
| 222 | 443 | 5'-mGps5mmCpsmApsmGpsmApsmGpsGpsTpsGpsApsApsGps5mmCpsmGpsmApsmApsmGpsmUpsmGps5mmC-GalNAc-3' | B | I | 8770.65 |

TABLE 13

| #ID | SEQ ID NO: | Sequence (5'-3') | 2215 HBsAg EC50 (nM) | 2215 CC50 (nM) | MW |
|---|---|---|---|---|---|
| 223 | 444 | 5'-mGpsm5meCpsmApsmGpsmApsmGpsGpsTpsGpsApsAps Gps5meCpsmGpsmApsmApsmGpsmUpsmGpsm5meC-3' | A | I | 6979.71 |
| 224 | 445 | 5'-mGpsm5meCpsmApsmGpsmApsmGpsGpsTpsGpsApsAps Gps5meCpsmGpsmApsmApsmGpsmUpsmGpsm5meC-po-Chol-3' | | I | 7735.67 |
| 225 | 446 | 5'-mGpsm5meCpsmApsmGpsmApsmGpsGpsTpsGpsApsAps Gps5meCpsmGpsmApsmApsmGpsmUpsmGpsm5meC-po-Tocopherol-3' | | I | 7678.62 |
| 226 | 447 | 5'-mGpsm5meCpsmApsmGpsmApsmGpsGpsTpsGpsApsAps Gps5meCpsmGpsmApsmApsmGpsmUpsmGpsm5meC-po-GalNAc-3' | B | I | 8740.62 |
| 227 | 448 | 5'-mGpsm5meCpsmApsmGpsmApsmGpsGpsTpsGpsApsAps Gps5meCpsGpsmApsmApsmGpsmUpsmGpsm5meC-3' | A | I | 6949.69 |
| 228 | 449 | 5'-mGpsm5meCpsmApsmGpsmApsmGpsGpsTpsGpsApsAps Gps5meCpsGpsmApsmApsmGpsmUpsmGpsm5meC-po-Chol-3' | | I | 7705.65 |
| 229 | 450 | 5'-mGpsm5meCpsmApsmGpsmApsmGpsGpsTpsGpsApsAps Gps5meCpsGpsmApsmApsmGpsmUpsmGpsm5meC-po-Tocopherol-3' | A | I | 7650.61 |
| 230 | 451 | 5'-mGpsm5meCpsmApsmGpsmApsmGpsGpsTpsGpsApsAps Gps5meCpsGpsmApsmApsmGpsmUpsmGpsm5meC-po-GalNAc-3' | B | I | 8710.59 |

TABLE 14

| #ID | SEQ ID NO: | Sequence (5'-3') | 2215 HBsAg EC50 (nM) | 2215 HBsAg CC50 (nM) | MW |
|---|---|---|---|---|---|
| 231 | 452 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-3 | A | I | 6967.62 |
| 232 | 453 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-Chol-3 | A | I | 7723.58 |
| 233 | 454 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-Toco-3 | A | I | 7666.53 |
| 234 | 455 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-GalNAc-3 | A | I | 8728.52 |
| 235 | 456 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-3 | A | I | 6937.59 |
| 236 | 457 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-Chol-3 | A | I | 7693.55 |
| 237 | 458 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-Toco-3 | A | I | 7636.50 |
| 238 | 459 | 5-mGps2-4-OCH$_2$-(5m)CpsmAps 2-4-OCH$_2$-GpsmAps2-4-OCH$_2$-GpsGpsTpsGpsApsApsGps(5m)CpsmGps2-4-OCH$_2$-ApsmAps2-4-OCH$_2$-GpsmUps2-4-OCH$_2$-Gps (5m)mC-GalNAc-3 | A | I | 8698.50 |

TABLE 14-continued

| #ID | SEQ ID NO: | Sequence (5'-3') | 2215 HBsAg EC50 (nM) | 2215 HBsAg CC50 (nM) | MW |
|---|---|---|---|---|---|
| 239 | 460 | 5-mGps2-4-$OCH_2$-(5m)CpsmAps 2-4-$OCH_2$-GpsmAps2-4-$OCH_2$-GpsGpsTpsGpsApsApsGps(5m)CpsmGps2-4-$OCH_2$-ApsmAps2-4-$OCH_2$-GpsmUps2-4-$OCH_2$-Gps (5m)mC-3 | A | I | 6881.57 |

TABLE 15

| #ID | SEQ ID NO: | Sequence (5'-3') | 2215 HBsAg EC 50 (nM) | 2215 CC50 (nM) | MW |
|---|---|---|---|---|---|
| 240 | 461 | 5-dTnpsGnpsCnpsAnpsGnpsApsGpsGpsTpsGpsApsApsGpsCpsGpsAnpsAnpsGnpsTnpsGn-3 | A | I | 6566.49 |
| 241 | 462 | 5-dTnpsfGnpsCnpsfAnpsfGnpsApsGpsGpsTpsGpsApsApsGpsCpsGpsfAnpsfAnpsfGnpsfUnpsfGn 3' | A | I | 6700.35 |

TABLE 16

| #ID | SEQ ID NO: | Sequence (5'-3') | 2215 HBsAg EC50 | 2215 CC50 | MW |
|---|---|---|---|---|---|
| 243 | 463 | 5-fGnpsCnpsfAnpsfGnpsfAnpsfGnpsGpsTpsGpsApsApsGpsCnpsfGnpsfAnpsfAnpsfGnpsfUnpsfGnpsCn-3' | A | I | 6731.41 |
| 242 | 464 | 5-fGnpsCnpsfAnpsfGnpsfAnpsfGnpsGpsTpsGpsApsApsGpsCpsGpsfAnpsfAnpsfGnpsfUnpsfGnpsCn-3' | A | I | 6715.39 |

TABLE 17

| #ID | Y Domain Size | SEQ ID NO: | Sequence (5' -3') | 2215 EC 50 | 2215 CC50 (nM) | MW |
|---|---|---|---|---|---|---|
| 244 | 6 | 465 | 5'-dGnpmCnpmAnpmGnpmAnpmGnpGpsTpsGpsApsApsGpsmCnpmGnpmAnpmAnpmGnpmUnpmGnpmCnp-3' | A | I | 6714.98 |
| 245 | 7 | 466 | 5'-dGnpmCnpmAnpmGnpmAnpmGnpGpsTpsGpsApsApsGpsCpsmGnpmAnpmAnpmGnpmUnpmGnpmCnp-3' | A | I | 6702.01 |
| 246 | 8 | 467 | 5'-dGnpmCnpmAnpmGnpmAnpmGnpGpsTpsGpsApsApsGpsCpsGpsmAnpsmAnpmGnpmUnpmGnpmCnp-3' | A | G | 6689.03 |
| 247 | 8 | 468 | 5'-dGnpmCnpmAnpmGnpmAnpGpsGpsTpsGpsApsApsGpsCpsmGnpmAnpmAnpmGnpmUnpmGnpmCnp-3' | A | I | 6689.03 |
| 248 | 9 | 469 | 5'-dGnpmCnpmAnpmGnpmAnpGpsGpsTpsGpsApsApsGpsCpsGpsmAnpmAnpmGnpmUnpmGnpmCnp-3' | A | I | 6676.06 |

TABLE 18

| #ID | SEQ ID NO: | Sequence (5'-3') | 2215 HBsAg EC50 | 2215 HBsAg CC50 | MW |
|---|---|---|---|---|---|
| 142 | 470 | 5'-mApsmApsmGpsmApsmGpsApsGpsGpsTpsGps5meCpsGps5meCps5meCps5memCpsmGpsmUpsmGpsmG 3' | A | I | 6869.64 |
| 196 | 471 | 5'-mApsmApsmGpsmApsmGpsmApsGpsGpsTpsGps5meCpsGps5meCps5meCps5memCps5memCpsmGpsmUpsmGpsmG 3' | A | I | 6929.69 |
| 197 | 472 | 5'-mApsmApsmGpsmApsmGpsmApsmGpsGpsTpsGps5meCpsGps5meCps5memCps5memCps5memCpsmGpsmUpsmGpsmG 3' | A | I | 6989.74 |
| 143 | 473 | 5'-mGpsmpsmUpsmGpsmApsApsGps5meCpsGpsApsApsGpsTpsGps5mCpsmAps5memCpsmAps5memeCpsmG 3' | A | I | 6863.64 |
| 198 | 474 | 5'-mGpsmGpsmUpsmGpsmApsApsGps5meCpsGpsApsApsGpsTpsGps5memCpsmAps5memCpsmAps5memeCpsmG 3' | A | I | 6923.69 |
| 199 | 475 | 5'-mGpsmGpsmUpsmGpsmApsmApsGps5meCpsGpsApsApsGpsTpsGps5memCpsmAps5memCpsmAps5memeCpsmG 3' | A | I | 6953.72 |
| 146 | 476 | 5'-mUpsmGpsmGps5memCpsmAps5meCpsTpsApsGpsTpsApsApsAps5meCpsTpsmGpsmApsmGps5memCps5memC 3' | A | I | 6987.62 |
| 200 | 477 | 5'-mUpsmGpsmGps5memCpsmAps5memCpsTpsApsGpsTpsApsApsApsAps5meCpsTpsmGpsmApsmGps5memCps5memC 3' | A | I | 6817.64 |
| 201 | 478 | 5'-mUpsmGpsmGps5memCpsmAps5meCpsTpsApsGpsTpsApsApsApsAps5meCpsTpsmGpsmApsmGps5memCps5memC 3' | A | I | |
| 147 | 479 | 5'-5memCpsmUpsmApsmGmGpsApsGpsTpsTps5meCps5meCpsGps5meCpsApsGpsmUpsmApsmUpsmGpsmG 3' | A | I | 6792.55 |
| 202 | 480 | 5'-5memCpsmUpsmApsmGmGpsmApsGpsTpsTps5meCps5meCpsGps5meCpsApsmGpsmUpsmApsmUpsmGpsmG 3' | A | I | 6852.60 |
| 203 | 481 | 5'-5memCpsmUpsmApsmGmGpsmApsmGpsTpsTps5meCps5meCpsGps5meCpsApsmGpsmUpsmApsmUpsmGpsmG 3' | A | I | 6882.62 |

TABLE 19

| #ID | SEQ ID NO: | Sequence (5'-3') | 2215 HBsAg EC50 | 2215 CC50 | MW |
|---|---|---|---|---|---|
| 128 | 482 | 5'-GnpsCnpsAnpsGnpsApsGpsGpsTpsGpsAnpsAnpsGnpsCnps-3-NH$_2$-G-3' | B | J | 4577.86 |
| 129 | 483 | 5'-CnpsGnpsTnpsGnpsCnpsApsGpsApsGpsGpsTnpsGnpsAnpsAnpsGnps-3-NH$_2$-C-3' | B | J | 5201.40 |
| 130 | 484 | 5'-GnpsCnpsAnpsGnpsAnpsGnpsGnpsTnpsGpsApsAnpsGnpsCnpsGnpsAnpsAnpsGnpsTnpsGnps-3 NH$_2$-C-3' | A | J | 6543.60 |
| 131 | 485 | 5'-GnpsCnpsAnpsGnpsAnpsGnpsGnpsTpsGpsAnpsAnpsGnpsCnpsGnpsAnpsAnpsGnpsTnpsGnps-3 NH$_2$-C-3' | B | J | 6543.60 |
| 132 | 486 | 5'-GnpsCnpsAnpsGnpsAnpsGnpsGnpsGpsTpsGnpsAnpsAnpsGnpsCnpsGnpsAnpsAnpsGnpsTnpsGnps-3 NH$_2$-C-3' | B | J | 6543.60 |
| 133 | 487 | 5'-GnpsCnpsAnpsGnpsAnpsGnpsGnpsGnpsTnpsGnpsApsApsGnpsCnpsGnpsAnpsAnpsGnpsTnpsGnps-3 NH$_2$-C-3' | B | J | 6543.60 |

TABLE 19-continued

| #ID | SEQ ID NO: | Sequence (5'-3') | 2215 HBsAg EC50 | 2215 CC50 | MW |
|---|---|---|---|---|---|
| 134 | 488 | 5'-GnpsCnpsAnpsGnpsAnpsGnpsGnpsTnpsGnpsAnpsAps GpsCnpsGnpsAnpsAnpsGnpsTnpsGnps-3 NH$_2$-C-3' | B | J | 6543.60 |
| 135 | 489 | 5'-GnpsCnpsAnpsGnpsAnpsGnpsGnpsGpsTpsGpsAnpsAnpsG npsCnpsGnpsAnpsAnpsGnpsTnpsGnps-3 NH$_2$-C-3' | B | J | 6544.58 |
| 136 | 490 | 5'-GnpsCnpsAnpsGnpsAnpsGnpsGnpsTnpsGpsApsApsG npsCnpsGnpsAnpsAnpsGnpsTnpsGnps-3 NH$_2$-C-3' | B | J | 6544.58 |
| 137 | 491 | 5'-GnpsCnpsAnpsGnpsAnpsGnpsGnpsTpsGpsApsAnpsG npsCnpsGnpsAnpsAnpsGnpsTnpsGnps-3 NH$_2$-C-3' | A | J | 6544.58 |
| 138 | 492 | 5'-GnpsCnpsAnpsGnpsAnpsGnpsGnpsTnpsGnpsApsAps GpsCnpsGnpsAnpsAnpsGnpsTnpsGnps-3 NH$_2$-C-3' | B | J | 6544.58 |
| 139 | 493 | 5'-GnpsCnpsAnpsGnpsAnpsGnpsGnpsTnpsGpsApsApsG psCnpsGnpsAnpsAnpsGnpsTnpsGnps-3 NH$_2$-C-3' | A | J | 6545.57 |
| 140 | 494 | 5'-GnpsCnpsAnpsGnpsAnpsGnpsGnpsTpsGpsApsApsGp sCnpsGnpsAnpsAnpsGnpsTnpsGnps-3 NH$_2$-C-3' | A | J | 6546.55 |

TABLE 20

| #ID | 2215 HBsAg EC50 (nM) | 2215 CC50 (nM) | 2217 sup HBVDNA (EC50 nM) | 2117 intra HBVNA EC50(nM) |
|---|---|---|---|---|
| 177 | B | J | D | F |
| 178 | B | J | E | F |
| 179 | B | J | F | F |
| 180 | A | J | D | F |
| 181 | B | J | D | F |
| 182 | A | J | D | E |
| 183 | A | J | D | E |
| 184 | A | J | D | D |
| 185 | A | J | D | E |
| 186 | B | J | D | D |
| 187 | B | J | E | E |
| 188 | B | J | E | F |
| 189 | A | J | D | F |
| 190 | C | J | E | F |
| 191 | B | J | E | F |
| 192 | B | J | D | D |
| 193 | B | J | E | D |
| 194 | C | J | E | E |
| 195 | B | J | E | D |

TABLE 21

| #ID | 2215 HBsAg EC50 (nM) | 2215 CC50 (nM) | 2217 sup HBVDNA (EC50 nM) | 2217 intra HBVDNA (EC50 nM) |
|---|---|---|---|---|
| 124 | B | J | B | B |
| 125 | B | J | B | B |
| 126 |   | J | B | A |
| 127 | A | J | A | A |
| 128 | B | J | C | B |
| 129 | B | J | B | B |

TABLE 22

| #ID | 2215 HBsAg EC50 (nM) | 2215 CC50 (nM) | 2217 sup HBVDNA (EC50 nM) | 2217 intra HBVDNA (EC50 nM) |
|---|---|---|---|---|
| 249 | C | G | F | F |
| 250 | B | G | F | E |
| 251 | B | G | F | F |
| 252 | B | G | E | E |
| 253 | B | G | E | E |
| 254 |   | G | E | D |
| 255 | A | G | D | D |
| 256 | B | G | F | E |
| 257 | B | G | E | E |

TABLE 23

| HBsAg EC50 (µM) | 2215 CC50 (µM) | SEQ ID NO: | Sequence (5'-3') | MW |
|---|---|---|---|---|
| A | E-F | 495 | GnpsCnpsAnpsGnpsAnpsGnpsGnpsTnpsGpsApsAnpsGnpsCnpsG npsAnpsAnpsGnpsTnpsGnps-3nh2-C | 6543.60 |
| A | E-F | 496 | GnpsCnpsAnpsGnpsAnpsGnpsGnpsTpsGpsAnpsAnpsGnpsCnpsG npsAnpsAnpsGnpsTnpsGnps-3nh2-C | 6543.60 |
| A | E-F | 497 | GnpsCnpsAnpsGnpsAnpsGnpsGnpsGpsTpsGnpsAnpsAnpsGnpsCnpsG npsAnpsAnpsGnpsTnpsGnps-3nh2-C | 6543.60 |
| A | E-F | 498 | GnpsCnpsAnpsGnpsAnpsGnpsGnpsTnpsGnpsApsApsGnpsCnpsG npsAnpsAnpsGnpsTnpsGnps-3nh2-C | 6543.60 |

TABLE 23-continued

| HBsAg 2215 EC50 (µM) | 2215 CC50 (µM) | SEQ ID NO: | Sequence (5'-3') | MW |
|---|---|---|---|---|
| A | E-F | 499 | GnpsCnpsAnpsGnpsAnpsGnpsGnpsTnpsGnpsAnpsApsGpsCnpsG npsAnpsAnpsGnpsTnpsGnps-3nh2-C | 6543.60 |
| A | E-F | 500 | GnpsCnpsAnpsGnpsAnpsGnpsGpsTpsGpsAnpsAnpsGnpsCnpsGn psAnpsAnpsGnpsTnpsGnps-3nh2-C | 6544.58 |
| A | E-F | 501 | GnpsCnpsAnpsGnpsAnpsGnpsGnpsTnpsGpsApsApsGnpsCnpsGn psAnpsAnpsGnpsTnpsGnps-3nh2-C | 6544.58 |
| A | E-F | 502 | GnpsCnpsAnpsGnpsAnpsGnpsGnpsTpsGpsApsAnpsGnpsCnpsGn psAnpsAnpsGnpsTnpsGnps-3nh2-C | 6544.58 |
| A | E-F | 503 | GnpsCnpsAnpsGnpsAnpsGnpsGnpsTnpsGnpsApsApsGpsCnpsGn psAnpsAnpsGnpsTnpsGnps-3nh2-C | 6544.58 |
| A | E-F | 504 | GnpsCnpsAnpsGnpsAnpsGnpsGnpsTnpsGpsApsApsGpsCnpsGnp sAnpsAnpsGnpsTnpsGnps-3nh2-C | 6545.57 |
| A | E-F | 505 | GnpsCnpsAnpsGnpsAnpsGnpsGnpsTpsGpsApsApsGpsCnpsGnps AnpsAnpsGnpsTnpsGnps-3nh2-C | 6546.55 |
| A | E-F | 506 | GnpsCnpsAnpsGnpsAnpsGnpsGpsTpsGpsApsApsGpsCpsGnpsAn psAnpsGnpsTnpsGnps-3nh2-C | 6548.52 |
| A | E-F | 507 | GnpsCnpsApsGnpsAnpsGpsGnpsTnpsGpsAnpsAnpsGpsCnpsGnp sApsAnpsGnpsTpsGnps-3nh2-C | 6547.54 |
| A | E-F | 508 | GpsCnpsAnpsGpsAnpsGnpsGpsTnpsGnpsApsAnpsGnpsCpsGnps AnpsApsGnpsTnpsGps-3nh2-C | 6548.52 |
| A | E-F | 509 | GnpsCpsAnpsGnpsApsGnpsGnpsTpsGnpsAnpsApsGnpsCnpsGps AnpsAnpsGpsTnpsGnps-3nh2-C | 6547.54 |
| A | E-F | 510 | GnpsCnpsAnpsGnpsAnpsGnpsGpsTpsGpsApsApsGpsCnpsGnpsA npsAnpsGnpsTnpsGnps-3nh2-C | 6547.54 |

Two oligonucleotides, the first containing 2'MOE PS modifications and the other containing 2'MOE NPS, were tested in vitro and in vivo. The following Tables 24-26 summarize the results of the testing.

TABLE 24

| Sequence | Tm (° C.) | Max HBsAg Reduction (nadir) 3 × 10 mg/kg | Max HBeAg Reduction (nadir) 3 × 10 mg/kg |
|---|---|---|---|
| 258 | 77.2 | 3.4 log | 2.7 log |
| 259 | 69.9 | 2.4 log | 1.9 log |
| Improvement | 7.3 | 1 log | 0.8 log |

| # | Sequence (5'-3') | Mol Wt. |
|---|---|---|
| 258 | 5'-mGnpsmoeCnpsmoeAnpsmGnpsmoeAnpsGpsGpsTpsGp sApsApsGpsCpsGpsApsmoeAnpsmGnpsmoeUnpsmGnpsm oeCnp-C6-NH-GalNAc6-3' (SEQ ID NO: 511) | 8862.97 |
| 259* | 5'-moeGps(5me)moeCpsmoeApsmoeGpsmoeApsGpsGpsTp sGpsApsApsGps(5me)CpsGpsApsmoeApsmoeGpsmoeTpsm oeGps(5me)moeC-po-GalNAc2-3' (SEQ ID NO: 512) | 9008.93 |

*Sequences 260 and 261 were also tested and provided similar results.

Figures 9A, 9B:
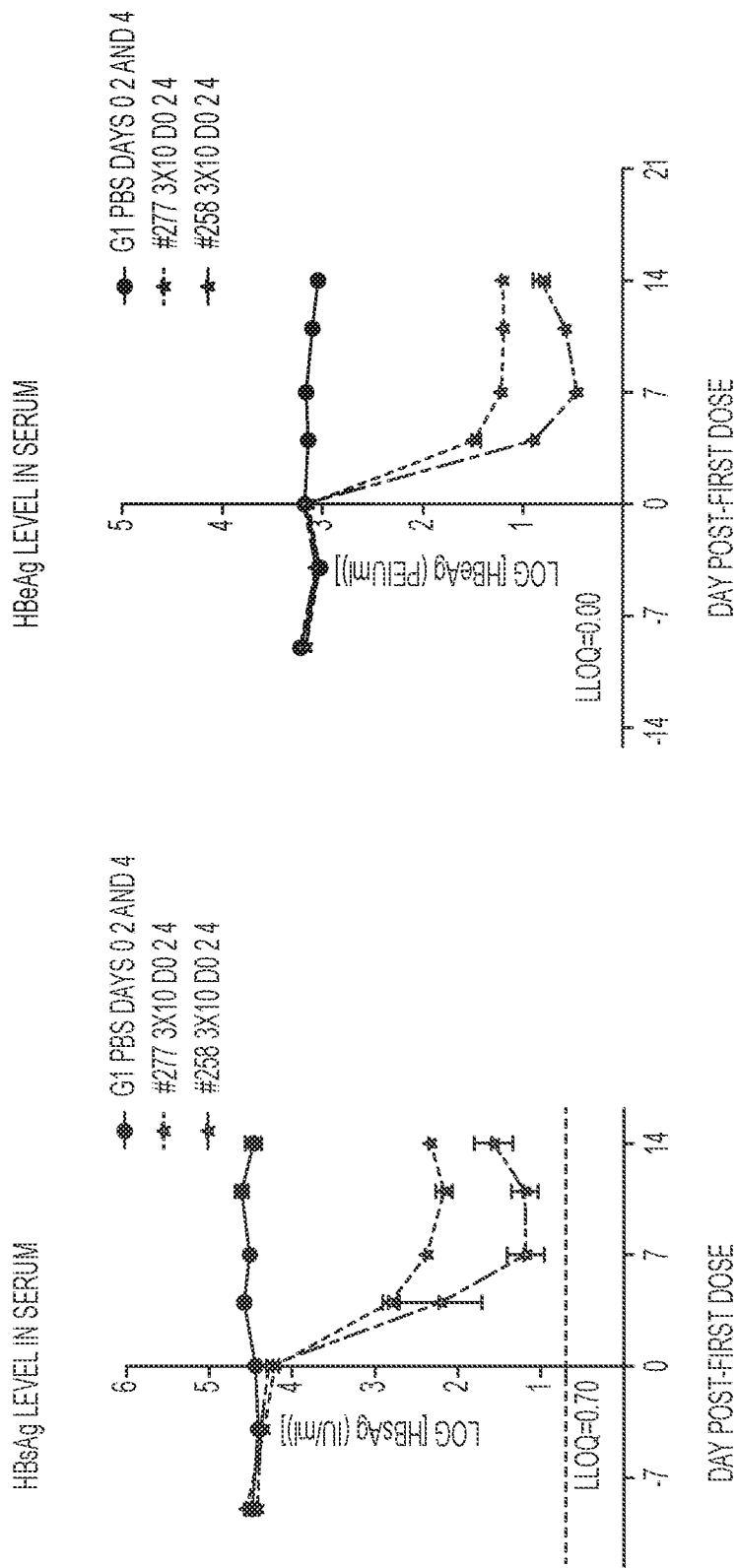
FIG. 9A shows HBsAg level in serum for two oligonucleotides described in Table 30.
FIG. 9B shows HBeAg level in serum for two oligonucleotides described in Table 30.

FIG. 9A shows HBsAg results of oligomers 1 and 2 in a HBV Mouse Model tested at 3×10 mg/kg on Days 0, 2, 4. FIG. 9B shows the HBeAg results.

TABLE 25

| Sequence | Tm (° C.) | Max HBsAg Reduction (nadir) 3 × 10 mg/kg | Max HBeAg Reduction (nadir) 3 × 10 mg/kg |
|---|---|---|---|
| 262 | 77.3 | 3.1 log | 2.5 log |
| 263 | 69.9 | 2.4 log | 1.9 log |
| Improvement | 7.4 | 0.7 log | 0.6 log |

| # | Sequence (5'-3') | | Mol Wt. |
|---|---|---|---|
| 262* | 5'-GalNAc 2-moeGnpsmoeCnpsmoeAnpsmoeGnpsmoeAnpsGpsGpsTpsGpsApsApsGpsCpsGpsApsmoeAnpsmoeGnpsmoeUnpsmoeGnpsmoeCn 3' (SEQ ID NO: 513) | | 8941.00 |
| 263 | 5'-moeGps(5me)moeCpsmoeApsmoeGpsmoeApsGpsGpsTpsGpsApsApsGps(5me)CpsGpsApsmoeApsmoeGpsmoeTpsmoeGps(5me)moeC-GalNAc2-3' (SEQ ID NO: 514) | | 9008.93 |

*5'-GalNac2-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn-3' (SEQ ID NO: 515) and 5'-GalNac-moeGnpsmoeCnpsmoeAnpsmoeGnpsmoeAnpsGpsGpsTpsGpsApsApsGpsCpsGpsApsmoeAnpsmoeGnpsmoeUnpsmoeGnpsmoeCn-3' (SEQ ID NO: 516) were also tested and provided similar results.

TABLE 26

| Sequence | Max HBsAg Reduction (nadir) 3 × 5 mg/kg | Max HBeAg Reduction (nadir) 3 × 5 mg/kg |
|---|---|---|
| 266 | 2.3 log | 2.1 log |
| 267 | 2.2 log | 1.9 log |
| Improvement | 0.1 log | 0.2 log |

| # | Sequence (5'-3') | | Mol Wt. |
|---|---|---|---|
| 266* | 5-GalNAc2-mGnpsmCnpsmAnpsmGnpsmAnpsGpsGpsTpsGpsApsApsGps(5m)CpsGpsApsmoeAnpsmoeGnpsmoeUnpsmoeGnpsmoeCn-3 (SEQ ID NO: 517) | | 8736.73 |
| 267 | 5'-GalNac6- NH-C6-moeGps(5m)moeCpsmoeApsmoeGpsmoeApsGpsGpsTpsGpsApsApsGps(5m)CpsGpsApsmoeApsmoeGpsmoeTpsmoeGps(5m)moeC-3' (SEQ ID NO: 518) | | 9105.14 |

*5'-GalNAc2-mGnpsmCnpsmAnpsmGnpsmAnpsGpsGpsTpsGpsApsApsGps(5m)CpsGpsApsmAnpsmGnpsmUnpsmGnpsmCn-3' (SEQ ID NO: 519) was also tested and provided similar results.

As can be seen above, the MOE NPS oligomers were more active than MOE PS in vivo and OMe NPS is as active as MOE PS oligomers.

Two oligonucleotides, the first containing OEt NPS substitution and the second having MOE NPS were tested in vitro and in vivo. The following Table 27 summarizes the results of the testing.

TABLE 27

| Sequence | Max HBsAg Reduction (nadir) 3 × 5 mg/kg | Max HBeAg Reduction (nadir) 3 × 5 mg/kg |
|---|---|---|
| 269 | 1.9 log | 1.7 log |
| 270 | 1.9 log | 1.8 |

TABLE 27-continued

| Difference0 log | -0.1 log |
|---|---|

| # | Sequence (5'-3') |
|---|---|
| 269 | 5'-GalNAc2-etoGnps(5m)etoCnpsetoAnpsetoGnpsetoAnpsGps GpsTpsGpsApsApsGps(5m)CpsGpsApsetoAnpsetoGnpsetoTnpse toGnps(5m)etoCn-3' (SEQ ID NO: 520) |
| 270 | 5-GalNAc2-moeGnpsmoeCnpsmoeAnpsmoeGnpsmoeAnpsGpsGpsTpsGpsApsApsGps (5m)CpsGpsApsmAnpsmGnpsmUnpsmGnpsmCn-3 (SEQ ID NO: 521) |

As can be seen above, the MOE NPS oligomers had similar activity to the OEt NPS oligomers.

Four oligonucleotides, the first containing MOE PS substitution, the second having MOE NPS substitution, the third having OME PS substitution, the fourth having OME NPS were tested in vitro. The following Table 28 summarizes the results of the testing. Comparing with Sequence #9 (MOE PS), Sequence #10 (MOE NPS) is 7 times more potent in vitro. Comparing with Sequence #11 (OME PS), Sequence #12 (OME NPS) is close to 6 times more potent.

TABLE 28

| Sequence | 2215 HBsAg EC50 (nM) | Tm (° C.) |
|---|---|---|
| 271 | 5 | 69.9 |
| 272 | 0.7 | 77.3 |
| 273 | 5 | 70.7 |
| 274 | 0.9 | 75.5 |

| # | Sequence (5'-3') | MW |
|---|---|---|
| 271 | 5'-moeGpsmoemCpsmoeApsmoeGpsmoeApsGpsGpsTpsGpsApsAps Gps5mCpsGpsApsmoeApsmoeGpsmoeTpsmoeGpsmoemC 3' (SEQ ID NO: 522) | 7344.19 |
| 272 | 5'moeGnpsmoeCnpsmoeApsmoeGnpsmoeAnpsGpsGpsTpsGpsA psApsGpsCpsGpsApsmoeAnpsmoeGnpsmoeUnpsmoeGnpsmoeCn 3' (SEQ ID NO: 523) | 7276.27 |
| 273 | 5'-mGps5mmCpsmApsmGpsmApsGpsGpsTpsGpsApsApsGps5mCps GpsApsmApsmGpsmUpsmGps5mmC-3' (SEQ ID NO: 524) | 6889.64 |
| 274 | 5'-mGnpsmCpsmAnpsmGnps mAnpsGpsGpsTpsGpsApsApsGpsCpsGpsApsmAnpsmGnpsmUnp smGnpsmCn-3' (SEQ ID NO: 525) | 6837.71 |

Figure 8:
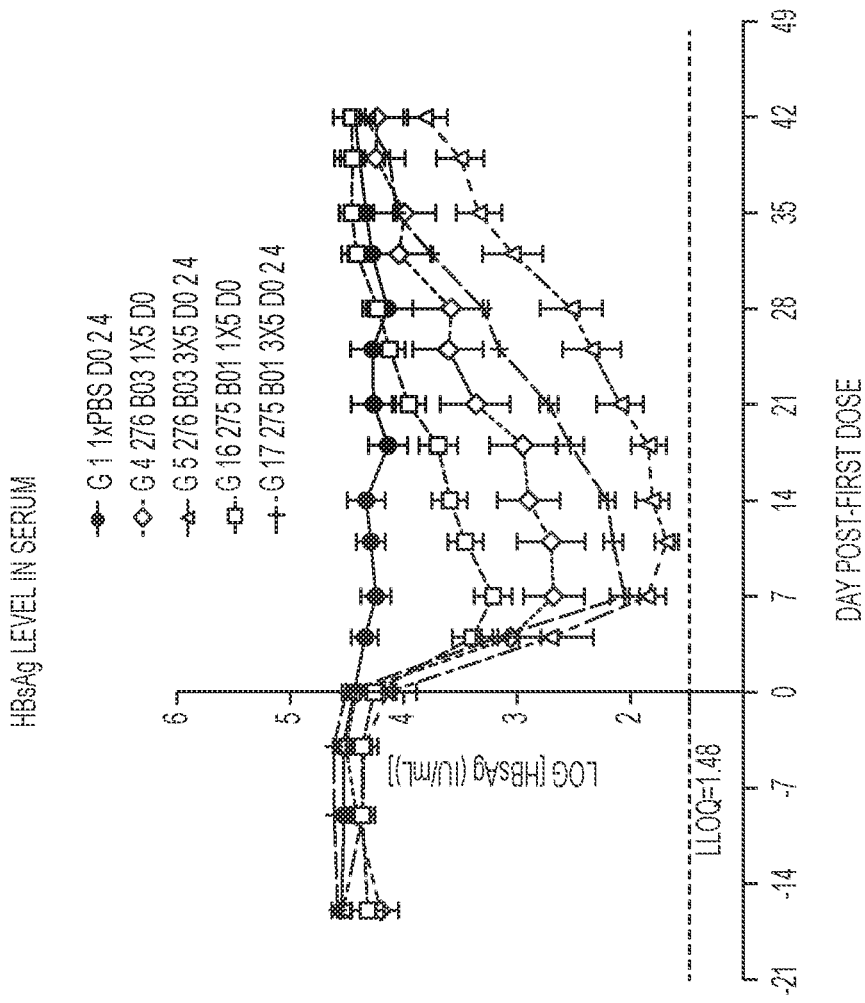
FIG. 8 shows HBsAg level in serum for two oligonucleotides described in Table 29.

Two oligonucleotides, the first containing 5'GalNAc-2'-MOE NPS substitution, the second having 5'-GalNAc-6:MOE PS substitution was tested in vivo. The following Table 29, along with FIG. 8, summarizes the results of the testing. Maximum HBsAg reduction (nadir) improvement is shown in Table 29. At certain times the advantage was as high as 0.8 log (6×) difference and the advantage of MOE NPS over MOE PS was maintained throughout most days of 42-day study duration.

TABLE 29

| # | Sequence (5'-3') | MW |
|---|---|---|
| 275 | 5'-GalNAc2-moeGnpsmoeCnpsmoeAnps moeGnpsmoeAnpsGpsGpsTpsGpsApsAps Gps(5m)CpsGpsApsmoeAnpsmoeGnps moeUnpsmoeGnpsmoeCn-3'(SEQ ID NO: 526) | 8957.00 |
| 276 | 5'-GalNac6-NH-C6-moeGps(5m)moeCps moeApsmoeGpsmoeApsGpsGpsTpsGpsAps ApsGps(5m)CpsGpsApsmoeApsmoeGps moeTpsmoeGps(5m)moeC-3' (SEQ ID NO: 527) | 9105.14 |

| Dose | Improvement of HBsAg Max Reduction (nadir) |
|---|---|
| 3 × 5 mg/kg | 0.4 Log (2.5 times) |
| 1 × 5 mg/kg | 0.5 log (3.2 times) |

Two oligonucleotides, the first containing 3'-GalNAc-2'-MOE NPS substitution, the second having 3'-GalNAc2'-MOE PS substitution was tested in vivo. The following Table 30 summarizes the results of the testing.

TABLE 30

| # | Sequence (5'-3') | MW |
|---|---|---|
| 277 | 5'moeGps(5m)moeCpsmoeApsmoeGpsmoe ApsGpsGpsTpsGpsApsApsGps(5m)CpsGps ApsmoeApsmoeGpsmoeTpsmoeGps(5me) moeC-GalNAc2-3'(SEQ ID NO: 528) | 9008.93 |
| 258 | 5'-mGnpsmoeCnpsmoeAnpsmGnpsmoeAnps GpsGpsTpsGpsApsApsGpsCpsGpsApsmoe AnpsmGnpsmoeUnpsmGnpsmoeCnp-C6-NH- GalNAc63'(SEQ ID NO: 529) | 8862.97 |

| Sequence | 277 | 258 | Improvement |
|---|---|---|---|
| Tm (° C.) | 69.9 | 77.2 | 7.3 |
| 2215 HBsAg In vitro EC50 (nM) | 5 | 0.7 | 7.1-fold |
| Max HBsAg Reduction (nadir) 3 × 10 mg/kg | 2.4 log | 3.4 log | 1 log (10 times) |
| Max HBeAg Reduction (nadir) 3 × 10 mg/kg | 1.9 log | 2.7 log | 0.8 log (6.3 times) |

Figure 10A:
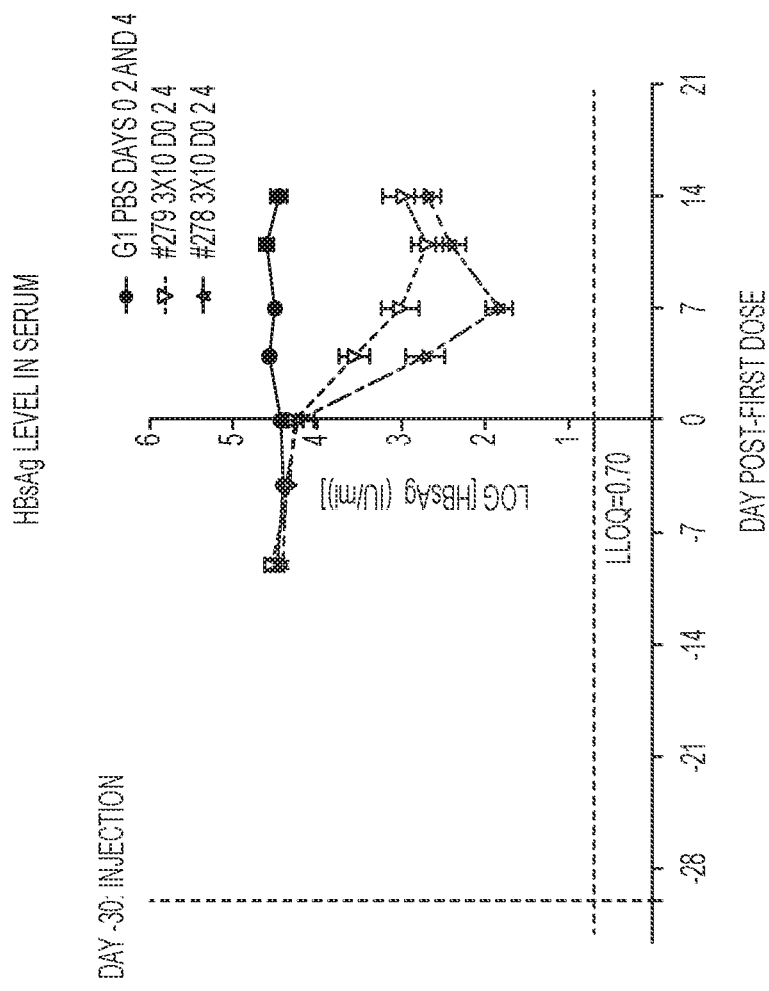
FIG. 10A shows HBsAg level in serum for two oligonucleotides described in Table 31.
Figure 10B:
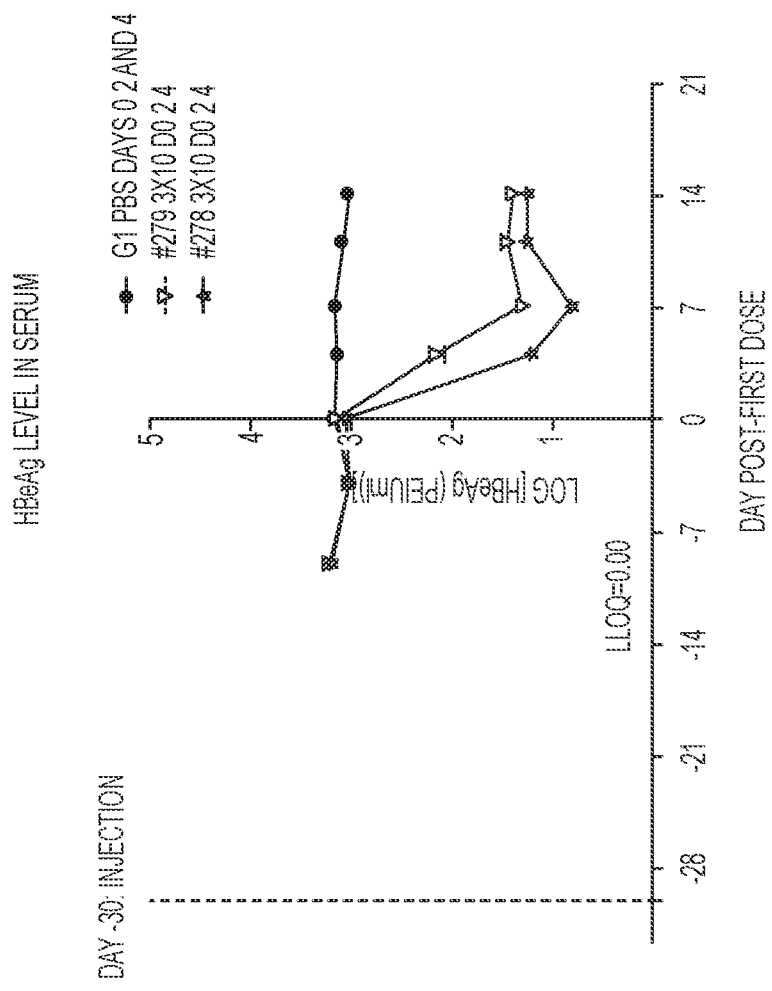
FIG. 10B shows HBeAg level in serum for two oligonucleotides described in Table 31.

Two oligonucleotides, the first containing OME NPS substitution, the second having OME PS substitution were tested in vivo. The following Table 31, along with FIGS. 10A-10B, summarizes the results of the testing. OME NPS is much more potent in vivo than OME PS.

TABLE 31

| # | Sequence (5'-3') | MW |
|---|---|---|
| 278 | 5-GalNAc2-mGnpsmCnpsmAnpsmGnpsm AnpsGpsGpsTpsGpsApsApsGpsCpsGps ApsmAnpsmGnpsmUnpsmGnpsmCn-3' (SEQ ID NO: 530) | 8502.45 |
| 279 | 5-mGps(5m)mCpsmApsmGpsmApsGpsGps TpsGpsApsApsGps(5m)CpsGpsApsmAps mGpsmUpsmGps(5m)mC-GalNAc-3' (SEQ ID NO: 531) | 8650.54 |

| Improvement of OME NPS over OME PS | Max HBsAg Reduction (nadir) improvement | Max HBeAg Reduction (nadir) |
|---|---|---|
| 3 × 10 mg/kg | 0.9 Log (8 times) | 0.5 Log (3.2 times) |

Figure 11A:
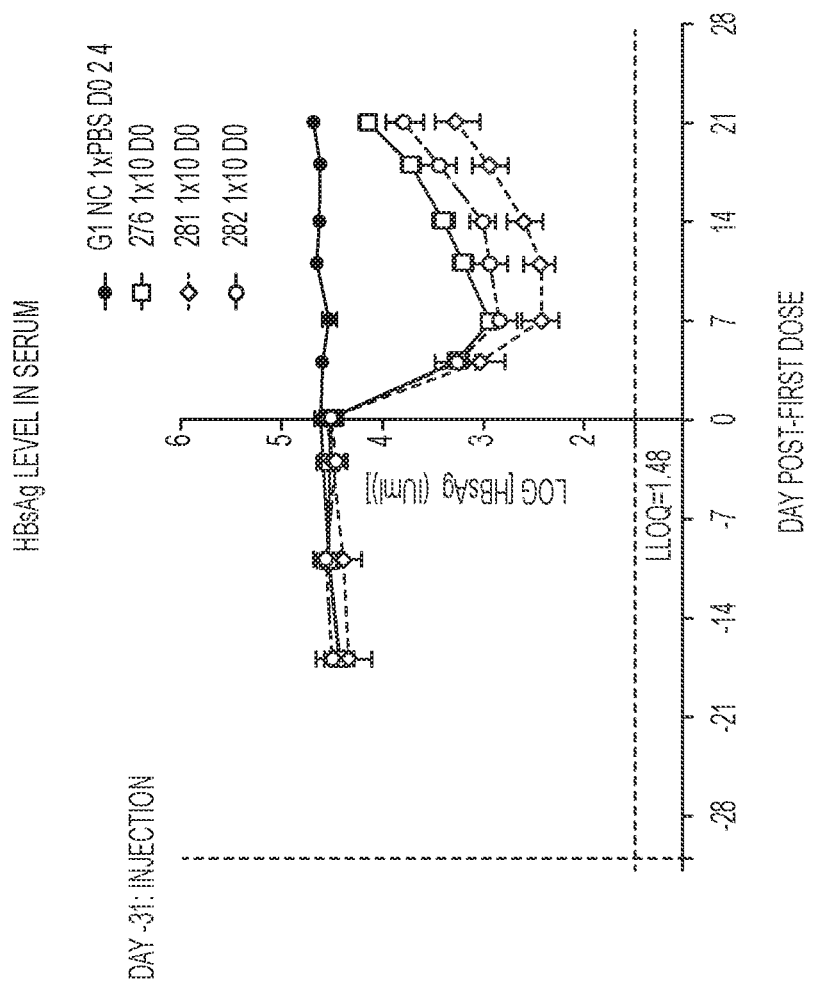
FIG. 11A shows HBsAg level in serum for oligonucleotides described in Table 33 as a single dose.
Figure 11B:
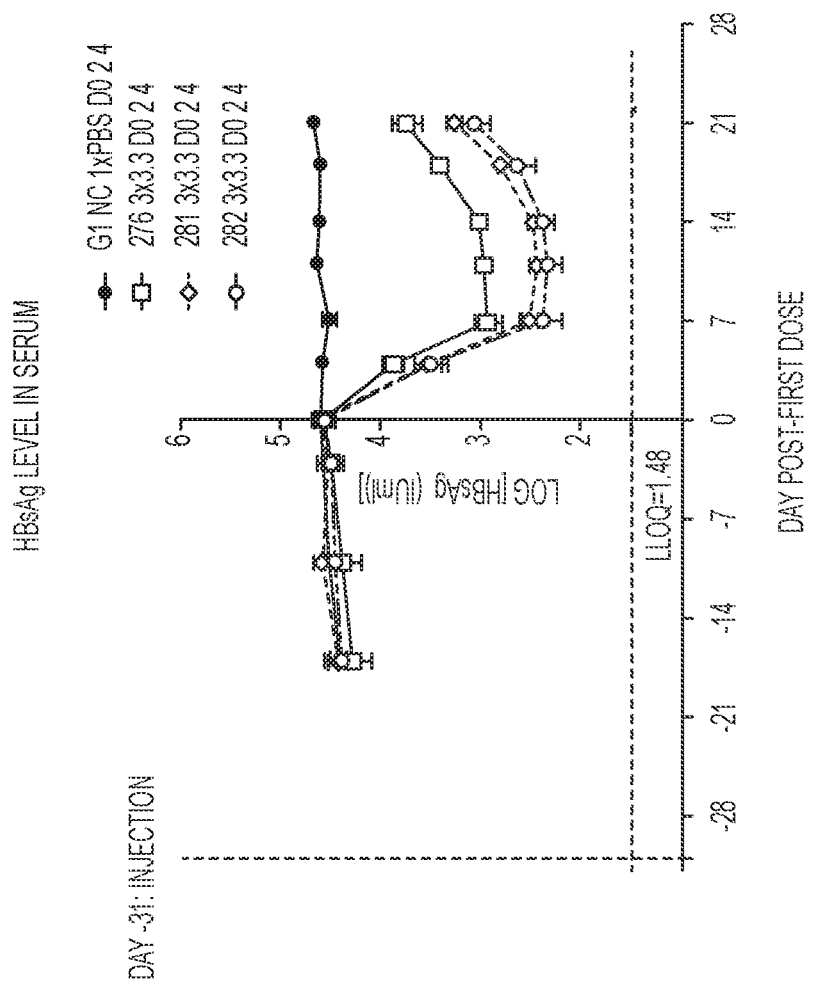
FIG. 11B shows HBsAg level in serum for oligonucleotides described in Table 33 for a dosing regimen of 3×3.3 mg/kg on Days 0, 2, 4.

The following sequences were tested in the HBV mouse model. The results are shown in FIGS. 11A-11B. In FIG. 11A, at 1×10 mg/kg dose, 3' GalNac MOE NPS maintained as high as 0.8 log (6 times) better efficacy than 5' GalNac MOE PS, advantage was maintained throughout most of the 21 day study. 5'GalNac MOE NPS maintained as high as 0.4 log (2.5 times) better efficacy than 5' GalNac MOE PS, advantage was maintained throughout most of the 21 day study. In FIG. 11B, at 3×3.3 mg/kg dose, 3' GalNac MOE NPS and 5'GalNac MOE NPS performed similarly, both maintained as high as 0.6 log (4 times) better efficacy than 5' GalNac MOE PS, advantages were maintained throughout most of the 21 day study.

TABLE 32

| # | Chemistry | SEQ ID NO: | Sequence (5'-3') | MW |
|---|---|---|---|---|
| 276 | MOE PS | 532 | 5'-GalNac6-NH-C6-moeGps(5m) moeCpsmoeApsmoeGpsmoeApsGps GpsTpsGpsApsApsGps(5m)Cps GpsApsmoeApsmoeGpsmoeTpsmoe Gps(5m)moeC-3' | 9105.14 |
| 280 | MOE NPS | 533 | 5'-GalNAc2-moeGnpsmoeCnpsmoe AnpsmoeGnpsmoeAnpsGpsGpsTps GpsApsApsGps(5m)CpsGpsApsmoe AnpsmoeGnpsmoeUnpsmoeGnpsmoe Cn-3' | 8957.00 |

The following sequences were tested in the HBV mouse model. The results are shown in FIG. 11A for a dosing regimen of a 10 mg/kg single dose, and FIG. 11B for a dosing regimen of 3×3.3 mg/kg on Days 0, 2, 4.

TABLE 33

| # | Chemistry | SEQ ID NO: | Sequence (5'-3') | MW |
|---|---|---|---|---|
| 276 | MOE PS | 534 | 5'-GalNac6-NH-C6-moeGps(5m)moe CpsmoeApsmoeGpsmoeApsGpsGpsTps GpsApsApsGps(5m)CpsGpsApsmoe ApsmoeGpsmoeTpsmoeGps(5m)moe C-3' | 9105.14 |
| 281 | MOE NPS | 535 | 5'-moeGnpsmoeCnpsmoeAnpsmoeGnps moeAnpsGpsGpsTpsGpsApsApsGps(5m) CpsGpsApsmoeAnpsmoeGnpsmoeUnps moeGnpsmoeCnp-C6-NH-GalNAc6-3' | 9053.85 |
| 282 | MOE NPS | 536 | 5'-GalNAc2-moeGnpsmoeCnpsmoeAnps moeGnpsmoeAnpsGpsGpsTpsGpsApsAps Gps(5m)CpsGpsApsmoeAnpsmoeGnps moeUnpsmoeGnpsmoeCn-3' | 8957.00 |

The following sequences were tested in the HBV mouse model. The values in the right column show max HBsAg reduction in LOG dosed at 3×10 mg/kg Days 0, 2, 4.

TABLE 34

| # | Chemistry | SEQ ID NO: | Sequence 5'-3' | Max HBsAg reduction (nadir) | MW |
|---|---|---|---|---|---|
| 283 | Deoxy NPS | 537 | 5'-GalNAc-GnpsCnpsAnps GnpsAnpsGpsGpsTpsGpsAps ApsGpsCpsGpsApsAnpsGnps TnpsGnpsCn-3' | 1.1 | 8312.38 |
| 265 | MOE NPS | 538 | 5'-GalNAc-moeGnpsmoeCnps moeAnpsmoeGnpsmoeAnpsGps GpsTpsGpsApsApsGpsCpsGps ApsmoeAnpsmoeGnpsmoeUnps moeGnpsmoeCn-3' | 3.1 | 9037.17 |

The following sequences were tested in the HBV mouse model. The values in the right column show max HBsAg reduction in LOG dosed at 3×10 mg/kg Days 0, 2, 4.

TABLE 35

| No. | Targeted HBV Region | Chemistry | SEQ ID NO: | Sequence 5'-3' | Max HBsAg reduction (nadir) in log | MW |
|---|---|---|---|---|---|---|
| 283 | DR2 #1 | Deoxy NPS | 539 | 5'-GalNAc-GnpsCnpsAnps GnpsAnpsGpsGpsTpsGpsAps ApsGpsCpsGpsApsAnpsGnps TnpsGnpsCn-3' | 1.1 | 8312.38 |
| 284 | DR2 #1 | OME NPS | 540 | 5'-GalNAc-mGnpsmCnpsm AnpsmGnpsmAnpsGpsGpsTps GpsApsApsGpsCpsGpsApsm AnpsmGnpsmUnpsmGnpsm Cn-3' | 2.1 | 8598.62 |
| 285 | DR2 #1 | F NPS | 541 | 5'-GalNAc-fGnpsfCnpsf AnpsfGnpsfAnpsGpsGpsTps GpsApsApsGpsCpsGpsApsf AnpsfGnpsfUnpsfGnps-3nh2-fC-3' | 2.5 | 8478.26 |
| 286 | DR2 #1 | Ara F NPS | 542 | 5'-GalNAc-afGnpsafCnps afAnpsafGnpsafAnpsGps GpsTpsGpsApsApsGpsCps GpsApsafAnpsafGnpsaf TnpsafGnpsafCn-3' | 0.5 | 8492.29 |
| 287 | DR2 #2 | Deoxy NPS | 543 | 5'-GalNAc-dTnpsGnpsCnps AnpsGnpsApsGpsGpsTpsGps ApsApsGpsCpsGpsAnpsAnps GnpsTnps-3nh2-G-3' | 1.1 | 8327.29 |
| 288 | DR2 #2 | OME NPS | 544 | 5'-GalNAc-mUnpsmGnpsm CnpsmAnpsmGnpsApsGpsGps TpsGpsApsApsGpsCpsGpsm AnpsmAnpsmGnpsmUnpsmG n-3' | 2.1 | 8599.60 |
| 289 | DR2 #2 | F NPS | 545 | 5'-GalNAc-fUnpsfGnpsf CnpsfAnpsfGnpsApsGpsGps TpsGpsApsApsGpsCpsGpsf AnpsfAnpsfGnpsfUnps-3nh2-fG-3' | 2.4 | 8479.24 |
| 290 | Pre-PolyA | OME NPS | 546 | 5'-GalNAc-mGnpsmCnpsm UnpsmCnpsmCnpsApsApsAps TpsTps5MeCpsTpsTpsTps ApsmUnpsmAnpsmAnpsmGnps mGnpsmGn-3' | 1.1 | 8807.84 |
| 291 | Pre-PolyA | MOE NPS | 547 | 5'-GalNAc-moeGnpsmoe CnpsmoeUnpsmoeCnpsmoe CnpsApsApsApsTpsTps5Me CpsTpsTpsTpsApsmoeUnps moeAnpsmoeAnpsmoeGnps moeGnpsmoeGn-3' | 2.0 | 9292.42 |

The following oligomers having MOE/NPS and MOE/PS substitution were tested using (1) a HepG2.2.15 HBsAg reduction potency comparison, (2) a HepG2.117 HBV DNA reduction potency comparison, (3) a Primary Human Hepatocyte (PHH) HBsAg reduction potency comparison, (4) a Primary Human Hepatocyte (PHH) HBeAg reduction potency comparison.

TABLE 36

| No. | SEQ ID NO: | Sequence (5'-3') | 1 2215 HBsAg EC50 (nM) | 2 2117 HBV DNA EC50 (nM) | 3 PHH HBsAg EC50 (nM) | 4 PHH HBeAg EC50 (nM) | MW |
|---|---|---|---|---|---|---|---|
| 292 | 548 | 5'-moeGps(5m)moeCpsmoeApsmoeGpsmoeApsGpsGpsTpsGpsApsApsGps(5m)CpsGpsApsmoeApsmoeGpsmoeTpsmoeGps(5m)moeC-3' | 5.1 | 11.4 | 16.2 | 20.1 | 7344.19 |
| 293 | 549 | 5'-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn-3' | 0.43 | 1.9 | 1.7 | 2.5 | 7292.26 |

TABLE 37

| No. | Chemistry | MW | SEQ ID NO: | Sequence |
|---|---|---|---|---|
| 294 | F NPS with OPO link to 3'GalNac | 85307.3 | 550 | 5'-fGnps(5m)fCnpsfAnpsfGnpsfAnpsGpsGpsTpsGpsApsApsGpsCpsGpsApsfAnpsfGnpsfTnpsfGnpsfC-C6-NH-GalNac6-3' |
| 295 | F NPS with NPO link to 3'GalNac | 8492.29 | 551 | 5'-fGnpsfCnpsfAnpsfGnpsfAnpsGpsGpsTpsGpsApsApsGps(5m)CpsGpsApsfAnpsfGnpsfUnpsfGnpsfCnp-C6-NH-GalNAc6-3' |

Figure 12A:
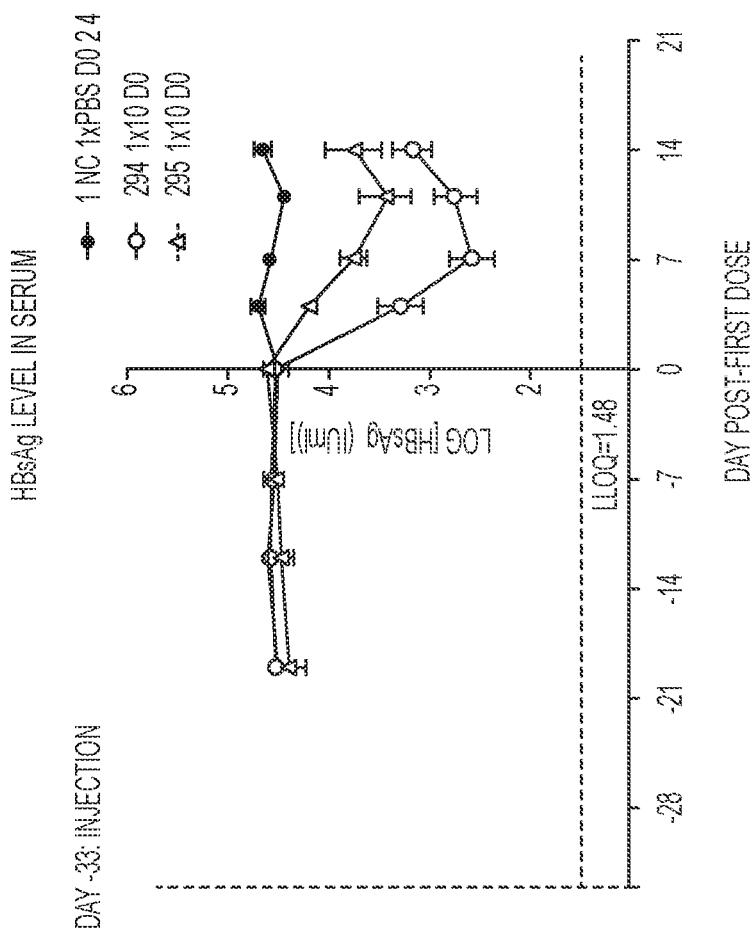
FIG. 12A shows HBsAg level in serum for oligonucleotides described in Table 37 as a single dose.

As shown in FIG. 12A, at 1×10 mg/kg, F NPS with OPO linkage to 3'GalNac significantly outperformed F NPS with NPO linkage, as high as 1.2 log (16 times) better at certain time points.

TABLE 38

| No. | Chemistry | MW | SEQ ID NO: | Sequence |
|---|---|---|---|---|
| 296 | OME NPS with NPO linkage to 3'GalNac | 8614.39 | 552 | 5-mGnpsmCnpsmAnpsmGnpsmAnpsGpsGpsTpsGpsApsApsGps(5m)CpsGpsApsmAnpsmGnpsmUnpsmGnpsmCnp-C6-NH-GalNAc6-3 |
| 297 | OME NPS with OPO linkage to 3'GalNac | 8614.43 | 553 | 5-mGnpsmCnpsmAnpsmGnpsmAnpsGpsGpsTpsGpsApsApsGps(5m)CpsGpsApsmAnpsmGnpsmUnpsmGnpsmC-C6-NH-GalNAc6-3 |

Figure 12B:
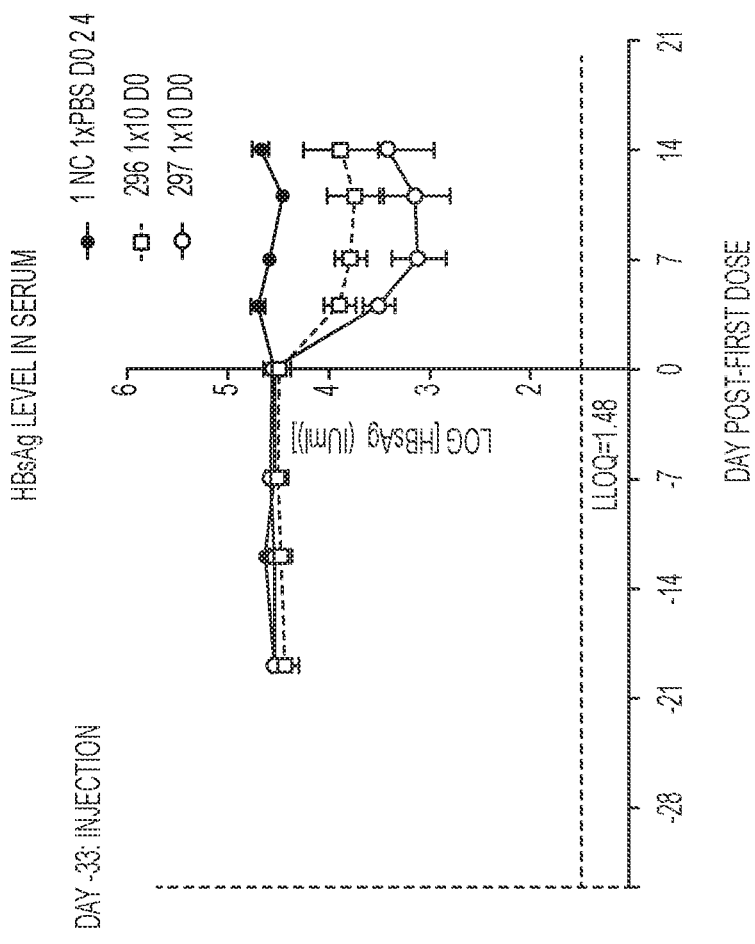
FIG. 12B shows HBsAg level in serum for oligonucleotides described in Table 38 as a single dose.

As shown in FIG. 12B, at 1×10 mg/kg, OME NPS with OPO linkage to 3'GalNac significantly outperformed OME NPS with NPO linkage, as high as 0.7 log (5 times) better at certain time points.

TABLE 39

| No. | Chemistry | MW | SEQ ID NO: | Sequence |
|---|---|---|---|---|
| 298 | MOE NPS with NPO linkage to 3'GalNac | 9053.85 | 554 | 5'-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCnp-C6-NH-GalNAc6-3' |
| 299 | MOE NPS with OPO linkage to 3'GalNac | 9069.62 | 555 | 5'-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnps(5m)moeC-C6-NH-GalNAc6-3' |

TABLE 40

| No. | Chemistry | MW | SEQ ID NO: | Sequence |
|---|---|---|---|---|
| 300 | 5'GalNAc MOE NPS | 8955.48 | 556 | 5-GalNAc2-moeGnpsmoeCnpsmoeAnpsmoeGnpsmoeAnpsGpsGpsTpsGpsApsApsGps(5m)CpsGpsApsmoeAnpsmoeGnpsmoeUnpsmoeGnpsmoeCn-3 |
| 301 | 5'GalNAc OEt NPS | 8697.6 | 557 | 5-GalNAc2-etoGnpseto(5m)CnpsetoAnpsetoGnpsetoAnpsGpsGpsTpsGpsApsApsGps(5m)CpsGpsApsetoAnpsetoGnpsetoTnpsetoGnpseto(5m)Cn-3' |

Figure 12C:
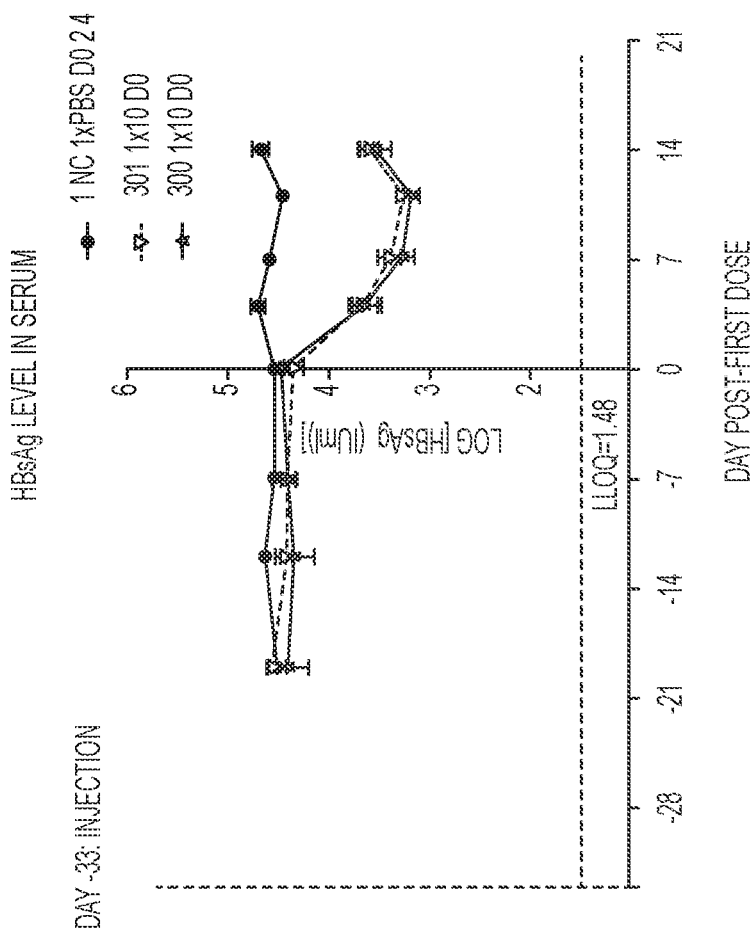
FIG. 12C shows HBsAg level in serum for oligonucleotides described in Table 40 as a single dose.

As shown in FIG. 12C, at 1×10 mg/kg, OEt NPS is as efficacious as MOE NPS.

TABLE 41

| SEQ ID No. | NO: | Sequence 5'-3' | Modification | MW | 2215 HBsAg EC50 (uM) | 2215 HBsAg CC50 (uM) |
|---|---|---|---|---|---|---|
| 302 | 558 | 5-mGnpsmCnps2-4-OCH$_2$ AnpsmGnpsmAnpsGpsGps TpsGpsApsApsGpsCps GpsAps2-4-OCH$_2$Anpsm GnpsmUnpsmGnps3-NH$_2$mC-3 | Anti-DR-1 with x2 3'-NH-LNA-A | 6835.3 | 0.0008 | 0.0148 |
| 303 | 559 | 5-mGnpsmCnps2-4-OCH$_2$ CH$_2$AnpsmGnpsmAnpsGps GpsTpsGpsApsApsGpsCps GpsAps2-4-OCH$_2$CH$_2$Anps mGnpsmUnpsmGnps3-NH$_2$mC-3 | Anti-DR-1 with x2 3'-NH-ENA-A | 6862.0 | 0.00067 | 0.0256 |
| 304 | 560 | 5-mGnpsmCnps2-4-OCH$_2$ CH$_2$AnpsmGnps2-4OCH$_2$ CH$_2$AnpsGpsGpsTpsGps ApsApsGpsCpsGpsAps2-4-OCH$_2$CH$_2$AnpsmGnpsm UnpsmGnps3-NH$_2$mC-3 | Anti-DR-1 with x3 3'-NH-ENA-A | 6874.7 | 0.0009 | 0.0214 |
| 305 | 561 | 5-mGnpsmCnpsmAnpsm Gnps2-4-OCH$_2$CH$_2$Anps GpsGpsTpsGpsApsAps GpsCpsGpsAps2-4-OCH$_2$ CH$_2$AnpsmGnpsmUnpsm Gnps3-NH$_2$mC-3 | Anti-DR-1 with x2 3'-NH-ENA-A | 6863.3 | 0.00029 | 0.0226 |
| 306 | 562 | 5-mGnpsmCnpsmUnpsm CnpsmCnps2-4-OCH$_2$CH$_2$ AnpsApsApsTpsTpsCps TpsTpsTpsmAnpsmUnps mAnps2-4-OCH$_2$CH$_2$Anps mGnpsmGnps3-NH$_2$mG-3 | Pre Poly A with x2 3'-NH-ENA-A | 7116.0 | 0.0005 | >1.00 |
| 307 | 563 | 5-mGnpsmCnpsmUnpsm CnpsmCnps2-4-OCH$_2$ CH$_2$AnpsApsApsTpsTps CpsTpsTpsTps2-4-OCH$_2$ CH$_2$AnpsmUnpsmAnps2-4-OCH$_2$CH$_2$AnpsmGnpsm Gnps3-NH$_2$mG-3 | Pre Poly A with x3 3'-NH-ENA-A | 7128.6 | 0.00055 | >1.00 |
| 308 | 564 | 5-mGnpsmCnpsmUnpsm CnpsmCnps2-4-OCH$_2$CH$_2$ AnpsApsApsTpsTpsCps TpsTpsTps2-4-OCH$_2$CH$_2$ AnpsmUnps2-4-OCH$_2$CH$_2$ AnpsmAnpsmGnpsmGnps 3-NH$_2$mG-3 | Pre Poly A with x3 3'-NH-ENA-A | 7127.9 | 0.0006 | >1.00 |

TABLE 42

| SEQ ID No. | NO: | Oligonucleotides (5'-3') | Modification | 2215 HBsAg EC50 (uM) | 2215 HBsAg CC50 (uM) |
|---|---|---|---|---|---|
| XX | 565 | 5-mGnpsmCnpsmAnpsmGnpsmAnpsGps GpsTpsGpsApsApsGpsCpsGpsApsm AnpsmGnpsmUnpsmGnps3-NH$_2$mC-3 | Control | — | — |
| 309 | 566 | 5-2-4 OCH$_2$CH$_2$GnpsmCnpsmAnpsm GnpsmAnpsGpsGpsTpsGpsApsApsGps CpsGpsApsmAnpsmGnpsmUnps2-4OCH$_2$CH$_2$Gnps3-NH$_2$mC-3 | DR-1 with 3'-NH-ENA-G (1 + 1) | 0.0013 | 0.0553 |

TABLE 42-continued

| SEQ ID No. NO: | | Modification | 2215 HBsAg EC50 (uM) | 2215 HBsAg CC50 (uM) |
|---|---|---|---|---|
| 310 | 567 5-2-4 OCH₂CH₂GnpsmCnpsmAnps2-4OCH₂CH₂GnpsmAnpsGpsGpsTpsGpsApsApsGpsCpsGpsApsmAnps2-4OCH₂CH₂GnpsmUnps2-4OCH₂CH₂Gnps3-NH₂mC-3 | DR-1 with 3'-NH-ENA-G 2 + 2 3'-NH-ENA-G | 0.0006 | 0.0230 |
| 311 | 568 5-2-4 OCH₂CH₂GnpsmCnps2-4-OCH₂CH₂AnpsmGnpsmAnpsGpsGpsTpsGpsApsApsGpsCpsGpsApsmAnpsmGnpsmUnpsmGnps3-NH₂mC-3 | DR-1 with 3'-ENA-G & 3'-ENA A (1 + 1) Asymmetric | 0.00078 | 0.0305 |
| 312 | 569 5-2-4 OCH₂CH₂GnpsmCnpsmUnpsmCnpsmCnp52-4-OCH₂CH₂AnpsApsApsTpsTpsCpsTpsTpsTpsmAnpsmUnpsmAnps2-4-OCH₂CH₂AnpsmGnpsm2-4OCH₂CH₂Gnps3-NH₂mG-3 | Pre Poly A with 1 + 1/1 + 1 3'-NH-ENA-G + A | 0.0015 | >1.00 |
| 313 | 570 5-2-4 OCH₂CH₂GnpsmCnpsmUnpsmCnpsmCnpsmAnpsApsTpsTpsCpsTpsTpsTpsmAnpsmUnpsmAnpsmAnpsmGnpsm2-4OCH₂CH₂Gnps3-NH₂mG-3 | Pre Poly A with 3'-NH-ENA-G 1 + 1 | 0.0017 | >1.00 |

TABLE 43

| No. | Found MW | SEQ ID NO: | Oligonucleotides (5'-3') | Modification | HPLC Purity | 2215 HBsAg EC50 (uM) | 2215 HBsAg CC50 (uM) |
|---|---|---|---|---|---|---|---|
| 314 | 6838 8 | 571 | 5-mGnpsmCnpsmAnpsmGnpsmAnpsGpsGpsTpsGpsApsApsGpsCpsGpsApsmAnpsmGnpsmUnpsmGnps3-NH₂mC-3 | Control | 86% | — | — |
| 315 | 6902.9 | 572 | 5-mGnps2-4OCH₂CH₂(5mc)CnpsmAnps2-4OCH₂CH₂GnpsmAnpsGpsGpsTpsGpsApsApsGpsCpsGpsApsmAnpsmGnps2-4OCH₂CH₂TnpsmGnps3-NHzmC-3 | DR-1 2 + 1 | 83% | 0.0033 | >1.00 |
| 316 | 69148 | 573 | 5-2-4OCH₂CH₂GnpsmCnps2-4OCH₂CH₂AnpsmGnpsmAnpsGpsGpsTpsGpsApsApsGpsCpsGpsApsmAnpsmGnps2-4OCH₂CH₂TnpsmGnps2-OCH₂CH₂3-NH₂(5me)C-3 | DR-1 2 + 2 | 94% | 0.0043 0.0025 | >1.00 |
| 317 | 7169 0 | 574 | 5-2-4OCH₂CH₂GnpsmCnps2-4OCH₂CH₂TnpsmCnpsmCnpsmAnpsApsApsTpsTpsCpsT;psTpsTpsmAnps2-4OCH₂CH₂TnpsmAnpsmAnpsmGnps2-4OCH₂CH₂Gnps3-NH₂mG-3 | Pre Poly A 2 + 2 | 84% | 0.0025 | >1.00 |
| 318 | 71822 | 575 | 5-mGnps2-4OCH₂CH₂(5me)CnpsmUnps2-4OCH₂CH₂(5me)CnpsmCnpsmAnpsApsApsTpsTpsCpsTpsTpsTpsmAnps2-4OCH₂CH₂TnpsmAnpsmAnps2-4OCH₂CH₂Gnpsm Gnps3-NH₂mG-3 | Pre Poly A 2 + 2 | 95% | 0.0051 | >1.00 |

In some embodiments, the oligonucleotide of the present disclosure also include an oligonucleotide that is selected from the nucleobase sequence listed in Tables 1-43, independent of the modifications of the sequences listed in Tables 1-43. Oligonucleotides of the present disclosure also include an oligonucleotide comprising a sequence that is at least 90% identical to a nucleobase sequence selected from the sequences listed in Tables 1-43, independent of the modifications of the sequences listed in Tables 1-43. In some embodiments, 1, 2, 3, 4, 5 nucleobases are different from the sequences listed in Tables 1-43, independent of the modifications of the sequences listed in Tables 1-43.

In some embodiments, the oligonucleotides of the present disclosure also include an oligonucleotide that is selected from the nucleotide sequences listed in Tables 1-43, independent of the nucleobases of the sequences listed in Tables 1-43. Oligonucleotides of the present disclosure also include an oligonucleotide comprising a sequence that is at least 90% identical to a nucleotide sequence selected from the sequences listed in Tables 1-43, independent of the nucleobases of the sequences listed in Tables 1-43. In some embodiments, 1, 2, 3, 4, 5 nucleobases are different from the sequences listed in Tables 1-43, independent of the modifications of the sequences listed in Tables 1-43.

The invention claimed is:

1. A chimeric antisense oligonucleotide represented by Formula (A):

$$5'-X-Y-Z3' \quad (A),$$

wherein
X-Y-Z is a chimeric oligonucleotide comprising a sequence of 18 to 22 nucleosides, optionally conjugated at the 5' and/or 3' end to a ligand targeting group;
X is a domain comprising a sequence of modified nucleosides that is 3 to 10 nucleosides in length;
Z is a domain comprising a sequence of modified nucleosides that is 3 to 10 nucleosides in length; and
Y is a domain comprising a sequence of 2 to 10 2'-deoxynucleosides linked through thiophosphate intersubunit linkages,
each modified nucleoside in the X domain and each modified nucleoside in the Z domain are nucleosides of Formula (1)

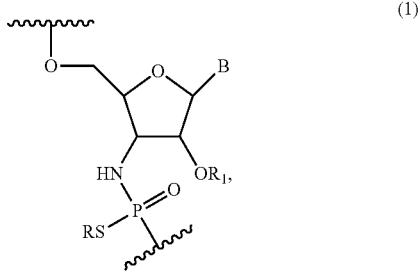

wherein
R is H or a positively charged counter ion,
B is a nucleobase independently selected from the group consisting of adenine, guanine, thymine, cytosine, uracil, 5-methylcytosine, 2,6-diaminopurine, and 5-methyluracil,
$R_1$ is —CR'$_3$, —CR'$_2$OCR'$_3$, —(CR'$_2$)$_3$OCR'$_3$, —(CR'$_2$)$_{1-2}$CR'$_3$, —(CR'$_2$)$_2$OCR'$_3$, or —Et, and
R' is independently in each instance H or F, and
wherein the oligonucleotide comprises a nucleobase sequence that is complementary or hybridizes to a target RNA.

2. The oligonucleotide of claim 1,
wherein R is H,
R is —(CR'$_2$)$_2$OCR'$_3$, and
each R' is H.

3. The oligonucleotide of claim 1, wherein the X domain and the Z domain each comprise a sequence of modified nucleosides that is 4-6 nucleosides in length.

4. The oligonucleotide of claim 1, wherein $R_1$ is —Et.

5. The oligonucleotide of claim 1, wherein $R_1$ is —(CH$_2$)$_2$OCH$_3$.

6. The oligonucleotide of claim 1, wherein the Y domain comprises 10 2'-deoxy-nucleosides.

7. The oligonucleotide of claim 6, wherein the X domain and the Z domain each comprise a sequence of modified nucleosides that is 5 nucleosides in length.

8. The oligonucleotide of claim 1, wherein the ligand targeting group comprises a GalNAc moiety.

9. The oligonucleotide of claim 1, wherein each B is independently selected from the group consisting of adenine, guanine, thymine, cytosine, uracil, 5-methylcytosine, 2,6-diaminopurine, and 5-methyluracil.

10. The oligonucleotide of claim 1, wherein each 2'-deoxy-nucleoside of the Y domain has a nucleobase independently selected from the group consisting of adenine, guanine, thymine, cytosine, uracil, 5-methylcytosine, 2,6-diaminopurine, and 5-methyluracil.

11. The oligonucleotide of claim 1, wherein the target RNA is viral RNA.

12. The oligonucleotide of claim 1, wherein the oligonucleotide comprises a nucleobase sequence that is complementary or hybridizes to the target RNA at a higher affinity than an unmodified oligonucleotide of the same sequence.

13. The oligonucleotide of claim 1, wherein the oligonucleotide complexed with the target RNA under physiological conditions has a melting temperature of >37° C.

14. A pharmaceutical composition comprising the oligonucleotide of claim 1 and a pharmaceutically acceptable excipient.

15. The pharmaceutical composition of claim 14, wherein the pharmaceutical composition is formulated for parenteral delivery.

* * * * *